United States Patent
Ritz et al.

(10) Patent No.: US 11,974,739 B1
(45) Date of Patent: *May 7, 2024

(54) COMPRESSION AND FIXATION SYSTEMS AND PROCESSES FOR USING THE SAME

(71) Applicant: Pressio Inc., San Antonio, TX (US)

(72) Inventors: Joseph Paul Ritz, Castroville, TX (US); Eric Alberto Marcano, San Antonio, TX (US); Daniel Paul Leas, Huntersville, NC (US)

(73) Assignee: Pressio Inc., San Antonio, TX (US)

( * ) Notice: Subject to any disclaimer, the term of this patent is extended or adjusted under 35 U.S.C. 154(b) by 122 days.

This patent is subject to a terminal disclaimer.

(21) Appl. No.: 17/699,990

(22) Filed: Mar. 21, 2022

Related U.S. Application Data

(63) Continuation of application No. 17/353,165, filed on Jun. 21, 2021, now Pat. No. 11,311,289.

(51) Int. Cl.
| | |
|---|---|
| *A61B 17/064* | (2006.01) |
| *A61B 17/10* | (2006.01) |
| *A61B 17/16* | (2006.01) |
| *A61B 17/17* | (2006.01) |
| *A61B 17/56* | (2006.01) |
| *A61B 17/00* | (2006.01) |

(52) U.S. Cl.
CPC .......... *A61B 17/0642* (2013.01); *A61B 17/10* (2013.01); *A61B 17/1671* (2013.01); *A61B 17/1757* (2013.01); *A61B 17/56* (2013.01); *A61B 2017/00867* (2013.01); *A61B 2017/0641* (2013.01); *A61B 2017/564* (2013.01)

(58) Field of Classification Search
CPC ............................ A61B 17/0642; A61B 17/10
See application file for complete search history.

(56) References Cited

U.S. PATENT DOCUMENTS

| | | | | |
|---|---|---|---|---|
| 2,544,492 | A * | 3/1951 | Francis | A61B 17/10 |
| | | | | 227/181.1 |
| 4,438,769 | A * | 3/1984 | Pratt | A61B 17/92 |
| | | | | 227/19 |
| 5,246,443 | A * | 9/1993 | Mai | A61B 17/8004 |
| | | | | 606/911 |
| 6,325,805 | B1 * | 12/2001 | Ogilvie | A61B 17/0642 |
| | | | | 606/911 |
| 6,336,928 | B1 | 1/2002 | Guerin | |
| 6,966,911 | B2 | 11/2005 | Ellington | |

(Continued)

*Primary Examiner* — Christian A Sevilla
(74) *Attorney, Agent, or Firm* — Morris, Manning & Martin, LLP; Daniel E. Sineway, Esq.; Adam J. Thompson, Esq.

(57) ABSTRACT

A staple apparatus can include a base member substantially coplanar to a first axis and a second axis perpendicular to the first axis. The base member can include a trapezoidal shape including two substantially equal length sides and two unequal length sides, the two unequal length sides comprising a first side and a second side with the first side being shorter than the second side and the first side being parallel with the second side on the first axis. The base member can include an aperture passing through a center point of the base member, a first indentation in the first side, and a second indentation in the second side. The staple apparatus can include a first pair of legs protruding from the first side of the base member and a second pair of legs protruding from the second side of the base member.

20 Claims, 74 Drawing Sheets

(56) References Cited

U.S. PATENT DOCUMENTS

| | | |
|---|---|---|
| 7,618,441 B2 | 11/2009 | Groiso |
| 7,635,367 B2 | 12/2009 | Groiso |
| 7,942,301 B2 | 5/2011 | Sater |
| 8,021,389 B2 | 9/2011 | Molz, IV |
| 8,062,297 B2 | 11/2011 | Groiso |
| 8,211,109 B2 | 7/2012 | Groiso |
| 8,343,194 B2 | 1/2013 | Alfatoon |
| 8,372,075 B2 | 2/2013 | Groiso |
| 8,475,493 B2 | 7/2013 | Bender |
| 8,584,853 B2 | 11/2013 | Knight |
| 8,721,646 B2 | 5/2014 | Fox |
| 8,801,753 B2 | 8/2014 | Bender |
| 8,864,764 B2 | 10/2014 | Groiso |
| 8,979,927 B2 | 3/2015 | Huntsman |
| 9,017,331 B2 | 4/2015 | Fox |
| 9,101,349 B2 | 8/2015 | Knight |
| 9,204,932 B2 | 12/2015 | Knight |
| 9,295,463 B2 | 3/2016 | Viola |
| 9,339,268 B2 | 5/2016 | Fox |
| 9,451,955 B2 | 9/2016 | Fox |
| 9,451,957 B2 | 9/2016 | Fox |
| 9,468,436 B2 | 10/2016 | Groiso |
| 9,649,108 B2 | 5/2017 | Weinstein |
| 9,700,362 B2 | 7/2017 | Knight |
| 9,743,926 B2 | 8/2017 | Fox |
| 9,839,458 B2 | 12/2017 | Bouduban |
| 9,855,036 B2 | 1/2018 | Palmer |
| 10,010,320 B2* | 7/2018 | Wahl ................ A61B 17/0682 |
| 10,058,366 B2 | 8/2018 | Bouduban |
| 10,117,647 B2 | 11/2018 | Cheney |
| 10,285,743 B2 | 5/2019 | Bouduban et al. |
| 10,368,860 B2 | 8/2019 | Nering |
| 10,512,459 B2 | 12/2019 | Fox |
| 10,779,816 B2 | 9/2020 | Goldstein |
| 10,820,902 B2 | 11/2020 | Cheney |
| 10,842,487 B2 | 11/2020 | Ritz |
| 10,918,484 B2 | 2/2021 | Ellington |
| 10,987,101 B2 | 4/2021 | Ducharme |
| 11,006,949 B2 | 5/2021 | Daniel |
| 11,020,110 B1 | 6/2021 | Blair |
| 11,033,311 B2 | 6/2021 | McIff |
| 11,045,190 B1 | 6/2021 | Anakwenze |
| 2002/0107575 A1* | 8/2002 | Metz-Stavenhagen ..................... A61F 2/442 623/17.16 |
| 2005/0021035 A1 | 1/2005 | Groiso |
| 2006/0058802 A1 | 3/2006 | Kofoed |
| 2007/0093839 A1 | 4/2007 | Beckendorf |
| 2007/0233187 A1 | 10/2007 | Lobello |
| 2008/0065153 A1 | 3/2008 | Allard |
| 2008/0065154 A1 | 3/2008 | Allard |
| 2008/0262541 A1 | 10/2008 | Sater |
| 2008/0269803 A1 | 10/2008 | Sater |
| 2008/0319443 A1 | 12/2008 | Focht |
| 2009/0131984 A1 | 5/2009 | Linares |
| 2010/0063506 A1* | 3/2010 | Fox ................ A61B 17/0642 606/151 |
| 2011/0022099 A1 | 1/2011 | Ashman |
| 2011/0118842 A1 | 5/2011 | Bernard |
| 2011/0297732 A1 | 12/2011 | Molz, IV |
| 2013/0206815 A1* | 8/2013 | Fox ................ A61B 17/0642 227/176.1 |
| 2013/0231667 A1 | 9/2013 | Taylor |
| 2014/0214037 A1 | 7/2014 | Mayer |
| 2014/0276830 A1 | 9/2014 | Cheney |
| 2014/0276881 A1* | 9/2014 | Taylor ................ A61B 17/17 606/96 |
| 2014/0309639 A1 | 10/2014 | Averous |
| 2014/0358187 A1* | 12/2014 | Taber ................ A61B 17/10 606/86 R |
| 2015/0230839 A1* | 8/2015 | Riccione ............ A61B 17/0642 606/297 |
| 2015/0238039 A1 | 8/2015 | Riccione |
| 2015/0313592 A1 | 11/2015 | Coillard-Lavirotte |
| 2016/0135808 A1 | 5/2016 | Anderson |
| 2016/0287230 A1 | 10/2016 | Hausen |
| 2017/0020537 A1* | 1/2017 | Tuten ................ A61B 17/0642 |
| 2017/0209193 A1 | 7/2017 | Hartegen |
| 2017/0215879 A1 | 8/2017 | Weinstein et al. |
| 2018/0008263 A1 | 1/2018 | Goldstein |
| 2018/0071001 A1 | 3/2018 | McIff |
| 2018/0289366 A1 | 10/2018 | Morgan |
| 2018/0353172 A1 | 12/2018 | Hartdegen |
| 2019/0105040 A1 | 4/2019 | Gordon |
| 2019/0357951 A1 | 11/2019 | Rogers |
| 2020/0000465 A1 | 1/2020 | MacLure |
| 2020/0038076 A1 | 2/2020 | Amis |
| 2020/0138433 A1 | 5/2020 | Fox |
| 2020/0146668 A1 | 5/2020 | Krumme |
| 2020/0214701 A1 | 7/2020 | Wahl |
| 2020/0229813 A1 | 7/2020 | Seykora |
| 2020/0281633 A1 | 9/2020 | Rogers |
| 2020/0375594 A1 | 12/2020 | Goldstein |
| 2020/0375639 A1 | 12/2020 | Rogers |
| 2020/0383684 A1 | 12/2020 | Weinstein |
| 2021/0068822 A1 | 3/2021 | Wahl |
| 2021/0128145 A1 | 5/2021 | Taylor |
| 2021/0161671 A1 | 6/2021 | Ellington |

\* cited by examiner

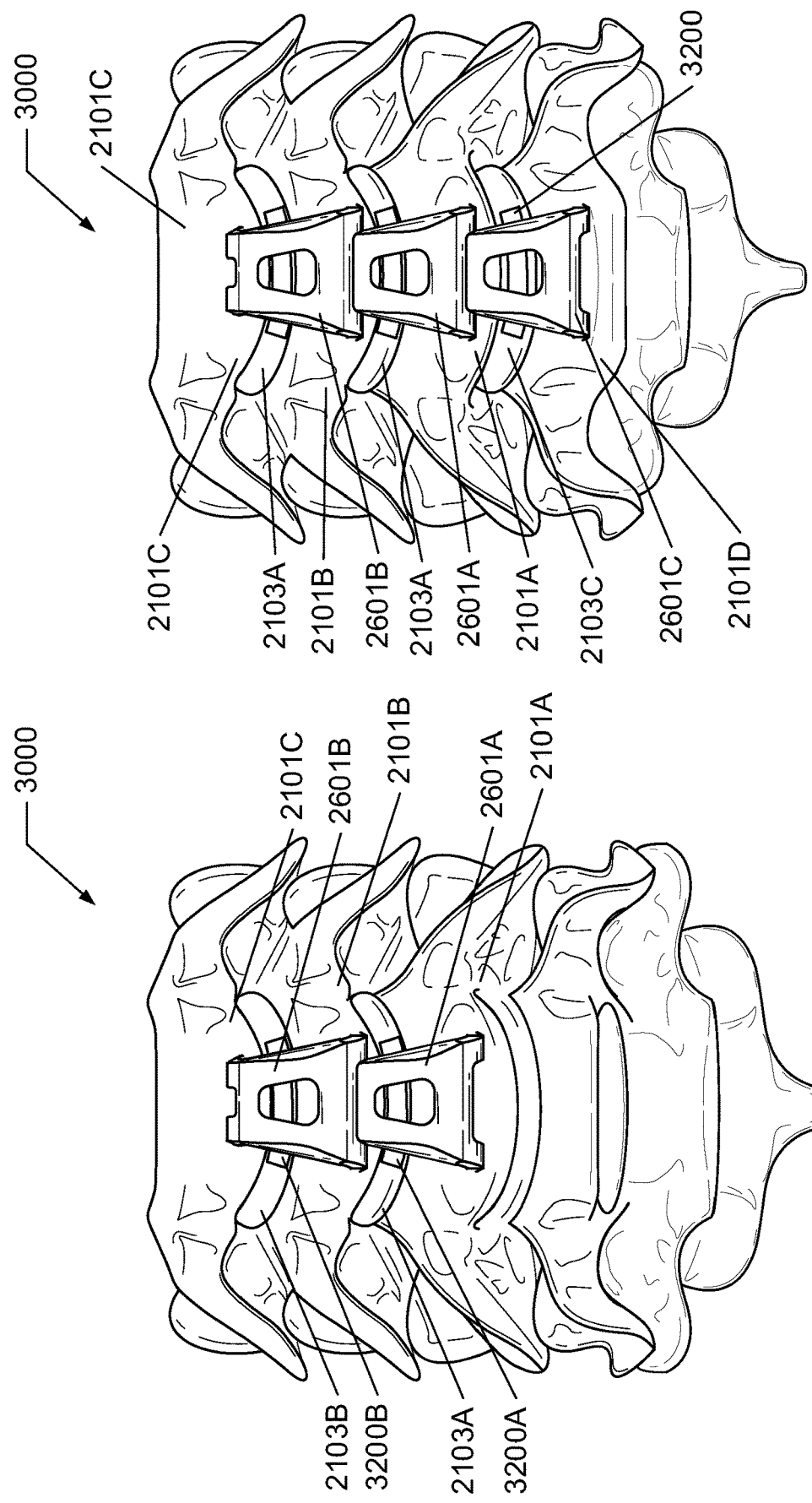

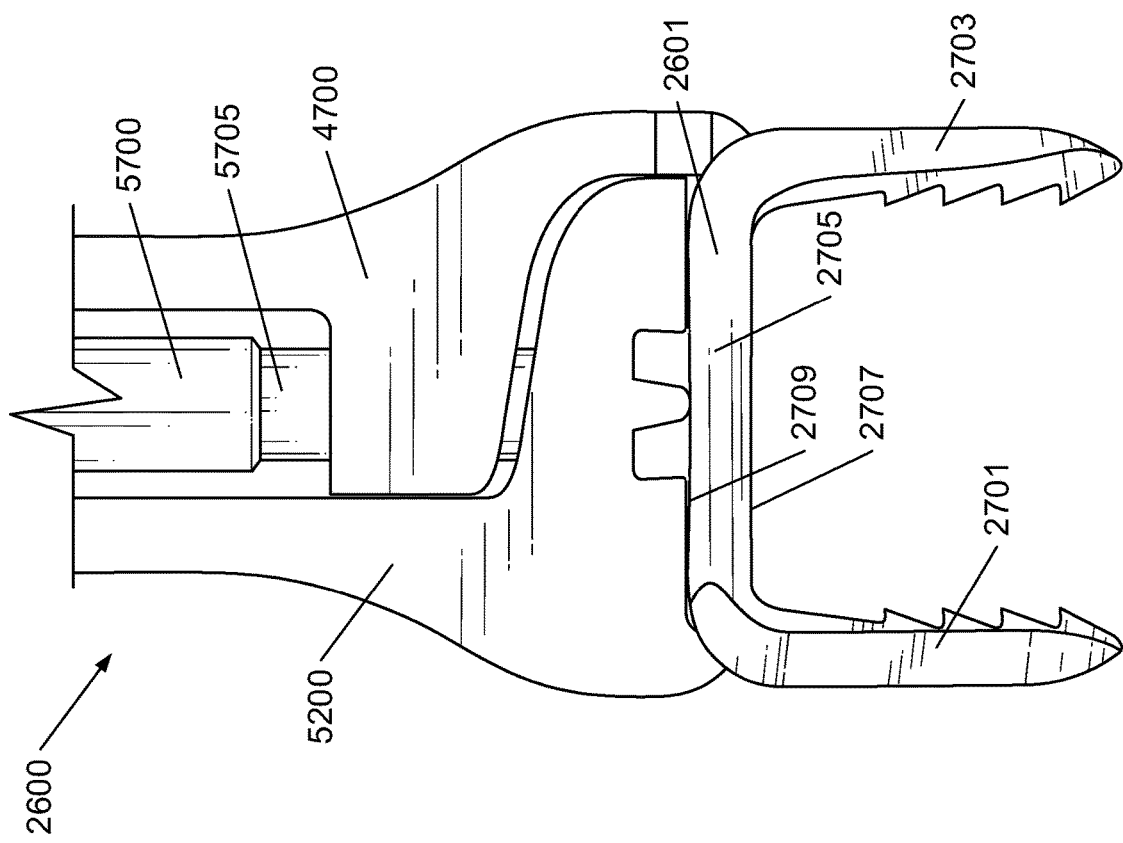
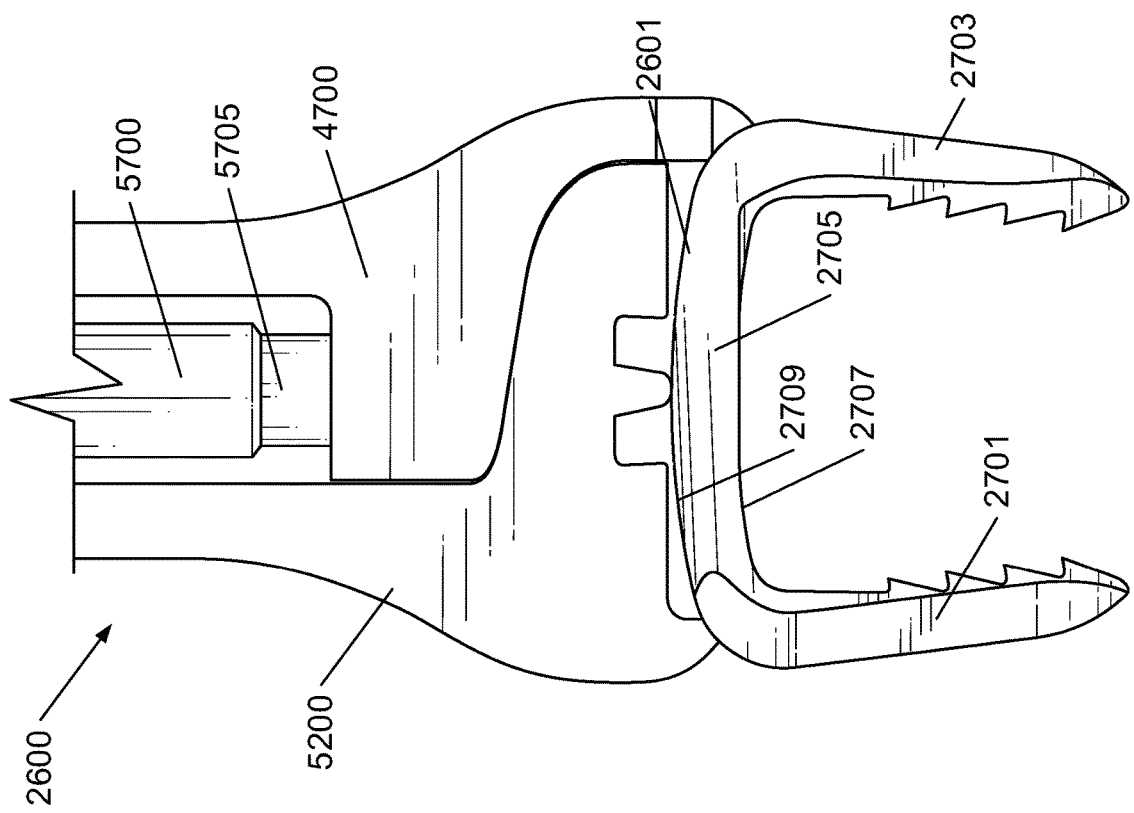
FIG. 31A
FIG. 31B

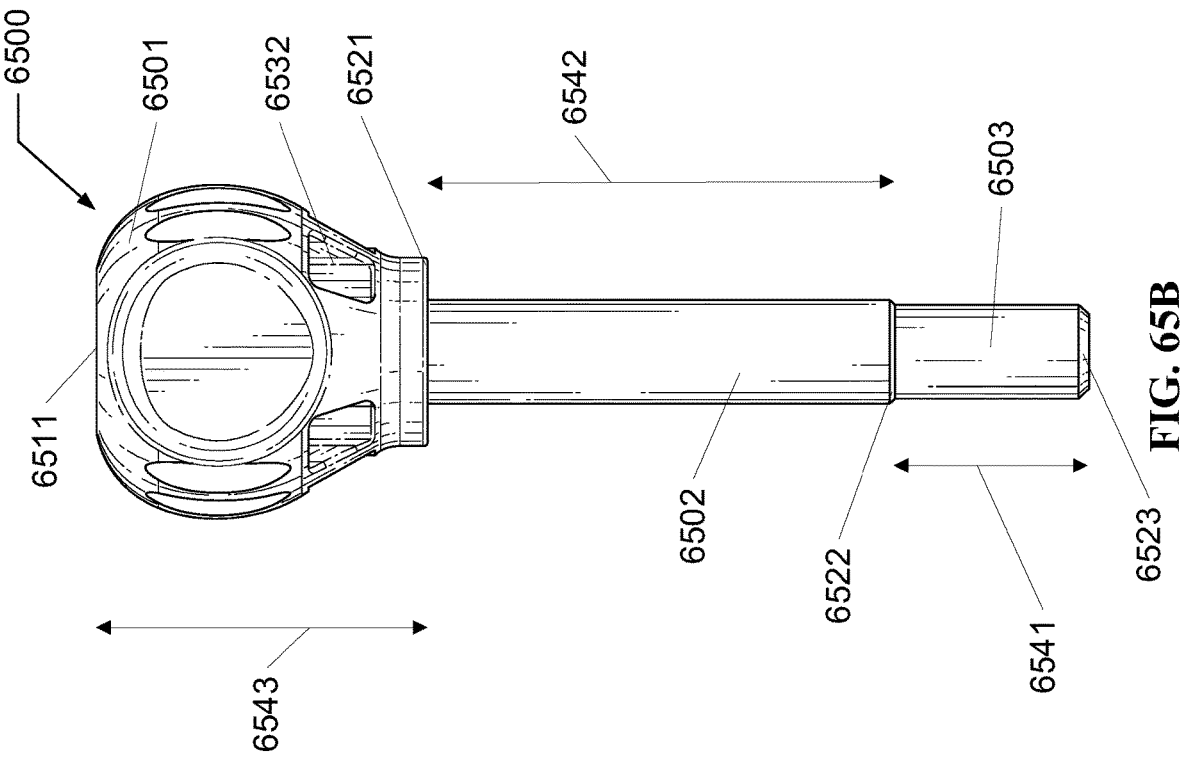
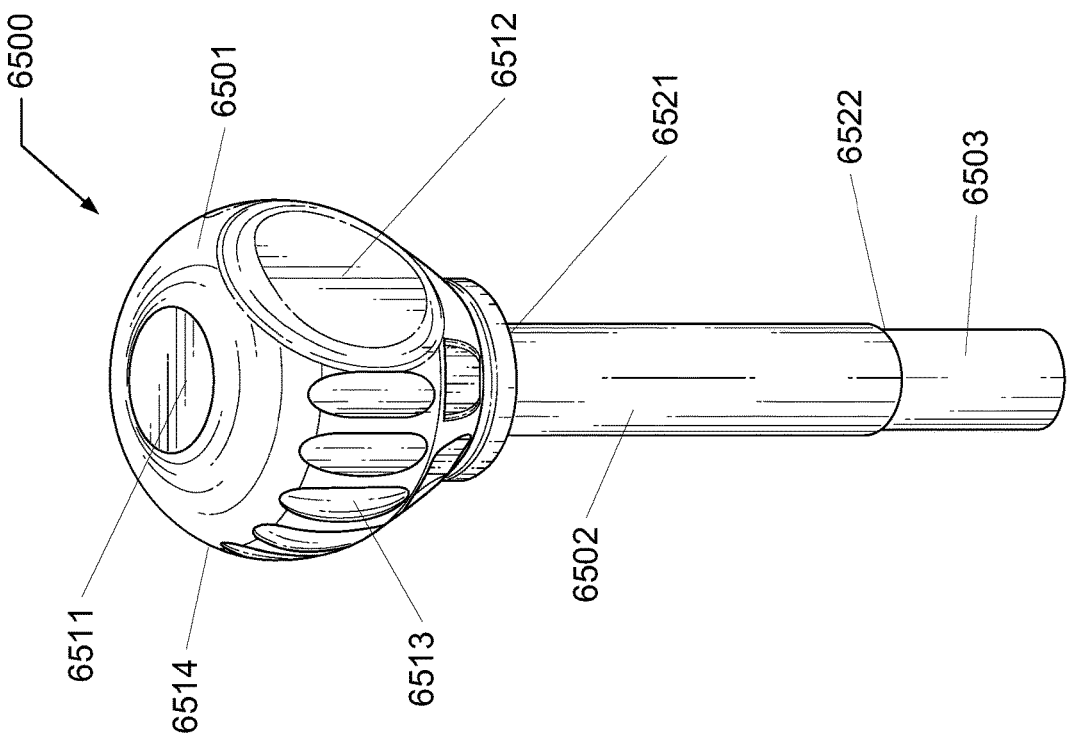
FIG. 65B
FIG. 65A

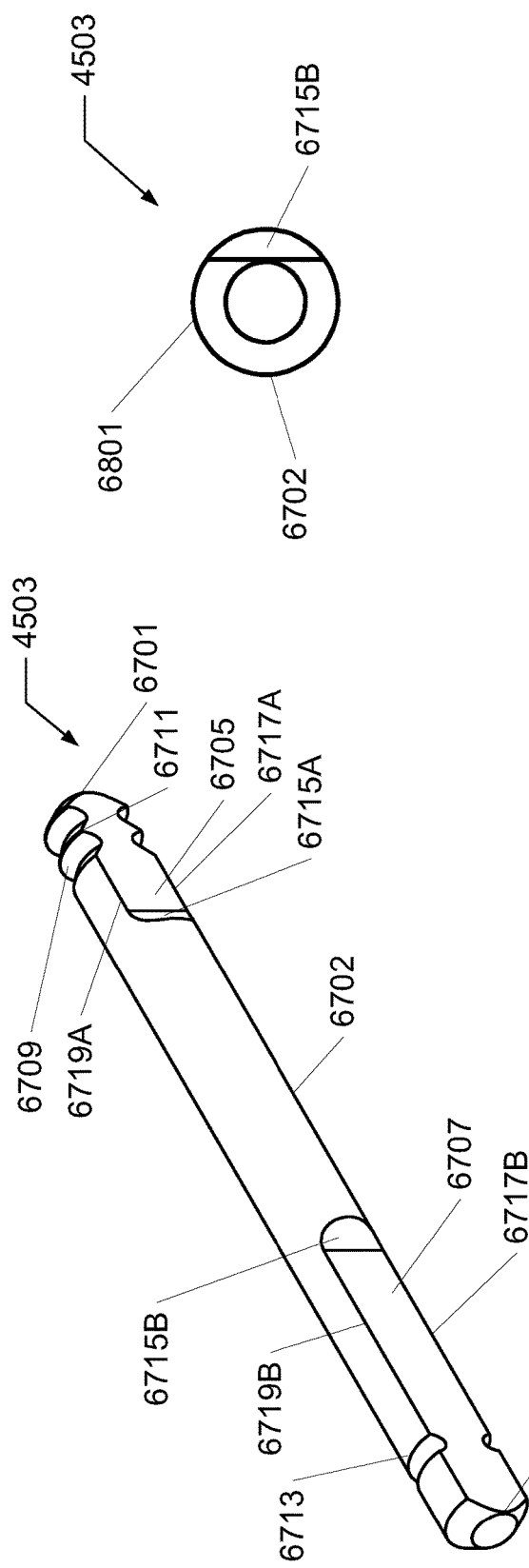
FIG. 67
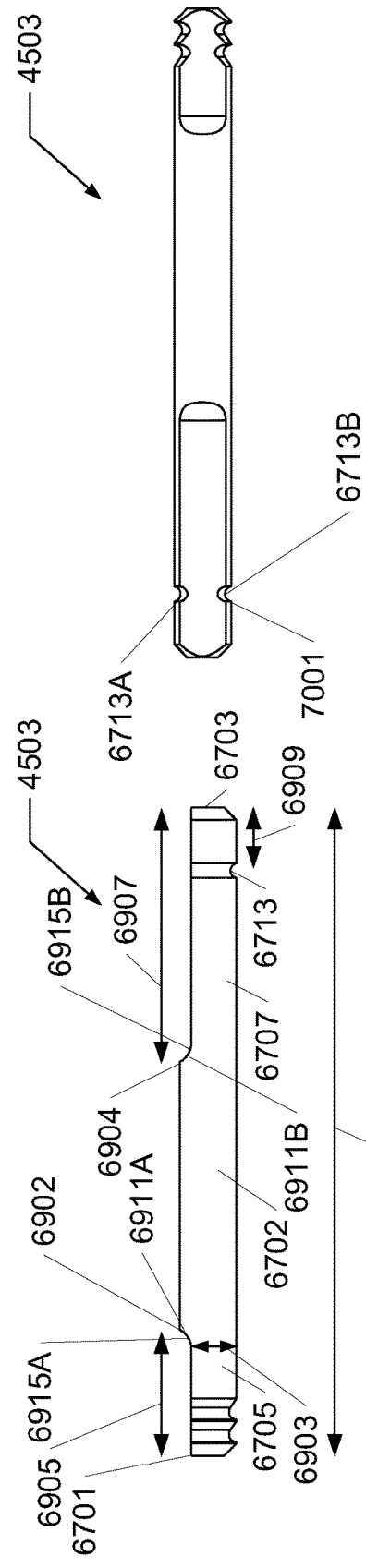
FIG. 68
FIG. 70
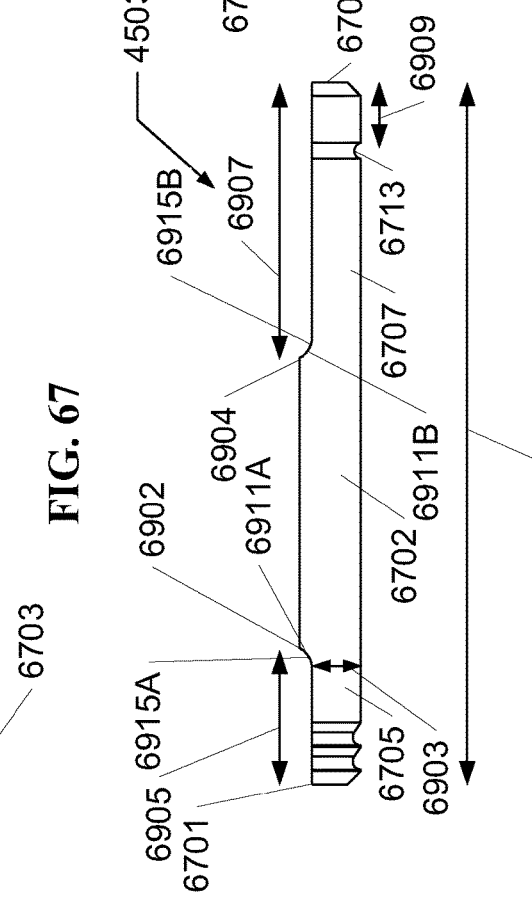
FIG. 69

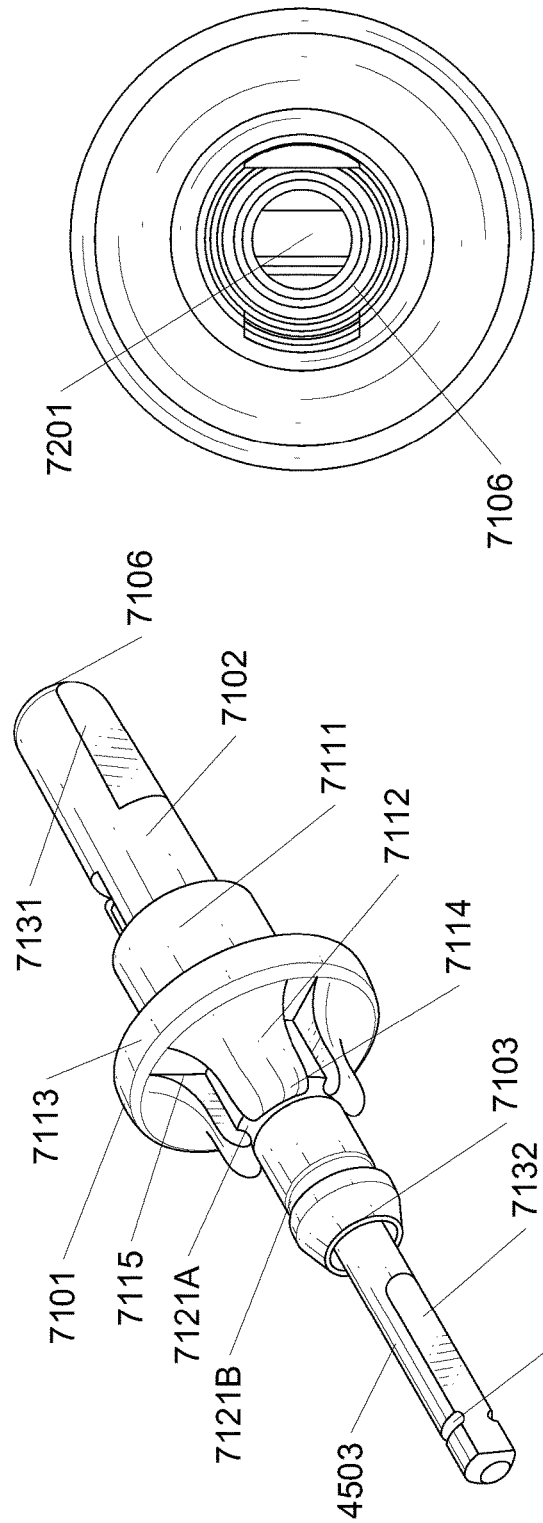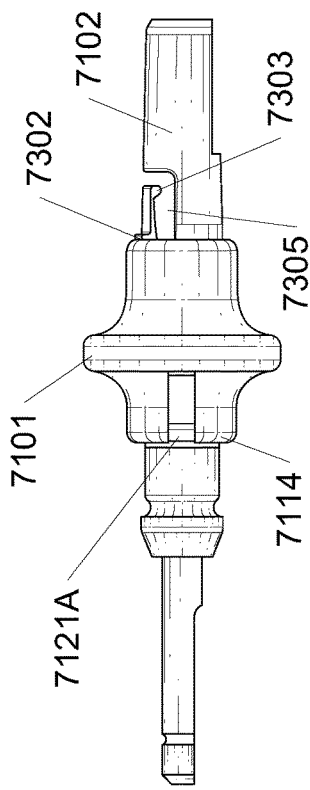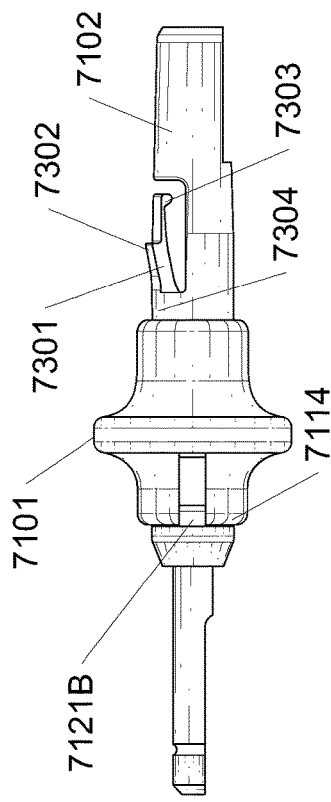

COMPRESSION AND FIXATION SYSTEMS AND PROCESSES FOR USING THE SAME

CROSS REFERENCE TO RELATED APPLICATIONS

This application is a continuation of U.S. patent application Ser. No. 17/353,165, filed Jun. 21, 2021, entitled "COMPRESSION AND FIXATION SYSTEMS AND PROCESSES FOR USING THE SAME," the disclosure of which is incorporated by reference herein its entirety.

TECHNICAL FIELD

The present systems and processes relate generally to fixation and compression of bony structures.

BACKGROUND

Surgical staples are used in orthopedic indications to apply compressive forces to two or more bone segments. Patients may require multiple staples to fixate and compress bone segments. For example, spinal fusion procedures may include fusing two adjacent vertebrae and some patients may require fusion of three or more vertebrae. As will be understood, space within a body is limited and space within a spinal column is especially limited due to prevalence of soft tissues and requirements for tolerating spinal articulation. Previous approaches to multi-implant compression procedures may rely on external alignment apparatuses for maintaining an inserted position and arrangement of compressive implants. However, external alignment apparatuses are typically bulky and cumbersome, thereby increasing a risk of patient discomfort and increasing a risk of inserted implants becoming disturbed or dislodged (for example, in instances where external alignment apparatuses experience a shock or other external force).

Therefore, there exists a need for improved staple systems that are spatially efficient and tolerant to target site articulation.

BRIEF SUMMARY OF THE DISCLOSURE

Briefly described, and according to one embodiment, aspects of the present disclosure generally relate to compression and fixation systems and processes for using the same. In particular embodiments, the compression and fixation system and processes are used for orthopedic procedures to fuse bone structures together.

Generally, surgical staples can be used in orthopedic indications to apply compressive forces to two or more bone segments or structures. Staples can compress bone structures together or toward an implant placed therebetween based on stored strain profiles of the staples. Such compression can limit the distance between broken bone segments, thereby possibly helping reduce bone healing time by eliminating gaps that need to be filled by the bones/body when healing. Further, such compression may help increase/speed bone growth.

In various embodiments, the compression and fixation system includes one or more staples and one or more insertion tools, such as, for example, a tool for preparing a target site and a tool for inserting a staple to the target site. In at least one embodiment, the staple is configured to compress two or more bony structures together and/or against an implant inserted therebetween. For example, in a spinal fusion procedure a staple is inserted into adjacent vertebrae and the staple compresses the adjacent vertebrae toward an intervertebral space between the vertebrae. In the same example, a second staple is inserted into one of the adjacent vertebrae and into an additional adjacent vertebra, and the second staple compresses the one of the adjacent vertebrae and the additional adjacent vertebra toward a second intervertebral space therebetween. In this example, a shape of the second staple conforms to a footprint of the first staple such that the first and second staples demonstrate a low profile and an improved stacking efficiency. As referenced herein, an improved stacking efficiency generally refers to a quality of two or more staples to be placed in a space such that a portion of one of the two or more staples is received into (e.g., "nests") into another of the two or more staples.

In at least one embodiment, the staple includes a base member and two or more legs. In one or more embodiments, the staple includes a first leg and a second leg that connect to a first side of the base member, and the staple includes a third and a fourth leg that connect to a second side of the base member (e.g., opposite the first side). In particular embodiments, the base member acts as a semi rigid component that connects to each of the four legs at its respective corners. In at least one embodiment, the semi rigid structure allows a user to bend the base member to a constrained state. In one or more embodiments, the base member is biased to return to an unconstrained state from the constrained state, and the bias of the base member toward the unconstrained state allows the staple to generate compressive forces at a target site. In various embodiments, the base member can include an aperture at its center point and can be shaped to any geometric configuration (e.g., rectangular, trapezoidal, square).

In some embodiments, the legs can be deformed relative to a vertical axis. For example, the legs can be deformed to a substantially parallel orientation or to an orientation in which opposed pairs of legs are angled away from each other. In some embodiments, the top surface of the base member is substantially smooth and extends continuously to the outer surface of the leg members. In at least one embodiment, each leg of the staple includes one or more teeth on the leg's inner surface. In one or more embodiments, two legs are placed into the first targeted vertebra, while the remaining two legs are placed into the adjacent targeted vertebra. In various embodiments, the four legs contact the bone once the staple has been placed into the drilled holes of the targeted bone structure and fastened into place. In particular embodiments, the four legs clasp to the bone by providing oppositional forces after the staple has been fastened. In at least one embodiment, this oppositional force compresses the bones together and/or into an implant inserted there between.

In some embodiments, the insertion tools are used to prepare the bone structure for the insertion of a staple and to fasten the staple to the targeted location. In at least one embodiment, the insertion tools used for preparing the bone structure for the insertion of a staple include boring apparatus, a boring apparatus handle, a target pin, a drill pin, and a tool adaptor (e.g., and may include other components described herein and/or shown in the accompanying drawings). In various embodiments, the boring apparatus is used to guide the target and drill pins relative to two vertebrae or bone structures and an intervertebral device. In particular embodiments, a boring apparatus handle can be attached to the boring apparatus to help stabilize the device during the boring process. In at least one embodiment, once the boring apparatus is positioned on the desired targeted location, the target pin is driven into the bottom vertebra to stabilize the device. In one or more embodiments, the drill pins are manually or mechanically turned into the targeting locations to create four independent boring locations. In particular embodiments, for a drill pin to be mechanically rotated, the tool adapter can be attached to the drill pin to continuously attach the drill pin to a drilling tool. In some embodiments, once the boring process is complete, the boring apparatus, the target pin, and the four drill pins can be removed to expose the four independent boring locations.

In one or more embodiments, the insertion tools used for inserting and fastening the staple include a spacer, a first shaft, a second shaft, a rod, a sleeve, a staple installation tool handle (e.g., and may include other components described herein and/or shown in the drawings). In various embodiments, the staple is grappled by both the first and second shaft with a spacer in between the staple and the shafts. In particular embodiments, the rod is placed in between both the first and second shaft and the sleeve is positioned over both of the shafts to maintain pressure on the staple. In at least one embodiment, the staple installation tool handle is attached to the top of the sleeve and can rotate freely. In some embodiments, once the previous system is assembled, the staple is placed into the four independent boring locations. In one or more embodiments, the rotation of the staple installation tool handle rotates the rod and applies downward pressure on the spacer and the staple. In various embodiments, as the spacer applies pressure on the staple within the targeted location, the base member of the staple is deformed for the teeth of the staple to catch and hold the bone structure of the targeted location. In particular embodiments, once the user has determined a desired amount of deformation, the attached tools can be disassembled and the implanted staple can remain grappled to the bone structure, thereby providing sustained compression in support of ossification and bone fusion.

According to a first aspect, a staple apparatus, comprising: A) a base member substantially coplanar to a first axis and a second axis perpendicular to the first axis, the base member comprising: 1) a trapezoidal shape comprising two substantially equal length sides and two unequal length sides, the two unequal length sides comprising a first side and a second side with the first side being shorter than the second side and the first side being parallel with the second side on the first axis; 2) an aperture passing through a center point of the base member; 3) a first indentation in the first side; and 4) a second indentation in the second side; B) a first pair of legs protruding from the first side of the base member; and C) a second pair of legs protruding from the second side of the base member.

According to a second aspect, the staple apparatus of the first aspect or any other aspect wherein the aperture is configured to align the staple apparatus on a decompression tool.

According to a third aspect, the staple apparatus of the first aspect or any other aspect wherein the first side and the second side are shorter than the two substantially equal length sides.

According to a fourth aspect, the staple apparatus of the first aspect or any other aspect wherein the staple apparatus is configured to receive a decompression tool and transition between an unconstrained state and a constrained state via the decompression tool.

According to a fifth aspect, the staple apparatus of the fourth aspect or any other aspect wherein the staple apparatus is configured to receive a first pulling component of the decompression tool at the first indentation, a second pulling component of the decompression tool at the second indentation, and a pushing component of the decompression tool at the base member.

According to a sixth aspect, the staple apparatus of the fourth aspect or any other aspect wherein the first pair of protruding legs and the second pair of protruding legs are substantially parallel to one another when in the constrained state.

According to a seventh aspect, the staple apparatus of the fourth aspect or any other aspect wherein the first pair of protruding legs and the second pair of protruding legs are parallel to a third axis when in the constrained state, the third axis being perpendicular to both the first axis and the second axis.

According to an eighth aspect, the staple apparatus of the fourth aspect or any other aspect wherein the first pair of protruding legs and the second pair of protruding legs are angled 7 degrees from parallel to a third axis in a respective direction of the second axis towards a center of the base member when in the unconstrained state, the third axis being perpendicular to both the first axis and the second axis.

According to a ninth aspect, the staple apparatus of the fourth aspect or any other aspect wherein the first pair of protruding legs are angled 17 degrees from parallel to a third axis in a direction of the second axis towards a center of the base member when in the unconstrained state, the third axis being perpendicular to both the first axis and the second axis.

According to a tenth aspect, the staple apparatus of the ninth aspect or any other aspect wherein the second pair of protruding legs are angled 3 degrees from parallel to the third axis in another direction of the second axis towards the center of the base member when in the unconstrained state.

According to an eleventh aspect, the staple apparatus of the fourth aspect or any other aspect wherein the first pair of protruding legs and the second pair of protruding legs are angled between 4.75 and 4.95 degrees from parallel to a third axis in a respective direction of the first axis away from a center of the base member when in the unconstrained state, the third axis being perpendicular to both the first axis and the second axis.

According to a twelfth aspect, the staple apparatus of the first aspect or any other aspect wherein the second indentation is longer than a length of the first side.

According to a thirteenth aspect, the staple apparatus of the first aspect or any other aspect wherein the staple apparatus comprises nitinol per ASTM F2063.

According to a fourteenth aspect, a staple system, comprising: A) a staple apparatus comprising: 1) a base member substantially coplanar to a first axis and a second axis perpendicular to the first axis, the base member comprising: i) a trapezoidal shape comprising two substantially equal length sides and two unequal length sides, the two unequal length sides comprising a first side and a second side with the first side being shorter than the second side and the first side being parallel with the second side on the first axis; ii) an aperture passing through a center point of the base member; iii) a first indentation in the first side; and iv) a second indentation in the second side; 2) a first pair of legs protruding from the first side of the base member; and 3) a second pair of legs protruding from the second side of the base member; and B) a decompression tool configured to transition the staple apparatus between an unconstrained state and a constrained state.

According to a fifteenth aspect, the staple system of the fourteenth aspect or any other aspect wherein the staple apparatus is configured to mechanically couple a first vertebra with a second vertebra, wherein the first vertebra and the second vertebra are adjacent.

According to a sixteenth aspect, the staple system of the fifteenth aspect or any other aspect further comprising a second staple apparatus configured to mechanically couple the second vertebra with a third vertebra, wherein the second vertebra and the third vertebra are adjacent According to a seventeenth aspect, the staple system of the sixteenth aspect or any other aspect wherein a first side of the second staple apparatus is configured to occupy a space corresponding to the second indentation in the second side of the staple apparatus when installed across adjacent intervertebral spaces.

According to an eighteenth aspect, a method, comprising: A) changing a staple apparatus from an unconstrained state to a constrained state by: 1) applying a pushing force on a central region of a base member of the staple apparatus, the base member being substantially coplanar to a first axis and a second axis perpendicular to the first axis and the base member comprising a trapezoidal shape with two substantially equal length sides and two unequal length sides, the two unequal length sides comprising a first side and a second side with the first side being shorter than the second side and the first side being parallel with the second side on the first axis, an aperture passing through a center point of the base member, a first indentation in the first side, and a second indentation in the second side; and 2) applying a pulling force on the first side and the second side via the first indentation and the second indentation; B) inserting a first pair of legs that protrude from the first side of the base member and a second pair of legs that protrude from the second side of the base member into a plurality of apertures in adjacent vertebrae; and C) subsequent to inserting the first pair of legs and the second pair of legs into the plurality of apertures, changing the staple apparatus from the constrained state to the unconstrained state to fuse the adjacent vertebrae.

According to a nineteenth aspect, the method of the eighteenth aspect or any other aspect wherein the pushing force and the pulling force are provided by a decompression tool.

According to a twentieth aspect, the method of the eighteenth aspect or any other aspect further comprising: A) changing a staple apparatus from the unconstrained state to the constrained state; B) removing the staple apparatus from the adjacent vertebrae; and C) changing the staple apparatus from the constrained state to the unconstrained state.

According to a twenty-first aspect, a tool apparatus, comprising: A) a first shaft comprising a first end and a second end, the second end comprising: 1) a first hooked portion; and 2) at least one protrusion; B) a second shaft comprising a third end and a fourth end, the fourth end comprising a second hooked portion; C) a sleeve portion comprising a first aperture, wherein the first shaft and the second shaft are configured to mate into a mated state, the sleeve portion is configured to slide over the first shaft and the second shaft by passing the first shaft and the second shaft through the first aperture when in the mated state; and D) a rod comprising a fifth end and a sixth end, wherein: 1) the fifth end comprises a knob; and 2) the rod is configured to pass through the first aperture between the first shaft and the second shaft, through the fourth end of the second shaft, and through the second end of the first shaft.

According to a twenty-second aspect, the tool apparatus of the twenty-first aspect or any other aspect wherein: A) the fourth end comprises a second aperture, wherein the second aperture comprises a plurality of female threads; B) the second end comprises a third aperture; C) the sixth end comprises a plurality of male threads; and D) the rod is configured to: 1) pass through the fourth end by rotating the plurality of male threads through the plurality of female threads; and 2) pass through the second end by passing through the third aperture.

According to a twenty-third aspect, the tool apparatus of the twenty-first aspect or any other aspect wherein the first hooked portion is configured to mate with a first indentation on a first side of a base member of a staple apparatus and the second hooked portion is configured to mate with a second indentation on a second side of the base member.

According to a twenty-fourth aspect, the tool apparatus of the twenty-third aspect or any other aspect wherein: when mating the first hooked portion with the first indentation and the second hooked portion with the second indentation, the first shaft and the second shaft are configured to be positioned at opposing angles relative to an axis, wherein the axis perpendicularly intersects a plane corresponding to the base member of the staple apparatus.

According to a twenty-fifth aspect, the tool apparatus of the twenty-fourth aspect or any other aspect wherein subsequent to mating of the first hooked portion with the first indentation and the second hooked portion with the second indentation, the first end of the first shaft and the third end of the second shaft are configured to move toward each other until the first shaft and the second shaft are parallel According to a twenty-sixth aspect, the tool apparatus of the twenty-first aspect or any other aspect wherein the apparatus comprises a decompression tool configured to cause a staple apparatus to transition between an unconstrained state and a constrained state.

According to a twenty-seventh aspect, a boring apparatus, comprising: A) a body comprising: 1) a first plurality of apertures extending from a first side to a second side opposite the first side, the first plurality of apertures spaced apart at a first spacing; 2) a second plurality of apertures extending from the first side to the second side, the second plurality of apertures spaced apart at a second spacing, the second spacing being greater than the first spacing; and 3) a window aperture extending from the first side to the second side, the window aperture being positioned between the first plurality of apertures and the second plurality of apertures; and B) a plurality of drill pins, wherein each of the plurality of drill pins comprises a respective length that exceeds a distance between the first side and the second side.

According to a twenty-eighth aspect, the boring apparatus of the twenty-seventh aspect or any other aspect wherein the body further comprises an affixing aperture positioned between two of the second plurality of apertures, the affixing aperture configured to receive a targeting pin to affix the boring apparatus to a vertebra.

According to a twenty-ninth aspect, the boring apparatus of the twenty-seventh aspect or any other aspect wherein a first subset of the plurality of drill pins comprise a first length and aa second subset of the plurality of drill pins comprise a second length.

According to a thirtieth aspect, the boring apparatus of the twenty-seventh aspect or any other aspect wherein the plurality of drill pins each comprise a point at a first side.

According to a thirty-first aspect, the boring apparatus of the twenty-seventh aspect or any other aspect further comprising a removable handle coupled to the body at the first side.

According to a thirty-second aspect, the boring apparatus of the thirty-first aspect or any other aspect, wherein the removable handle comprises a third plurality of apertures that align with the second plurality of apertures from the body, and a subset of the plurality of drill pins are configured to individually extend through a respective one of the plurality of the third apertures and a corresponding one of the plurality of second apertures.

According to a thirty-third aspect, the boring apparatus of the twenty-seventh aspect or any other aspect wherein the first plurality of apertures comprises two apertures and the second plurality of apertures comprises two apertures.

According to a thirty-fourth aspect, the boring apparatus of the twenty-seventh aspect or any other aspect wherein the boring apparatus is configured to be positioned on against a first vertebra and a second vertebra.

According to a thirty-fifth aspect, the boring apparatus of the thirty-fourth aspect or any other aspect, wherein the first plurality of apertures are configured to align with the first vertebra, the second plurality of apertures are configured to align with the second vertebra, and the window aperture is configured to align with an intervertebral space between the first vertebra and the second vertebra.

According to a thirty-sixth aspect, the boring apparatus of the twenty-seventh aspect or any other aspect wherein the body further comprises a side aperture on a third side perpendicular to the first side and the second side.

According to a thirty-seventh aspect, the boring apparatus of the thirty-sixth aspect or any other aspect, wherein the body further comprises a second side aperture on a fourth side perpendicular to the first side and the second side, the fourth side being non-parallel, non-perpendicular, and non-adjacent to the third side.

According to a thirty-eighth aspect, the boring apparatus of the thirty-fifth aspect or any other aspect, wherein: A) a first subset of the plurality of drill pins are individually configured to pass through a respective one of the first plurality of apertures to generate boring holes in the first vertebra; and B) a second subset of the plurality of drill pins are individually configured to pass through a respective one of the second plurality of apertures to generate boring holes in the second vertebra.

According to a thirty-ninth aspect, the boring apparatus of the twenty-seventh aspect or any other aspect further comprising a plurality of stops individually formed in a respective one of: the first plurality of apertures and the second plurality of apertures, wherein each of the plurality of stops prevent a respective one of the plurality of drill pins from moving beyond the second side of the body more than a predetermined amount.

According to a fortieth aspect, a boring apparatus, comprising: A) a body comprising: 1) a first set of apertures comprising a first aperture and a second aperture extending from a first side to a second side opposite the first side, the first aperture spaced a first distance from the second aperture along a first axis; 2) a second set of apertures comprising a third aperture and a fourth aperture extending from the first side to the second side, the third aperture spaced a second distance from the fourth aperture substantially along the first axis, where the second distance is greater than the first distance; 3) an affixing aperture extending from the first side to the second side and positioned between the third aperture and the fourth aperture; and 4) a window aperture extending from the first side to the second side, the window aperture being positioned between the first set of apertures and the second set of apertures; B) a first two drill pins comprising a first length, the first two drill pins configured to be inserted into the first aperture and the third aperture; C) a second two drill pins comprising a second length that exceeds the first length, the second two drill pins configured to be inserted into the second aperture and the third aperture; and D) a targeting pin configured to be inserted into the affixing aperture to affix the boring apparatus to a vertebra.

According to a forty-first aspect, the boring apparatus of the fortieth aspect or any other aspect further comprising an implant configured to be positioned within an intervertebral space between the vertebra and a second vertebra adjacent to the vertebra.

According to a forty-second aspect, the boring apparatus of the forty-first aspect or any other aspect, wherein the window aperture is configured to provide a viewing window to the implant within the intervertebral space.

According to a forty-third aspect, the boring apparatus of the fortieth aspect or any other aspect wherein the first two drill pins are configured to be inserted prior to insertion of the second two drill pins, and the second length is greater than the first length to prevent the first two drill pins from interfering with the second two drill pins during insertion.

According to a forty-fourth aspect, a boring system, comprising: A) a body comprising: 1) a first set of apertures comprising a first aperture and a second aperture extending from a first side to a second side opposite the first side, the first aperture spaced a first distance from the second aperture along a first axis; 2) a second set of apertures comprising a third aperture and a fourth aperture extending from the first side to the second side, the third aperture spaced a second distance from the fourth aperture substantially along the first axis, where the second distance is greater than the first distance; 3) a first affixing aperture extending from the first side to the second side and positioned between the third aperture and the fourth aperture; and 4) a window aperture extending from the first side to the second side, the window aperture being positioned between the first set of apertures and the second set of apertures; and B) a removable handle configured to couple to the handle and comprising a third set of apertures comprising a fifth aperture, a sixth aperture, and a second affixing aperture, wherein the fifth aperture is configured to align with the third aperture, the sixth aperture is configured to align with the fourth aperture, and the second affixing aperture is configured to align with the first affixing aperture when the removable handle is coupled to the body.

According to a forty-fifth aspect, the boring system of the forty-fourth aspect or any other aspect wherein the second side comprises a concave surface.

According to a forty-sixth aspect, the boring system of the forty-fourth aspect or any other aspect wherein the removable handle protrudes in a direction parallel to the first axis.

According to a forty-seventh aspect, a method, comprising: A) positioning a first side of a body of a boring apparatus against a first vertebra of a pair of vertebrae, the pair of vertebrae comprising the first vertebra and a second vertebra adjacent to the first vertebra; B) aligning the first side of the body against the first vertebra and the second vertebra; C) inserting, through an affixing aperture extending from a second side to the first side, a targeting pin into the first vertebra; D) driving, through a plurality of boring apertures extending from the second side to the first side, a plurality of drill pins into a respective one of the first vertebra and the second vertebra; E) removing, the boring apparatus from the first vertebra and the second vertebra; F) inserting, via a staple installation tool, a staple into the pair of vertebrae, wherein: 1) the staple installation tool attaches to the staple; 2) the staple comprises a first pair of legs and a second pair of legs; and 3) inserting the staple into the pair of vertebrae comprises: i) inserting the first pair of legs into a first set of the plurality of boring apertures corresponding to the first vertebra; and ii) inserting the second pair of legs into a second set of the plurality of boring apertures corresponding to the second vertebra; and G) engaging, via the staple installation tool, contraction of the staple with the first pair of legs and the second pair of legs positioned in the plurality of boring apertures in the pair of vertebrae.

According to a forty-eighth aspect, the method of the forty-seventh aspect or any other aspect wherein the step of inserting the staple into the pair of vertebrae is performed while the staple is in a constrained state.

According to a forty-ninth aspect, the method of the forty-eighth aspect or any other aspect wherein engaging contraction of the staple comprises allowing the staple to transition from the constrained state to an unconstrained state.

According to a fiftieth aspect, the method of the forty-ninth aspect or any other aspect, wherein allowing the staple to transition from the constrained state to the unconstrained state comprises detaching the staple installation tool from the staple.

According to a fifty-first aspect, the method of the forty-eighth aspect or any other aspect further comprising expanding, via the staple installation tool, the staple to the constrained state prior to inserting the staple into the pair of vertebrae.

According to a fifty-second aspect, the method of the forty-seventh aspect or any other aspect further comprising removing anterior osteophytes from the vertebrae.

According to a fifty-third aspect, the method of the forty-seventh aspect or any other aspect further comprising inserting an implant into an intervertebral space between the first vertebra and the second vertebra, wherein the step of aligning the first side of the body against the first vertebra and the second vertebra further comprises aligning an aperture of the body with the implant.

According to a fifty-fourth aspect, the method of the forty-seventh aspect or any other aspect further comprising exposing and preparing a fusion site.

According to a fifty-fifth aspect, the method of the forty-seventh aspect or any other aspect further comprising verifying, via a fluoroscopy image, a trajectory of the targeting pin relative to the first vertebra and the second vertebra.

According to a fifty-sixth aspect, the method of the forty-seventh aspect or any other aspect further comprising: A) determining that a tip of the targeting pin is directed towards the first vertebra; and B) verifying that a cranial side of the first side is in contact with the second vertebra.

According to a fifty-seventh aspect, the method of the forty-seventh aspect or any other aspect wherein driving, through the plurality of boring apertures extending from the second side to the first side, the plurality of drill pins into the respective one of the first vertebra and the second vertebra comprises: A) driving, through a first boring aperture extending from the second side to the first side, a first drill pin into the second vertebra; B) driving, through a second boring aperture extending from the second side to the first side, a second drill pin into the first vertebra; C) driving, through a third boring aperture extending from the second side to the first side, a third drill pin into the second vertebra; and D) driving, through a fourth boring aperture extending from the second side to the first side, a forth drill pin into the first vertebra.

According to a fifty-eighth aspect, the method of the forty-seventh aspect or any other aspect wherein: A) the first drill pin and the third drill pin comprise a first length; B) the second drill pin and the fourth drill pin comprise a second length; and C) the first length is greater than the second length.

According to a fifty-ninth aspect, the method of the forty-seventh aspect or any other aspect wherein engaging, via the staple installation tool, contraction of the staple comprises: A) removing a rod of the staple installation tool from an aperture in a first shaft of the staple installation tool, the rod being removed from a first end of the staple installation tool opposite a second end coupled to the staple; B) sliding a sleeve portion over and off of the first shaft and a second shaft in a direction of the first end; C) moving the first shaft and the second shaft at the first end in opposite directions; and D) removing a first hooked portion of the first shaft and a second hooked portion of the second shaft from the staple.

According to a sixtieth aspect, the method of the forty-seventh aspect or any other aspect wherein removing the rod of the staple installation tool comprises rotating, in a first direction, a knob coupled to the rod.

According to a sixty-first aspect, a method, comprising: A) boring, via a boring tool, a first set of apertures in a first vertebra; B) boring, via the boring tool, a second set of apertures in a second vertebra adjacent to the first vertebra; C) applying, via the staple insertion tool, a force onto the staple to transition from an unconstrained state to a constrained state; D) aligning a first pair of legs of the staple with the first set of apertures in the first vertebra; E) aligning a second pair of legs of the staple with the second set of apertures in the second vertebra; F) inserting the staple into the first vertebra and the second vertebra; and G) withdrawing, via the staple insertion tool, the force from the staple to transition from the constrained state to the unconstrained state.

According to a sixty-second aspect, the method of the sixty-first aspect or any other aspect wherein: A) the force comprises: 1) a pushing force applied to a base member of the staple; 2) a first pulling force applied to a first side of the base member; and 3) a second pulling force applied to a second side of the base member, wherein the second side is opposite the first side; and B) withdrawing the force from the staple comprises: 1) removing the pushing force by rotating a rod of the staple insertion tool; and 2) removing the first pulling force and the second pulling force by increasing an angle between a first shaft and a second shaft of the staple insertion tool.

According to a sixty-third aspect, the method of the sixty-first aspect or any other aspect wherein rotating the rod comprises rotating a knob of the staple insertion tool, wherein the knob is attached to the rod.

According to a sixty-fourth aspect, the method of the sixty-first aspect or any other aspect further comprising coupling the staple insertion tool to the staple, wherein the step of applying the force onto the staple occurs in response to coupling the staple insertion tool to the staple.

According to a sixty-fifth aspect, the method of the sixty-fourth aspect or any other aspect, wherein coupling the staple insertion tool onto the staple comprises: A) positioning a first hooked end of a first shaft of a staple insertion tool against a first side of a base member of the staple; B) positioning a second hooked end of a second shaft of the staple insertion tool against a second side of the base member of the staple; C) moving a third end of the first shaft and a fourth end of the second shaft to be parallel to each other; D) sliding a sleeve over the first shaft and the second shaft; E) inserting a rod through the sleeve and into an aperture in at least one of the first hooked end and the second hooked end; and F) screwing the rod into the aperture.

According to a sixty-sixth aspect, the method of the sixty-fifth aspect or any other aspect, wherein applying the force onto the staple to transition from the unconstrained state to the constrained state comprises screwing the rod into the aperture.

According to a sixty-seventh aspect, the method of the sixty-fifth aspect or any other aspect, wherein applying the force onto the staple to transition from the unconstrained state to the constrained state comprises moving the third end of the first shaft and the fourth end of the second shaft to be parallel to each other.

According to a sixty-eighth aspect, a method, comprising: A) positioning a first hooked end of a first shaft of a staple removal tool against a first side of a trapezoidal shaped base member of the staple, wherein the staple is coupled to a first vertebra and a second vertebra adjacent to the first vertebra via a plurality of legs, wherein a first subset of the plurality of legs are positioned in a first subset of a plurality of apertures corresponding to the first vertebra and a second subset of the plurality of legs are positioned in a second subset of the plurality of apertures that correspond to the second vertebra; B) positioning a second hooked end of a second shaft of the staple removal tool against a second side of the trapezoidal shaped base member of the staple; C) moving a third end of the first shaft and a fourth end of the second shaft to be parallel to each other; D) sliding a sleeve over the first shaft and the second shaft; E) inserting a rod through the sleeve and into an aperture in at least one of the first hooked end and the second hooked end; F) screwing the rod into the aperture; and G) removing the plurality of legs of the staple from the plurality of apertures in the first vertebra and the second vertebra to decouple the staple from the first vertebra and the second vertebra.

According to a sixty-ninth aspect, the method of the sixty-eighth aspect or any other aspect wherein moving the third end of the first shaft and the fourth end of the second shaft to be parallel to each other causes the staple to transition from an unconstrained state to a constrained state.

According to a seventieth aspect, the method of the sixty-eighth aspect or any other aspect wherein screwing the rod into the aperture causes the staple to transition from an unconstrained state to a constrained state.

According to a seventy-first aspect, the method of the sixty-eighth aspect or any other aspect further comprising transitioning the staple from an unconstrained state to a constrained state by performing the steps of: A) moving the third end of the first shaft and the fourth end of the second shaft to be parallel to each other; and B) screwing the rod into the aperture.

According to a seventy-second aspect, the method of the seventy-first aspect or any other aspect, wherein: A) the rod comprises a first end and a second end; B) the first end of the rod screws into the aperture; C) the staple removal tool comprises a knob; and D) the method further comprises securing the knob to the second end of the rod.

According to a seventy-third aspect, the method of the seventy-second aspect or any other aspect, wherein screwing the rod into the aperture comprises rotating the knob in a first direction while the knob is secured to the second end of the rod.

According to a seventy-fourth aspect, a system, comprising: A) a boring apparatus comprising: 1) a body comprising: i) a first plurality of apertures extending from a first side to a second side opposite the first side; and ii) a second plurality of apertures extending from the first side to the second side; and 2) a plurality of drill pins configured to create a first plurality of bone apertures in a first vertebra and a second plurality of bone apertures in a second vertebra adjacent to the first vertebra, wherein each of the plurality of drill pins comprises a respective length that exceeds a distance between the first side and the second side; and B) a staple comprising: 1) a base member comprising a third side and a fourth side, the third side being opposite the fourth side; 2) a first pair of legs protruding from the third side of the base member, the first pair of legs being configured to align with and be inserted to the first plurality of bone apertures when the staple is in a constrained state; and 3) a second pair of legs protruding from the fourth side of the base member, the second pair of legs being configured to align with and be inserted to the second plurality of bone apertures when the staple is in the constrained state; and C) a tool apparatus comprising: 1) a first shaft comprising a first end, the first end comprising a first aperture; 2) a second shaft comprising a second end, wherein the first end is configured to mate with the third side of the base member and the second end is configured to match with the fourth side of the base member; 3) a sleeve portion comprising a second aperture configured to pass over the first shaft and the second shaft; and 4) a rod configured to: i) pass through the first aperture and the second aperture; ii) apply a pressure onto the staple to change the staple from an unconstrained state to the constrained state; and iii) remove the pressure from the staple to change the staple from the constrained state to the unconstrained state.

According to a seventy-fourth aspect, the system of the seventy-fourth aspect or any other aspect wherein: A) the tool apparatus further comprises a spacer; and B) the second shaft receives the spacer, wherein the spacer is configured to receive the rod and apply the pressure from the rod onto the staple to change the staple from the unconstrained state to the constrained state.

According to a seventy-sixth aspect, the system of the seventy-fourth aspect or any other aspect wherein: A) the base member comprises a third side and a fourth side, wherein the fourth side is opposite the third side; B) the first shaft is configured to attach to the third side; C) the second shaft is configured to attach to the fourth side; and D) the first shaft and the second shaft are configured to, while attached to the third side and the fourth side, rotate to a substantially parallel position to change the staple from the unconstrained state to the constrained state.

According to a seventy-seventh aspect, the system of the seventy-fourth aspect or any other aspect further comprising an implant, wherein: A) the implant is configured to be inserted to an intervertebral space between the first vertebra and the second vertebra; and B) the staple is configured to compress the first vertebra and the second vertebra toward the intervertebral space when changed to the unconstrained state.

According to a seventy-eighth aspect, a method, comprising: A) creating an incision at a target site, wherein the target site comprises: 1) a first bony structure; 2) a second bony structure adjacent to the first bony structure; and 3) a space between the first bony structure and a second bony structure; B) inserting an implant to the space between the first bony structure and the second bony structure; C) placing a boring apparatus against the first bony structure and the second bony structure, wherein a portion of the boring apparatus is aligned with the implant; D) boring, via the boring apparatus, a first plurality of boreholes into the first bony structure and a plurality of boreholes in to the second boring apparatus; E) removing the boring apparatus; F) inserting a staple to the first plurality of boreholes of the first bony structure and the second plurality of boreholes of the second bony structure, wherein: 1) the staple is inserted in a constrained state; and 2) a portion of the staple is aligned over the implant; and G) compressing, via the staple, the first bony structure and the second bony structure against the implant, wherein compressing comprises releasing the staple from the constrained state.

According to a seventy-ninth aspect, the method of the seventy-eighth aspect or any other aspect wherein the staple is coupled to a staple installation tool and releasing the staple from the constrained state comprises decoupling the staple installation tool from the staple.

According to an eightieth aspect, the method of the seventy-eighth aspect or any other aspect wherein the first bony structure comprises a first vertebra, the second bony structure comprises a second vertebra, and the space between the first bony structure and the second bony structure comprises an intervertebral space.

According to an eighty-first aspect, the method of the seventy-eighth aspect or any other aspect wherein the portion of the boring apparatus aligned with the implant comprises a window for viewing the implant.

According to an eighty-second aspect, the method of the seventy-eighth aspect or any other aspect wherein: A) the staple comprises a first pair of legs and a second pair of legs; B) inserting the staple to the first plurality of boreholes comprises inserting the first pair of legs to the first plurality of boreholes; and C) inserting the staple to the second plurality of boreholes comprises inserting the second pair of legs to the second plurality of boreholes.

According to an eighty-third aspect, the method of the seventy-eighth aspect or any other aspect further comprising verifying a trajectory of the first plurality of boreholes and the second plurality of boreholes under fluoroscopy.

According to an eighty-fourth aspect, the method of the seventy-eighth aspect or any other aspect further comprising removing anterior osteophytes from the first bony structure and the second bony structure prior to inserting the staple.

According to an eighty-fifth aspect, the method of the seventy-eighth aspect or any other aspect wherein inserting the implant comprises aligning an anterior edge of the implant with an anterior edge of the first bony structure and an anterior edge of the second bony structure.

According to an eighty-sixth aspect, a method for detaching a staple from a staple installation tool, comprising: A) removing a pushing force from a top portion of a staple coupled to a staple insertion tool; B) removing a first pulling force from a first side of the staple; C) removing a second pulling force from a second side of the staple, wherein the second side is opposite the first side; and D) decoupling the staple installation tool from the staple.

According to an eighty-seventh aspect, the method of the eighty-sixth aspect or any other aspect, wherein removing the pushing force comprises rotating a rod of the staple installation tool.

According to an eighty-eighth aspect, the method of the eighty-seventh aspect or any other aspect, wherein rotating the rod comprises rotating a knob connected to the rod.

According to an eighty-ninth aspect, the method of the eighty-eighth aspect or any other aspect, wherein rotating the rod causes disconnection of a threaded connection between the rod and a first shaft of the staple installation tool.

According to a ninetieth aspect, the method of the eighty-ninth aspect or any other aspect, wherein: A) the staple installation tool comprises: 1) the rod; 2) the knob; 3) the first shaft, wherein the first shaft applies the first pulling force; and 4) a second shaft, wherein the second shaft applies the second pulling force; and B) removing the first pulling force and the second pulling force comprises rotating the first shaft and the second shaft away from a substantially parallel position.

According to a ninety-first aspect, the method of the ninetieth aspect or any other aspect, wherein: A) the staple installation tool further comprises a sleeve for maintaining the first shaft and the second shaft in the substantially parallel position; and B) the method further comprises removing the sleeve from the staple installation tool, wherein removal of the sleeve permits rotation of the first shaft and the second shaft away from the substantially parallel position.

According to a ninety-second aspect, the method of the ninety-first aspect or any other aspect, wherein decoupling the staple installation tool comprises: A) detaching the first shaft from the first side of the staple; and B) detaching the second shaft from the second side of the staple.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 30B shows an exemplary multi-staple system according to one embodiment of the present disclosure;

FIG. 30C shows an exemplary multi-staple system according to one embodiment;

FIG. 31A shows an exemplary staple installation tool and an exemplary staple configured to an unconstrained state according to one embodiment;

FIG. 31B shows an exemplary staple installation tool and an exemplary staple configured to a first constrained state according to one embodiment;

FIG. 65A shows a perspective view of an exemplary handle according to one embodiment of the present disclosure;

FIG. 65B shows a side view of an exemplary handle according to one embodiment of the present disclosure;

FIG. 67 shows a perspective view of an exemplary adapter pin according to one embodiment of the present disclosure;

FIG. 68 shows a top view of an exemplary adapter pin according to one embodiment of the present disclosure;

FIG. 69 shows a side view of an exemplary adapter pin according to one embodiment of the present disclosure;

FIG. 70 shows a side view of an exemplary adapter pin according to one embodiment of the present disclosure;

FIG. 71 shows a perspective view of an exemplary tool adapter according to one embodiment of the present disclosure;

FIG. 72 shows a bottom view of an exemplary tool adapter according to one embodiment of the present disclosure;

FIG. 73A shows a side view of an exemplary tool adapter in an unlocked state according to one embodiment of the present disclosure;

FIG. 73B shows a side view of an exemplary tool adapter in a locked state according to one embodiment of the present disclosure;

DETAILED DESCRIPTION

Figure 1:
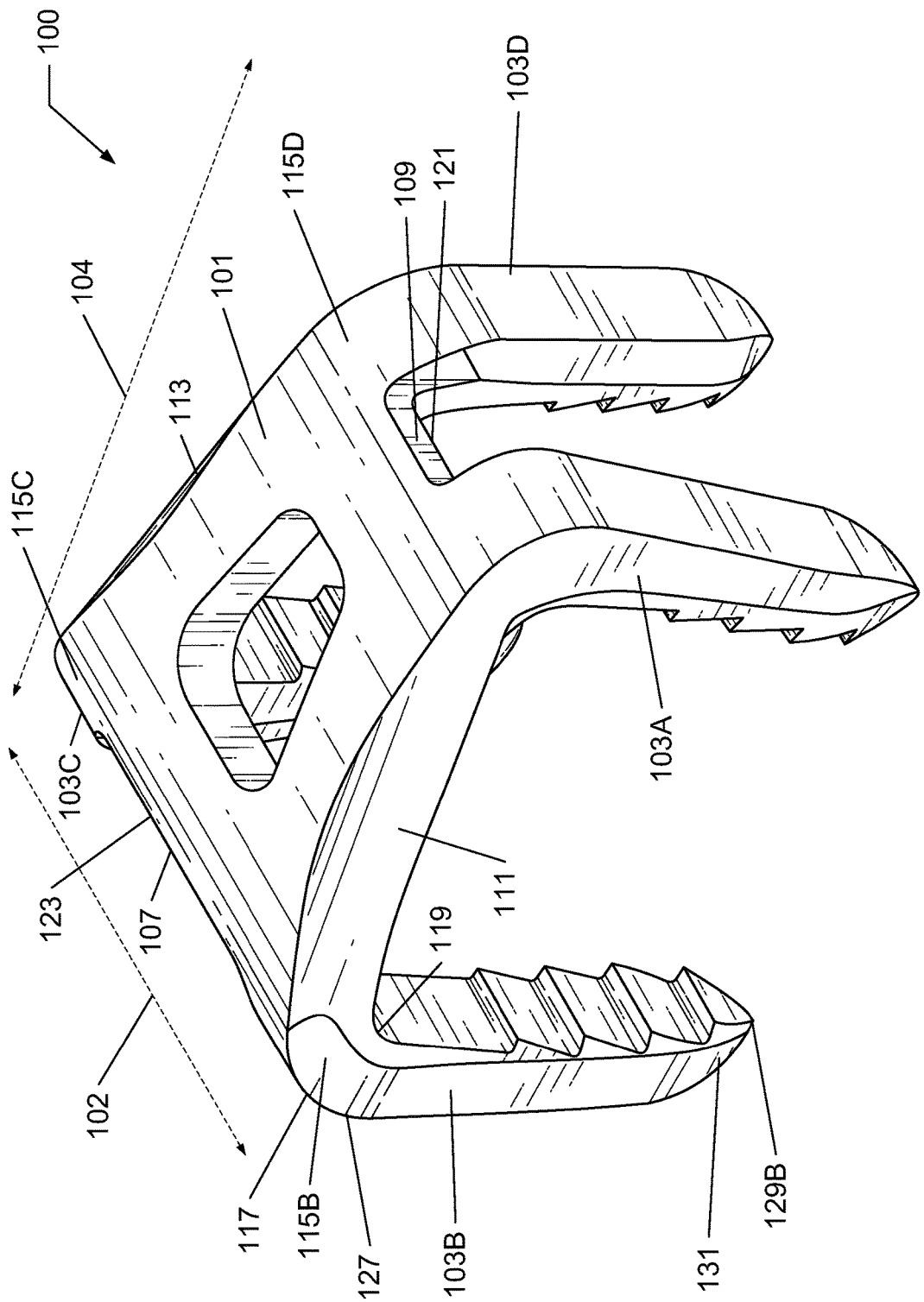
FIG. 1 shows a perspective view of an exemplary staple according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to systems and processes for fixation and compression of bony structures.

Exemplary Staples

Referring now to the figures, for the purposes of example and explanation of the fundamental processes and components of the disclosed systems and processes, reference is made to FIG. 1, which illustrates an exemplary staple 100. As will be understood and appreciated, the exemplary staple 100 shown in FIG. 1 represents merely one approach or embodiment of the present system, and other aspects are used according to various embodiments of the present system.

In one or more embodiments, the staple 100 deforms between an unconstrained state and a constrained state. According to one embodiment, the staple 100 is biased to return to the unconstrained state from the constrained state (e.g., upon removal of a force that deforms and/or maintains the staple 100 in the constrained state). In one or more embodiments, the bias of the staple 100 toward the unconstrained state allows the staple 100 to generate and apply compressive forces at a target site. In at least one embodiment, the staple 100 (e.g., and other staples described herein) receives one or more tools for deforming the staple 100 from an unconstrained state to a constrained state.

In one example, while held in the constrained state, the staple 100 is inserted to a target site such that a first portion of the staple 100 lies in a first bony structure (e.g., a first bony fragment or a first bone) and a second portion of the staple 100 lies in a second bony structure (e.g., a second bony fragment or a second bone). In the same example, following insertion, the staple 100 is unconstrained and attempts to return to the unconstrained state by movement of the first portion and the second portion toward each other. In this example, the biased movement of the first portion and the second portion compresses the first bony structure and the second bony structure together, which may promote fixation and/or fusion at the target site via ossification (e.g., under Wolff's Law). In at least one embodiment, the staple 100 includes one or more super-elastic and/or shape memory materials that provide bias of the staple 100 toward an unconstrained state. In one example, the staple 100 includes nitinol (e.g., per ASTM F2063) and/or other shape memory alloys.

In one or more embodiments, the staple 100 (e.g., and/or other staples described and illustrated herein) is manufactured in a non-constrained state and may be formed into the non-constrained state while the staple 100 is maintained within a martensite temperature range. In various embodiments, during manufacturing, the staple 100 is deformed to a constrained state while the staple is maintained within an austenite temperature range. In one example, while in the martensite temperature range, the staple 100 is formed such that legs 103A,D are positioned at an acute angle to relative to legs 103B,C (e.g., the pair of legs 103A,D and the pair of legs 103B,C are angled toward each other). In this example, while in the austenite temperature range, the staple 100 is deformed such that the legs 103A,D are substantially parallel or are angled away from the legs 103B,C.

In various embodiments, the staple 100 includes a base member 101 and legs 103A-D that connect to the base member 101. In particular embodiments, the legs 103A-D can be referred to as protruding legs. In one or more embodiments, the base member is referred to as a "bridge." The base member 101 can include any suitable shape, such as, for example, a generally trapezoidal, rectangular, or triangular shape. In at least one embodiment, the base member 101 includes sides 107, 109, 111, 113. According to one embodiment, each of the sides 107, 109, 111, 113 defines a surface of the base member 101. In one or more embodiments, the sides 107, 109 are opposed, parallel, and substantially unequal in length, and the sides 111, 113 are opposed, substantially equal in length, and are not parallel. In various embodiments, a first end of each side 111, 113 connects to the side 107 and a second end of each side 111, 113 connects to the side 109 (e.g., thereby forming a generally trapezoidal shape).

In one or more embodiments, the staple 100 includes corners 115A-D that define connections between the sides 107, 109, 111, and 113, and that define connections between the base member 101 and each leg 103A-D. In various embodiments, the corners 115A-D are substantially rounded (e.g., as opposed to including substantially angular or other sharp corners). The term "substantially rounded" can be used to describe the corners 115A-D having one or more radius forming a substantially rounded shape. As an example, the corners 115A-D can define an outer radius 117 and an inner radius 119 for transitioning the base member 101 to each leg 103A-D. In various embodiments, the outer radius 117 measures about 0.5-4.0 mm, 0.5-1.0 mm, 1.0-1.5 mm, 1.5-2.0 mm, 2.0-2.5 mm, 2.5 mm, 2.5-3.0 mmm, 3.0-3.5 mm, or 3.5-4.0 mm. In at least one embodiment, the inner radius 119 measures about 0.5-4.0 mm, 0.5-1.0 mm, 1.0-1.5 mm, 1.5-2.0 mm, 1.5 mm, 2.0-2.5 mm, 2.5-3.0 mmm, 3.0-3.5 mm, or 3.5-4.0 mm.

In at least one embodiment, the base member 101 is substantially coplanar to a first axis represented by a reference line 102 and to a second axis represented by a reference line 104. According to one embodiment, the first axis defined by the reference line 102 is perpendicular to the second axis represented by the reference line 104. In at least one embodiment, the base member 101 is non-coplanar with the first axis and/or the second axis. In one or more embodiments, the side 107 is substantially parallel with the side 109 along the first axis represented by the reference line 102.

In one or more embodiments, the side 109 defines an indentation 121 and the side 107 defines an indentation 123. In at least one embodiment, the base member 101 includes one or more apertures 125. According to one embodiment, the aperture 126 passes through a center point 301 of the base member 101 (see FIG. 3).

In various embodiments, each leg 103A-D includes a first end 127 and a second end 129 (e.g., opposite the first end 127). In at least one embodiment, each leg 103A-D is generally straight between the first end 127 and the second end 129. In some embodiments, one or more of the legs 103A-D demonstrate curvature between the first end 127 and the second end 129. In one example, one or more of the legs 103A-D demonstrate a concave curvature (e.g., toward the base member center point 301 shown in FIG. 3). In one or more embodiments, the legs 103A-D demonstrate a generally rectangular cross-section. The legs 103A-D can demonstrate any suitable shape including, but not limited to, generally cylindrical shapes, serpentine shapes, obround shapes, oval shapes, and tubular shapes. In various embodiments, the end 129 includes one or bone penetrating features, such as, for example, a wedge-like shape for easier insertion of a staple leg into a target site (e.g., a bone, bore hole, etc.). In at least one embodiment, each leg 103A-D includes a tip 131 at the end 129. In one or more embodiments, the tip 131 includes any suitable shape (e.g., wedges, points, rounded edges, blocked edges, etc.) or combination of suitable shapes.

Figure 2:
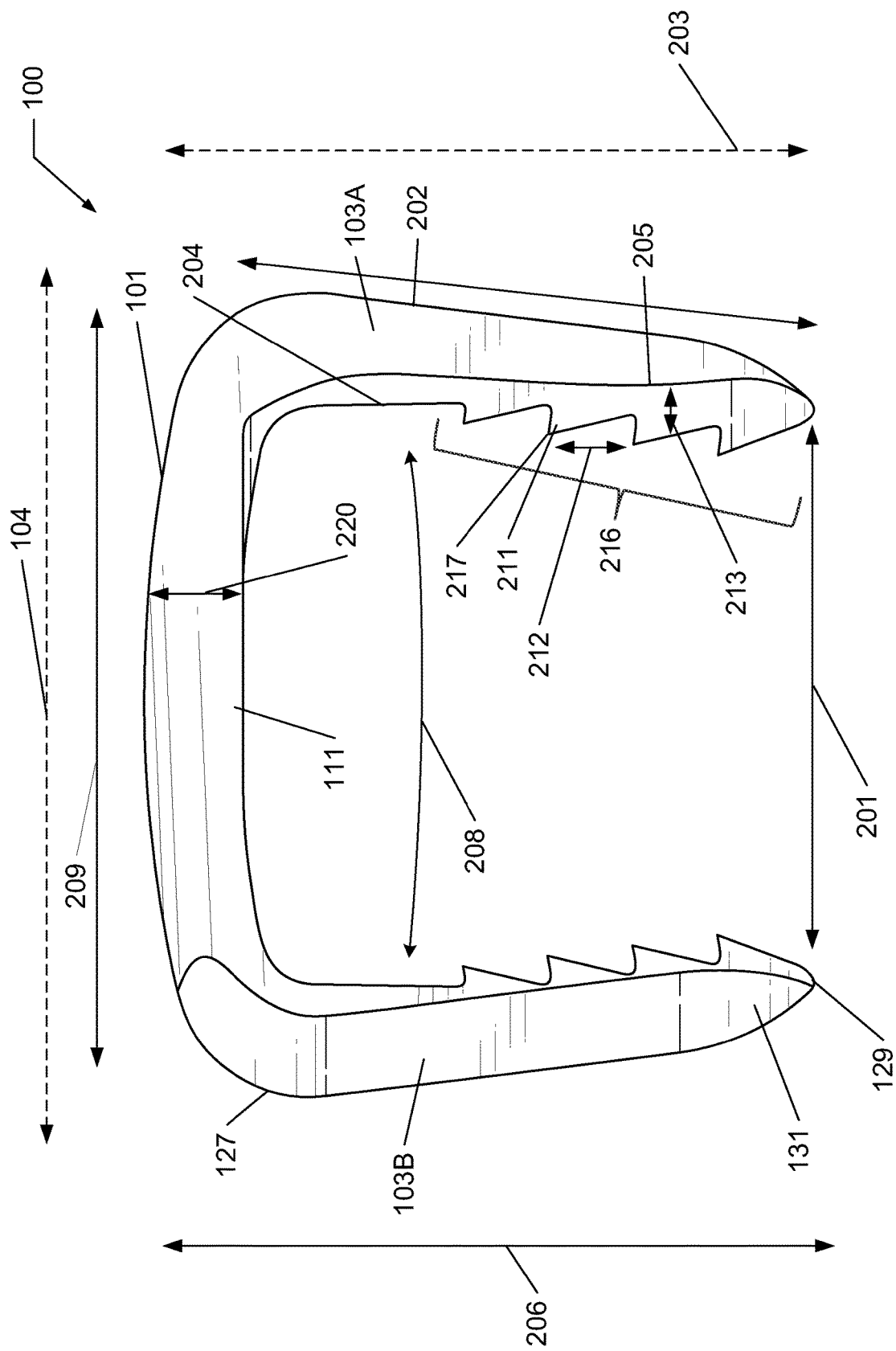
FIG. 2 shows a side view of an exemplary staple according to one embodiment of the present disclosure.

FIG. 2 shows a side view of the staple 100, according to one embodiment of the present disclosure. In various embodiments, a separation distance 201 measures the distance between the leg 103B and the leg 103A between their respective ends 129. In one or more embodiments, the leg 103D and the leg 103C share the same separation distance 201. In particular embodiments, the separation distance 201 measures at least around 8.0 mm, or around 8.0-19.0 mm, 8.0-10.0 mm, 10.0-12.0 mm, 12.9 mm, 12.0-14.0 mm, 14.0-16.0 mm, 16.0-19.0 mm, or less than about 19.0 mm. A leg length 206 may measure the vertical distance from the end 129 to the first end 127 for the legs 103A-D, and may measure at least around 10.0 mm, or around 10.0-15.0 mm, 10.0-11.0 mm, 11.9 mm, 11.0-13.0 mm, 13.0-15.0 mm, or less than about 15.0 mm. The leg length 206 may equal the leg length of leg 103A. The length 206 may differ for each leg 103A-D. A first subset of the legs 103A-D can demonstrate a first length 206 that is greater than a second length 206 demonstrated by a second subset of the legs 103A-D (e.g., the second subset excluding the first subset). In at least one embodiment, the base member 101 includes a distance 209 that measures the separation between first end 127 of each leg 103A and 103B. The distance 209 may measure at least 14.0 mm, or about 14.0-22.0 mm, 14.0-15.0 mm, 15.89 mm, 15.0-17.0 mm, 17.0-19.0 mm, 19.0-21.0 mm, 21.65 mm, or about 21.0-22.0 mm, or less then about 22.0 mm.

In various embodiments, the base member 101 includes a thickness 220. The thickness 220 may represent a thickness of the side 111 and/or the side 113 (not shown). In various embodiments, the thickness 220 measures at least around 1.5 mm, or around 1.5-2.5 mm, 1.5-2.0 mm, 2.26 mm, 2.0-2.5 mm, or less than about 2.5 mm.

In some embodiments, each leg 103A-D includes a first inner leg surface 204, a first outer leg surface 202, and a second outer leg surface 205. In one or more embodiments, at the leg tip 131 and/or toward the end 129, the first inner leg surface 204, the first outer leg surface 202, and the second outer leg surface 205 converge. The end 129 may represent the point where all three surfaces converge. The inner section, which will be described in further detail herein, may converge at the end 129 to create a vertex.

In particular embodiments, the outer leg surface 202 is not parallel to a third axis 203 and includes an increased angle 208 of inwards bend relative to the third axis 203. The third axis 203 may represent one arbitrary coordinate plane of a three-dimensional coordinate system (x, y, and z). The angle 208 at which the outer leg surface 202 varies with respect to the third axis 203 may measure at least around 5.0 degrees, or around 5.0-45.0 degrees, 5.0-10.0 degrees, 10.0-15.0 degrees, 15.0-20.0 degrees, 20.0-25.0 degrees, 25.0-30.0 degrees, 30.0-35.0 degrees, 35.0-40.0 degrees, 40.0-45.0 degrees, or less than about 45.0 degrees. The leg 103A-D may include the angle 208. In one or more embodiments, the angle 208 may be reduced to zero such that the first outer leg surface 202 is parallel to the third axis 203.

In various embodiments, the second outer leg surface 205 represents the location where the outer surface of leg 103A-D transition to the first inner leg surface 204. The distance between the first outer leg surface 202 and the second outer leg surface 205 may measure about 1.1-1.7 mm, 1.1-1.3 mm, 1.3-1.5 mm, 1.53 mm, 1.5-1.7 mm, or about 1.7 mm. The distance between the first inner leg surface 204 and the second outer leg surface 205 may measure about 0.4-0.8 mm, 0.42 mm, 0.4-0.6 mm, 0.63 mm, 0.6-0.8 mm or less than about 0.8 mm.

In particular embodiments, a tooth section 216 includes one or more teeth 211. According to one embodiment, the tooth 211 demonstrates a tooth depth 213 relative to the first inner leg surface 204. Each tooth 211 may include varying tooth depths 213 to create an increasing (or decreasing)

tooth size along the length of the first inner leg surface 204 of the leg 103A-D. The tooth depth 213 may measure at least around 0.3 mm, or around 0.5-2.0 mm, 0.5-1.0 mm, 1.02 mm, 1.18 mm, 1.34 mm, 1.6 mm, 1.0-2.0 mm, or less than about 2.0 mm. In particular embodiments, each successive tooth depth 213 increases in size from top (e.g., furthest from the end 129) to bottom (e.g., closest to the end 129). In one or more embodiments, a tooth length 212 measures the distance between each successive tooth tip 217, the vertex of each successive tooth, with respect to the third axis 203. The tooth length 212 may measure at least about 1.8 mm, 1.80-1.85 mm, 1.88 mm, 1.85-1.90 mm, or less than about 1.90 mm. In at least one embodiment, the tooth length 212 is substantially equal, or unequal, for each successive tooth 211.

Figure 3:
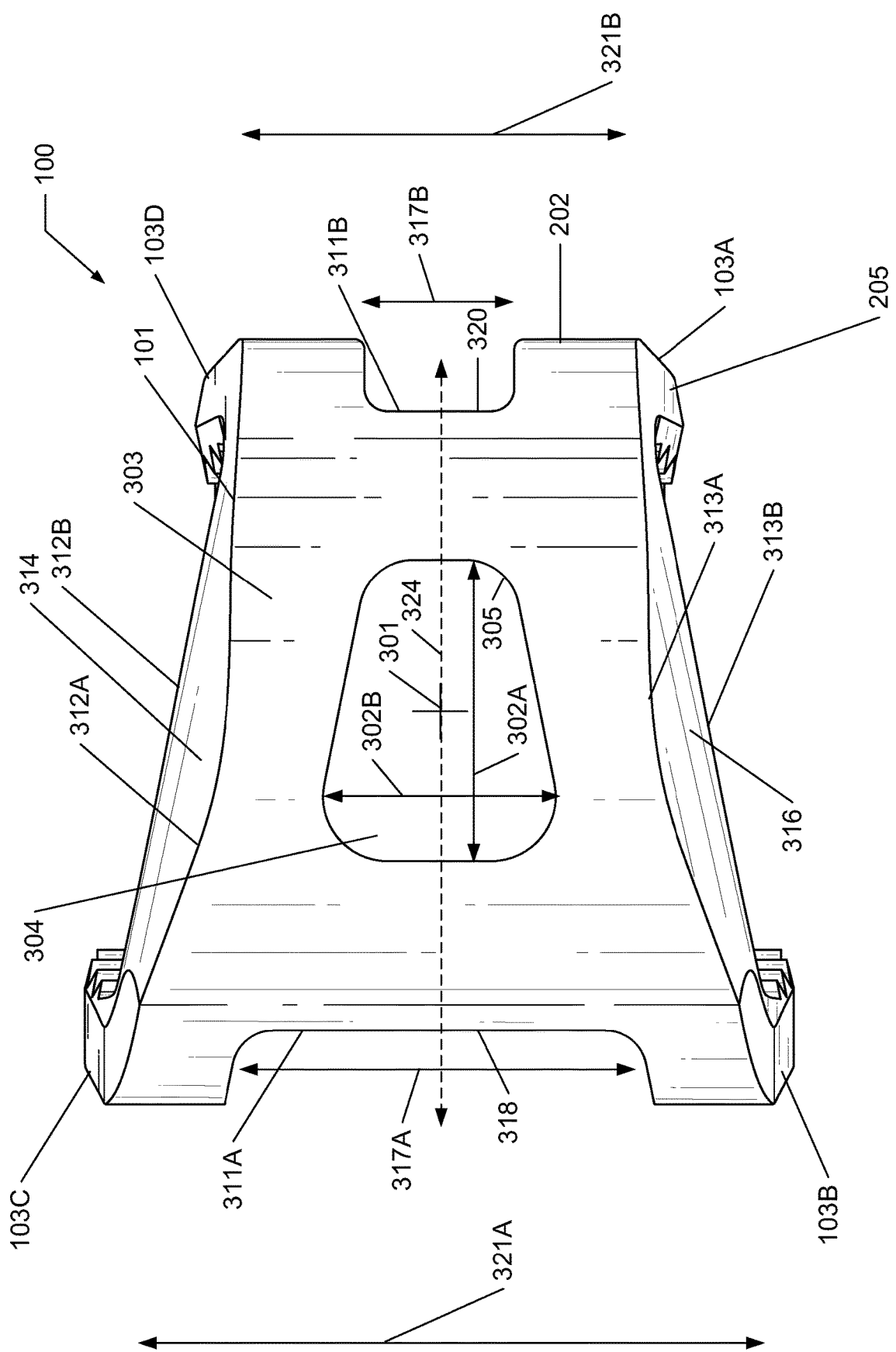
FIG. 3 shows a top view of an exemplary staple according to one embodiment of the present disclosure.

FIG. 3 shows a top view of the staple 100, according to one embodiment of the present disclosure. In various embodiments, the base member 101 includes a center point 301. In various embodiments, the staple 100 demonstrates bi-symmetry along an axis 324 aligned with center point 301 324 and bisecting edges 311A, 311B of the base member 101.

In one or more embodiments, the base member 101 includes a top surface 303. In at least one embodiment, the top surface 303 extends between edges 311A, 311B and between edges 312A, 313A. In various embodiments, the base member 101 includes one or more apertures 304 that extend through the base member 101. In at least one embodiment, the aperture 304 is aligned with the center point 301. The aperture 304 size may be determined by a length 302A and a depth 302B. The length 302A may measure at least about 4.0 mm, or about 4.0-10.0 mm, 4.0-6.0 mm, 6.0-7.0 mm, 7.05 mm, 7.0-8.0 mm, 8.0-10.0 mm, or less than about 10.0 mm. The depth 302B may measure at least about 2.0 mm, or about 2.0-6.0 mm, 2.0-4.0 mm, 4.54 mm, 4.0-6.0 mm, or less than about 6.0 mm. The aperture 304 may take on any suitable shape, such as, for example, trapezoidal, rectangular, or triangular shapes, or other suitable polygons or irregular shapes. In particular embodiments, the aperture 304 include a radius 305 that measures at least about 1.2 mm, or about 1.2-1.6 mm, 1.25 mm, 1.2-1.3 mm, 1.3-1.4 mm, 1.4-1.5 mm, 1.5 mm, or about 1.5-1.6 mm, or less than about 1.6 mm. In various embodiments, the top surface 303 includes continuous transitions to each leg 103A-D. In one or more embodiments, at the connection between each leg 103A-D and the base member 101, the top surface 303 transitions downwards to the first outer leg surface 202 (see FIG. 2).

In various embodiments, the base member 101 includes edges 312A, 313A and edges 312B, 313B. According to one embodiment, the edges 312A, 312B define a side surface 314 of the base member 101 and the edges 313A, 313B define a side surface 316 of the base member 101. The edge 312A may define the transition between the side surface 314 and the top surface 303. The edge 313A may define the transition between the side surface 316 and the top surface 303. The edge 311A may define the transition between a side surface 318 of the base member 101 and the top surface 303. The edge 311B may define the transition between a side surface 320 of the base member 101 and the top surface 303. In various embodiments, the transition between top surface 303 and side surfaces 314 and 316 are substantially non-breaking (for example, the transitions are rounded and/or demonstrate continuous curvature). In one example, the edges 312A and 312B are rounded to create a non-breaking transition between the top surface 303 and the side surfaces 314, 316.

In one or more embodiments, the edges 313A, 313B transition the side surface 316 to the second outer leg surface 205 of each leg 103A-B. In various embodiments, the edge 313B defines the transition between the first inner leg surface 204 (see FIG. 4) and the second outer leg surface 205. In at least one embodiment, the side 111 (see FIG. 1) includes the outer leg surfaces 205 of legs 103A, 103B, and substantially similar for side 113 and legs 103C-D. In at least one embodiment, the edges 312B, 313B define a non-breaking transition between the outer leg surface 205 and the side surfaces 316, 318.

Figure 4:
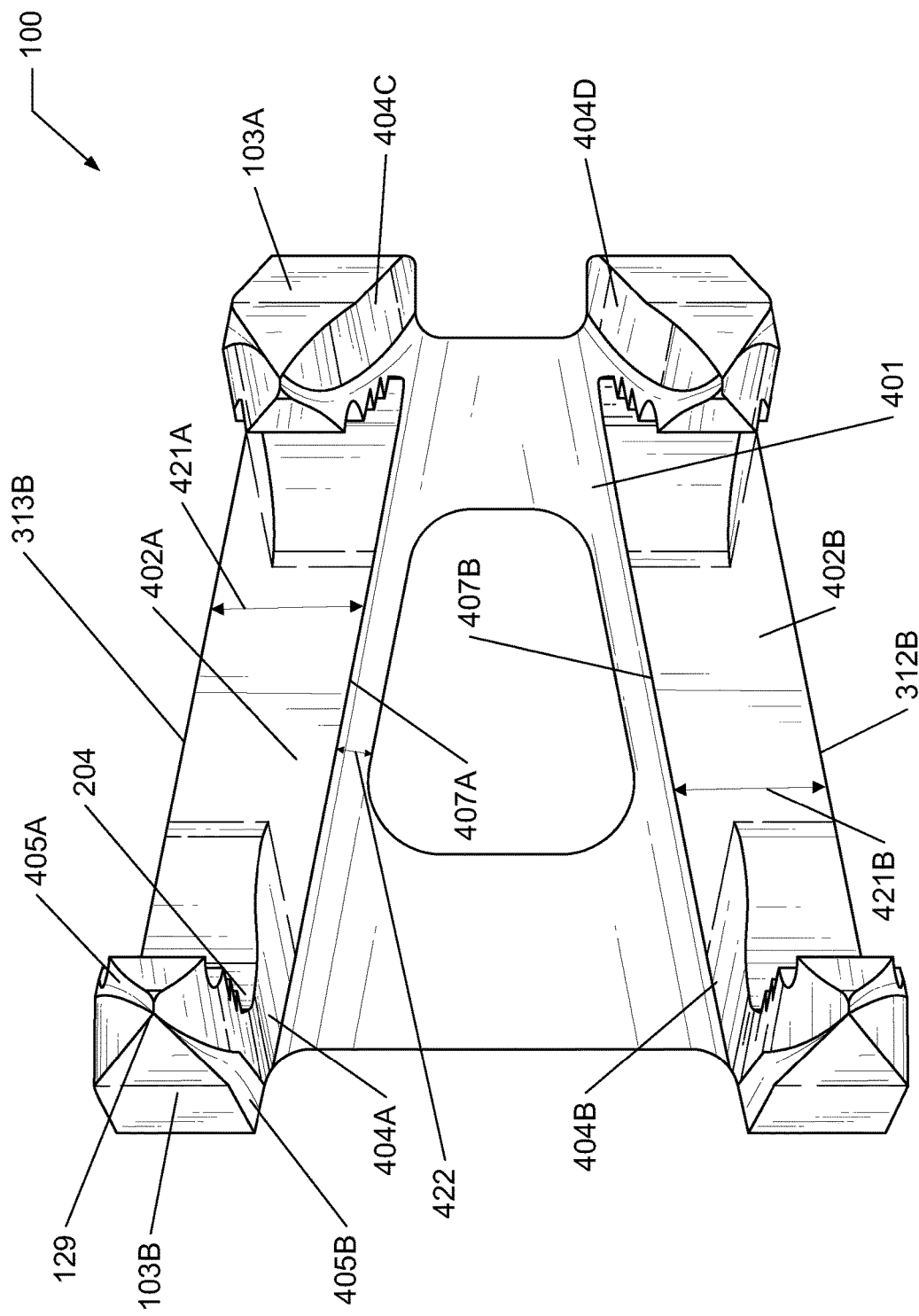
FIG. 4 shows a bottom view of an exemplary staple according to one embodiment of the present disclosure.

In various embodiments, the size of the staple is further defined by a base member depth 321A, a base member depth 321B, a separation distance 317A, and a separation distance 317B. In one or more embodiments, the separation distance 317A measures a distance between legs 103B and 103D. In at least one embodiment, the separation distance 317B measures a distance between leg 103A and leg 103Cleg 103D. The separation distance 317A may measure at least about 7.0-12.0 mm, 7.0-9.0 mm, 9.67 mm, 9.0-11.0 mm, 11.0-12.0 mm, or less than about 12.0 mm. The separation distance 317B may measure about 1.0-5.0 mm, 1.0-3.0 mm, 3.5 mm, 3.0-4.0 mm, 4.0-5.0 mm, or less than about 5.0 mm. The separation distance 317A may be equal to, greater than, or less than the separation distance 317B. The base member depths 321A-B may extend between the edge 312A the edge 313A of each corresponding leg 103A-D (e.g., as measured from the transitions between the edges 312A, 313A and the corresponding leg 103A-D). The depth 321A may measure about 10.0-18.0 mm, 10.0-12.0 mm, 12.0-14.0 mm, 14.03 mm, 14.0-16.0 mm, 16.0-18.0 mm, or less than about 18.0 mm. The depth 321B may measure at least about 6.0 mm, or about 6.0-14.0 mm, 6.0-8.0 mm, 8.0-9.0 mm, 9.22 mm, 9.0-12.0 mm, 12.0-14.0 mm, or less than about 14.0 mm. The depth 321A may be equal to, less than, or greater than the depth 321B FIG. 4 shows a bottom view of the staple 100, according to one embodiment of the present disclosure. In various embodiments, the base member 101 includes a bottom surface 401. In one or more embodiments, the bottom surface 401 demonstrates a non-breaking, curved transition to inner surfaces 404A-D of the legs 103A-D. In various embodiments, an edge 407A and an edge 407B define a transition between the inner surfaces 404A-D and shoulders 402A-B. In particular embodiments, the inner surfaces 404A-D demonstrate a non-breaking, curved transition to the inner leg surface 204 of each shoulder 402A-B. In various embodiments, edges 407A, 313B bound the shoulder 404A, and edges 407B, 312B bound the shoulder 404B. A distance 422, measuring the vertical distance between the bottom surface 401 and edge 407A or 407B, may measure about 0.1-0.5 mm, 0.1-0.3 mm, 0.39 mm, 0.3-0.5 mm, or less than 0.5 mm. In one or more embodiments, a depth 421A-B of the shoulder 402A or 402B, calculated by the distance between either edge 407A and 313B, or 407B and 312B, measures about 1.0-5.0 mm, 1.0-2.0 mm, 2.6 mm, 2.0-3.0 mm, 3.7 mm, 3.0-4.0 mm, 4.0-5.0 mm, or less than 5.0 mm.

In various embodiments, one or more of the legs 103A-D include chamfers 405A, 405B. In particular embodiments, the chamfers 405A-B, the inner surface of shoulder 404A, the inner leg surface 204, the outer leg surface 202 (not shown, see FIG. 2), and the outer leg surface 205 (not shown, see FIG. 2) converge at the end 129.

Figure 5:
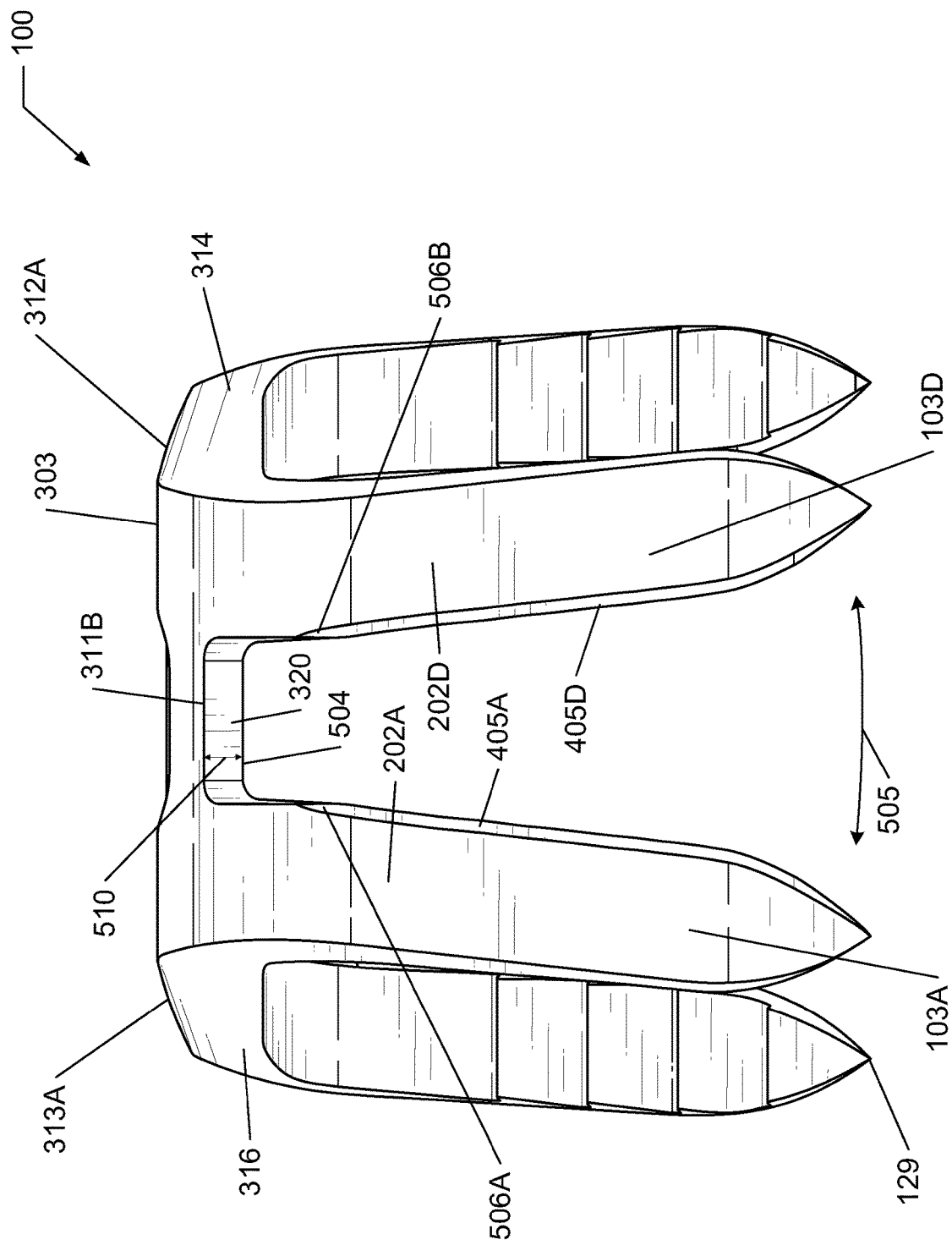
FIG. 5 shows a front view of an exemplary staple according to one embodiment of the present disclosure.

FIG. 5 shows a front view of the staple 100, according to one embodiment of the present disclosure. In one or more embodiments, a leg angle 505 measures the equivalent outward curve of the legs 103A and 103D relative to the third axis 203 (see FIG. 2). The angle 505 may measure at least around 5.0 degrees, or around 5.0-45.0 degrees, 5.0-10.0 degrees, 10.0-15.0 degrees, 15.0-20.0 degrees, 20.0-25.0 degrees, 25.0-30.0 degrees, 30.0-35.0 degrees, 35.0-40.0 degrees, 40.0-45.0 degrees, or less than about 45.0 degrees.

In various embodiments, the chamfer 405A and 405D, the outer leg surface 202, and the side 111 and 113 converge at the end 129 of each leg 103A and 103 D respectively. The top surface 303 may demonstrate a non-breaking, curved transition to the outer surface 202A, 202D of the legs 103A and 103D, respectively. The edge 313A and 312A extend continuously along the face of sides 111 and 113 down each corresponding leg pairs (e.g., 103A and 103B, or 103C and 103D).

In various embodiments, the side 320 is co-planar with the third axis 203 and includes a thickness 510 measured by the edge 311B and an edge 504. The side 320 may include a measured thickness of at least about 0.5 mm, or about 0.5-1.0 mm, 0.5-0.7 mm, mm, 0.81 mm, 0.8-1.0 mm, or less than about 1.0 mm. In one or more embodiments, the side 320 extends to a chamfer tip 506A-B of the chamfers 405A, 405D.

Figure 6:
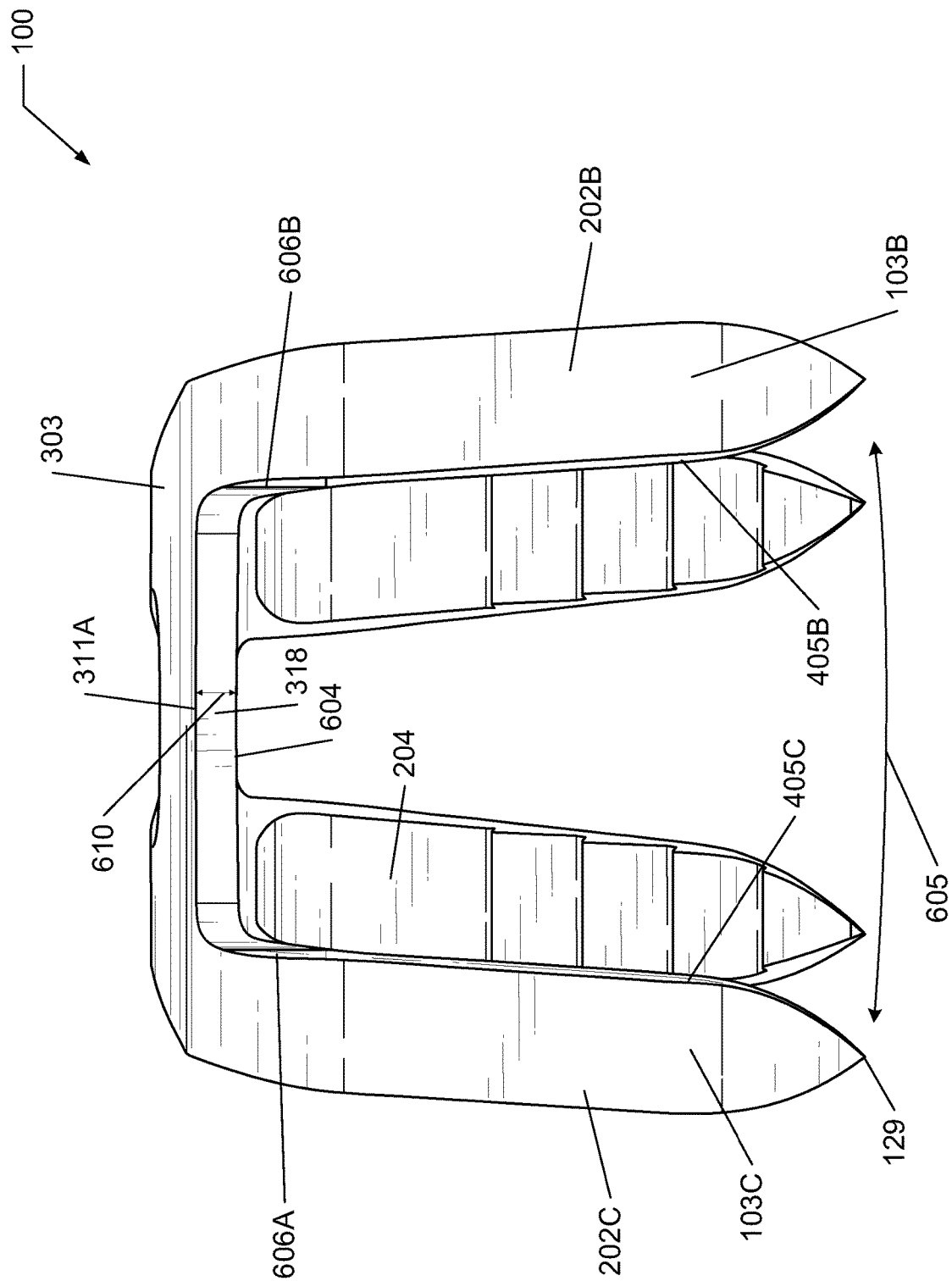
FIG. 6 shows a back view of an exemplary staple according to one embodiment of the present disclosure.

FIG. 6 shows a back view of the staple 100, according to one embodiment of the present disclosure. In one or more embodiments, a leg angle 605 measures the equivalent outward curve of the legs 103B and 103C relative to the third axis 203 (see FIG. 2). The angle 605 may measure at least around 5.0 degrees, or around 5.0-45.0 degrees, 5.0-10.0 degrees, 10.0-15.0 degrees, 15.0-20.0 degrees, 20.0-25.0 degrees, 25.0-30.0 degrees, degrees, 35.0-40.0 degrees, 40.0-45.0 degrees, or less than about 45.0 degrees.

In various embodiments, the chamfer 405B and 405C, the outer leg surface 202, and the side 111 and 113 (not pictured) converge at the end 129 of each leg 103B and 103C respectively. The top surface 303 may demonstrate a non-breaking, curved transition to the outer surface 202B, 202C of the legs 103B and 103C, respectively.

In various embodiments, the side 318 is co-planar with the third axis 203 and includes a thickness 610 measured by the edge 311A and an edge 604. The side 318 may include a measured thickness about 0.5-1.0 mm, 0.5-0.7 mm, 0.7-0.8 mm, 0.81 mm, 0.8-1.0 mm, or less than about 1.0 mm. the side 318 may extend to a chamfer tip 606A,B of the chamfers 405B, 405C.

Figure 7:
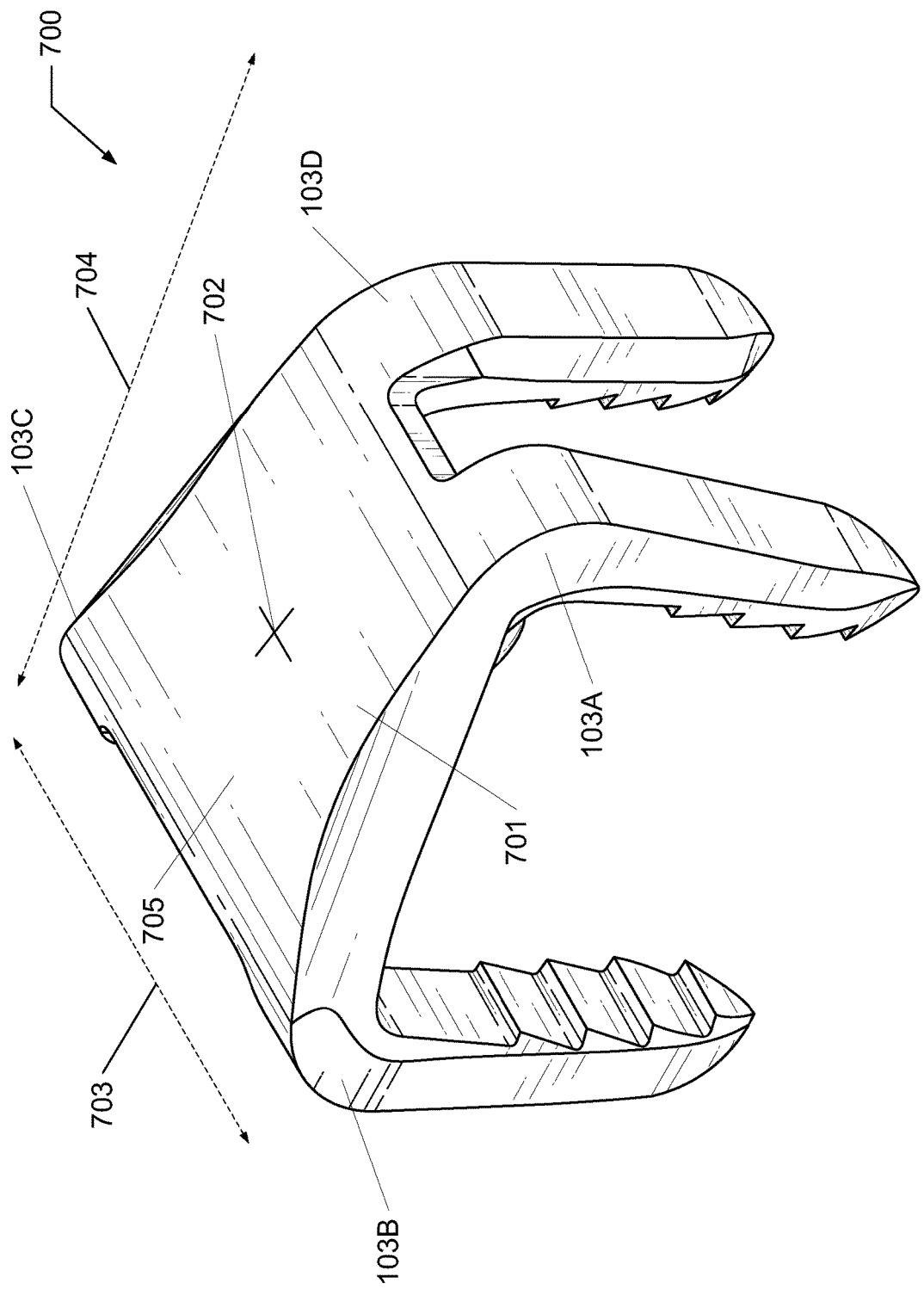
FIG. 7 shows a perspective view of an exemplary staple according to one embodiment of the present disclosure.

FIG. 7 shows a perspective view of an exemplary staple 700, according to one embodiment of the present disclosure. In various embodiments, the staple 700 is generally similar to the staple 100 (see FIG. 1). In one or more embodiments, the staple 700 includes a base member 701. In at least one embodiment, a base member 701 includes a center point 702. In particular embodiments, the base member 701 does not include an aperture, or any other opening, centered about the center point 702. In various embodiments, the staple 700 includes legs 103A-D. A top surface 705 of base member 701 may include a smooth surface that may extend continuously down the legs 103A-D, similarly to staple 100.

In at least one embodiment, the base member 701 is substantially coplanar to a first axis represented by a reference line 703 and to a second axis represented by a reference line 704. According to one embodiment, the first axis defined by the reference line 703 is perpendicular to the second axis represented by the reference line 704. In at least one embodiment, the base member 701 is non-coplanar with the first axis and/or the second axis.

Figure 8:
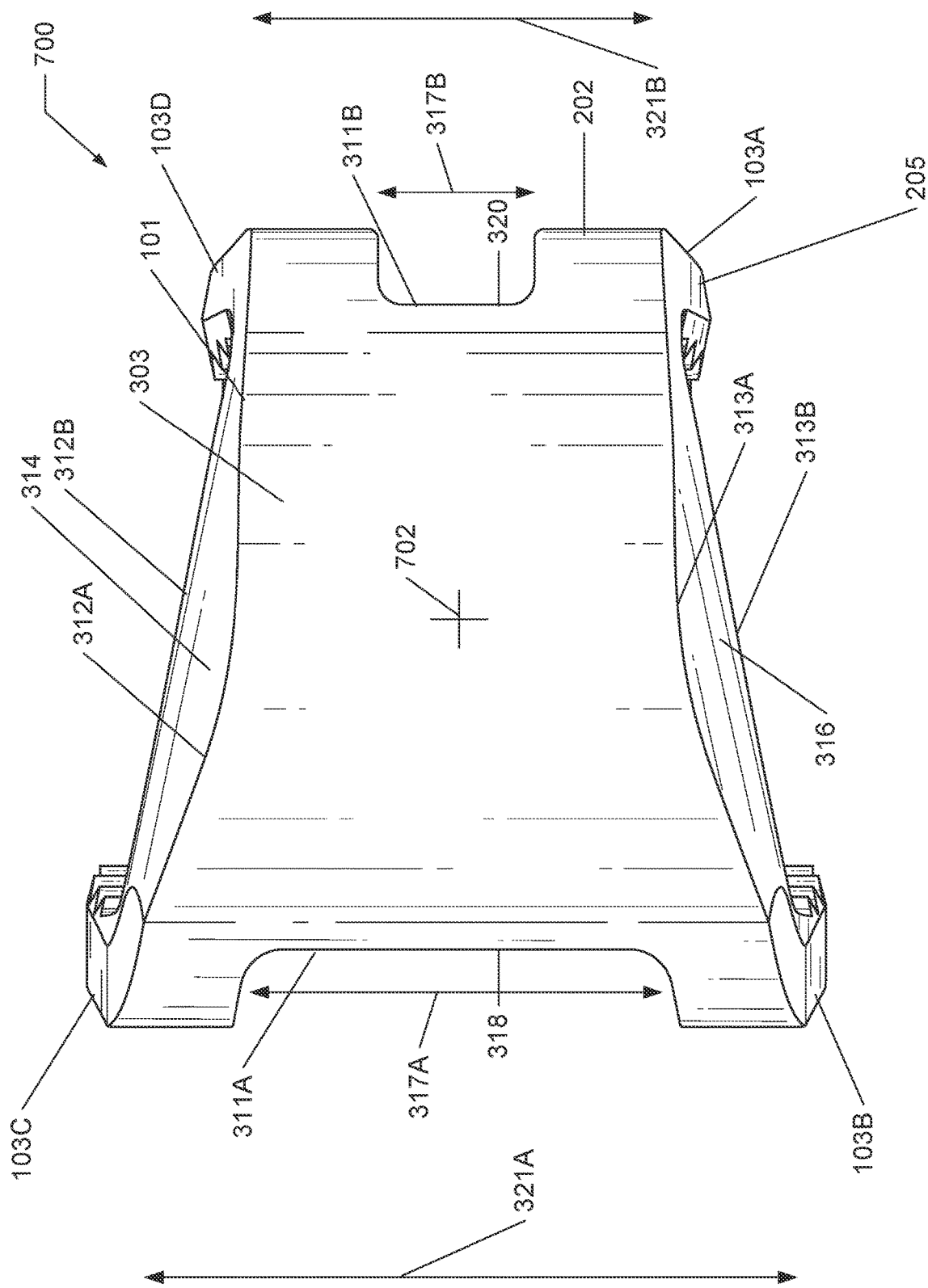
FIG. 8 shows a top view of an exemplary staple according to one embodiment of the present disclosure.

FIG. 8 shows a top view of the staple 700, according to one embodiment of the present disclosure. In various embodiments, the top view of staple 700 is generally similar to the staple 100, lacking only the aperture centered about the center point 702.

Figure 9:
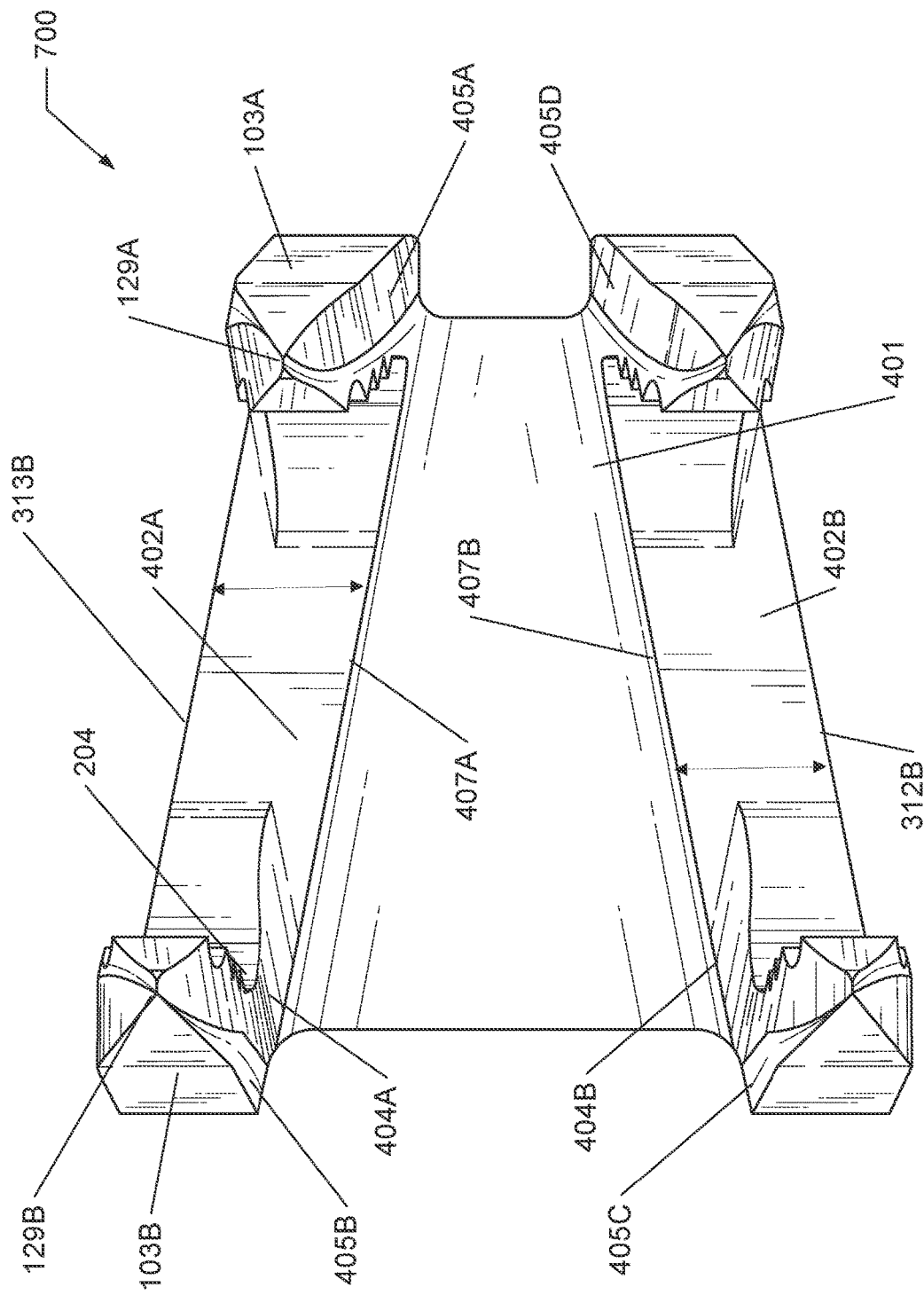
FIG. 9 shows a bottom view of an exemplary staple according to one embodiment of the present disclosure.

FIG. 9 shows a bottom view of the staple 700, according to one embodiment of the present disclosure.

Figure 10:
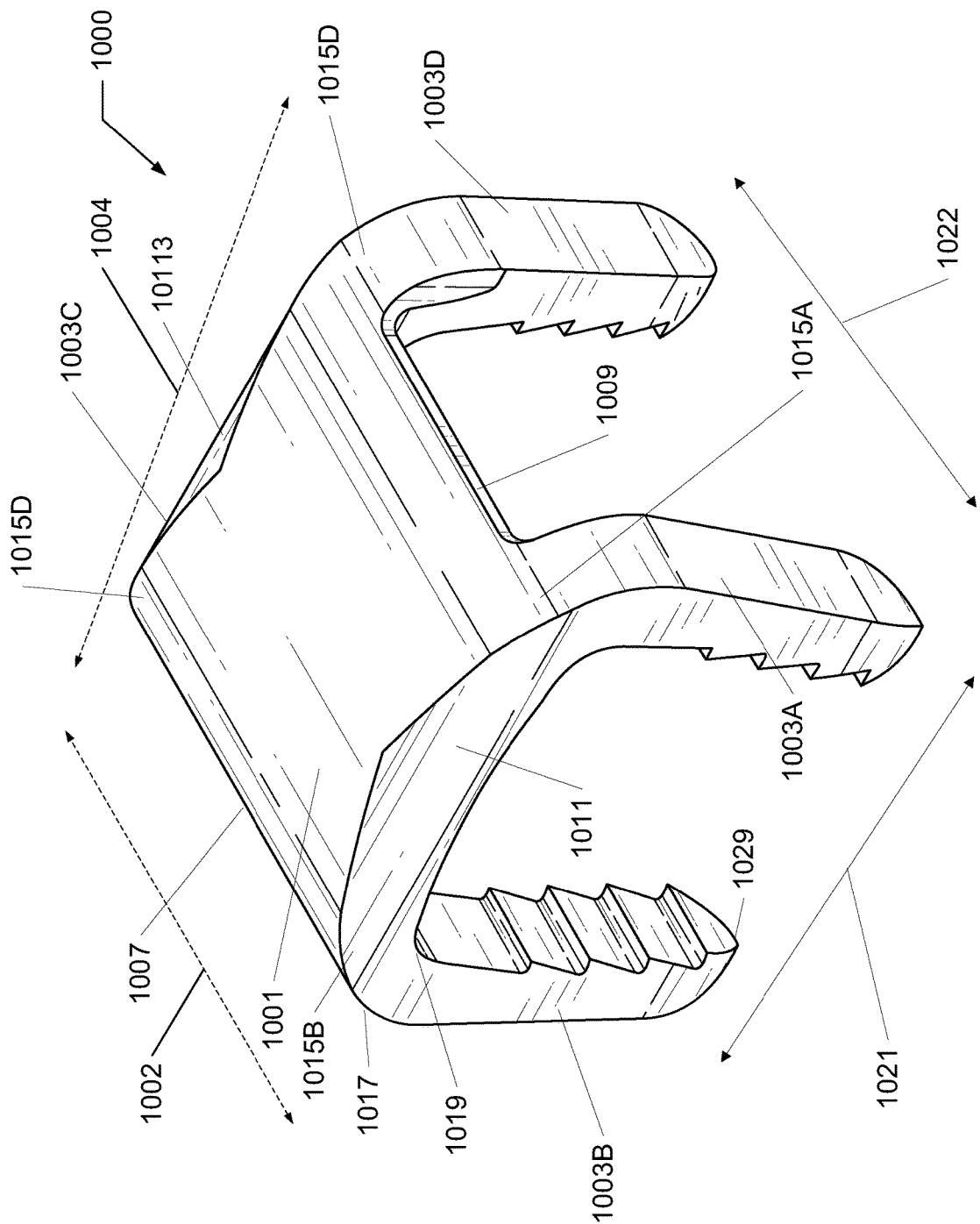
FIG. 10 shows a perspective view of an exemplary staple according to one embodiment of the present disclosure.

FIG. 10 shows a perspective view of an exemplary staple 1000, according to one embodiment of the present disclosure. In various embodiments, the staple 1000 is generally similar to the staple 100 (FIG. 1). In various embodiments, the staple 1000 includes a base member 1001 and legs 1003A-D that connect to the base member 1001. In one or more embodiments, the base member is referred to as a "bridge." The base member 1001 can include any suitable shape, such as, for example, a generally rectangular, trapezoidal, or triangular shape. In at least one embodiment, the base member 1001 includes sides 1007, 1009, 1011, 1013. According to one embodiment, each of the sides 1007, 1009, 1011, 1013 defines a surface of the base member 1001. In one or more embodiments, the sides 1007, 1009 are opposed, parallel, and substantially equal in length, and the sides 1011, 1013 are opposed, substantially equal in length, and are parallel. In various embodiments, a first end of each side 1011, 1013 connects to the side 1007 and a second end of each side 1011, 1013 connects to the side 1009.

In some embodiments, the legs 1003A-D include a second end 1029. A length 1021 may measure the distance between the end 1029 of legs 1003A and 1003B, while a length 1022 may measure the distance between the end 1029 of legs 1003A and 1003D. The length 1021 may measure at least 5.0 mm, or about 5.0-20.0 mm, 5.0-7.0 mm, 7.0-9.0 mm, 9.0-11.0 mm, 11.0-13.0 mm, 13.01 mm, 13.0-15.0 mm, 15.0-18.0 mm, 18.0-20.0 mm, or less than about 20.0 mm. The length 1022 may measure at least 5.0 mm, or about 5.0-20.0 mm, 5.0-7.0 mm, 7.0-9.0 mm, 9.0-11.0 mm, 11.0-13.0 mm, 13.01 mm, 13.0-15.0 mm, 15.0-18.0 mm, 18.0-20.0 mm, or less than about 20.0 mm. In particular embodiments, the length 1021 is greater than, equal to, or less than the length of 1022. In various embodiments, when the lengths 1021 and 1022 are unequal, the base member 1001 is rectangular, while when the lengths 1021 and 1022 are equal, the base member 1001 is a square.

In one or more embodiments, the staple 1000 includes corners 1015A-D that define connections between the sides 1007, 1009, 1011, and 1013, and that define connections between the base member 1001 and each leg 1003A-D. In various embodiments, the corners 1015A-D are substantially rounded (e.g., as opposed to including substantially angular or other sharp corners). In one or more embodiments, the corners 1015A-D define an outer radius 1017 and an inner radius 1019 for transitioning the base member 1001 to each leg 1003A-D. In various embodiments, the inner radius 1019 measures about 0.5-4.0 mm, 0.5-1.0 mm, 1.0-1.5 mm, 1.5 mm, 1.5-2.0 mm, 2.0-2.5 mm, 2.5-3.0 mmm, 3.0-3.5 mm, or 3.5-4.0 mm. In at least one embodiment, the inner radius 119 measures about 0.5-4.0 mm, 0.5-1.0 mm, 1.0-1.5 mm, 1.5-2.0 mm, 1.5 mm, 2.0-2.5 mm, 2.5-3.0 mmm, 3.0-3.5 mm, or 3.5-4.0 mm.

In at least one embodiment, the base member 1001 is substantially coplanar to a first axis represented by a reference line 1002 and to a second axis represented by a reference line 1004. According to one embodiment, the first axis defined by the reference line 1002 is perpendicular to the second axis represented by the reference line 1004. In at least one embodiment, the base member 1001 is non-coplanar with the first axis and/or the second axis. In one or more embodiments, the side 1007 is substantially parallel with the side 109 along the first axis represented by the reference line 1002.

Figure 11:
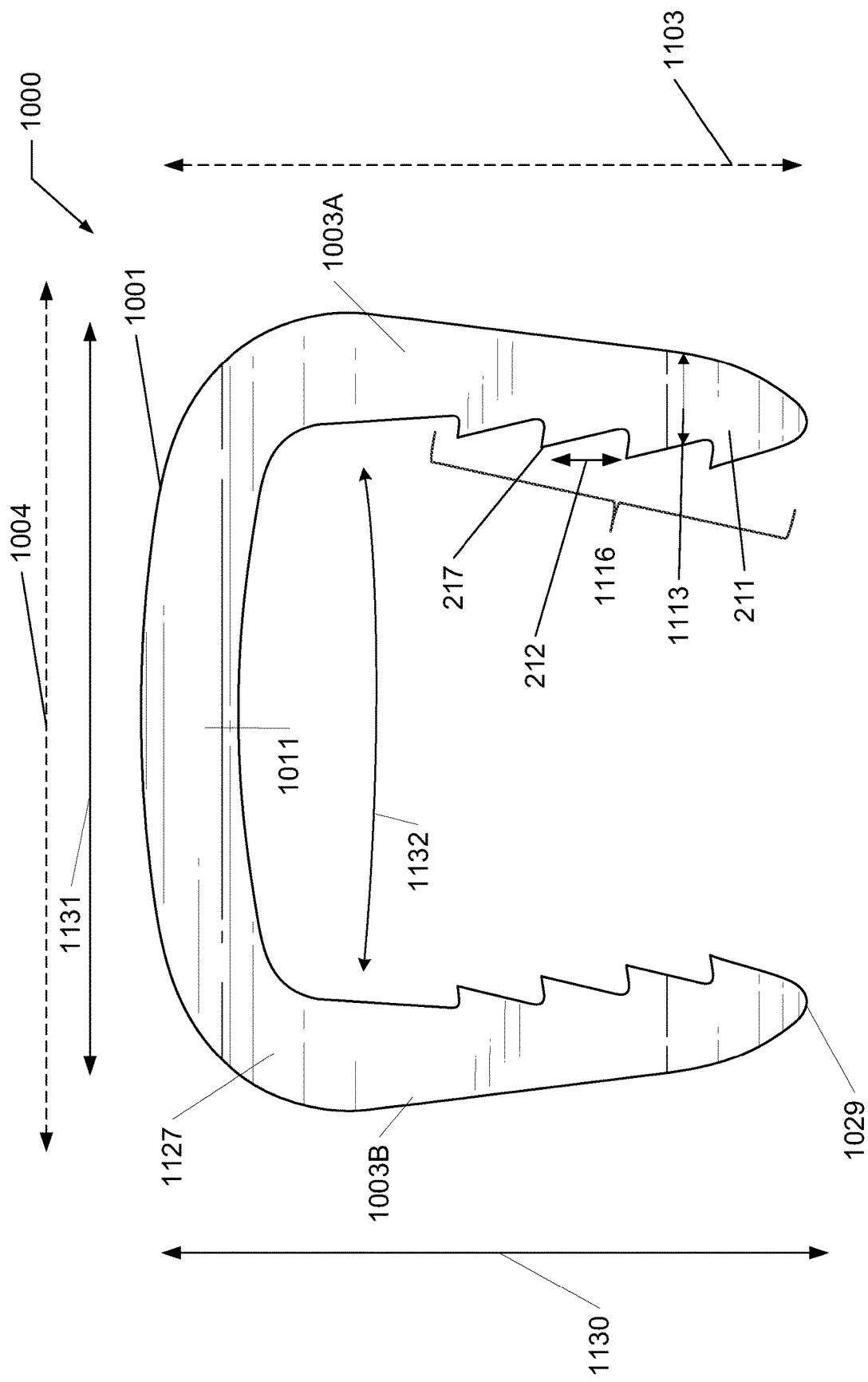
FIG. 11 shows a side view of an exemplary staple according to one embodiment of the present disclosure.

FIG. 11 shows a side view of the staple 1000, according to one embodiment of the present disclosure. In particular embodiments, a third axis 1103 marks one of the three axes in a three-dimensional coordinate system (x, y, and z). A tooth section 1116 is substantially similar to the tooth section 216 in staple 100, with a difference of a tooth depth 1113. The tooth depth 1113 may measure at least about 0.5 mm, or about 0.5-5.0 mm, 0.5-1.0 mm, 1.0-2.0 mm, 2.37 mm, 2.0-4.0 mm, 4.0-5.0 mm, or about less than 5.0 mm.

In at least one embodiment, a leg angle 1132 measures the angle between the third axis 1103 and either leg 1003A or 1003B. In various embodiments, the leg angle 1132 measures at least around 5.0 degrees, or around 5.0-45.0 degrees, 5.0-10.0 degrees, 10.0-15.0 degrees, 15.0-20.0 degrees, 20.0-25.0 degrees, 25.0-30.0 degrees, 30.0-35.0 degrees, degrees, 40.0-45.0 degrees, or less than about 45.0 degrees.

In various embodiments, the side 1011 extends through each leg 1003A-B, reaching to each respective end 1029. In one or more embodiments, the legs 1003A-D include a first end 1127. A length 1130 may measure the distance between the first end 1127 and the second end 1029. In particular embodiments, the length 1130 measures at least about 5.0 mm, or about 5.0-15.0 mm, 5.0-7.0 mm, 7.0-9.0 mm, 9.0-11.0 mm, 11.0-13.0 mm, 13.22 mm, 13.0-15.0 mm, or less than about 15.0 mm. In one or more embodiments, a length 1131 measures the distance between the first end 1127 of each leg 1003A and 1003B. The length 1131 may measure at least 7.0 mm, or about 7.0-20.0 mm, 7.0-10.0 mm, 10.0-13.0 mm, 13.0-16.0 mm, 16.0-17.0 mm, 17.76 mm, 17.0-20.0 mm, or less than about 20.0 mm. In particular embodiments, the end 1029 are vertices that converge all sides of each leg 1003A-D.

Figure 12:
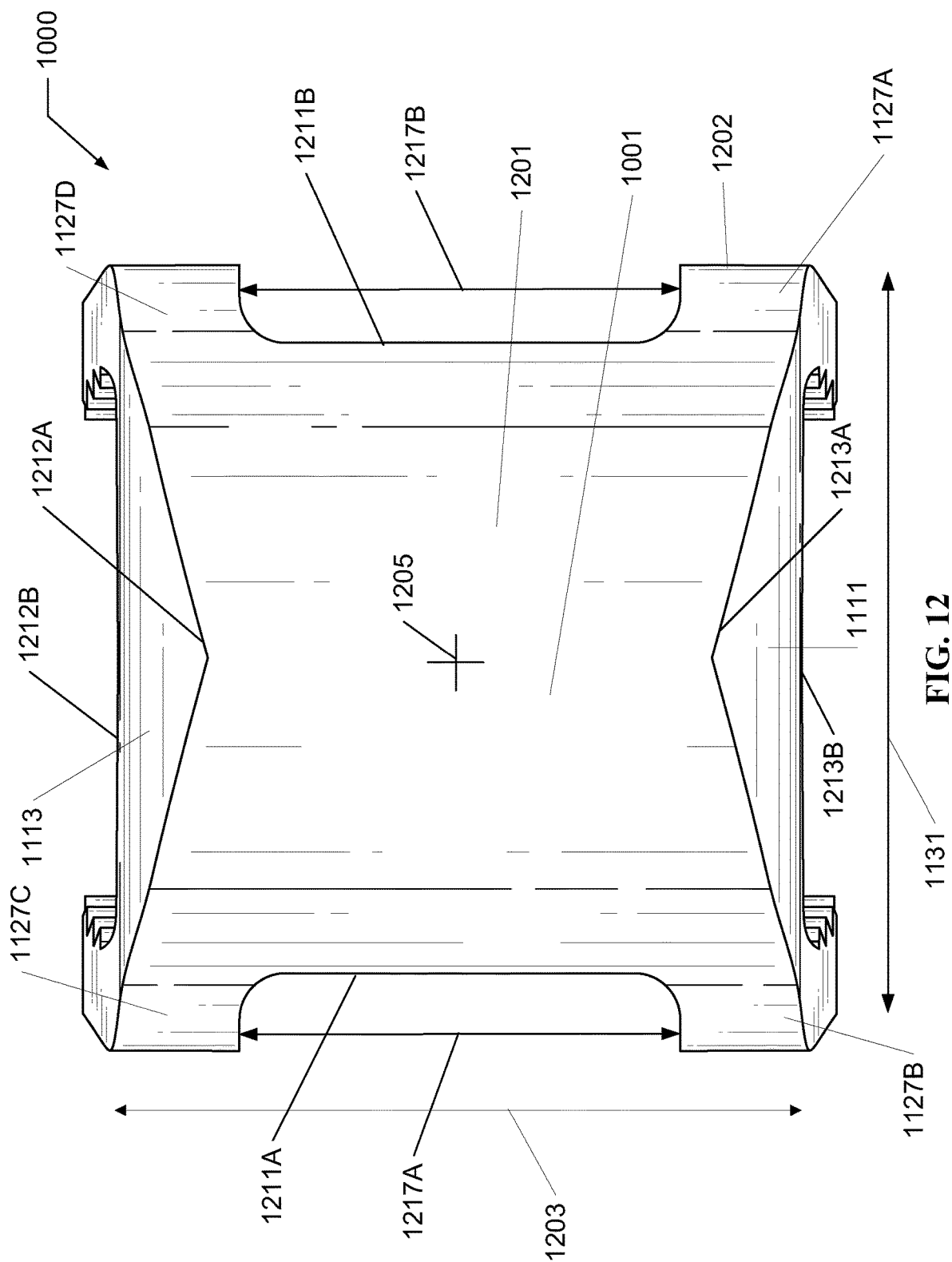
FIG. 12 shows a top view of an exemplary staple according to one embodiment of the present disclosure.

FIG. 12 shows a top view of the staple 1000, according to one embodiment of the present disclosure. In particular embodiments, the base member 1001 includes a top surface 1201. In various embodiments, the top surface 1201 is significantly smooth and lacks an aperture. The top surface 1201 may include an aperture centered at a center point 1205. In at least one embodiment, the top surface is bounded by edges 1212A, 1213A, 1211A, and 1211B. In particular embodiments, the legs 1003A-D each include an outer leg surface 1202. The top surface 1201 may extend continuously through the outer leg surface 1202 and through the rounded corners 1127A-D. In one or more embodiments, the side surfaces 1111 and 1113 are bounded by edges 1213A, 1213B and edges 1212A, 1212B, respectively.

In particular embodiments, a length 1203 extends from the top end 1127C, to the top end 1127B. The length of 1203 may measure at least 10.0 mm, or about 10.0-20.0 mm, 10.0-12.0 mm, 12.0-14.0 mm, 14.0-15.0 mm, 15.45 mm, 15.0-17.0 mm, 17.0-20.0 mm, or less than about 20.0 mm.

In one or more embodiments, a length 1217A, and 1217B measures the distance between the furthest sides of edges 1211A and 1211B, respectively. In particular embodiments, the length 1217A is substantially similar to the length 1217B. The length 1217A may measure at least about 8.0 mm, 8.0-12.0 mm, 8.0-10.0 mm, 10.0 mm, 10.0-12.0 mm, or less than about 12.0 mm.

Figure 13:
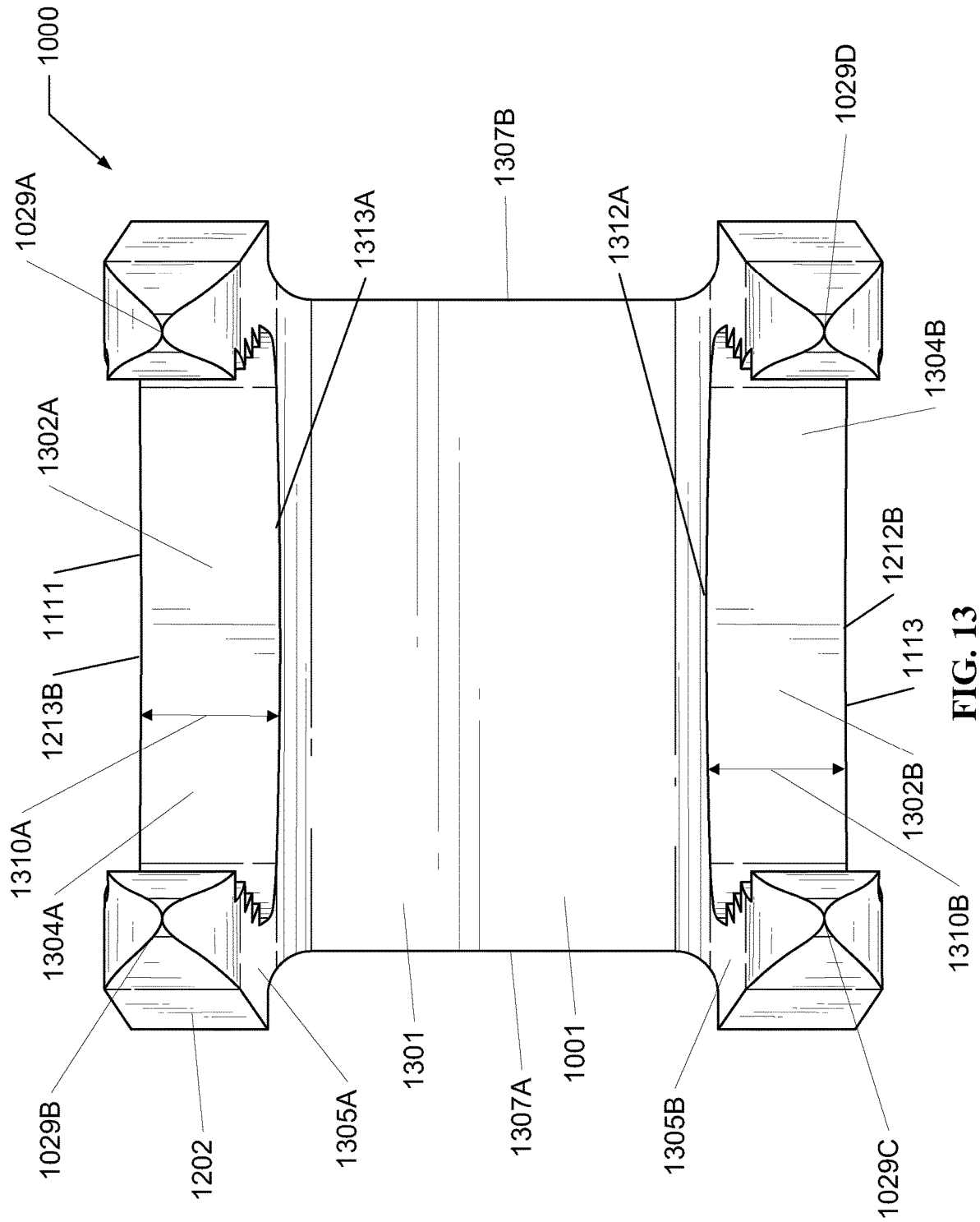
FIG. 13 shows a bottom view of an exemplary staple according to one embodiment of the present disclosure.

FIG. 13 shows a bottom view of the staple 1000, according to one embodiment of the present disclosure. In particular embodiments, the base member 1001 includes a bottom surface 1301. In at least one embodiment, the bottom surface 1301 transitions continuously to a second inner surface 1305A and 1305B, and is bounded by an edge 1312A, and 1313A. The edge 1312A and 1313A may mark the transition line between the second inner surfaces 1305A-B and shoulders 1302A-B, respectively. In various embodiments, the shoulders 1302A are protruding surfaces with respect to base member 1001, and contain the first inner surface 1304A and 1304B. In particular embodiments, the shoulders 1302A-B are bounded by 1313A, 1213B, and 1312A, 1212B respectively.

A length 1310A and 1310B may measure the distance between edges 1213B and 1313A, and edges 1312A and 1212B, respectively. In various embodiments, the length 1210A and the length 1310B are substantially similar. In at least on embodiment, the length 1310A measures at least 1.0 mm, or about 1.0-5.0 mm, 1.0-3.0 mm, 3.0 mm, 3.0-5.0 mm, or less than about 5.0 mm.

In one or more embodiments, the surfaces 1111, 1304A, 1305A, and 1202, converge at end 129 of legs 1003A-B. In various embodiments, the surfaces 1111, 1304B, 1305B, and 1202 converge at end 129 of legs 1003C-D.

Figure 14:
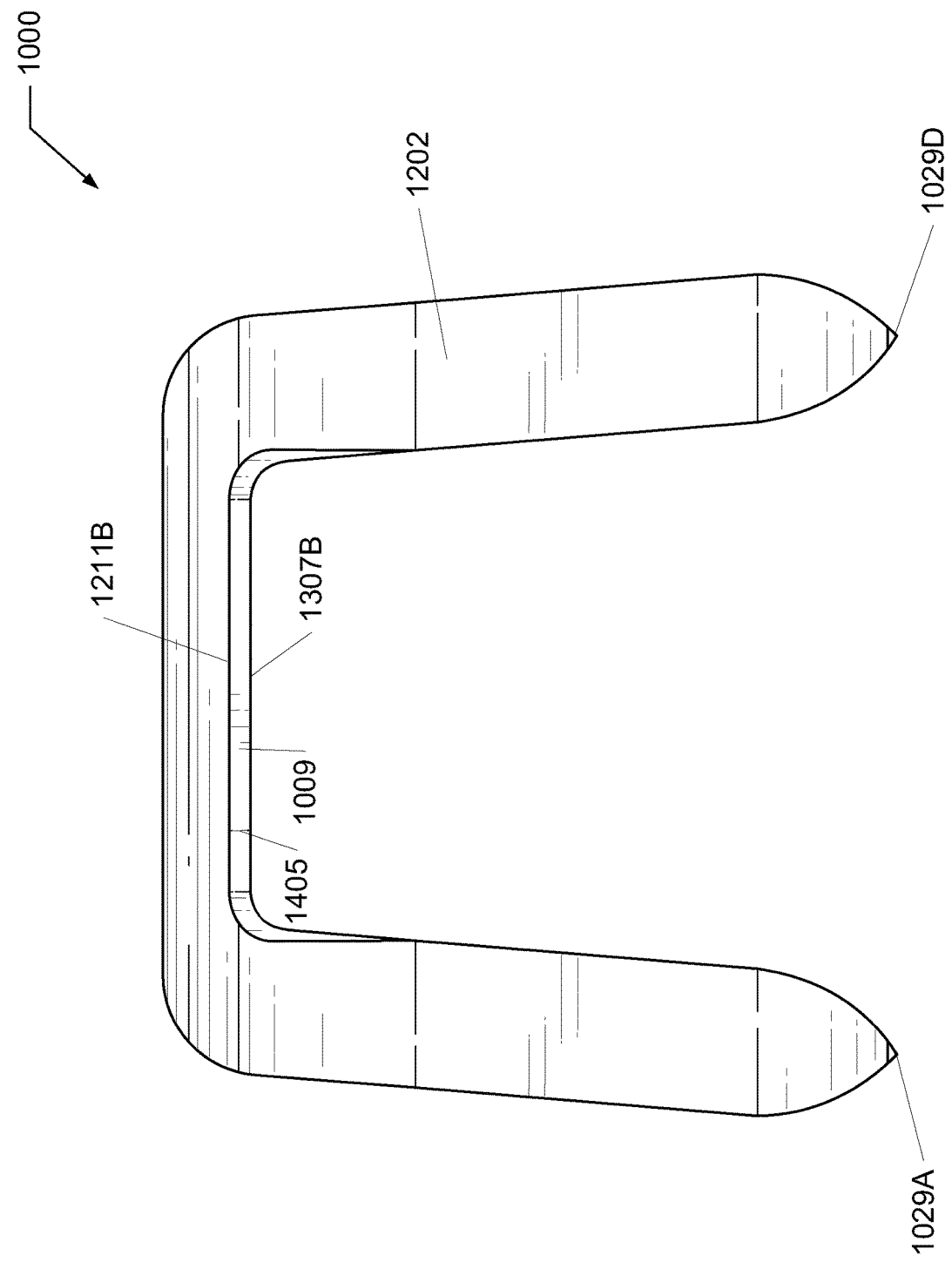
FIG. 14 shows a front view of an exemplary staple according to one embodiment of the present disclosure.

FIG. 14 shows a front view of the staple 1000, according to one embodiment of the present disclosure. In various embodiments, the front views of staple 1000 is substantially similar to the front view of staple 100. In one or more embodiments, the front view of staple 1000 is substantially similar to the back view of staple 1000. In particular embodiments, a depth 1405 is measured as the distance between edge 1307B and 1211B. The depth 1405 may measure at least 0.1 mm, or about 0.1-0.8 mm, 0.1-0.3 mm, 0.3-0.4 mm, 0.42 mm, 0.4-0.6 mm, or about 0.6-0.8 mm, or less than about 0.8 mm.

Figure 15:
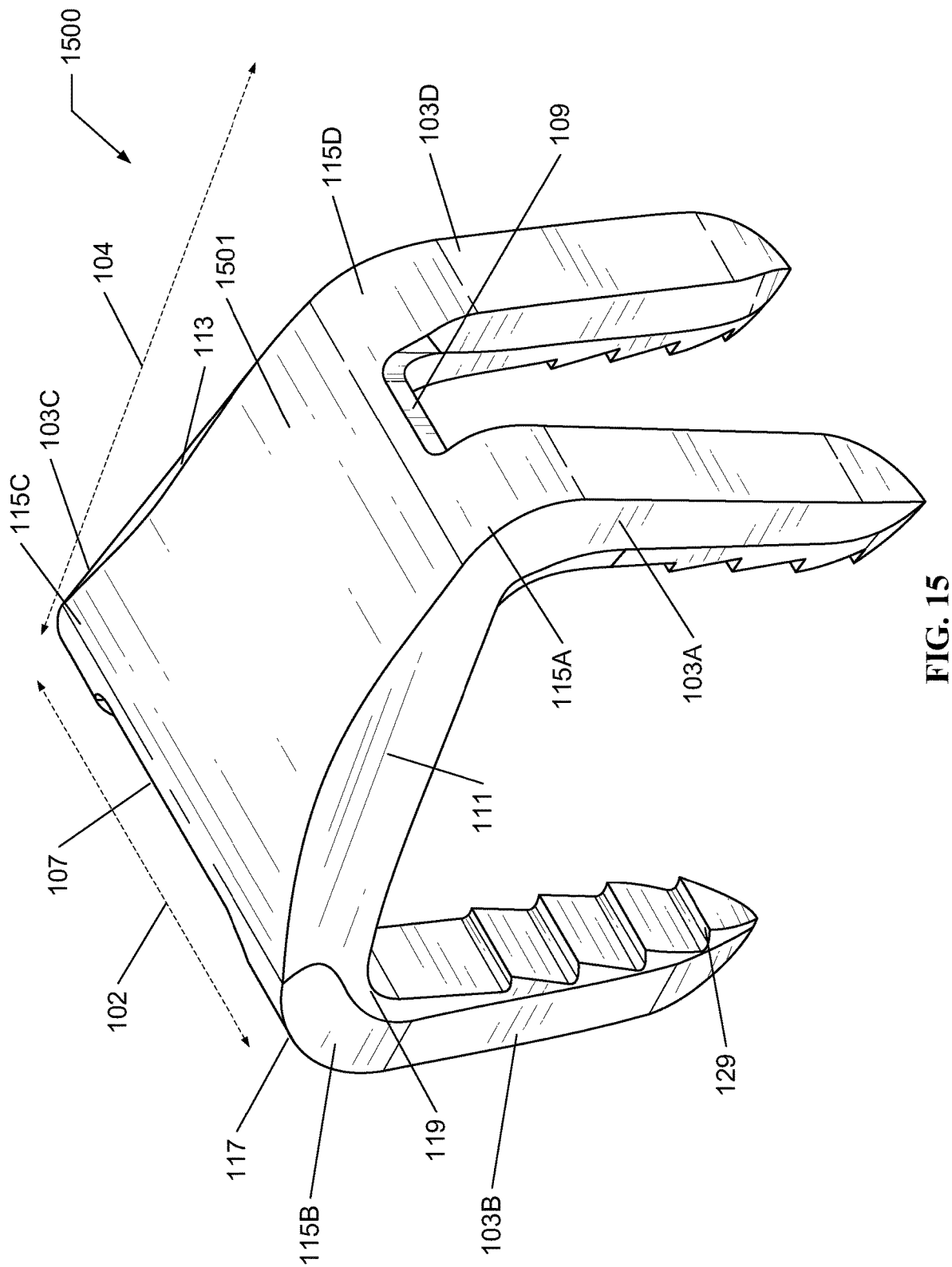
FIG. 15 shows a perspective view of an exemplary staple according to one embodiment of the present disclosure.

FIG. 15 shows a perspective view of an exemplary staple 1500, according to one embodiment of the present disclosure. In various embodiments, the staple 1500 is generally similar to the staple 100 (FIG. 1).

Figure 16:
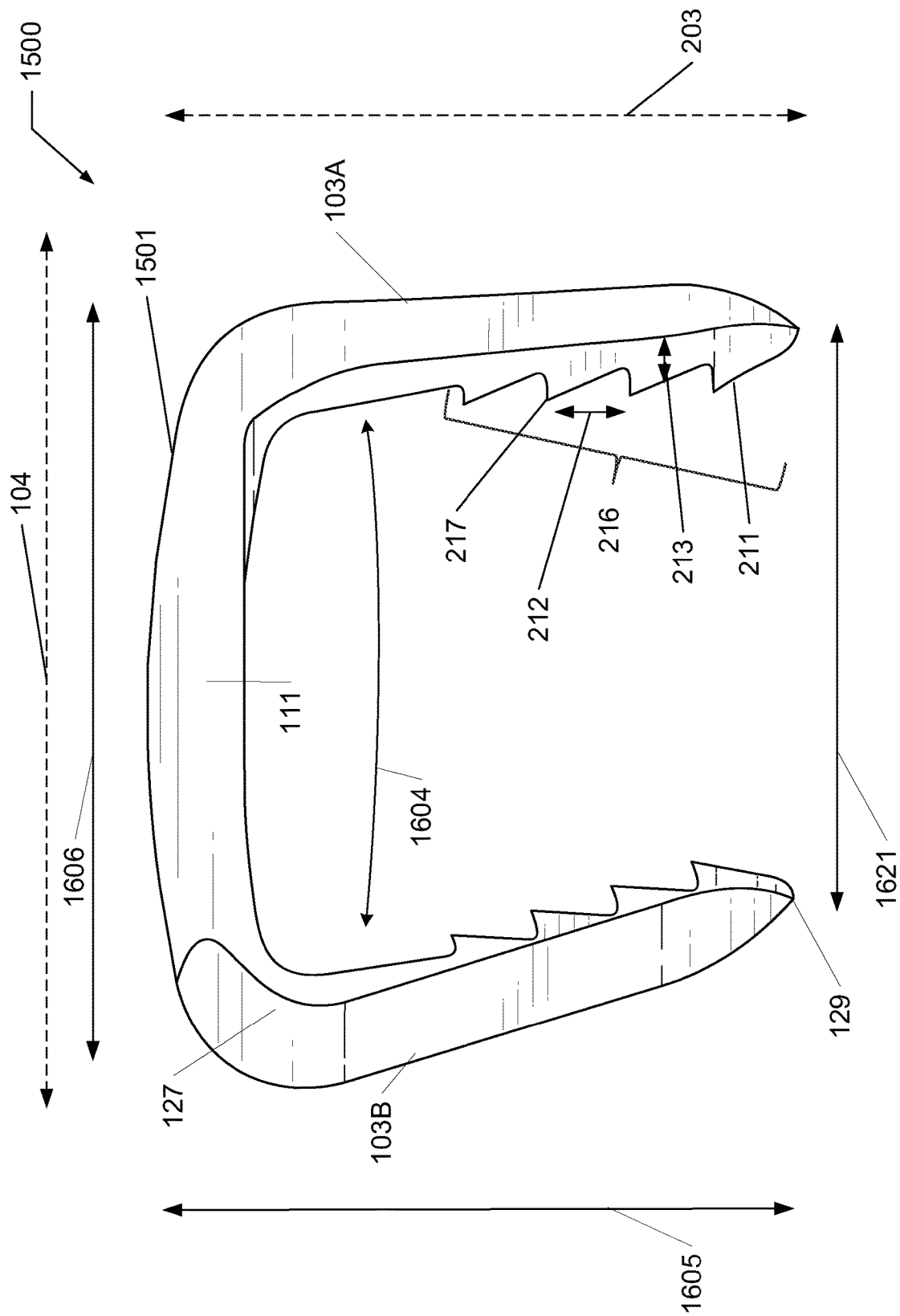
FIG. 16 shows a side view of an exemplary staple according to one embodiment of the present disclosure.

FIG. 16 shows a side view of the staple 1500, according to one embodiment of the present disclosure. In particular embodiments, the leg separation 1621 measures the distance between end 129 of each leg 103A and 103B. The leg separation 1621 may measure at least 6.0 mm, or about 6.0-12.0 mm, 6.0-8.0 mm, 8.8 mm, 8.0-10.0 mm, 10.7 mm, 10.0-12.0 mm, or less than about 12.0 mm. In at least one embodiment, a leg angle 1604 measures the degree of bend of leg 103B relative to a third axis 1603. In particular embodiments, the leg angle 1604 may measure at least 15.0 degrees, or about 15.0-30.0 degrees, 15.0-20.0 degrees, 17.0 degrees, 20.0-25.0 degrees, 25.0-30 degrees, or less than about 30.0 degrees. In particular embodiments, a leg length 1605 measures the distance between first end 127 and end 129. The leg length 1605 may measure at least 10.0 mm, 10.0-16.0 mm, 10.0-12.0 mm, 12.36 mm, 12.0-14.0 mm, 14.0-16.0 mm, or less than about 16.0 mm.

In various embodiments, the base member 1501 includes a length 1606 measured by the distance between first end 127 of each leg 103A and 103B. The length 1606 may measure at least 14.0 mm, or about 14.0-18.0 mm, 14.0-15.0 mm, 15.46 mm, 15.0-16.0 mm, 16.0-17.0 mm, 17.32 mm, 17.0-18.0 mm, or less than about 18.0 mm.

Figure 17:
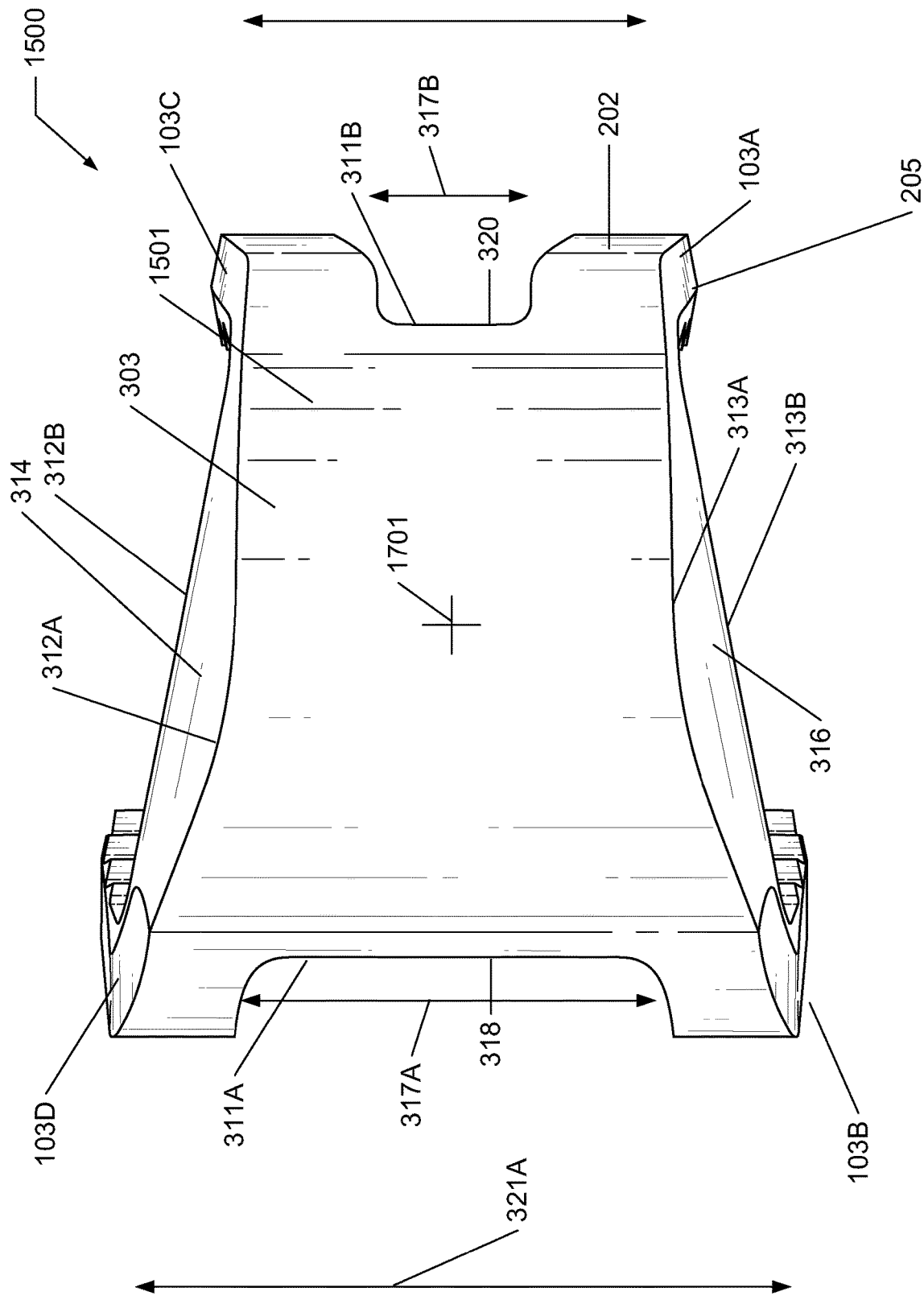
FIG. 17 shows a top view of an exemplary staple according to one embodiment of the present disclosure.

FIG. 17 shows a top view of the staple 1500, according to one embodiment of the present disclosure. In various embodiments, the staple 1500 is generally similar to the staple 100 (FIG. 1). In particular embodiments, the base member 1501 excludes an aperture centered about a center point 1701.

Figure 18:
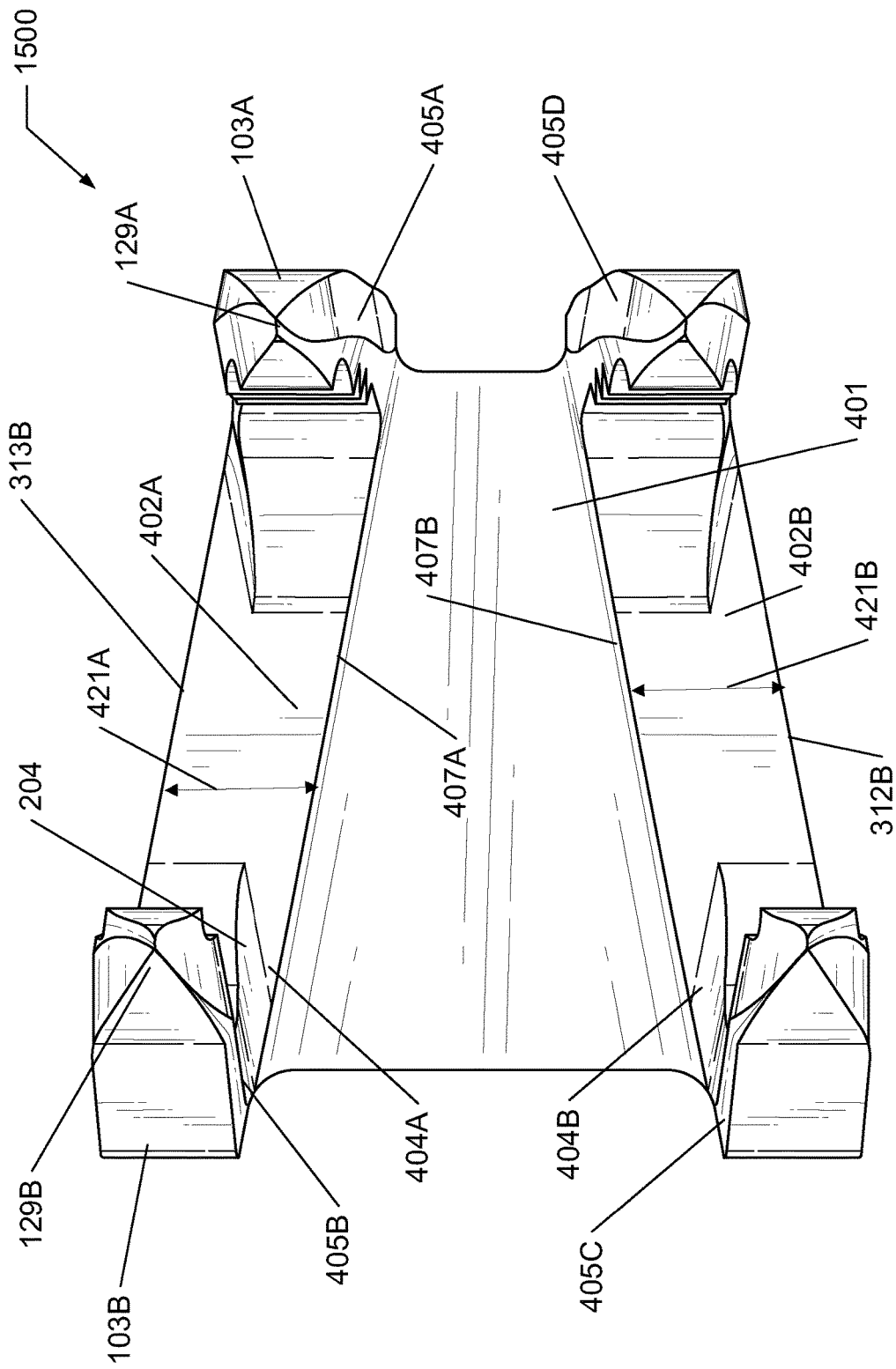
FIG. 18 shows a bottom view of an exemplary staple according to one embodiment of the present disclosure.

FIG. 18 shows a bottom view of the staple 1500, according to one embodiment of the present disclosure. In various embodiments, the staple 1500 is generally similar to the staple 100 (FIG. 1).

Figure 19:
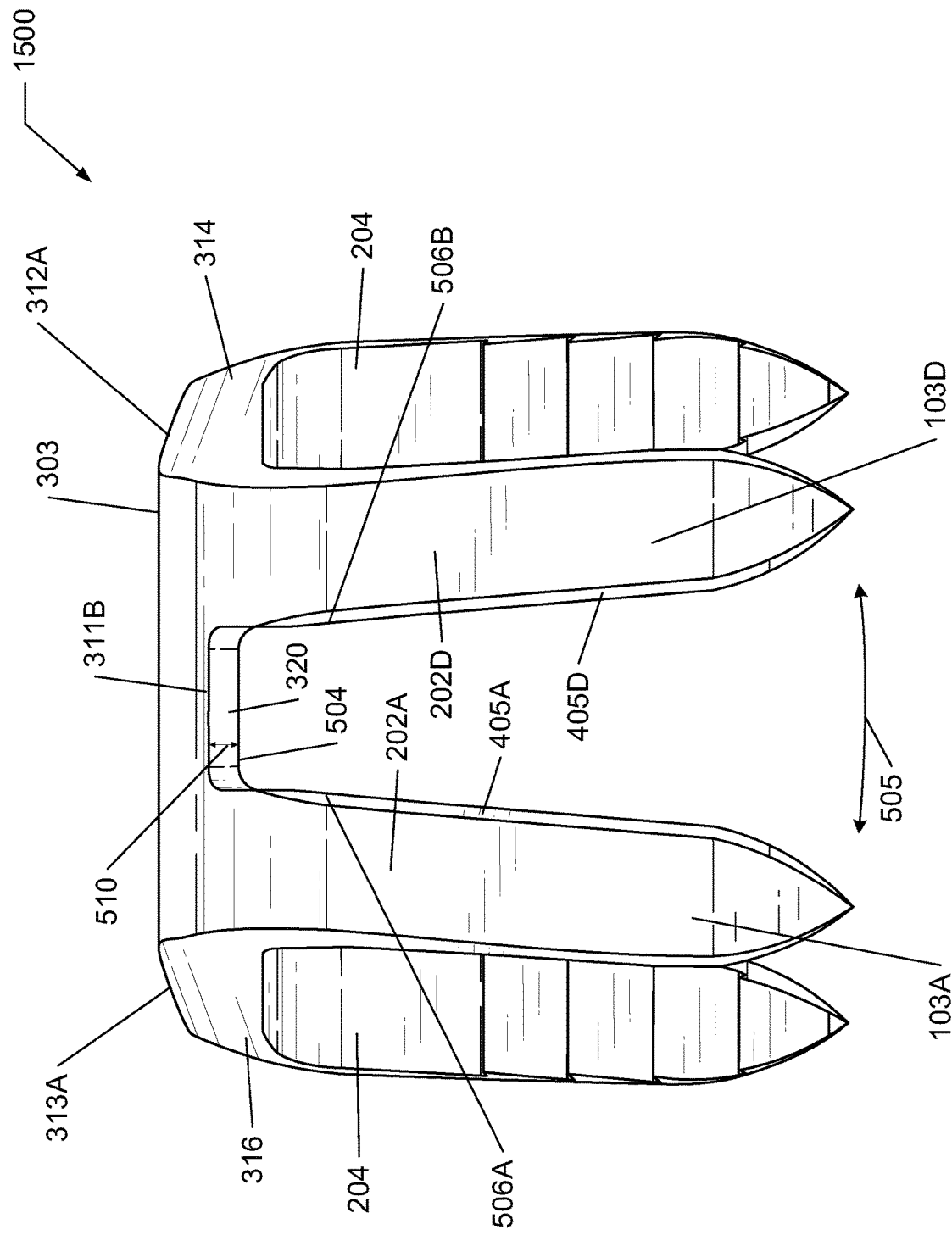
FIG. 19 shows a front view of an exemplary staple according to one embodiment of the present disclosure.

FIG. 19 shows a front view of the staple 1500, according to one embodiment of the present disclosure. In various embodiments, the staple 1500 is generally similar to the staple 100 (FIG. 1).

Figure 20:
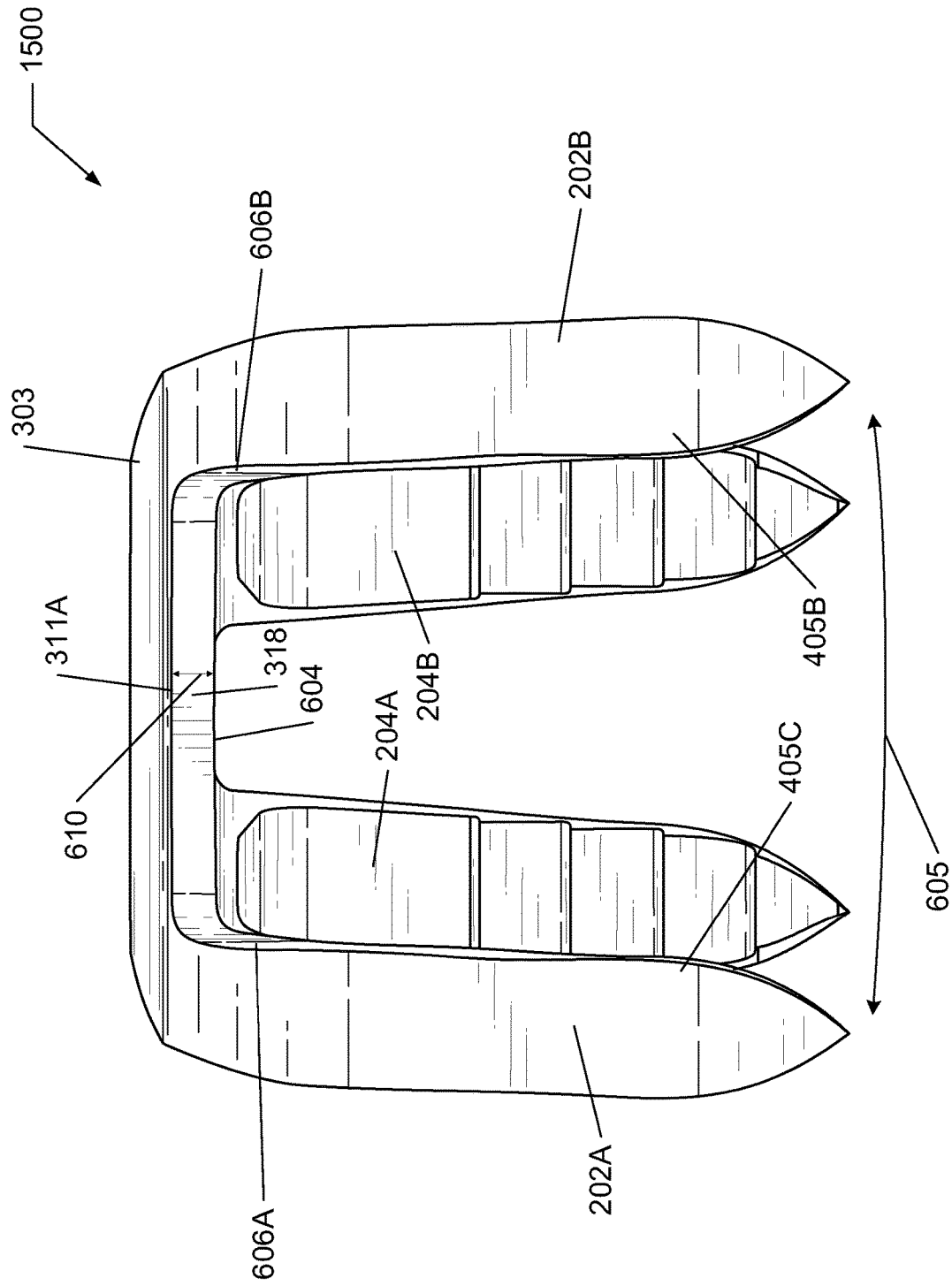
FIG. 20 shows a back view of an exemplary staple according to one embodiment of the present disclosure.

FIG. 20 shows a back view of the staple 1500, according to one embodiment of the present disclosure. In various embodiments, the staple 1500 is generally similar to the staple 100 (FIG. 1).

Exemplary Staple Systems

Figure 21:
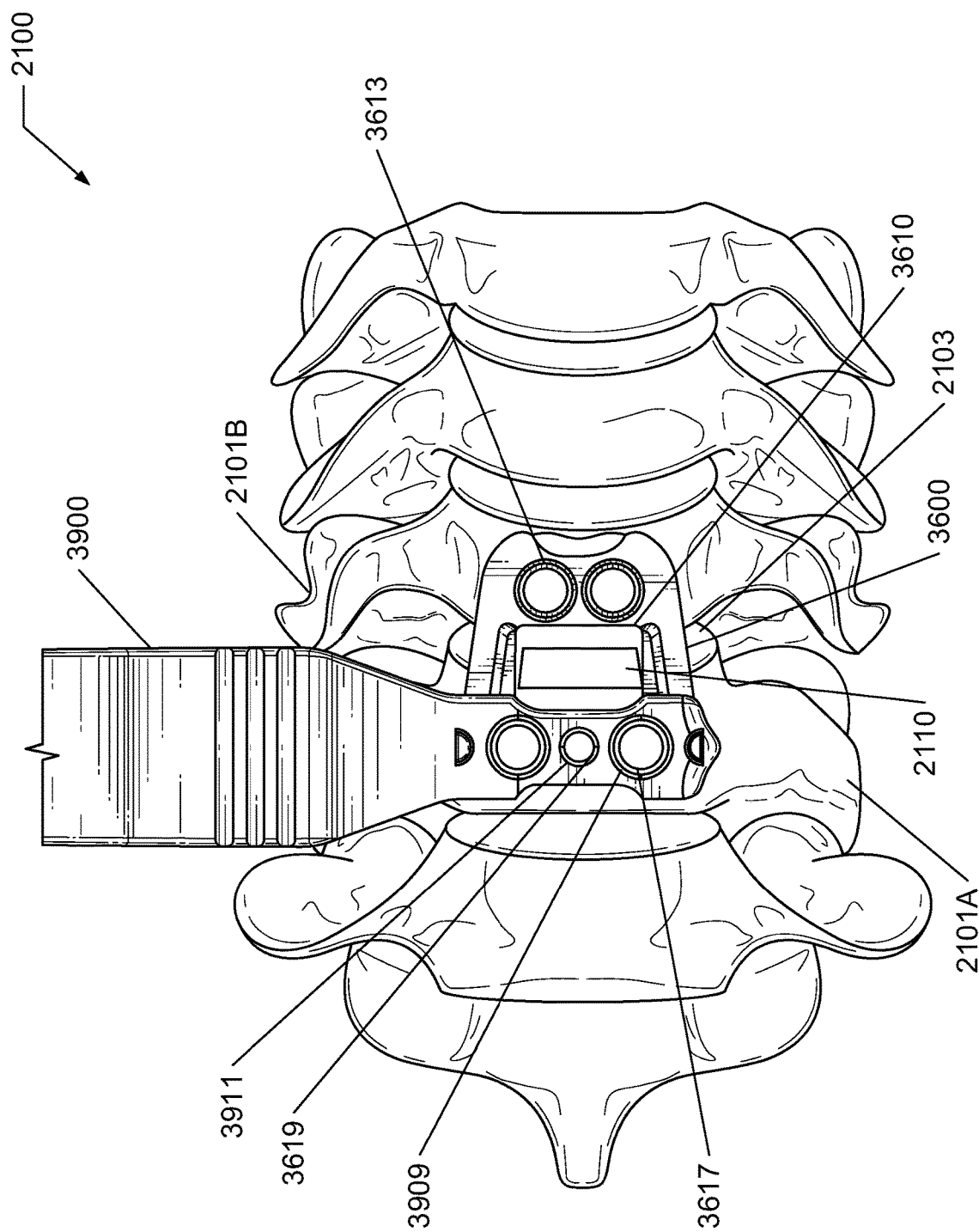
FIG. 21 shows an exemplary staple system according to one embodiment of the present disclosure.

FIG. 21 shows an exemplary staple system 2100, according to one embodiment of the present disclosure. According to one embodiment, FIGS. 21-30 show an exemplary sequence of staple system 2100 functions including, but not limited to, alignment, insertion, removal, and (dis)engagement of staples described and shown herein.

In various embodiments, the staple system 2100 compresses a first bony structure 2101A and a second bony structure 2101B toward each other and/or towards an implant 2110 that may be inserted in a space adjacent to the bony structures 2101A-B. In one example, the staple system 2100 compresses adjacent vertebrae for purposes of spinal fusion. In this example, the space adjacent to the bony structures 2101A-B is an intervertebral space 2103 and an implant 2110 is inserted into the intervertebral space 2103 to promote spinal fusion via osseointegration. In one or more embodiments, the staple system 2100 includes, but is not limited to, a boring apparatus 3600 and a handle 3900. In particular embodiments, the boring apparatus 3600 can also be referred to as the boring system and/or the boring tool. In various embodiments, the staple system 2100 includes one or more of, but is not limited to, the boring apparatus 3600, the handle 3900, a spacer 3200 (see, for example, FIGS. 26-29, 31A-B, and 32), an implant 2110, a staple (e.g., such as staples 100, 700, 1000, or 1500 shown in FIGS. 1, 7, 10, and 15), and a staple installation tool 2600 (see FIG. 26).

Figure 25:
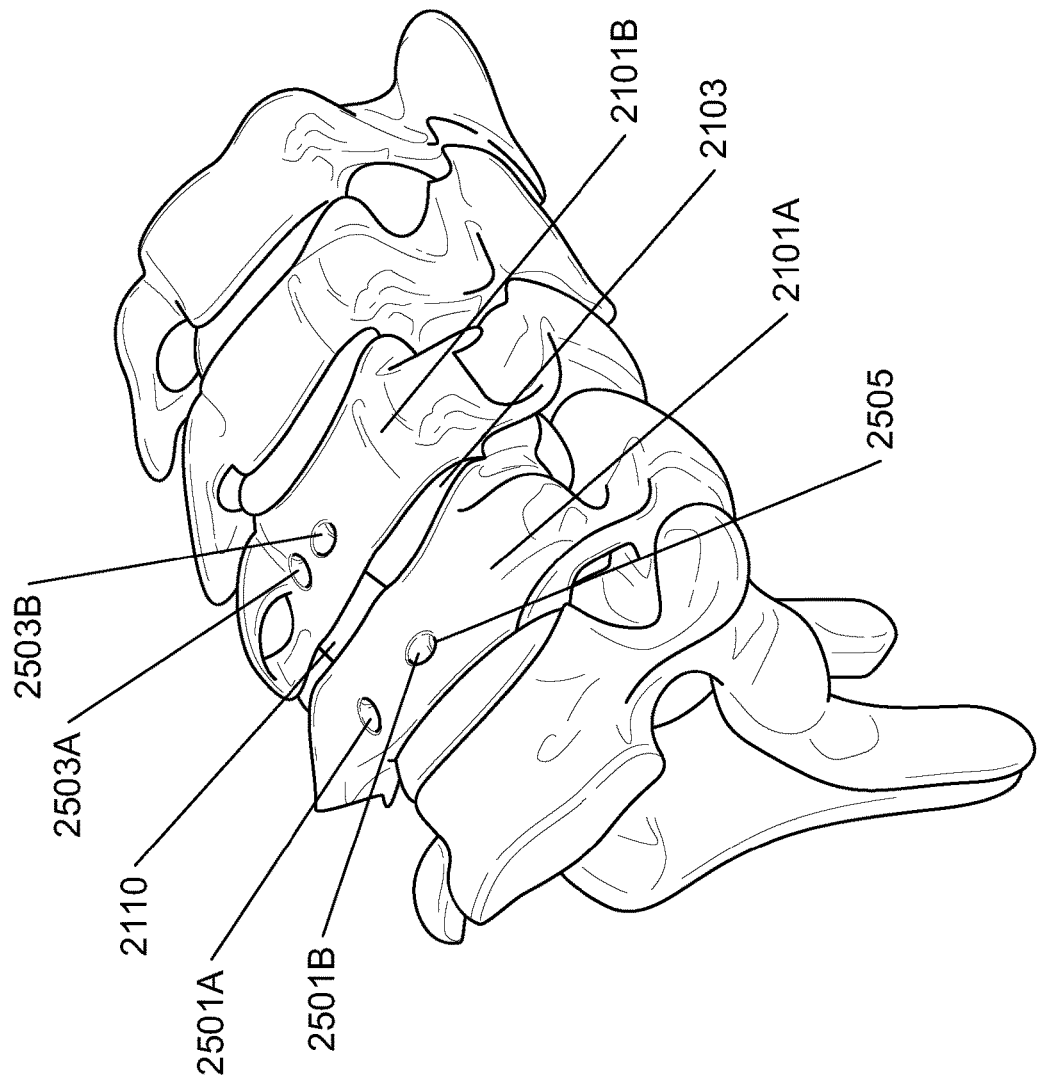
FIG. 25 shows the first and second bony structures 2101A-B following a boring process according to one embodiment of the present disclosure.

According to one embodiment, use of the boring apparatus 3600 provides for accurate insertion of a staple to a target site by supporting alignment and arrangement of one or more boreholes at the target site (e.g., such as boreholes 2501A-B, 2503A-B shown in FIG. 25). In some embodiments, the boreholes 2501A-B and 2503A-B can be referred to as a bone aperture and/or boring holes. In one or more embodiments, the boring apparatus 3600 is positioned against the first bony structure 2101A and the second bony structure 2101B. According to one embodiment, the boring apparatus 3600 is positioned against the first bony structure 2101A and the second bony structure 2101B such that one or more apertures 3617 of the boring apparatus 3600 align with the first bony structure 2101A and such that one or more apertures 3613 of the boring apparatus 3600 align with the second bony structure 2101B. In various embodiments, the handle 3900 connects to the boring apparatus 3600, thereby allowing accurate and precise manipulation of the boring apparatus 3600 via the handle 3900 in an offset manner that allows for substantially unobstructed observation of the boring apparatus position. In some embodiments, the handle 3900 is connected to the boring apparatus 3600 during an assembly stage of the staple system 2100. For example, the staple system 2100 is a kit in which the handle 3900 is pre-attached to the boring apparatus 3600. In at least one embodiment, a user (e.g., a surgeon, technician, etc.) connects the handle 3900 to the boring apparatus 3600 during a process for inserting a staple to a target site. For example, the staple system 2100 is a kit in which the handle 3900 is disconnected from the boring apparatus 3600 until assembly by the user at a predetermined step of a staple insertion process.

In at least one embodiment, positioning of the boring apparatus 3600 against the first bony structure 2101A and the second bony structure 2101B includes positioning the handle 3900 such that one or more apertures 3909 align with the first bony structure 2101A or the second bony structure 2101B. In one or more embodiments, positioning of the boring apparatus 3600 against the first bony structure 2101A and the second bony structure 2101B includes positioning the boring apparatus 3600 and the handle 3900 such that an aperture 3619 of the boring apparatus 3600 and an aperture 3911 of the handle 3900 are co-aligned and are further aligned with the first bony structure 2101A. In various embodiments, the boring apparatus 3600 is positioned against the first bony structure 2101A and the second bony structure 2101B such that each corner of the boring apparatus 3600 contacts bone. In some embodiments, positioning the boring apparatus 3600 includes removing anterior osteophytes at that target site, which may inhibit proper seating of the boring apparatus 3600, an implant 2110, and/or one or more staples.

In one or more embodiments, the implant 2110 is inserted to an intervertebral space 2103 of the first bony structure 2101A and the second bony structure 2101B. For example, a surgeon inserts the implant 2110 into an intervertebral space between adjacent vertebrae (e.g., a space typically by an intervertebral disk). Insertion of the implant 2110 can occur before, during, or following positioning of the boring apparatus 3600. In various embodiments, a process for inserting the implant 2110 includes inserting the implant 2110 into an intervertebral space 2103 such that an anterior edge of the implant 2110 aligns with the anterior edge of the first bony structure 2101A and/or the anterior edge of the second bony structure 2101B. According to one embodiment, a process for inserting the implant 2110 includes removing osteophytes (e.g., anterior osteophytes) from the bony structures 2101A-B. In one or more embodiments, the boring apparatus 3600 includes an aperture 3610 (e.g., also referred to as a "window") that allows observation of the implant 2110 during positioning of the boring apparatus 3600, thereby promoting precise and accurate placement.

In at least one embodiment, the implant 2110 includes one or more materials for promoting fusion of the first bony structure 2101A and the second bony structure 2101B. For example, the implant 2110 includes bone graft or bone graft substitute that promotes ossification at adjacent bony fragments and osseointegration into the implant 2110 and into corresponding bony fragments, thereby achieving fusion. According to one embodiment, the implant 2110 reduces a likelihood of incomplete fusion by providing a platform for directing and aligning bone growth toward bone fusion. In one or more embodiments, bone fusion refers to osseointegration of adjacent bone into the implant 2110. In at least one embodiment, bone fusion refers to osseointegration of adjacent bone structures into the implant 2110 and formation of new bone that connects the adjacent bone structures.

Figure 22:
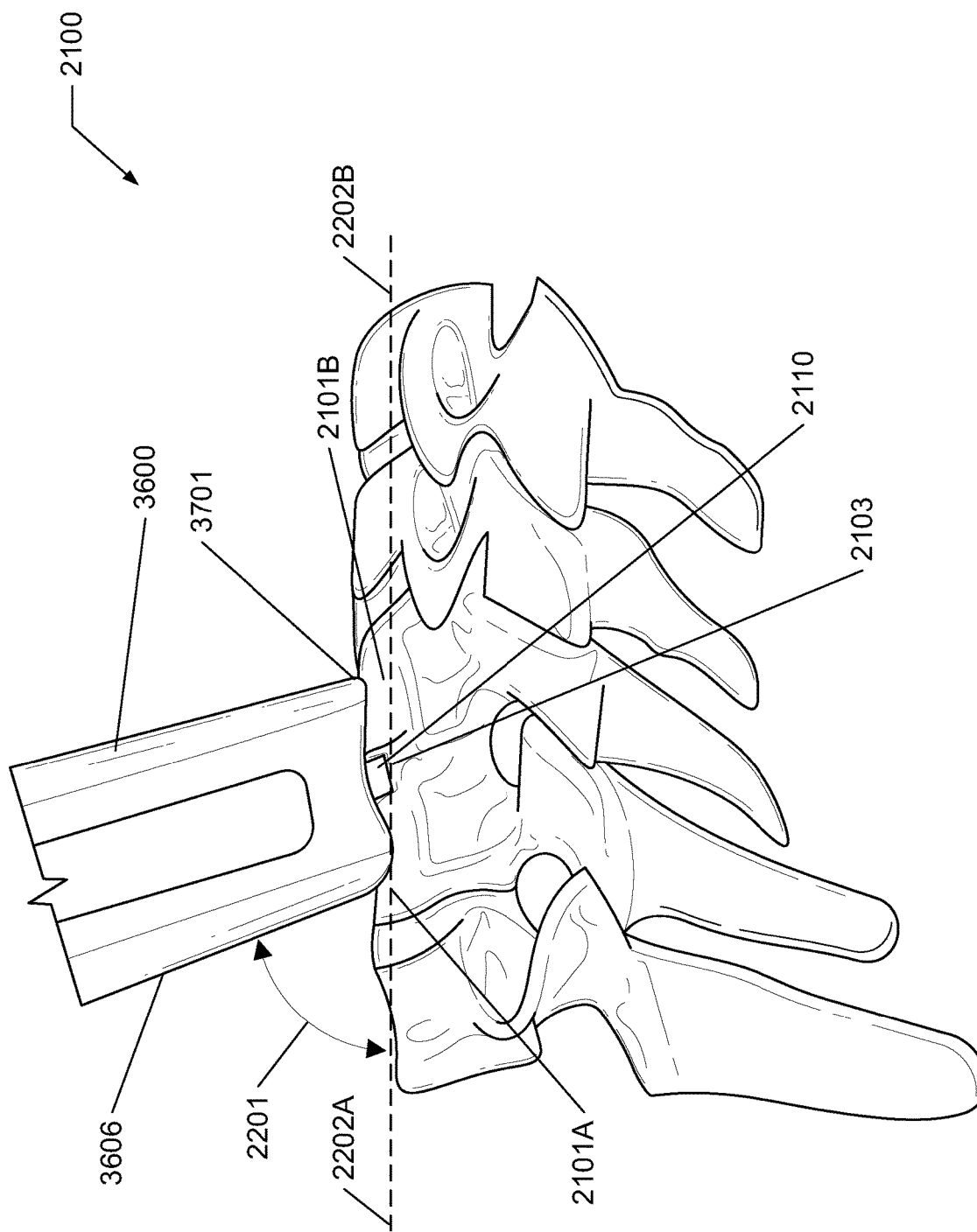
FIG. 22 shows the staple system according to one embodiment of the present disclosure.

FIG. 22 shows the staple system 2100, according to one embodiment of the present disclosure.

As described herein, the boring apparatus 3600 may be positioned against the first bony structure 2101A and the second bony structure 2101B such that each corner 3701 of the boring apparatus 3600 contacts bone. In at least one embodiment, the boring apparatus 3600 is oriented such that an insertion angle 2201 is achieved following positioning of the boring apparatus 3600 against the first bony structure 2101A and the second bony structure 2101B. In various embodiments, the insertion angle 2201 defines an angle between a side 3606 of the boring apparatus 3600 and a plane defined by a longitudinal axis 2202A, 2202B of the first bony structure 2101A. According to one embodiment, the insertion angle 2201 measures at least about 15 degrees, or about 15-85 degrees, 15-25 degrees, 25-35 degrees, 35-45 degrees, 45-55 degrees, 55-65 degrees, 65-75 degrees, or 75-85 degrees, or less than about 85 degrees.

In one or more embodiments, the implant 2110 is inserted into the intervertebral space 2103 such that the implant 2110 contacts the first bony structure 2101A and the second bony structure 2101B.

Figure 23:
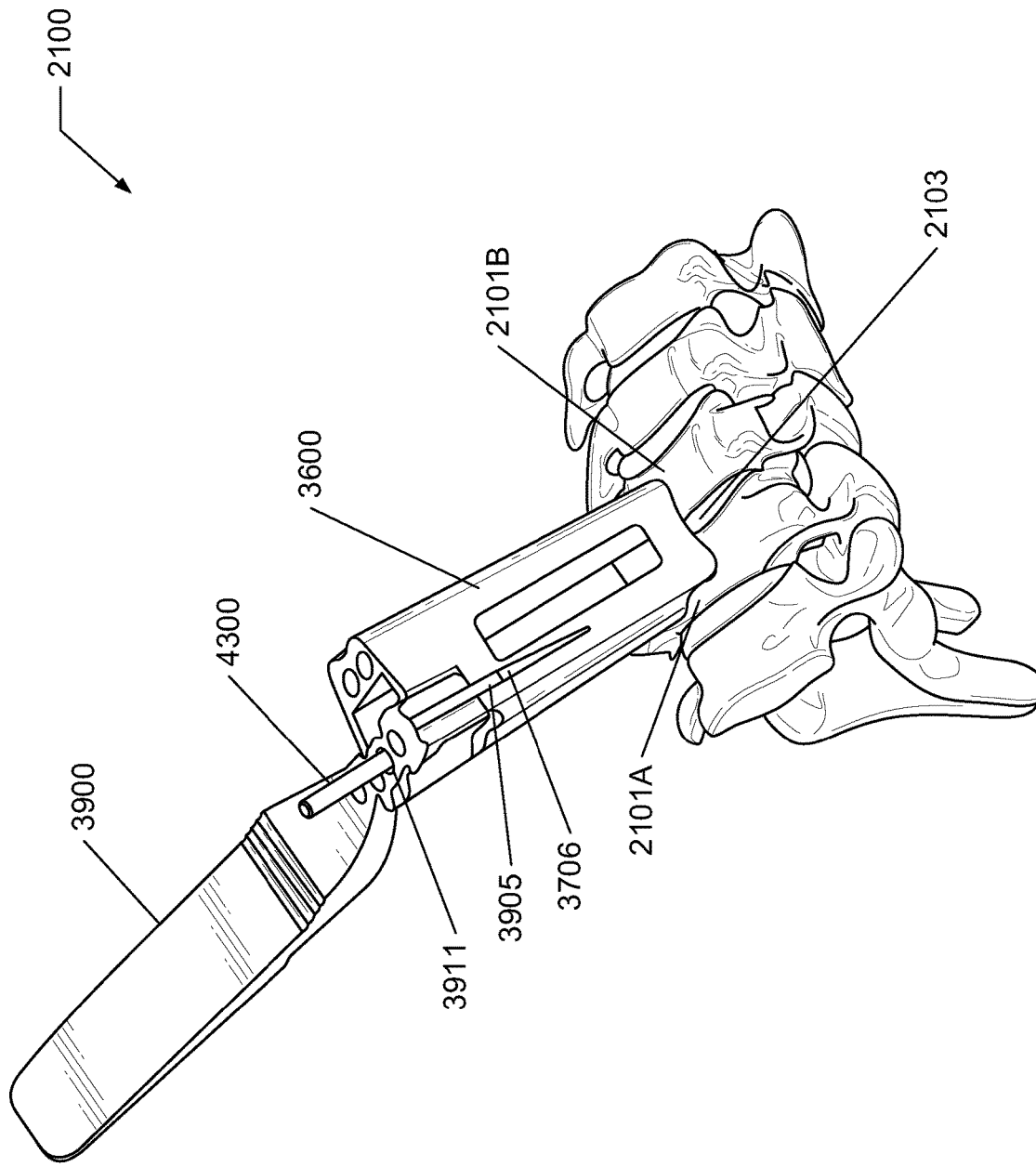
FIG. 23 shows the staple system according to one embodiment of the present disclosure.

FIG. 23 shows the staple system 2100, according to one embodiment of the present disclosure.

In one or more embodiments, the staple system 2100 includes a targeting pin 4300. In at least one embodiment, the targeting pin 4300 affixes to the first bony structure 2101A or the second bony structure 2101B. In various embodiments, the handle 3900 and the boring apparatus 3600 receive the targeting pin 4300 through aperture 3911 and aperture 3619 (not shown, see FIG. 36). In at least one embodiment, the targeting pin 4300 is passed through the handle 3900 and the boring apparatus 3600, and the targeting pin 4300 penetrates into the first bony structure 2101A. In one or more embodiments, insertion of the targeting pin 4300 includes imaging the first bony structure 2101A (e.g., and adjacent anatomy) under one or more imaging techniques to confirm precise and accurate placement of the targeting pin 4300. In one example, a process for inserting the targeting pin 4300 includes imaging the first bony structure 2101A and adjacent anatomy under fluoroscopy and verifying that the inserted targeting pin 4300 penetrates the first bony structure 2101A (e.g., at a mid-section thereof, or another suitable position) and the targeting pin 4300 follows a correct trajectory. In another example, following insertion, fluoroscopy is performed to verify that a tip of the target pin 4300 is directed toward a caudal aspect of the intervertebral space 2103. In another example, fluoroscopy is performed to confirm that that a tip of the target pin 4300 is directed towards the first vertebra of a pair of adjacent vertebrae that, with an intervertebral space therebetween, define the target site. In another example, fluoroscopy is performed to confirm that a cranial side of the boring apparatus 3600 (e.g., and/or implant 2110) is in contact with the second vertebra of the pair of adjacent vertebrae. Performing fluoroscopy can generally refer to capturing fluoroscopic images of a target site for review and/or imaging the target site under fluoroscopy in virtually real time.

In at least one embodiment, to ensure sufficient bone stock between the intervertebral space 2103 and the targeting pin 4300, the boring apparatus 3600 is biased caudally by at least about 0.5 mm, or about 0.5-2.0 mm, 0.5-1.0 mm, 1.0 mm, 1.0-1.5 mm, 1.5-2.0 mm, or less than about 2.0 mm.

In at least one embodiment, the handle 3900 includes one or more arms 3905 for securely connecting the handle 3900 to the boring apparatus 3600. According to one embodiment, the boring apparatus 3600 includes one or more channels 3706 configured to receive the arm 3905. In various embodiments, the connection between the arms 3905 and the channel 3706 is a snap-fit connection, a friction-based connection, or any other suitable connection.

Figure 24:
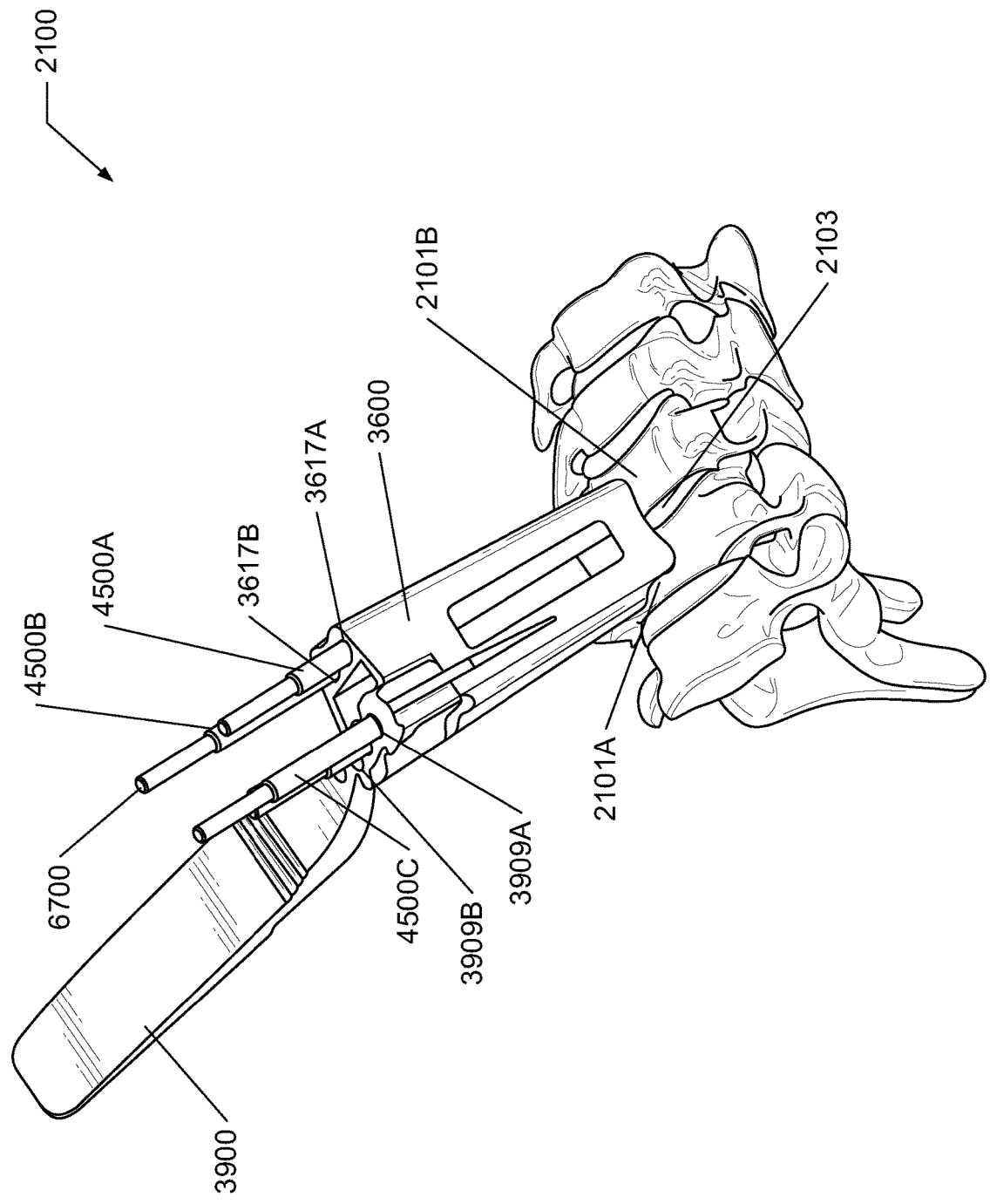
FIG. 24 shows the staple system according to one embodiment of the present disclosure.

FIG. 24 shows the staple system 2100, according to one embodiment of the present disclosure.

In one or more embodiments, the staple system 2100 includes one or more drill pins 4500A-C. In various embodiments, the handle 3900 and the boring apparatus 3600 are configured to receive the one or more drill pins 4500A-C. For example, the staple system 2100 includes 2, 3, 4, or any suitable number of drill pins, and the handle 3900 and the boring apparatus 3600 include aligned apertures through which the drill pins are inserted and drilled into bone. In one or more embodiments, each drill pin 4500A-C includes an adapter pin 4503 (see also, FIGS. 45, 67-70) for connecting a drilling tool to the drill pin.

According to one embodiment, the pins 4500A-C can be drilled into the first bony structure 2101A and/or the second bony structure 2101B for purposes of providing boreholes into which a staple may be inserted. In at least one embodiment, to ensure sufficient bone stock between the intervertebral space 2103 and the drill pin 4500A (e.g., or another drill pin), the boring apparatus 3600 is biased downwards (e.g., caudally) by at least about 0.5 mm, or about 0.5-2.0 mm, 0.5-1.0 mm, 1.0 mm, 1.0-1.5 mm, 1.5-2.0 mm, or less than about 2.0 mm. In one example, a fluoroscopy image can confirm the trajectory of the drill pins 4500A-C.

In at least one embodiment, the aperture 3617A of the boring apparatus 3600 receives the drill pin 4500A. For example, the drill pin 3600A is inserted through the aperture 3617A, through a corresponding aperture (not shown) opposite the aperture 3617A, and into the second bony structure 2101B. In various embodiments, the aperture 3617B of the boring apparatus 3600 receives the drill pin 4500B. In at least one embodiment, the aperture 3909A of the handle 3900 and another aperture (not shown) of the boring apparatus 3600 receive the drill pin 4500C. According to one embodiment, the aperture 3909B of the handle 3900 and another aperture (not shown) of the boring apparatus 3600 receive a drill pin substantially similar to the drill pins 4500A-C(e.g., in particular, drill pin 4500A).

In various embodiments, the drill pins are inserted through the boring apparatus 3600 (e.g., and, when applicable, the handle 3900) according to a particular sequence (e.g., such as an opposite and alternating sequence).

In an exemplary scenario, the drill pin 4500A is inserted through the aperture 3617A of the boring apparatus 3600 and into the second bony structure 2101B. Following insertion of the drill pin 4500A, a drill pin (not shown) is inserted through the aperture 3909B of the handle 3900 and an aperture of the boring apparatus 3600, and is further inserted into the first bony structure 2101A. Following insertion of the above drill pin, the drill pin 4500B is inserted through the aperture 3617B of the boring apparatus 3600, and is further inserted into the second bony structure 2101B. Following insertion of the drill pin 4500B, the drill pin 4500C is inserted through the aperture 3909A of the handle 3900 and another aperture of the boring apparatus 3600, and is further inserted into the first bony structure 2101A. In various embodiments, all drill pins are inserted to substantially equal depths within the first and second bony structures 2101A-B. In at least one embodiment, each drill pin includes indicia or a surface modification (e.g., such as an area of decreased or increased diameter, also referred to as a "stop") that visually indicates a predetermined depth to which the drill pin may be inserted.

In at least one embodiment, the drill pins 4500B, 4500C are longer than the drill pin 4500A (e.g., and longer than a drill pin inserted through the aperture 3909B). In various embodiments, the differing lengths of the drill pin length allows for easier manipulation of the drill pins (e.g., shorter pins may be less likely to obstruct insertion of longer pins). For example, the difference in drill pin length may permit easier access of a drilling tool, thereby reducing a likelihood of dislodging or otherwise disturbing the position of the boring apparatus 3600. According to one embodiment, the stops of drill pins demonstrating different lengths are configured such that drill pins of differing length are inserted to substantially equal depths within the first and second bony structures 2101A-B.

In one or more embodiments, following insertion of all drill pins, an imaging technique is performed to ensure that tips of the drill pins are substantially equidistant from the intervertebral space 2103 and to ensure that each drill pin is inserted such that sufficient bone stock is provided between the drill pin and the intervertebral space 2103. In at least one embodiment, the sufficient bone stock is at least about 1 mm, about 1-7 mm, 1-2 mm, 2-3 mm, 3-4 mm, 4-5 mm, 5-6 mm, or about 6-7 mm, or less than about 7 mm. For example, the drill pins are inserted such that 2 mm of bone stock (e.g., or 3 mm, 4 mm, 5 mm, or another suitable quantity of bone stock) between the intervertebral space 2103 and legs of a staple inserted to the first bony structure 2101A or second bony structure 2101B. According to one embodiment, the sufficient bone stock is about ##. In one or more embodiments, following the insertion of the drill pins (e.g., and/or following verification under imaging), the drill pins 4500A-C(e.g., and the drill pin inserted through the aperture 3909B), targeting pin 4300, boring apparatus 3600, and the handle 3900 are removed from the first and second bony structures 2101A-B.

FIG. 25 shows the first and second bony structures 2101A-B following a boring process, according to one embodiment of the present disclosure.

In various embodiments, insertion of drill pins into the first and second bony structures 2101A-B via the handle 3900 and the boring apparatus 3600 forms boreholes 2501A-B, 2503A-B. In one or more embodiments, each borehole 2501A-B, 2503A-B is sized to receive a leg of a staple (e.g., such as staples 100, 700, 1000, 1500, or 2601). According to one embodiment, each borehole 2501A-B, 2503A-B includes a diameter 2505 of at least about 1.0 mm, or about 1.0-5.0 mm, 1.0-2.0 mm, 2.0-3.0 mm, 3.1 mm, 3.0-4.0 mm, or 4.0-5.0 mm, or less than about 5.0 mm. According to one embodiment, an arrangement of the boreholes 2501A-B, 2503A-B generally matches a spatial footprint of legs of a staple that is to be inserted into the first and second bony structures 2101A-B. In one or more embodiments, imaging is used to verify that the boreholes 2501A-B, 2603A-B are equidistant from the implant 2110 or from the intervertebral space 2103.

Figure 26:
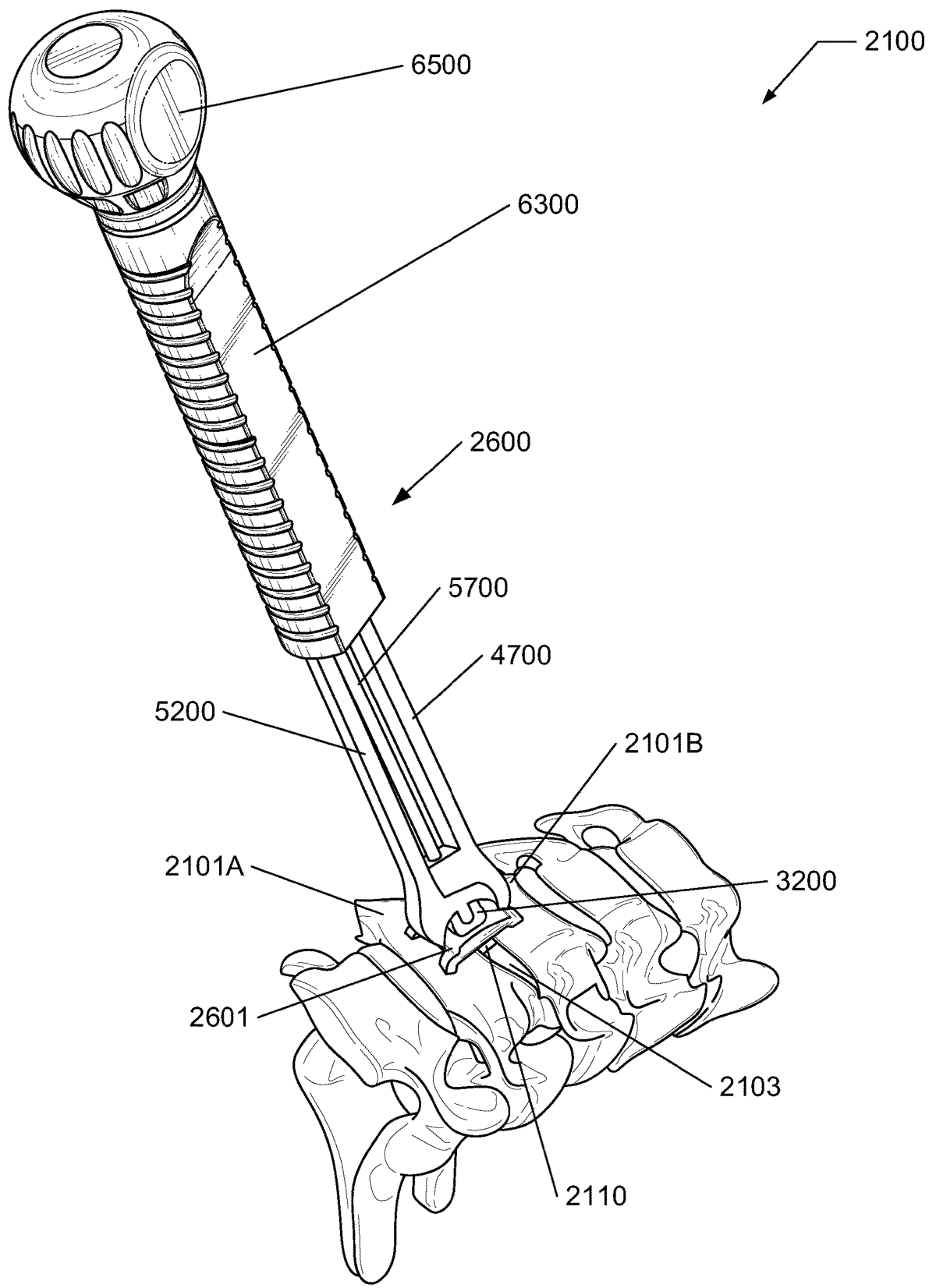
FIG. 26 shows the staple system according to one embodiment of the present disclosure.

FIG. 26 shows the staple system 2100, according to one embodiment of the present disclosure. In various embodiments, the staple system 2100 includes a staple installation tool 2600 and a staple 2601. In particular embodiments, the installation tool 2600 can be referred to as a staple insertion tool, a staple removal tool, and/or a tool apparatus. The staple 2601 can generally refer to any staple described herein, such as, for example, any embodiment of staples 100, 700, 1000, or 1500 (see FIGS. 1-20). According to one embodiment, the staple 2601 deforms from an unconstrained state to a constrained state by receiving a pushing force on a central region of a base member of the staple 2601 and by receiving a pulling force on a first side and an opposed second side of the base member. In various embodiments, the staple installation tool 2600 deforms the staple 2601 to the constrained state by applying a pushing force to the staple 2601 base member and by applying pulling forces to opposed sides of the base member (e.g., thereby causing the base member to deform and increasing an angle between opposed pairs of legs connected to the opposed base member sides).

In various embodiments, the staple installation tool 2600 includes, but is not limited to, a first shaft 4700, a second shaft 5200, a rod 5700, a sleeve 6300, and a handle 6500. According to one embodiment, the rod 5700 includes a pin 6100 (not shown, see FIG. 61) for engaging the second shaft 5200 and, thereby, deforming (e.g., and maintaining in a deformed state) the staple 2601. In one or more embodiments, the first shaft 4700 and the second shaft 5200 attach to the staple 2601 and secure the staple 2601 to the staple installation tool 2600. In one example, the staple 2601 is substantially similar to the staple 100 (FIG. 1) and the first shaft 4700 and the second shaft 5200 each include a hooked portion that hooks to an indentation of the staple 2601. In particular embodiments, the hooked portion can be referred to as a hooked end. In this example, the hooked portion of the first shaft 4700 attaches to an indentation 123 (see FIG. 1) and the hooked portion of the second shaft 5200 attaches to an indentation 121 (see FIG. 1). According to one embodiment, the first shaft 4700 and the second shaft 5200 orient substantially perpendicular to a base member of the staple 2601.

In various embodiments, the spacer 3200 acts as a fulcrum over which bending of the staple 2601 occurs. In one or more embodiments, the pulling forces of the first shaft 4700 and the second shaft 5200 pull the base member of the staple 2601 against the spacer 3200, thereby forming a three-point bending arrangement to deform the staple 2601 into a constrained state. In at least one embodiment, the second shaft 5200 receives the spacer 3200. For example, a prong portion of the second shaft 5200 receives a U-shaped portion of the spacer 3200. In particular embodiments, the combination of the installation tool 2600 and the spacer 3200 can be referred to as a decompression tool. In one or more embodiments, the spacer 3200 applies a pushing force to the staple 2601. In at least one embodiment, the spacer 3200 can be referred to as a pushing component. According to one embodiment, at least a portion of the pushing force applied by the spacer 3200 is generated in response to the pulling forces applied by the first shaft 4700 and the second shaft 5200. In some embodiments, the first shaft 4700 and the second shaft 5200 can be referred to as pulling components. In various embodiments, the pushing force applied by the spacer 3200 (e.g., or at least a portion of the pushing force) is generated by the rod 5700 that inserts through the first shaft 4700 and the second shaft 5200, and applies a force to the spacer 3200. In one example, as the rod 5700 is rotated through the first shaft 4700, a pin 5705 attached to the end of the rod 5700 contacts the spacer 3200. In this example, as the rod 5700 is further rotated through the first shaft 4700, the pin 5705 applies an increasing force to the spacer 3200. In the same example, as the pin 5705 applies the force to the spacer 3200, the spacer 3200 translates the applied force to the staple 2601 in the form of a pushing force that further deforms the staple 2601 into a constrained state.

In one or more embodiments connecting the staple installation tool 2600 to the staple 2601 includes attaching hooked portions of the first shaft 4700 and the second shaft 5200 to opposed sides of the staple 2601. For example, the staple 2601 includes two opposed sides that each include an indentation to which the hooked portion of the first shaft 4700 or the second shaft 5200 attaches. In at least one embodiment, while attached to the staple 2601, the first shaft 4700 and the second shaft 5200 move toward each other (e.g., via rotation about the staple connections) until the first shaft 4700 and the second shaft 5200 are substantially parallel. In at least one embodiment, a rod 5700 secures the relative position of the first shaft 4700 and the second shaft

5200. In one example, the first shaft 4700 includes female threads and the rod 5700 includes a pin including male threads and a tip. In this example, after connecting hooked portions of the first shaft 4700 and the second shaft 5200 to the staple 2601, the female threads of the first shaft 4700 and an aperture of the second shaft 5200 are aligned. Continuing the example, the female threads of the first shaft 4700 receive the male threads of the pin and the aperture of the second shaft 5200 receives the tip of the pin, thereby securing the relative positions of the first shaft 4700 and the second shaft 5200. In one or more embodiments, the sleeve 6300 slides over the first shaft 4700 and the second shaft 5200 and prevents relative movement thereof. In various embodiments, the sleeve 6300 receives a handle 6500 for rotating the rod 5700 and, thereby, controlling deformation of the staple 2601.

In at least one embodiment, the spacer 3200 is inserted between the second shaft 4700 and the staple 2601 prior to insertion of the rod 5700. In various embodiments, the first shaft 4700 and the second shaft 5200 each apply an upward force to sides (e.g., opposed sides) of the staple 2601. According to one embodiment, the rod 5700 (e.g., or a pin 6100 connected thereto) applies a force to the spacer 3200 (e.g., or, in some embodiments, the second shaft 5200) that causes application of a downward force to the spacer 3200 and, thereby, to a mid-section of the staple 2601. In at least one embodiment, the downward force of the rod 5700 and/or spacer 3200 and the upward forces of the first shaft 4700 and the second shaft 5200 deforms and maintains the staple 2601 in a deformed state. In at least one embodiment, the rod 5700 can be rotated to further engage a threaded connection between the rod 5700 and the second shaft 5200, and, thereby, increase the downward force applied to the spacer 3200 and/or the staple 2601. In various embodiments, increase of the downward force further deforms the staple 2601 into a constrained state. For example, at a first level of downward force, the staple 2601 is deformed such that opposed pairs of legs of the staple 2601 are drawn to a substantially parallel position. In the same example, at a second, increased level of downward force (e.g., caused by further rotation of the rod 5700), the staple 2601 is further deformed such that opposed pairs of legs of the staple 2601 are angled away from each other.

In an exemplary scenario, the upward and downward forces of the staple installation tool 2601 cause the staple 2601 to undergo bending substantially at a base member (for example, base member 101 shown in FIG. 1). The bending of the base member causes opposed legs of the staple 2601 (see legs 103A-D shown in FIG. 1) to deform from a first position to a second position (e.g., referred to as a "deformed" position). The legs of the staple 2601 are biased to return to the first position and, therefore, the legs generate and apply compressive forces to a target site in which the staple 2601 is inserted by compressing target site material while attempting to return to the first position.

In one or more embodiments, the sleeve 6300 receives a portion of the first shaft 4700 and the second shaft 5200, and the sleeve 6300 maintains a mated state of the first shaft 4700 and the second shaft 5200. For example, the sleeve 6300 slides over the first shaft 4700 at the end 4721 (see FIG. 47) and over the second shaft 5200 at the end 5221 (see FIG. 52). According to one embodiment, the sleeve 6300 maintains a position of the first shaft 4700 against the second shaft 5200, thereby preventing dislodging of the first shaft 4700 and the second shaft 5200 from the staple 2601. In one or more embodiments, the handle 6500 secures the position of the sleeve 6300 over a portion of the first shaft 4700 and a portion of the second shaft 5200. In at least one embodiment, the handle 6500 secures a connection between the rod 5700 and the first shaft 4700 by preventing upward movement of the rod 5700. In one or more embodiments, the rod 5700 receives a first end of a pin 5705 (see FIG. 57) and the first shaft 4700 receives a second end of the pin 5705. In various embodiments, the first shaft 4700 and the second end of the pin 5705 connect via a threaded fitting, a bayonet fitting, a luer lock fitting, a press fitting, or other suitable fitting.

According to one embodiment, the handle 6500 secures the connection between the rod 5700 and the pin 5705 by preventing upward movement of the rod 5700. In one or more embodiments, the handle 6500 connects to the rod 5700 such that the rod 5700 can be rotated via rotation of the handle 6500. In at least one embodiment, rotation of the handle 6500 in a first direction causes rotation of the rod 5700 in the first direction and, as a result, rotation of the pin 5705 in the first direction. According to one embodiment, rotation of the rod 5700 in the first direction applies a downward force to the second shaft 5200 and the downward force causes the spacer 3200 to apply a downward force to the staple 2601. In one or more embodiments, the downward force of the spacer 3200 causes the staple 2601 to deform to the constrained state, and the downward force maintains the staple 2601 in the constrained state. In at least one embodiment, rotation of the handle 6500 in a second direction, opposite the first direction, causes rotation of the rod 5700 in the second direction and, thereby, rotation of the pin 5705 in the second direction. In one or more embodiments, rotation of the pin 5705 in the second direction reduces or removes the downward force from the spacer 3200 and, thereby, reduces or removes the downward force applied to the staple 2601. According to one embodiment, removal of the downward force from the prong 5212 permits the staple 2601 to attempt to transition from the constrained position to an unconstrained (e.g., non-deformed) position. In one or more embodiments, the transition from the constrained position to the unconstrained position causes the legs of the staple 2601 to apply opposed forces to the first bony structure 2101A and the second bony structure 2101B, thereby causing compression of the bony structures 2101A-B toward the implant 3100.

In at least one embodiment, the staple system 2100 includes the staple installation tool 2600 attached to the staple 2601. For example, the staple system 2100 is a kit including the staple installation tool 2600 attached to the staple 2601 such that the staple 2601 deforms to the deformed position. In one or more embodiments, a user of the staple system 2100 (e.g., a surgeon, technician, etc.) attaches the staple installation tool 2600 to the staple 2601.

Figure 27A:
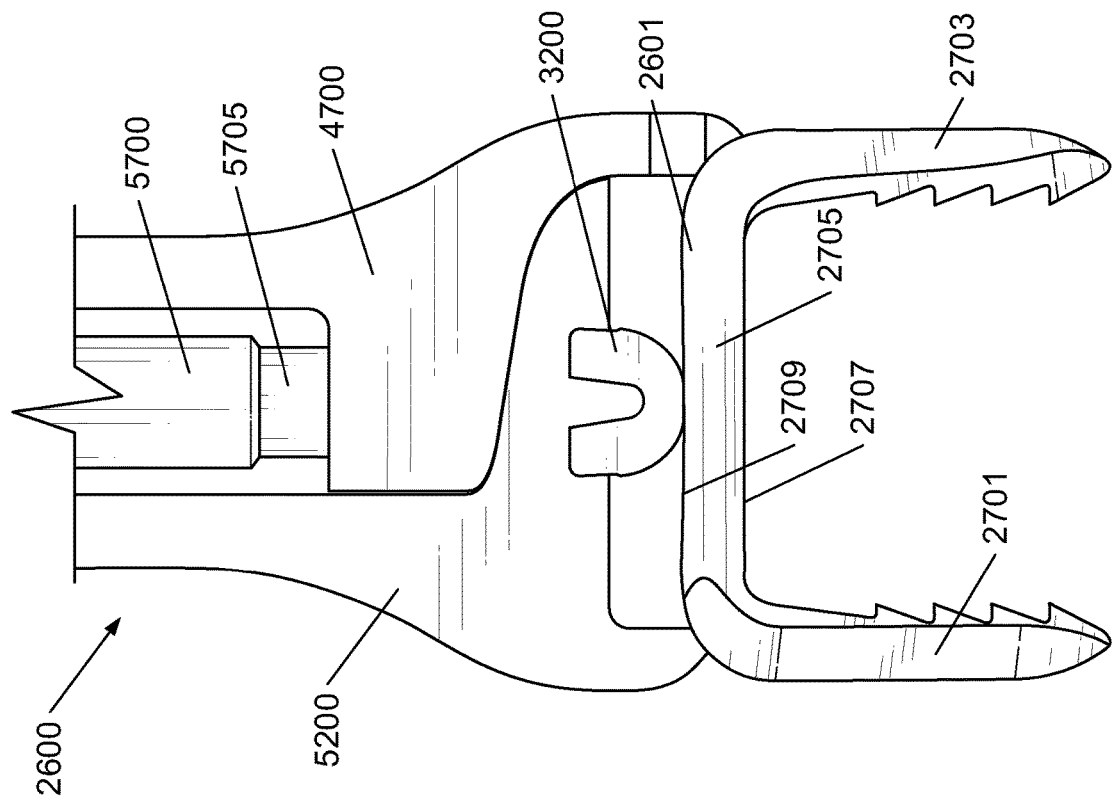
FIG. 27A shows an exemplary staple installation tool and an exemplary staple configured to a second constrained state according to one embodiment.

FIG. 27A shows the staple 2601 configured to a second constrained state, according to one embodiment. In one or more embodiments, FIG. 27A shows the staple 2601 and the staple installation tool 2600 in a post-manufacturing configuration. For example, the embodiment of the staple system shown in FIG. 27A may be provided to a surgeon in the form of a kit including a staple installation tool 2600 pre-attached to a staple 2601, the staple 2601 being pre-configured to the second constrained state. According to one embodiment, the second constrained state includes the staple 2601 deformed such that opposed leg portions 2701, 2703 of the staple 2601 are oriented away from each other. In at least one embodiment, in a first constrained state, opposed leg portions 2701, 2703 of the staple 2601 are oriented substantially parallel (for example, see FIG. 27B). In some embodiments, the second constrained state includes the staple 2601 deformed such that a base member 2705 of the staple 2601 demonstrates a convex curvature along a bottom surface 2707 and/or demonstrates a concave surface along a top surface 2709.

Figure 27B:
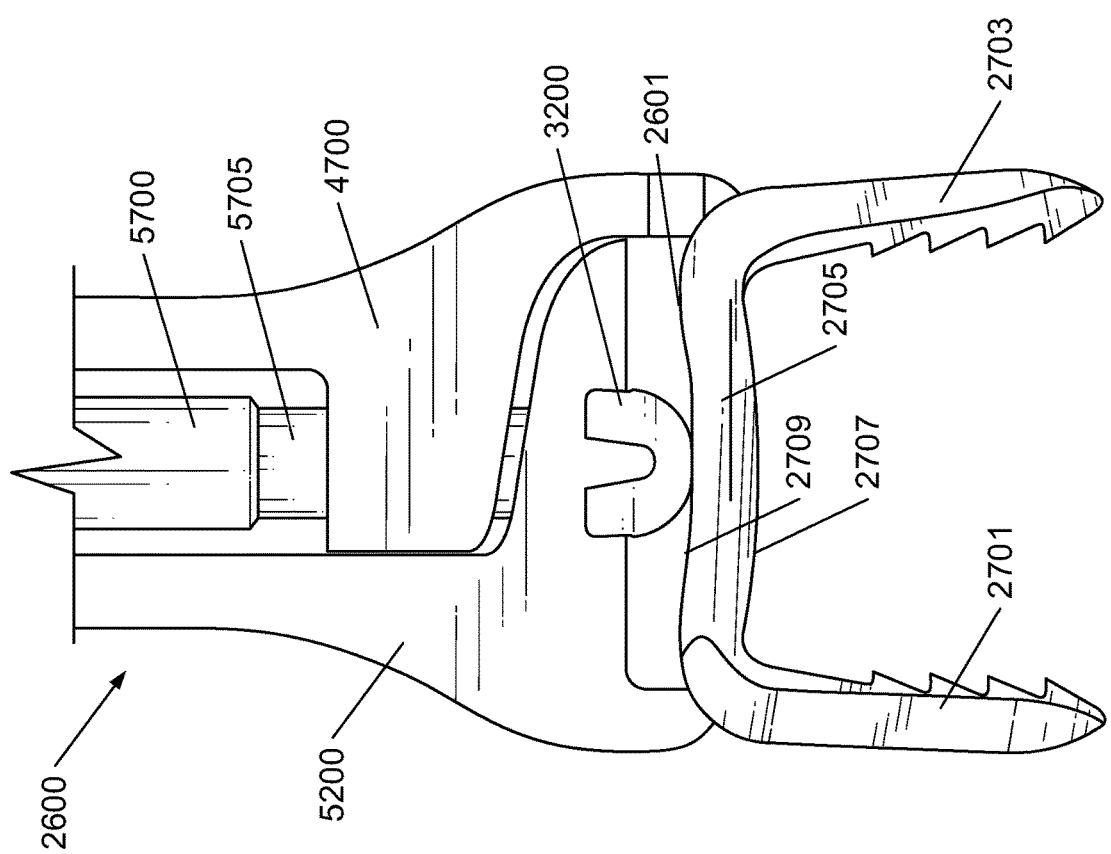
FIG. 27B shows an exemplary staple installation tool and an exemplary staple configured to a first constrained state according to one embodiment.

In one or more embodiments, the staple installation tool 2600 is attached to the staple 2601 such that the first shaft 4700 and the second shaft 5200 apply upward forces to opposed sides of the base member 2705. In at least one embodiment, a rod 5700 of the attached staple installation tool 2600 is rotated in a first direction to cause a pin 5705 to apply a downward force to the spacer 3200 and, thereby, apply a downward force to the staple 2601. In various embodiments, as shown in FIG. 27B, the downward force is applied at a first level to deform the staple 2601 to a first constrained state in which opposed pairs of legs of the staple 2601 are oriented substantially parallel. In at least one embodiment, as shown in FIG. 27A, the downward force is applied at a second level (e.g., via further rotation of the rod 5700) to further deform the staple 2601 to a second constrained position in which the opposed pairs of legs are oriented away from each other. In some embodiments, assembling the staple system 2100 includes configuring the staple 2601 to the second constrained state prior to the staple system 2100 being provided to a user (for example, a surgeon). According to one embodiment, maintaining the staple 2601 in the second constrained state allows the staple system 2100 to resist or tolerate external events (e.g., shocks, vibrations, etc.) and internal events (e.g., material creep, fitting creep, etc.) while maintaining the staple 2601 in a sufficiently deformed state.

FIG. 27B shows the staple 2601 configured to a first constrained state, according to one embodiment. In one or more embodiments, FIG. 27B shows the staple 2601 and the staple installation tool 2600 in an insertion configuration. For example, the embodiment of the staple system shown in FIG. 27B is achieved by rotating the rod 5700 of the staple system embodiment shown in FIG. 27A to reduce the downward force applied to the base member 2705 of the staple 2601 and, thereby, configure the staple to a first constrained state. According to one embodiment, the first constrained state includes the staple 2601 deformed such that opposed leg portions 2701, 2703 of the staple 2601 are oriented substantially parallel. In some embodiments, the first constrained state includes the staple 2601 deformed such that a base member 2705 of the staple 2601 demonstrates minimal curvature along the bottom surface 2707 and/or top surface 2709.

In at least one embodiment, a rod 5700 of the attached staple installation tool 2600 is rotated in a second direction (e.g., opposite the first direction used to configure the second constrained state) to cause a pin 5705 to partially withdraw a downward force from the spacer 3200 and, thereby, reduce a downward force to the staple 2601. In some embodiments, a process for inserting the staple 2601 includes configuring the staple 2601 to the first constrained state prior to the staple system 2100 being provided to a user (for example, a surgeon). According to one embodiment, configuring the staple 2601 in the second constrained state aligns the leg portions 2701, 2703 with corresponding boreholes in a first bony structure and a second bony structure into which the staple 2601 may be inserted.

Figure 28:
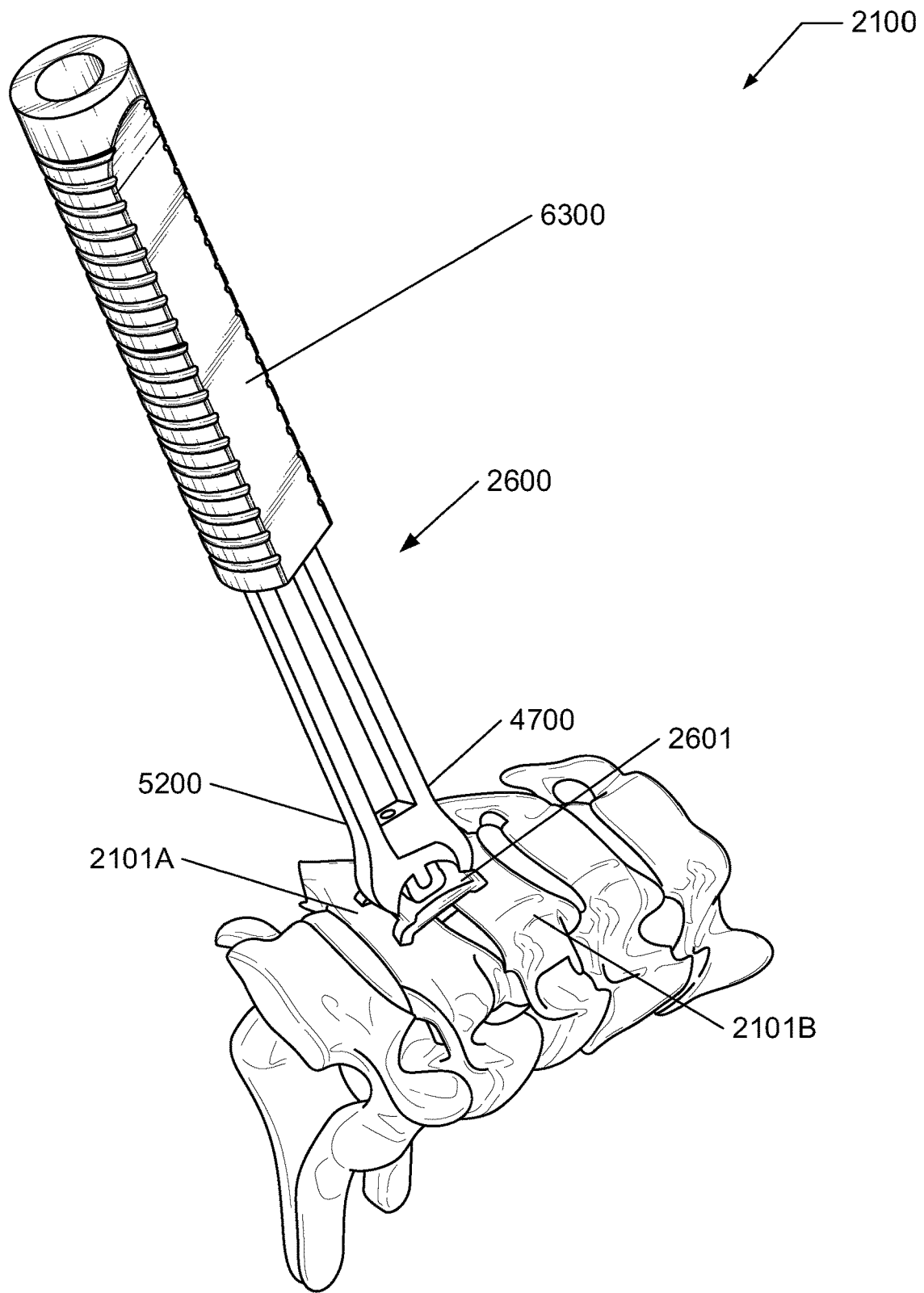
FIG. 28 shows the staple system according to one embodiment of the present disclosure.

FIG. 28 shows the staple system 2100, according to one embodiment of the present disclosure.

In at least one embodiment, FIG. 28 shows the staple installation tool 2600 following removal of the handle 6500 and the rod 5700, and during removal of the sleeve 6300. According to one embodiment, the handle 6500 rotates in the second direction such that the rod 5700 (e.g., or a pin 6100 connected thereto) disconnects from the first shaft 4700. In one or more embodiments, following disconnection of the rod 5700 from the shaft 4700, the handle 6500 and the rod 5700 (e.g., and the pin 1200) can be removed from the staple installation tool 2600. In various embodiments, the following removal of the handle 6500 the sleeve 6300 can be removed from the staple installation tool 2600. In at least one embodiment, removal of the rod 5700 removes a downward force applied to the spacer 3200 and, thereby, removes (or substantially reduces) a downward force applied to the staple 2601. In one or more embodiments, withdrawal of the downward force from the staple 2601 permits the staple 2601 to transition from the constrained state to an unconstrained state. In particular embodiments, the transition from the constrained state to an unconstrained state by removing the downward force from the staple 2601 can be referred to as engaging contraction. According to one embodiment, in the unconstrained state, opposed leg portions of the staple 2601 attempt to move toward each other (e.g., due to mechanical bias), thereby compressing the first bony structure 2101A and the second bony structure 2101B.

Figure 29:
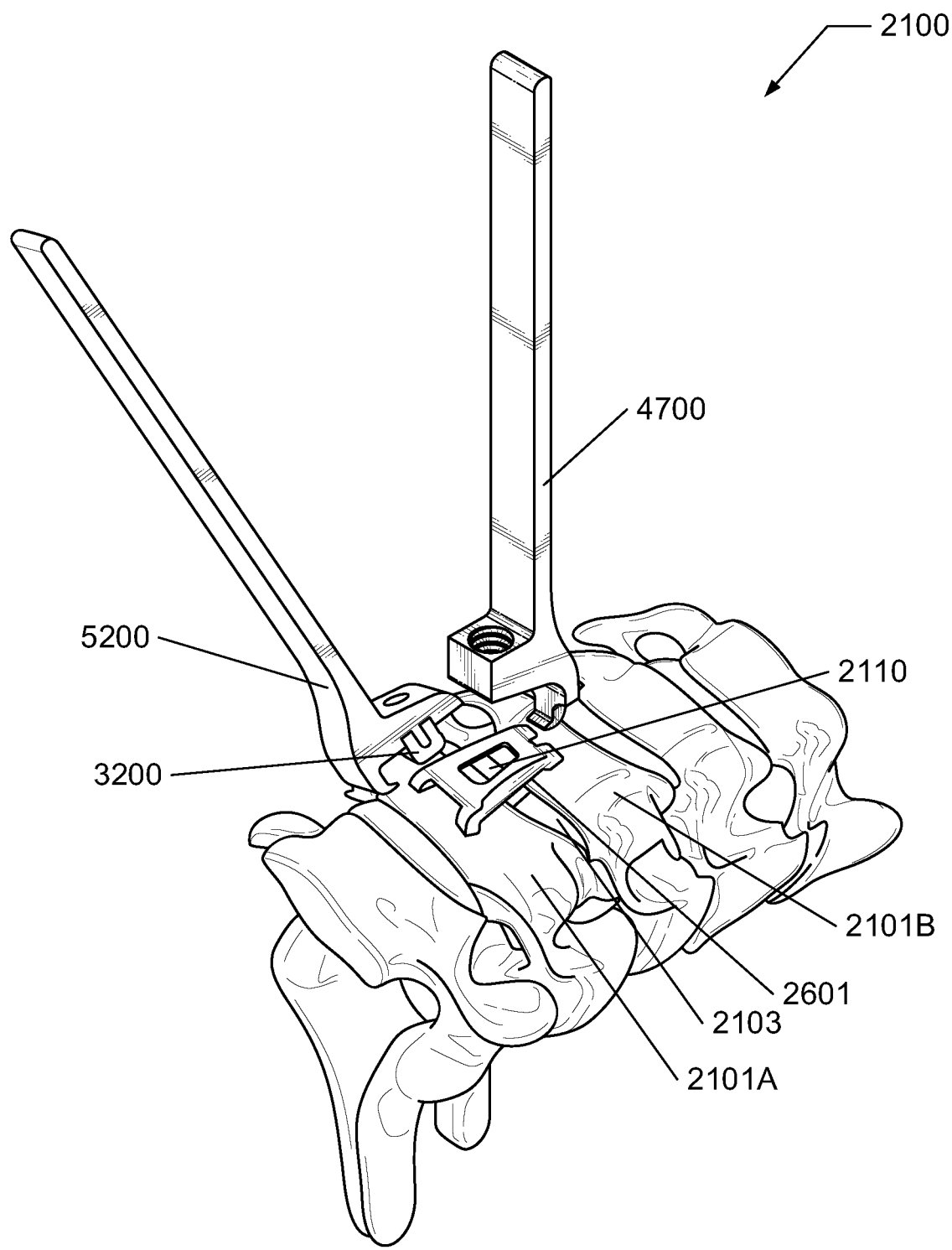
FIG. 29 shows the staple system according to one embodiment of the present disclosure.

FIG. 29 shows the staple system 2100, according to one embodiment of the present disclosure.

In one or more embodiments, FIG. 29 shows the staple installation tool 2600 following removal of the sleeve 6300. According to one embodiment, following removal of the sleeve 6300, the first shaft 4700 and the second shaft 5200 can detach from the staple 2601. In at least one embodiment, the spacer 3200 is removed from the staple 2601 (e.g., via removal of the second shaft 5200 or separate recovery of the spacer 3200). In one or more embodiments, the staple 2601 applies compressive forces to the first bony structure 2101A and the second bony structure 2101B, thereby promoting bony fusion toward and within the intervertebral space 2103. In one or more embodiments, the compressive forces of the staple 2601 cause the first and second bony structures 2101A-B to grow and fuse over the implant 2110.

Figure 30A:
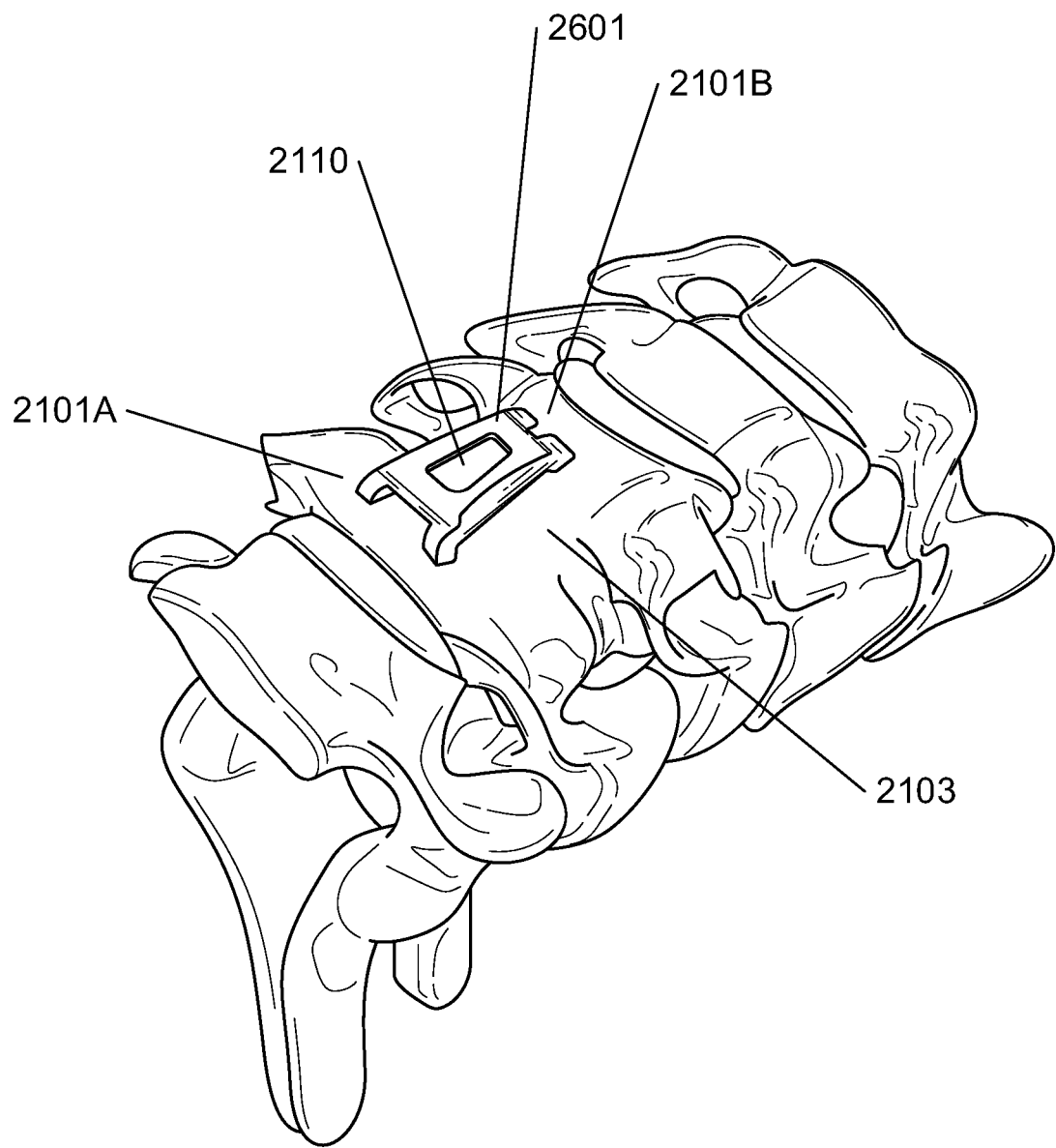
FIG. 30A shows an exemplary staple inserted into bony structures according to one embodiment of the present disclosure.

FIG. 30A shows the staple 2601, according to one embodiment of the present disclosure. In one or more embodiments, FIG. 30A shows the staple 2601 following fusion of the first bony structure 2101A and the second bony structure 2101B (e.g., over the implant 3100).

FIG. 30B shows an exemplary multi-staple system 3000, according to one embodiment of the present disclosure.

In one or more embodiments, the multi-staple system 3000 includes two or more staples for fusing three or more bony structures. In at least one embodiment, the multi-staple system 3000 includes a staple 2601A and a staple 2601B. The multi-staple system 3000 can include any suitable number of staples (e.g., 2, 3, 4, or any suitable quantity). In various embodiments, the staple 2601A compresses and, thereby, fuses the first bony structure 2101A and the second bony structure 2101B. In one or more embodiments, the staple 2601B compresses and fuses the second bony structure 2101B and a third bony structure 2101C. In various embodiments, the multi-staple system 3000 includes a spacer that is inserted to a space between each pair of bony structures to be compressed. In one or more embodiments, an implant 2110A is inserted into an intervertebral space 2103A between the first and second bony structures 2101A-B. In at least one embodiment, an implant 2110B is inserted into an intervertebral space 2103B between the second and third bony structures 2601B-C.

In one or more embodiments, the shape of the staples 2601A-B allows for improved packing efficiency and a reduced likelihood of staple contact occurring in response to movement of the bony structures 2101A-C. In various embodiments, the increased width of the staple 2601B toward the staple 2601A and the narrowed width of the staple 2601A toward the staple 2601B provides for a greater range of articulation between the staples 2601A-B before contact may occur. For example, the bony structures 2101A-C are vertebrae that form a portion of a spinal column. In this example, during straightening of the spinal column, the bony structures 2101A-C rotate and, thereby, shift the position of the staple 2601A relative to the position of the staple 2601B (e.g., the staple 2601A shifts toward the staple 2601B). Continuing the example, the tapered shape of the staple 2601A allows the staple 2601A to shift position toward the staple 2601B without contacting (e.g., or at least without significantly disturbing) the staple 2601B.

FIG. 30C shows an exemplary multi-staple system 3000, according to one embodiment. In at least one embodiment, the multi-staple system 3000 includes three or more staples 2601A-C. In one or more embodiments, the staple 2601C is inserted into the bony structure 2101A and an adjacent bony structure 2101D. In various embodiments, the staple 2601C aligns over an implant 3100 inserted into an intervertebral space 2103C between the bony structures 2101A, 2101D. In one or more embodiments, the nesting arrangement of the staples 2601A-C allows for improved packing efficiency and the generally trapezoidal shape of the staples 2601A-C provides a reduced likelihood of staple dislodging or misalignment occurring in response to movement of the bony structures 2601A-D. In some embodiments, intervertebral spaces that abut the same vertebra (e.g., or other bony structure) are referred to as adjacent intervertebral spaces. For example, in FIG. 30C the intervertebral space 2103A may be described as being adjacent to intervertebral spaces 2103B, 2103C.

FIG. 31A shows the staple 2601 configured to an unconstrained state, according to one embodiment. In one or more embodiments, FIG. 31A shows the staple 2601 and the staple installation tool 2600 in a removal configuration. In at least one embodiment, in the removal configuration, the staple installation tool 2600 is attached to the staple 2601 for purposes of removing the staple 2601 from a target site (e.g., two or more bony structures). For example, the embodiment of the staple system shown in FIG. 31B is achieved by attaching the staple installation tool 2600 to the staple 2601 such that the first shaft 4700 and the second shaft 5200 attach to opposing sides of the base member 2705 of the staple 2601, and such that the pin 5705 of the rod 5700 contacts the top surface 2709 of the base member 2705. The removal configuration can include attaching the staple installation tool 2600 to the staple 2601 such that the first shaft 4700 and the second shaft 5200 are attached to the staple 2601 and rotated to a substantially parallel position. In some embodiments, the substantially parallel position of the first shaft 4700 and the second shaft 5200 is referred to as a "mated" state. The removal configuration can include sliding a sleeve 6300 (not shown, see, for example, FIG. 26) over the first shaft 4700 and the second shaft 5200 to maintain the substantially parallel position. The removal configuration can include inserting the rod 5700 (e.g., or the pin 5705 attached to the rod 5700) through the first shaft 4700 and the second shaft 5200, and can include securing a handle 6500 (not shown, see, for example, FIG. 26) to the rod 5700 to prevent movement of the rod 5700. In at least one embodiment, the removal configuration includes rotating the rod 5700 (e.g., or a handle 6500 connected thereto) in a first direction such that a threaded connection between the rod 5700 (e.g., or pin 5705) and the first shaft 4700 are engaged. According to one embodiment, the engaging of the threaded connection at the first shaft 4700 applies a force to the second shaft 5200, thereby causing the second shaft 5200 to apply a downward force to the staple 2601. In at least one embodiment, the downward force of the second shaft 5200 and the upward forces of the second shaft 5200 and the first shaft 4700 secure the staple installation tool to the staple 2601.

FIG. 31B shows the staple 2601 configured to a first constrained state, according to one embodiment. In one or more embodiments, FIG. 31B shows the staple 2601 and the staple installation tool 2600 in a second removal configuration. According to one embodiment, in the second removal configuration, the staple installation tool 2600 is adjusted such that the staple installation tool 2600 applies an increased downward force to the base member 2705 and, thereby, deforms the staple 2601 to the first constrained position. In at least one embodiment, in the first constrained position, the leg portions 2701, 2703 are deformed, via bending of the base member 2705, to a substantially parallel orientation. In one or more embodiments, the substantially parallel orientation of the leg portions 2701, 2703 allows the staple 2601 to decouple from the boreholes such that the staple 2601 can be extracted from boreholes at the target site (for example, boreholes 2501A-B, 2503A-B shown in FIG. 25).

In one example, the embodiment of the staple system shown in FIG. 31B is achieved by attaching the staple installation tool 2600 to the staple 2601 such that the first shaft 4700 and the second shaft 5200 attach to opposing sides of the base member 2705 of the staple 2601, and such that the pin 5705 of the rod 5700 contacts the top surface 2709 of the base member 2705. In the same example, the rod 5700 is rotated in a first direction to increase a force applied by the pin 5705 to the top surface 2709 and, thereby, cause the staple 2601 to deform such that the leg portions 2701, 2703 are substantially parallel.

Exemplary Staple Instruments

Figure 32:
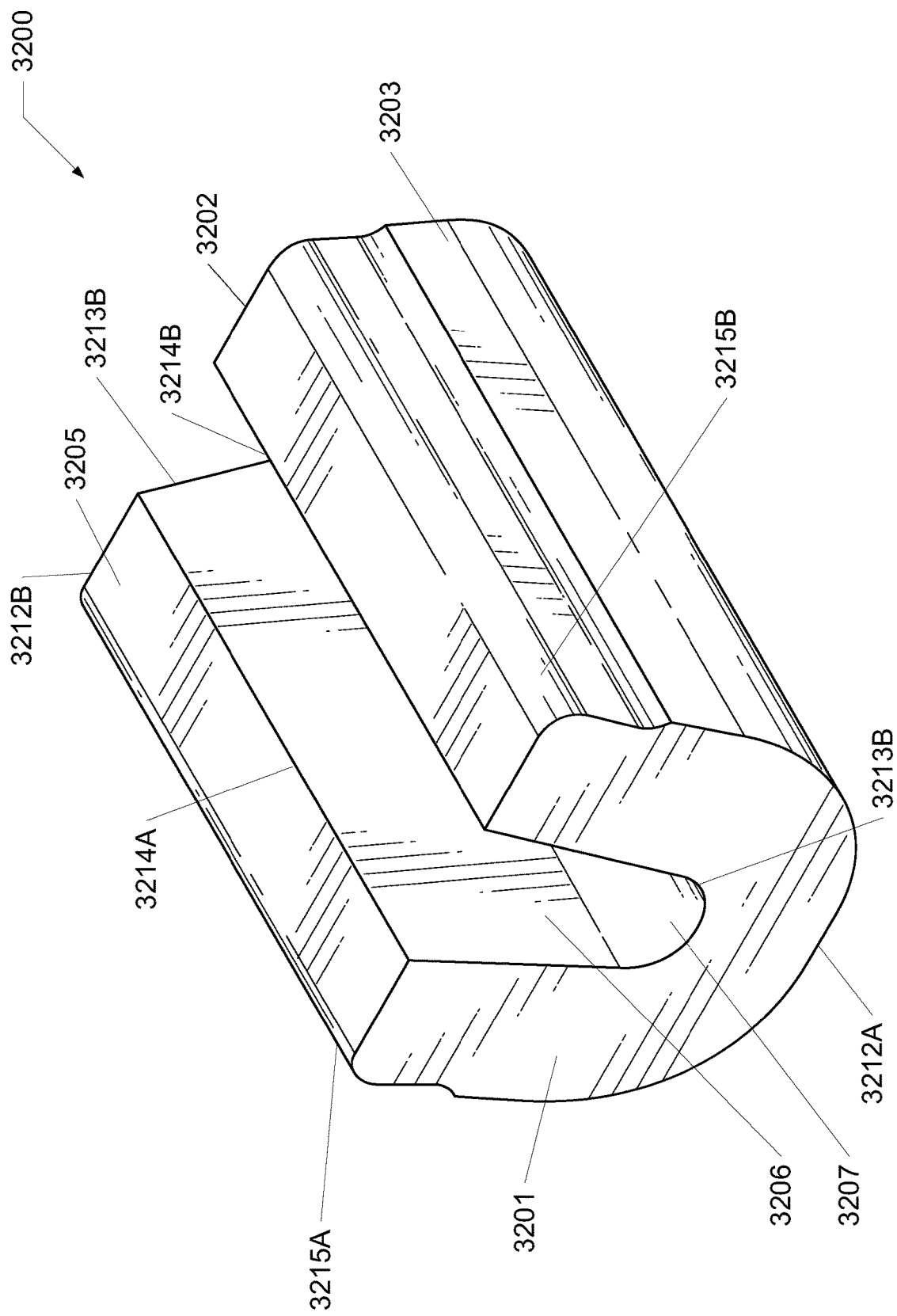
FIG. 32 shows a perspective view of an exemplary spacer according to one embodiment of the present disclosure.

FIG. 32 shows a perspective view of a spacer 3200, according to one embodiment of the present disclosure. In various embodiments, the spacer 3200 is configured to apply a pushing force to staples described herein. For example, while attached to the second shaft 5200, the spacer 3200 receives a pushing force from a rod 5700 and the spacer 3200 translates the pushing force to a staple to which the second shaft 5200 and a first shaft 4700 are attached. In this example, the pushing force of the spacer 3200 and pulling forces generated by the attached shafts 4700, 5200 cause the staple to deform to a constrained state.

Figure 52:
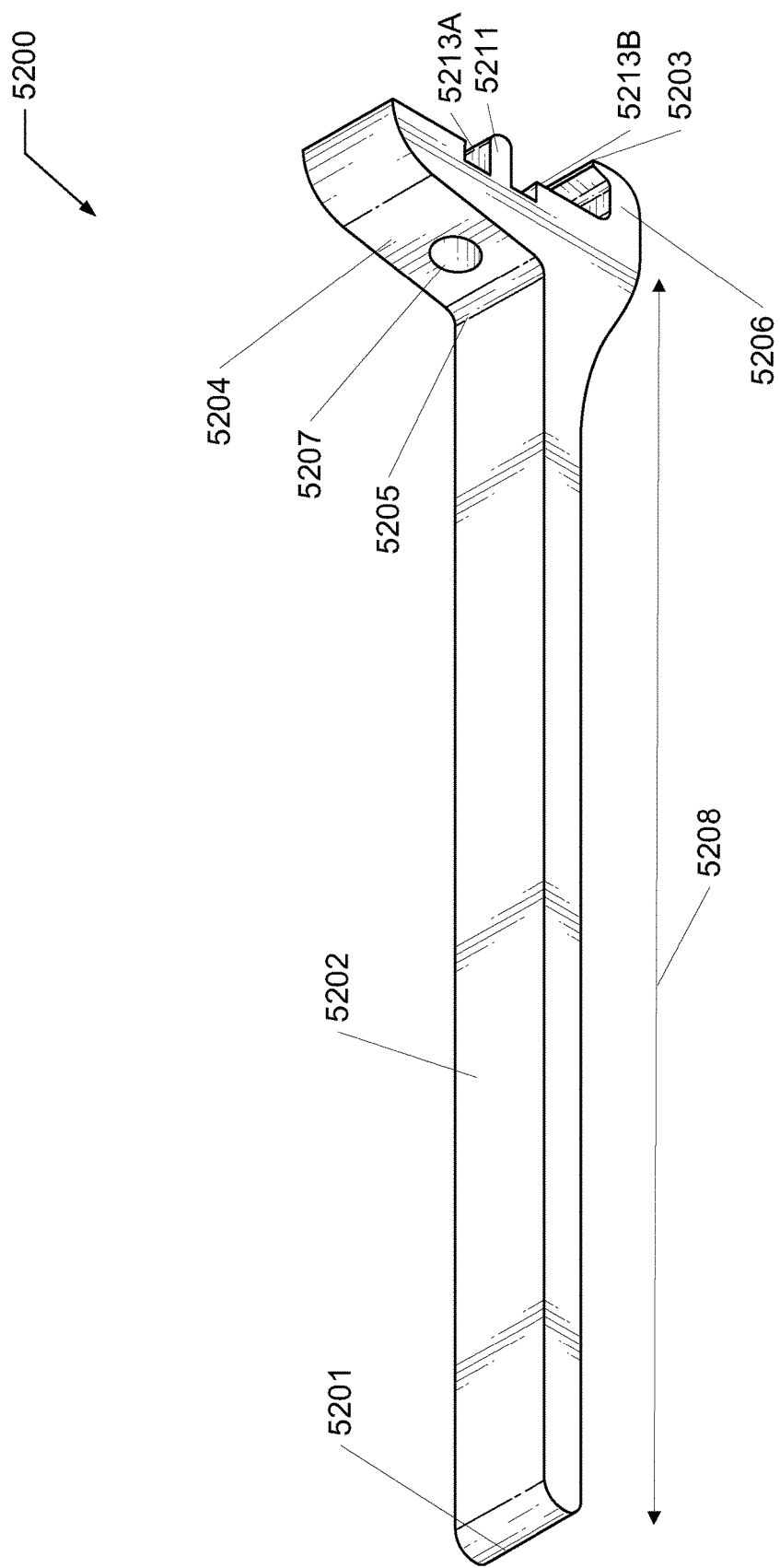
FIG. 52 shows a perspective view of an exemplary second shaft according to one embodiment of the present disclosure.

In particular embodiments, the spacer 3200 includes a front surface 3201 and a back surface 3202. In one or more embodiments, the spacer 3200 includes a top surface 3205 and an interior surface 3206. In various embodiments, the spacer 3200 includes a side surface 3203 that transitions between the top surface 3205 and a bottom surface 3400 (see FIG. 34). In one or more embodiments, the interior surface 3206 demonstrates a concave shape. In at least one embodiment, the interior surface 3206 is shaped to conform to a footprint of a prong 5211 of the second shaft 5200 (FIG. 52). In various embodiments, the interior surface 3206 defines a channel 3207 for receiving one or more prongs.

In at least one embodiment, the front surface 3201 is bounded by edges 3212A, 3213A, and the back surface 3202 is bounded by edges 3212B, 3213B. In various embodiments, the side surface 3203 is bounded by edges 3211A, 3211B and by edges 3215A, 3215B. In one or more embodiments, the edges 3215A, 3125B are curved and substantially non-breaking, and transition the side surface 3203 to the top surface 3205.

According to one embodiment, the interior surface 3206 is bounded by edges 3213A-B and by edges 3214A, 3214B. In various embodiments, the top surface 3205 is bounded by the edges 3215A-B, 3212A-B, and 3214A-B. In one or more embodiments, the one or more of the edges 3215A-B, 3212A-B, and 3214A-B demonstrate substantially non-breaking curvature for transitioning between corresponding surfaces of the spacer 3200.

Figure 33A:
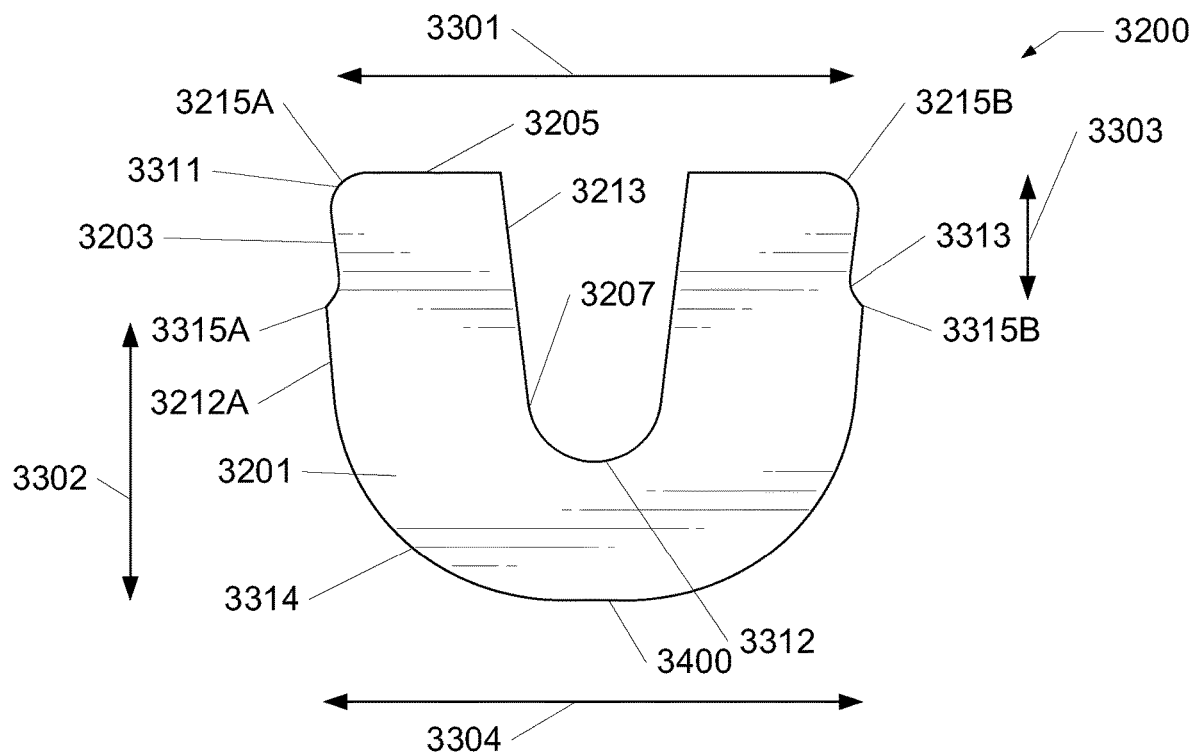
FIG. 33A shows a front view of an exemplary spacer according to one embodiment of the present disclosure.

FIG. 33A shows a front view of spacer 3200, according to one embodiment of the present disclosure. In one or more embodiments, the spacer 3200 includes radii 3311 for transitioning the top surface 3205 to the side surface 3203. In at least one embodiment, the radii 3311 measure at least about 0.3 mm, or about 0.3-0.5 mm, 0.3-0.4 mm, 0.4 mm, 0.4-0.5 mm, or less than about 0.5 mm. In various embodiments, the channel 3207 includes a radius 3312 that measures at least about 0.65 mm, or about 0.65-0.85 mm, 0.65-0.75 mm, 0.75 mm, 0.75-0.85 mm, or less than about 0.85 mm.

In one or more embodiments, the side surface 3203 includes radii 3313 that transition the spacer 3200 between a first depth 3301 and a second depth 3304. In at least one embodiment, the radii 3313 measure at least about 1.5 mm, or about 1.5-3.5 mm, 1.5-2.5 mm, 2.5 mm, 2.5-3.5 mm, or less than about 3.5 mm. In various embodiments, the first depth 3301 extends between edges 3215A-B and measures at least about 4.0 mm, 4.0-8.0 mm, 4.0-6.0 mm, 6.0 mm, 6.0-8.0 mm, or less than about 8.0 mm. In one or more embodiments, the second depth 3304 extends between radial points 3315A-B and measures at least about 2.0 mm, or about 2.0-10.0 mm, 2.0-3.0 mm, 3.0-4.0 mm, 4.0-5.0 mm, 5.0-6.0 mm, 6.0 mm, 6.0-7.0 mm, 7.0-8.0 mm, 8.0-9.0 mm, 9.0-10.0 mm, or less than about 10.0 mm. In at least one embodiment, the first depth 3301 and/or the second depth 3304 taper toward the bottom surface 3400. In one or more embodiments, the side surface 3203 includes radii 3314 that transition the side surface 3203 to the bottom surface 3400. In at least one embodiment, the radii 3314 measure at least about 1.5 mm, or about 1.5-3.5 mm, 1.5-2.5 mm, 2.5 mm, 2.5-3.5 mm, or less than about 3.5 mm.

Figure 33B:
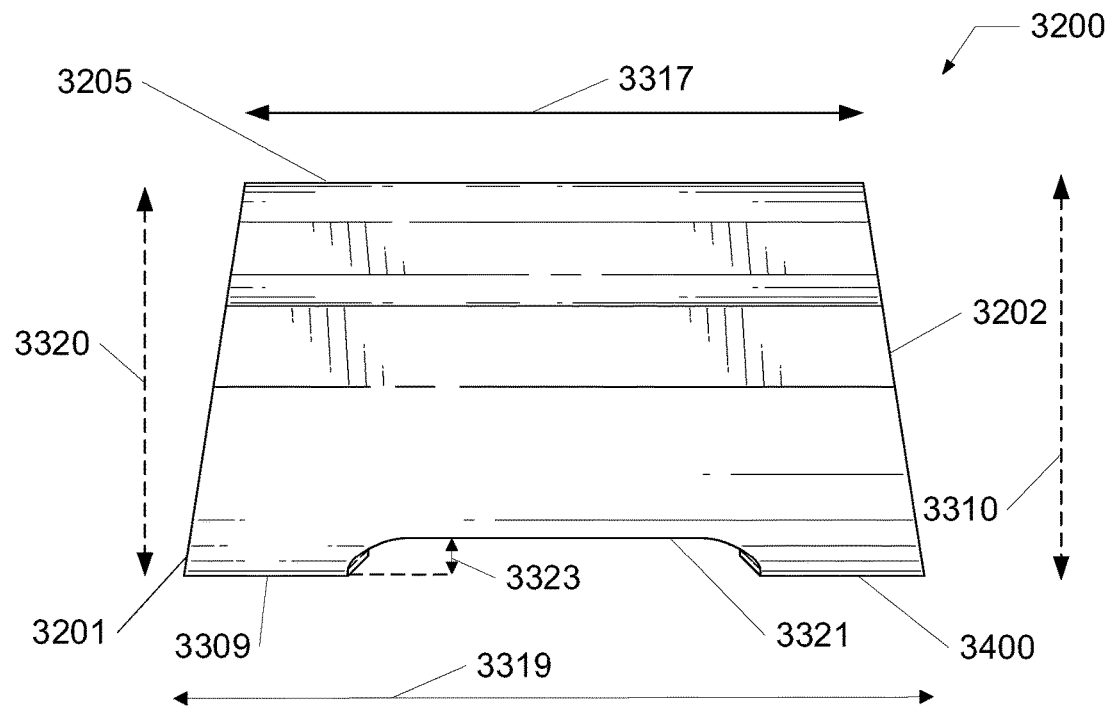
FIG. 33B shows a side view of an exemplary spacer according to one embodiment of the present disclosure.

In particular embodiments, a separation distance 3302 measures a distance between the radial points 3315A-B and the bottom surface 3400. In various embodiments, the separation distance 3302 measures at least about 2.0 mm, or about 2.0-4.0 mm, 2.0-3.0 mm, 2.9 mm, 3.1 mm, 3.3 mm, or about 3.0-4.0 mm, or less than about 4.0 mm. In various embodiments, a separation distance 3303 measures a distance between radial points 3315A-B and the top surface 3205. According to one embodiment, the separation distance 3303 measures at least about 1.0 mm, or about 1.5 mm, 1.0-3.0 mm, or less than about 3.0 mm. In at least one embodiment, separation distances 3302, FIG. 33B shows a side view of spacer 3200, according to one embodiment of the present disclosure. In at least one embodiment, the front surface 3201 and back surface 3202 are nonparallel to each other and nonparallel to a vertical axis 3310 (e.g., oriented perpendicular to the top surface 3205 and the bottom surface 3400). In one or more embodiments, the spacer 3200 includes a length 3317 along the top surface 3205. In at least one embodiment, the length 3317 measures at least about 7.0 mm, or about 7.5 mm, 7.0-8.0 mm, or less than about 8.0 mm. In various embodiments, the spacer 3200 includes a second length 3319 along the bottom surface 3400. In at least one embodiment, the length 3319 measures at least about 8.0 mm, 9.0 mm, or about 8.0-10.0 mm, or less than about 10.0 mm. According to one embodiment, the nonparallel orientation of the front surface 3201 and the back surface 3202 transitions (e.g., tapers) the spacer 3200 between the first length 3317 and the second length 3319. In one or more embodiments, the spacer 3200 includes a height 3320 between the top surface 3205 and the bottom surface 3400. In various embodiments, the height 3320 measures at least about 2.0 mm, or about 2.0-10.0 mm, 2.0-3.0 mm, 3.0-4.0 mm, 4.0-5.0 mm, 4.8 mm, 5.0-6.0 mm, 6.0-7.0 mm, 7.0-8.0 mm, 8.0-9.0 mm, or 9.0-10.0 mm, or less than about 10.0 mm.

In at least one embodiment, the spacer 3200 includes an indention 3321 that extends from the bottom surface 3400 into the spacer 3200. In one or more embodiments, the indentation 3321 includes a depth 3323 between the bottom surface 3400 and a surface 3401 of the indentation 3321 (see FIG. 34). In at least one embodiment, the depth measures at least about 0.25 mm, or about 0.25-0.75 mm, 0.25-0.5 mm, 0.5 mm, 0.5-0.75 mm, or less than about 0.75 mm.

Figure 34:
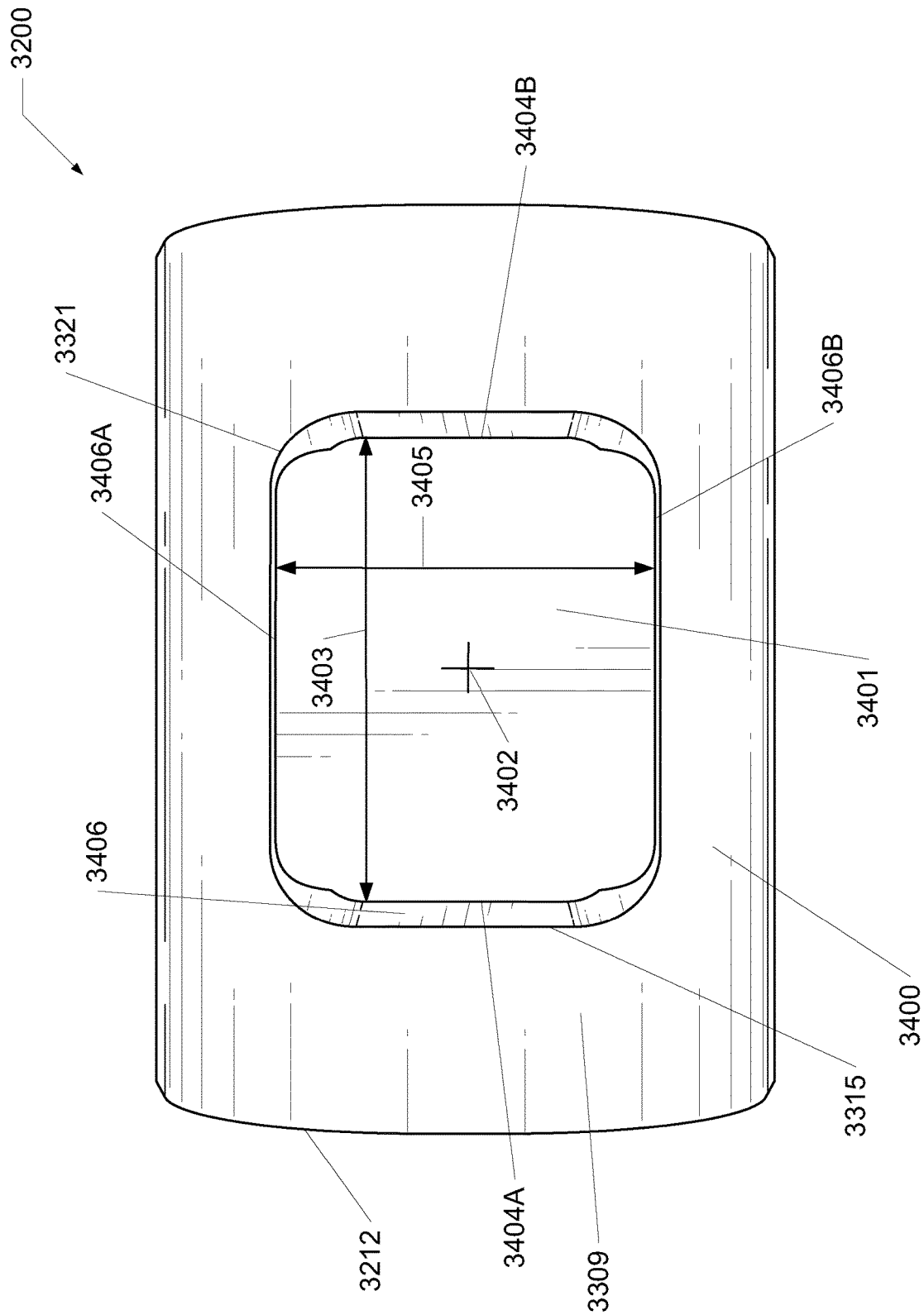
FIG. 34 shows a bottom view of an exemplary spacer according to one embodiment of the present disclosure.

FIG. 34 shows a bottom view of the spacer 3200, according to one embodiment of the present disclosure. In various embodiments, the spacer 3200 includes a center point 3402 and an indentation 3321 centered about the center point 3402. In various embodiments, the indentation 3321 includes a generally rectangular shape, or includes any suitable shape or shape combination (e.g., circular, rectangular, triangular, obround, and other shapes). In one or more embodiments, the indentation 3321 includes a length 3403 between inner edges 3404A, 3404B. In at least one embodiment, the length 3403 measures at least about 2.5 mm, or about 2.5-6.5 mm, 2.5-4.5 mm, 4.5 mm, 4.5-6.5 mm, or less than about 6.5 mm. In various embodiments, the indentation 3321 includes a width 3405 between edges 3406A, 3406B. According to one embodiment, the width 3405 measures at least about 1.0 mm, or about 1.0-3.0 mm, 1.0-1.5 mm, 1.5-2.0 mm, 1.8 mm, 2.0-2.5 mm, 2.5-3.0 mm, or less than about 3.0 mm. In at least one embodiment, the indentation 3321 includes an inner surface 3407 between the edges 3404A-B, 3406A-B and an edge 3408. In one or more embodiments, the inner surface 3407 defines a chamfer, curvature, or bevel for transitioning the bottom surface 3400 to the surface 3401 of the indentation 3321.

In one or more embodiments, the indentation 3321 is configured to receive a portion of a staple during deformation of the staple and, thereby, prevent movement of warped staple material into undesirable regions, such as, for example, a target site or an aperture of the staple. In at least one embodiment, the indentation 3321 reduces a likelihood that deformation of the staple causes undesirable warping of staple structures by allowing movement of warped staple material into the spacer 3200.

Figure 35:
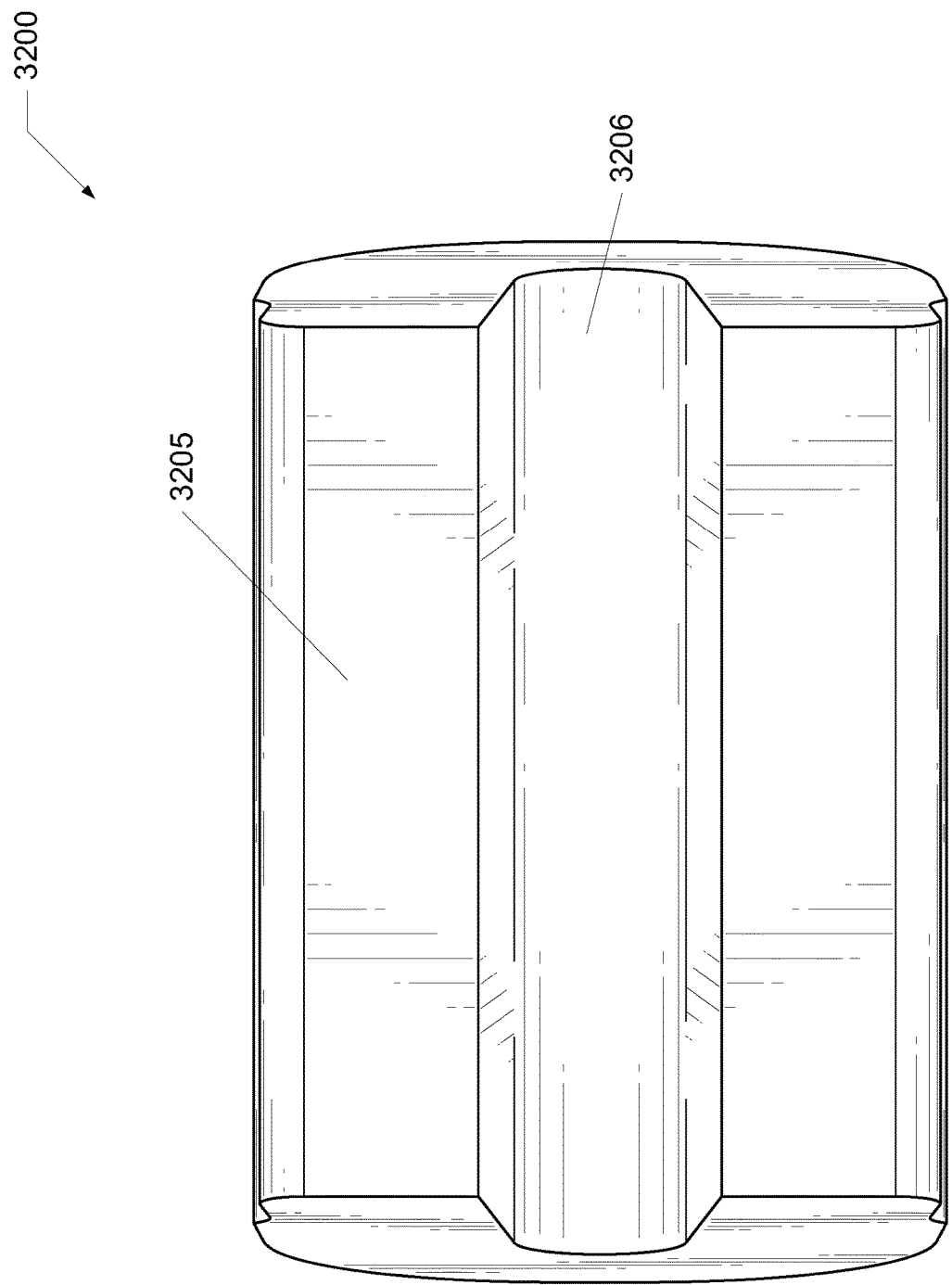
FIG. 35 shows a top view of an exemplary spacer according to one embodiment of the present disclosure.

FIG. 35 shows a top view of the spacer 3200, according to one embodiment of the present disclosure. In some embodiments, the indentation 3321 (see FIG. 34) includes an aperture that extends through the top surface 3205.

Figure 36:
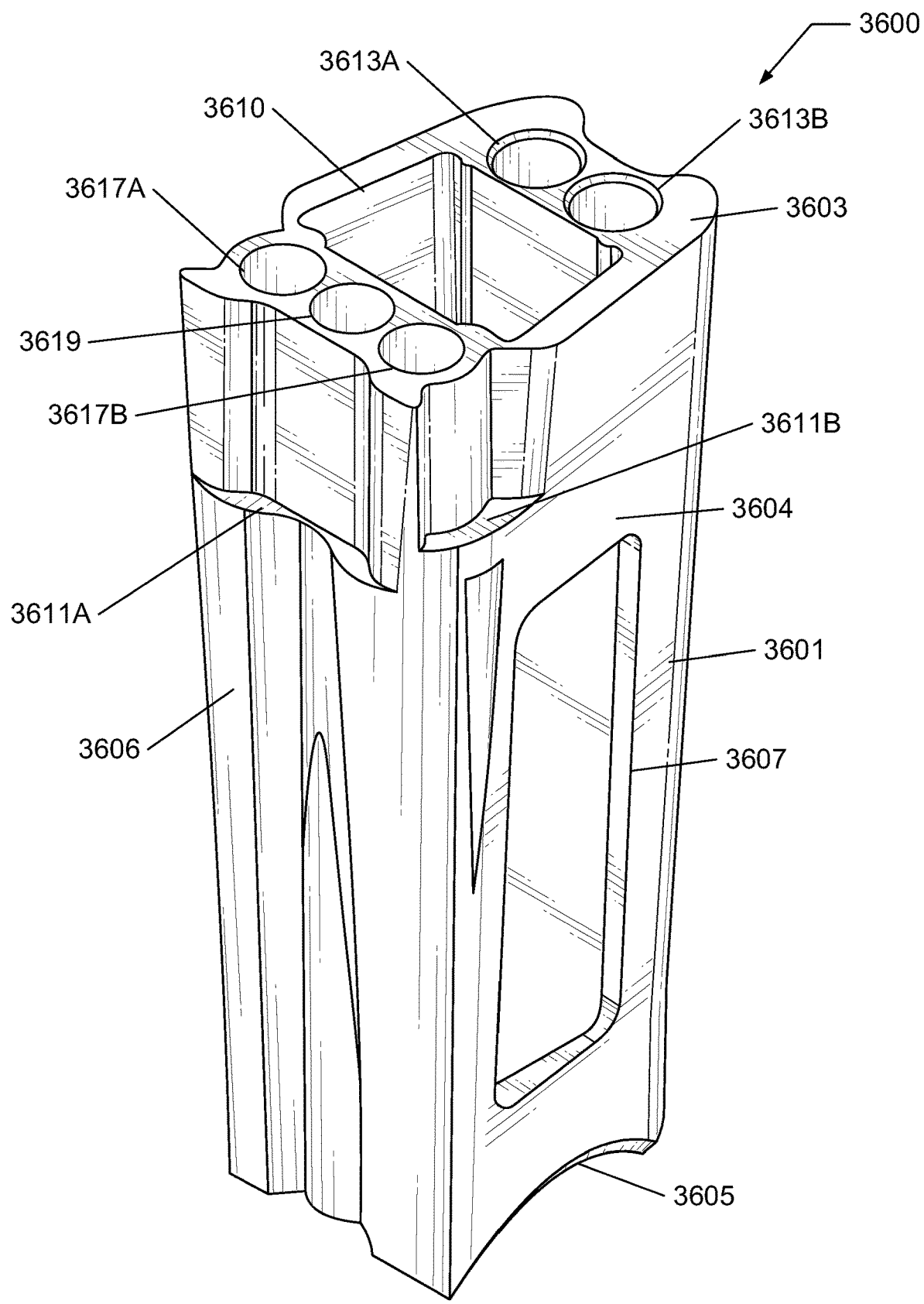
FIG. 36 shows a perspective view of an exemplary boring apparatus according to one embodiment of the present disclosure.

FIG. 36 shows a perspective view of an exemplary boring apparatus 3600, according to one embodiment of the present disclosure. In various embodiments, the boring apparatus 3600 includes a body 3601 that includes a top surface 3603 and a bottom surface 3605. In one or more embodiments, the body 3601 includes a generally rectangular prism- or trapezoidal prism-derived shape. In at least one embodiment, the body 3601 includes a side 3604 spaced from an opposed side (not shown), and the body 3601 includes a side 3606 spaced from a second opposed side (not shown). In various embodiments, the side 3604 connects to the side 3606 and the second opposed side, and the side 3606 connects to the side 3604 and the opposed side. In one or more embodiments, the side 3604 is generally perpendicular to the side 3606.

Figure 43:
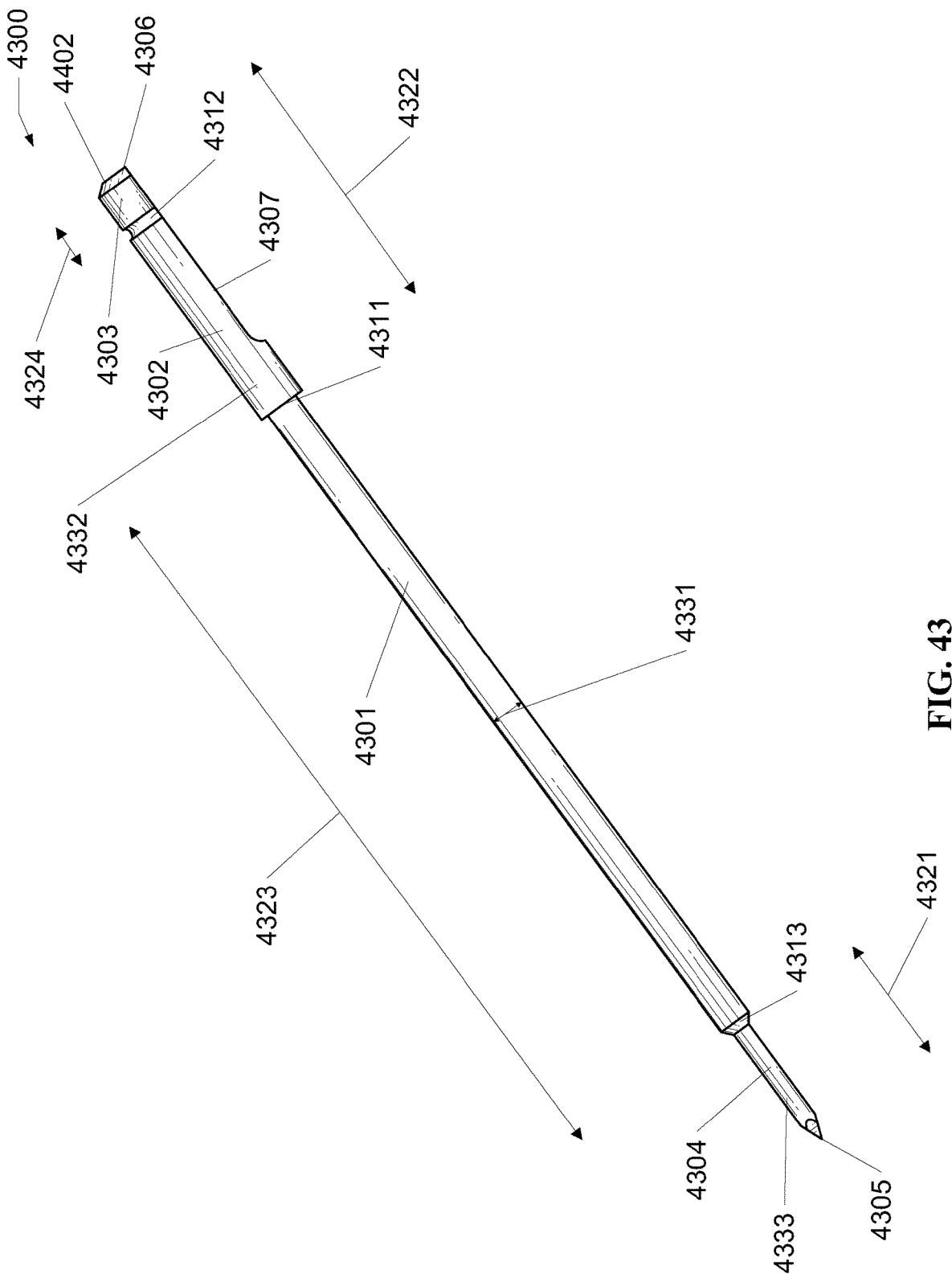
FIG. 43 shows a side view of an exemplary target pin according to one embodiment of the present disclosure.

In various embodiments, the side 3604 includes an aperture 3607 that extends into an opening 3608 of the body 3601. In one or more embodiments, the side opposed to the side 3604 includes an aperture substantially similar to the aperture 3607. In particular embodiments, the aperture 3607 can be referred to as a side aperture. In one or more embodiments, the top surface 3603 includes an aperture 3610 that extends into the opening 3608 and through the bottom surface 3605. According to one embodiment, the aperture 3610 and the aperture 3607 allow observation of a spacer (e.g., a spacer 3200) during alignment of the boring apparatus 3600 to a target site. In various embodiments, the top surface 3603 includes apertures 3613A-B, 3617A-B, and 3619 that extend through the body 3601 and the bottom surface 3605. In particular embodiments, the apertures 3613A-B and 3617A-B can be referred to as boring apertures. In some embodiments, the aperture 3619 can be referred to as an affixing aperture. In one or more embodiments, the apertures 3613A-B and 3617A-B are each configured to receive a drill pin 4500 (FIG. 45) and the aperture 3619 is configured to receive a targeting pin 4300 (FIG. 43).

Figure 39:
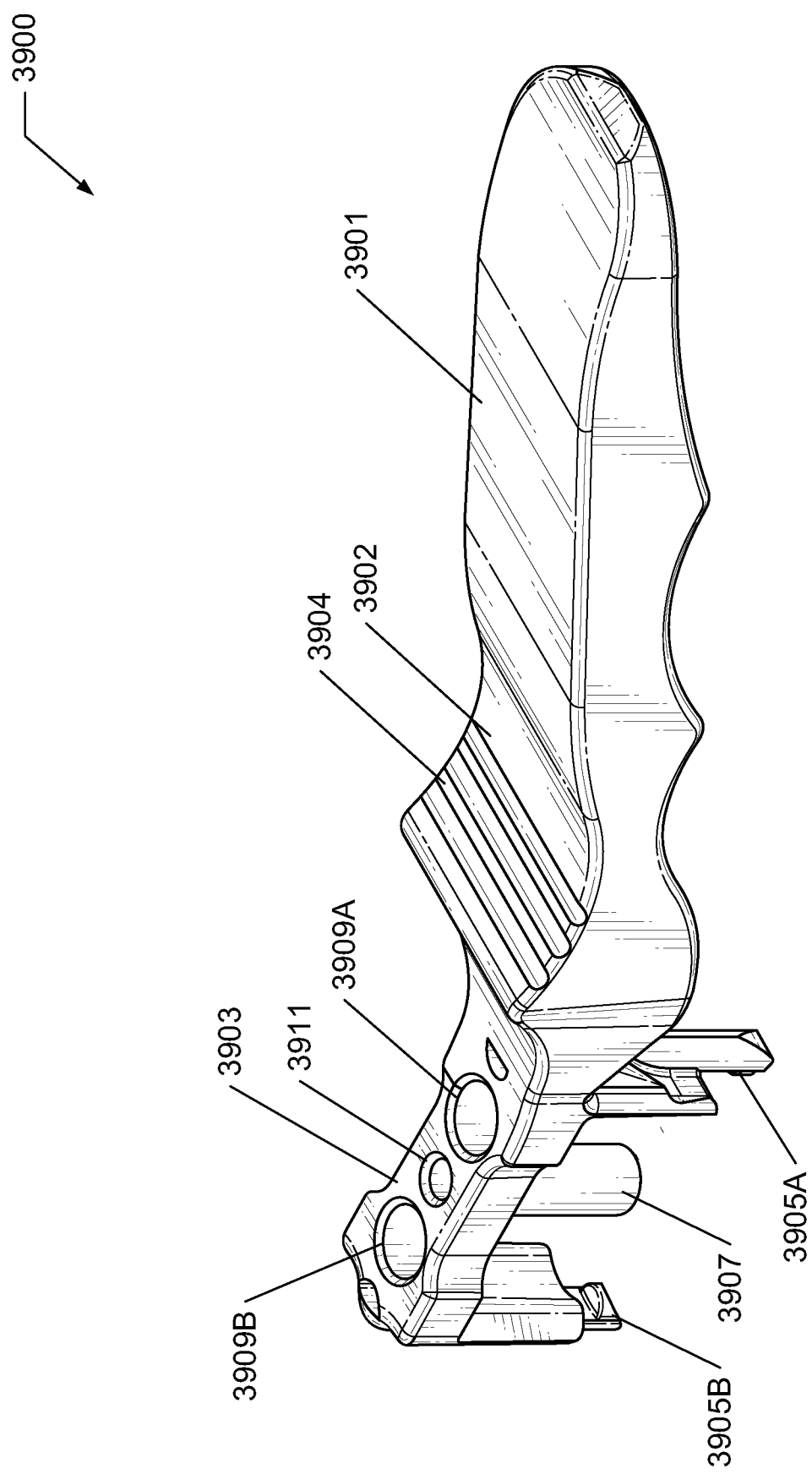
FIG. 39 shows an exemplary handle according to one embodiment of the present disclosure.

In various embodiments, the body 3601 includes a top portion 3609 that receives a handle 3900 (FIG. 39). In particular embodiments the handle 3900 can be referred to as a removable handle. In at least one embodiment, the top portion 3609 includes indentations 3611A-B (e.g., and another indentation on the opposed side not shown) for aligning the handle 3900 onto the boring apparatus 3600. According to one embodiment, a shape of the top portion 3609 generally matches a footprint of the handle 3900 (e.g., in particular, a footprint of the insert 3903 shown in FIG. 39). In various embodiments, the apertures 3617A-B and the apertures 3619 extend through the top portion 3609.

Figure 37:
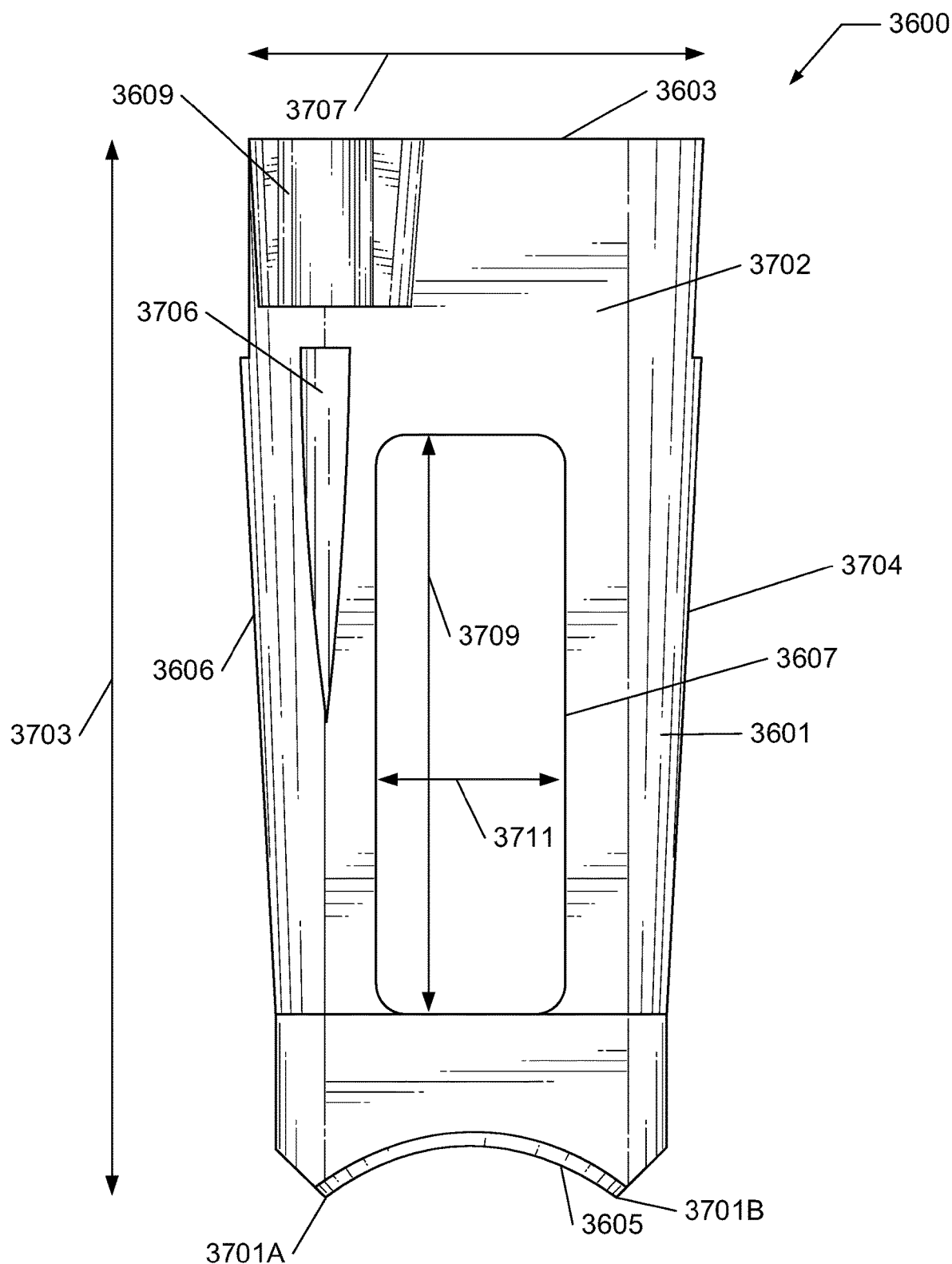
FIG. 37 shows a side view of an exemplary boring apparatus according to one embodiment of the present disclosure.

FIG. 37 shows a side view of the boring apparatus 3600, according to one embodiment of the present disclosure. In at least one embodiment, the body 3601 includes a side 3702 opposite the side 3604. In one or more embodiments, at the bottom surface 3605, the body 3601 includes corners 3701A, 3701B. According to one embodiment, the body 3601 includes corresponding corners on the opposing side 3604. In one or more embodiments, the corners 3701A, 3701B contact a target surface and stabilize a position of the boring apparatus 3600. In various embodiments, the side 3702 and the side 3604 each include a channel 3706 for receiving an arm 3905A, 3905B of the handle 3900 (see FIG. 39). In at least one embodiment, each channel 3706 provides a snap-fit connection between the arms 3905A-B and the top portion 3609. The side 3702, 3604, 3606, or 3704 can include any suitable number of channels 3706 for receiving prongs (e.g., or other connecting features) of the handle 3900.

In various embodiments, the boring apparatus 3600 includes a length 3703 between the top surface 3603 and the corner 3701A. In one or more embodiments, the length 3703 measures at least about 50 mm, or about 50-100 mm, 50-60 mm, 60-70 mm, 73 mm, 70-80 mm, 80-90 mm, 90-100 mm, or less than about 100 mm. In at least one embodiment, the boring apparatus 3600 includes a width 3707 between the side 3606 and an opposed side 3704. In various embodiments, the width 3707 tapers between the top surface 3603 and the bottom surface 3605. In one or more embodiments, the width 36707 measures at least about 20 mm, about 20-50 mm, 20-30 mm, 30-40 mm, 40-50 mm, or less than about 50 mm.

In at least one embodiment, the aperture 3607 includes a length 3709 that measures at least about 30 mm, or about 30-70 mm, 30-40 mm, 40-50 mm, 50-60 mm, 60-70 mm, or less than about 70 mm. In various embodiments, the aperture 3607 includes a depth 3711 that measures at least about 10 mm, or about 10-60 mm, 10-20 mm, 20-30 mm, 30-40 mm, 40-50 mm, 50-60 mm, or less than about 60 mm.

Figure 38:
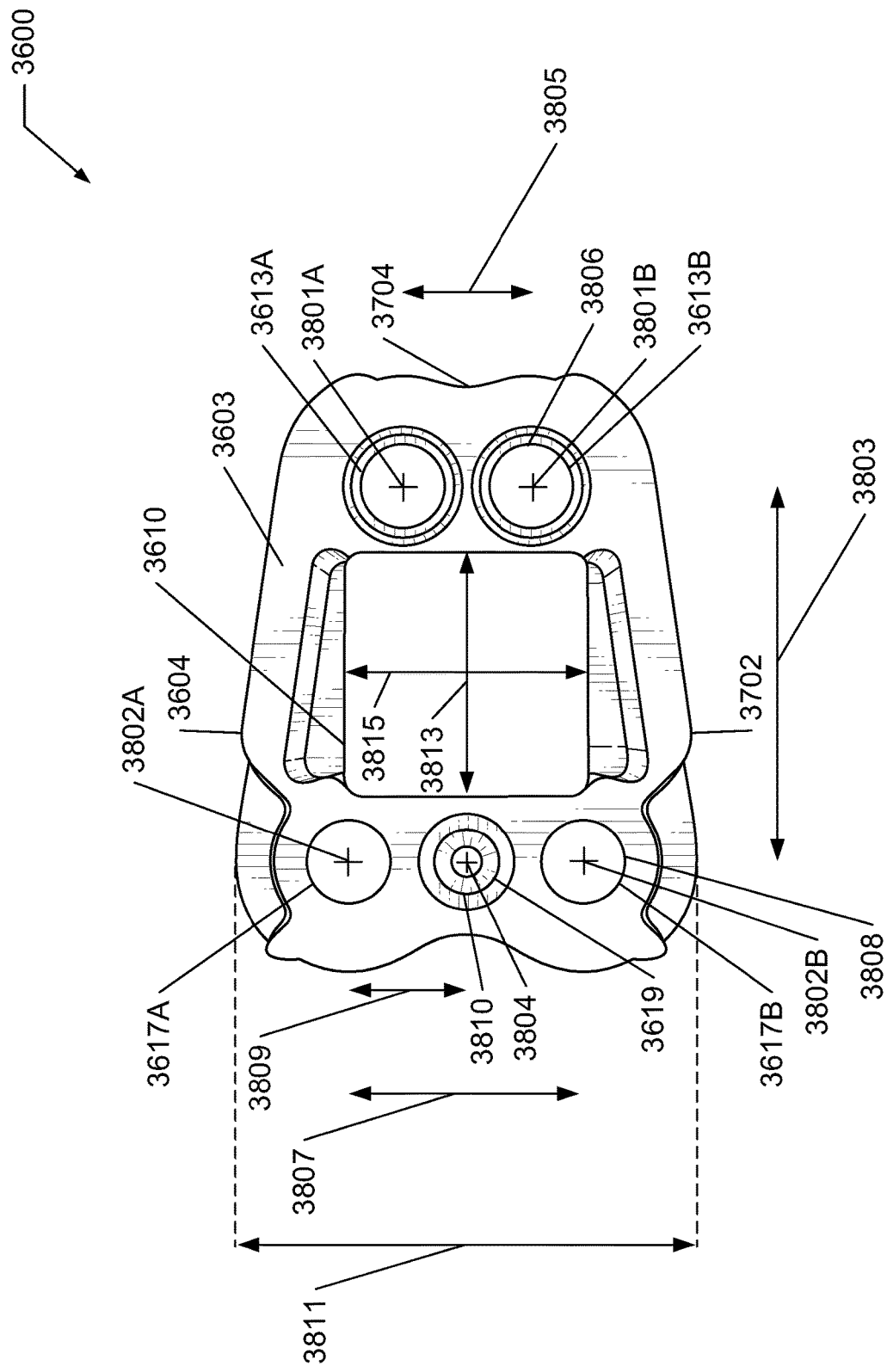
FIG. 38 shows a top view of an exemplary boring apparatus according to one embodiment of the present disclosure.

FIG. 38 shows a top view of the boring apparatus 3600, according to one embodiment of the present disclosure. In one or more embodiments, the apertures 3613A-B include center points 3801A-B, the apertures 3617A-B include center points 3802A-B, and the aperture 3619 includes a center point 3804. In various embodiments, a distance 3803 between the center points 3801A-B and the center points 3802A-B, 3804 measures at least about 5 mm, or about 5-30 mm, 5-10 mm, 12 mm, 14 mm, 10-15 mm, 16 mm, 18 mm, 15-20 mm, 20 mm, 20-25 mm, or 25-30 mm, or less than about 30 mm. In at least one embodiment, a distance 3805 between the center point 3801A and the center point 3801B measures at least about 3.0 mm, or about 3.0-10.0 mm, 3.0-4.0 mm, 4.0-5.0 mm, 5.0-6.0 mm, 6.8 mm, 6.0-7.0 mm, 7.0-8.0 mm, 8.0-9.0 mm, or 9.0-10.0 mm, or less than about 10.0 mm. In various embodiments, a distance 3807 between the center point 3802A and the center point 3802B measures at least about 4.0 mm, or about 4.0-20.0 mm, 4.0-6.0 mm, 6.0-8.0 mm, 8.0-10.0 mm, 10.0-12.0 mm, 12.5 mm, 12.0-14.0 mm, 14.0-16.0 mm, 16.0-18.0 mm, or 18.0-20.0 mm, or less than about 20.0 mm. In one or more embodiments, the center point 3804 is centrally located between the center points 3802A-B. In at least one embodiment, a distance 3809 between the center point 3802A (e.g., or center point 3802B) and the center point 3804 measures at least about 1.0 mm, or about 1.0-6.0 mm, 1.0-2.0 mm, 2.0-3.0 mm, 3.0-4.0 mm, 4.0-5.0 mm, or 5.0-6.0 mm, or less than about 6.0 mm.

In various embodiments, the apertures 3613A-B each include a diameter 3806 that measures at least about 2.0 mm, or about 2.0-10.0 mm, or 2.0-4.0 mm, 4.0-6.0 mm, 5.16 mm, 6.0-8.0 mm, or 8.0-10.0 mm, or less than about 10.0 mm. In one or more embodiments, the apertures 3617A-B each include a diameter 3808 that measures at least about 2.0 mm, or about 2.0-10.0 mm, or 2.0-4.0 mm, 4.0-6.0 mm, 5.16 mm, 6.0-8.0 mm, or 8.0-10.0 mm, or less than about 10.0 mm. In at least one embodiment, the aperture 3619 includes a diameter 3810 that measures at least about 2.0 mm, or about 2.0-10.0 mm, or 2.0-4.0 mm, 4.0-6.0 mm, 4.46 mm, 6.0-8.0 mm, or 8.0-10.0 mm, or less than about 10.0 mm.

In one or more embodiments, the boring apparatus 3600 includes a distance 3811 between opposed sides 3604, 3702. In at least one embodiment, the depth 3811 tapers toward the side 3704. In various embodiments, the distance 3811 measures at least about 10 mm, or about 10-30 mm, 10-15 mm, 13 mm, 15-20 mm, 20-25 mm, 25 mm, or 25-30 mm, or less than about 30 mm. In one or more embodiments, the aperture 3610 includes a width 3815 that measures at least about 6.0 mm, or about 6.0-18.0 mm, 6.0-8.0 mm, 8.0-10.0 mm, 10.0-12.0 mm, 12.0-14.0 mm, 13.0 mm, 14.0-16.0 mm, or 16.0-18.0 mm, or less than about 18.0 mm. In various embodiments, the aperture 3610 includes a width 3815 that measures at least about 6.0 mm, or about 6.0-18.0 mm, 6.0-8.0 mm, 8.0-10.0 mm, 10.0-12.0 mm, 12.0-14.0 mm, 13.0 mm, 14.0-16.0 mm, or 16.0-18.0 mm, or less than about 18.0 mm.

FIG. 39 shows an exemplary handle 3900, according to one embodiment of the present disclosure. According to one embodiment, the handle 3900 attaches to the boring apparatus 3600 (see FIG. 36). In one or more embodiments, the handle 3900 includes a first portion 3901 (also referred to as a "grip") and a second portion 3903 (also referred to as an "insert"). In at least one embodiment, the first portion 3901 and the second portion 3903 are integrally formed. In various embodiments, the second portion 3903 is received by the top portion 3609 of the boring apparatus 3600 (FIG. 6), thereby connecting the handle 3900 and the boring apparatus 3600. In one or more embodiments, the second portion 3903 includes arms 3905A, 3905B that secure into channels 3706 and, thereby, secure the connection between the boring apparatus 3600 and the handle 3900.

In one or more embodiments, the second portion 3903 includes a peg 3907 that can be received into the boring apparatus 3600. For example, the peg 3907 includes a generally cylindrical shape that matches a footprint of aperture 3619 of the boring apparatus 3600. In this example, during attachment of the handle 3900 to the boring apparatus 3600, the aperture 3619 receives the peg 3907. In various embodiments, the second portion 3903 includes apertures 3909A-B and aperture 3911. According to one embodiment, apertures 3909A-B each receive a drill pin 4500. In one or more embodiments, the apertures 3909A-B demonstrate a size similar to apertures 3617A-B of the boring apparatus 3600. In various embodiments, the aperture 3911 receives a targeting pin 4300. In at least one embodiment, the aperture 3911 demonstrates a size similar to the aperture 3619 of the boring apparatus 3600. In at least one embodiment, the apertures 3909A-B, 3911 extend through the handle 3900 such that a drill pin or targeting pin can pass through the handle 3900 and into the boring apparatus 3600.

In at least one embodiment, the first portion 3901 includes a top surface 3902. According to one embodiment, the top surface 3902 includes one or more ridges 3904 for improving grip of the first portion 3901.

Figure 40:
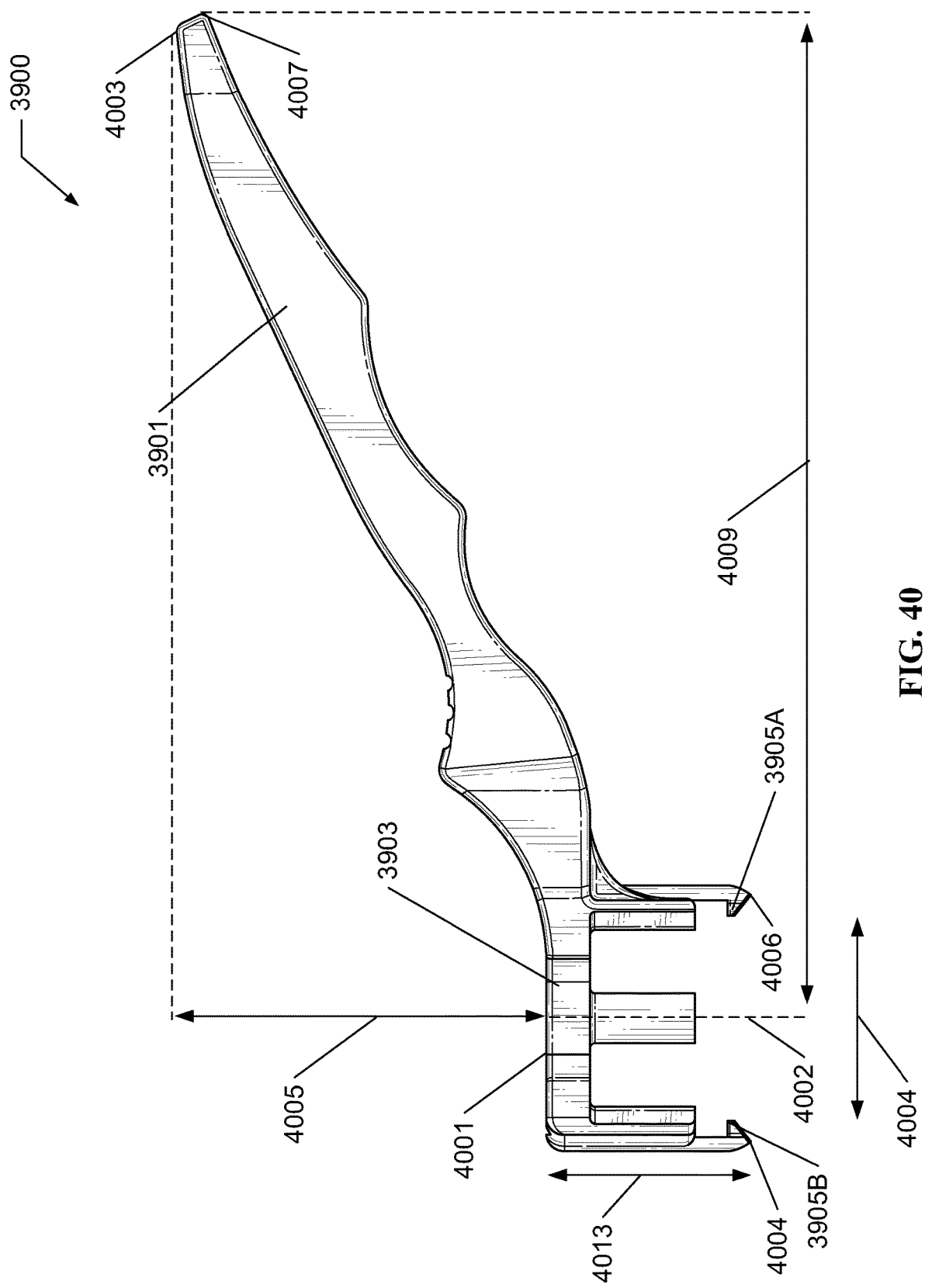
FIG. 40 shows a side view of an exemplary handle according to one embodiment of the present disclosure.

FIG. 40 shows a side view of the handle 3900, according to one embodiment of the present disclosure. In various embodiments, the first portion 3901 includes a top surface 4001. According to one embodiment, the second portion includes a top end 4003. In one or more embodiments, the handle 3900 includes a height 4005 between the top surface 4001 and the top end 4003, and the height 4005 measures at least about 30 mm, or about 30-60 mm, 30-35 mm, 35-40 mm, 40-45 mm, 45-50 mm, 50-55 mm, or 55-60 mm, or less than about 60 mm. In at least one embodiment, the first portion 3901 includes a side end 4007. In various embodiments, the handle 3900 includes a length 4009 between the side end 4007 and a centerline 4002 of the second portion 3903. In one or more embodiments, the length 4009 measures at least about 80 mm, or about 80-140 mm, 80-90 mm, 90-100 mm, 100-110 mm, 108 mm, 110-120 mm, 120-130 mm, 130-140 mm, or less than about 140 mm.

In at least one embodiment, the second portion 3903 includes a height 4013 between the top surface 4001 and an end 4004 of the arm 3905B. According to one embodiment, the height 4013 measures at least about 10 mm, or about 10-30 mm, 10-15 mm, 15-20 mm, 20 mm, 20-25 mm, 25-30 mm, or less than about 30 mm.

Figure 41:
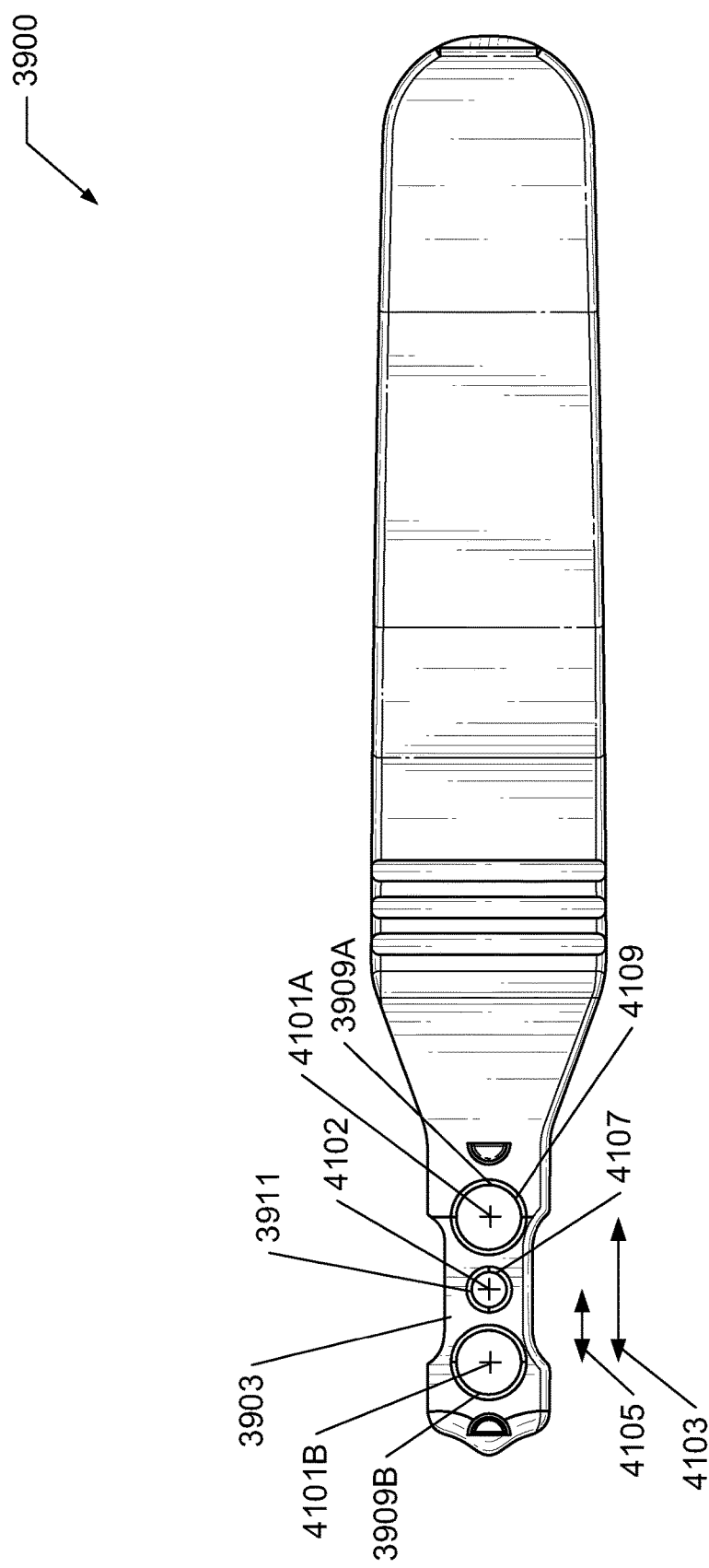
FIG. 41 shows a top view of an exemplary handle according to one embodiment of the present disclosure.

FIG. 41 shows a top view of the handle 3900, according to one embodiment of the present disclosure. According to one embodiment, a center point 4101A of the aperture 3909A is separated from a center point 4101B of the aperture 3909B by a distance 4103. In various embodiments, the distance 4103 measures at least about 4.0 mm, or about 4.0-20.0 mm, 4.0-6.0 mm, 6.0-8.0 mm, 8.0-10.0 mm, 10.0-12.0 mm, 12.5 mm, 12.0-14.0 mm, 14.0-16.0 mm, 16.0-18.0 mm, or 18.0-20.0 mm, or less than about 20.0 mm. In one or more embodiments, the center point 4101A is separated from a center point 4102 by a distance 4105. According to one embodiment, the distance 4105 measures at least about 1.0 mm, or about 1.0-6.0 mm, 1.0-2.0 mm, 2.0-3.0 mm, 3.0-4.0 mm, 4.0-5.0 mm, or 5.0-6.0 mm, or less than about 6.0 mm.

Figure 42:
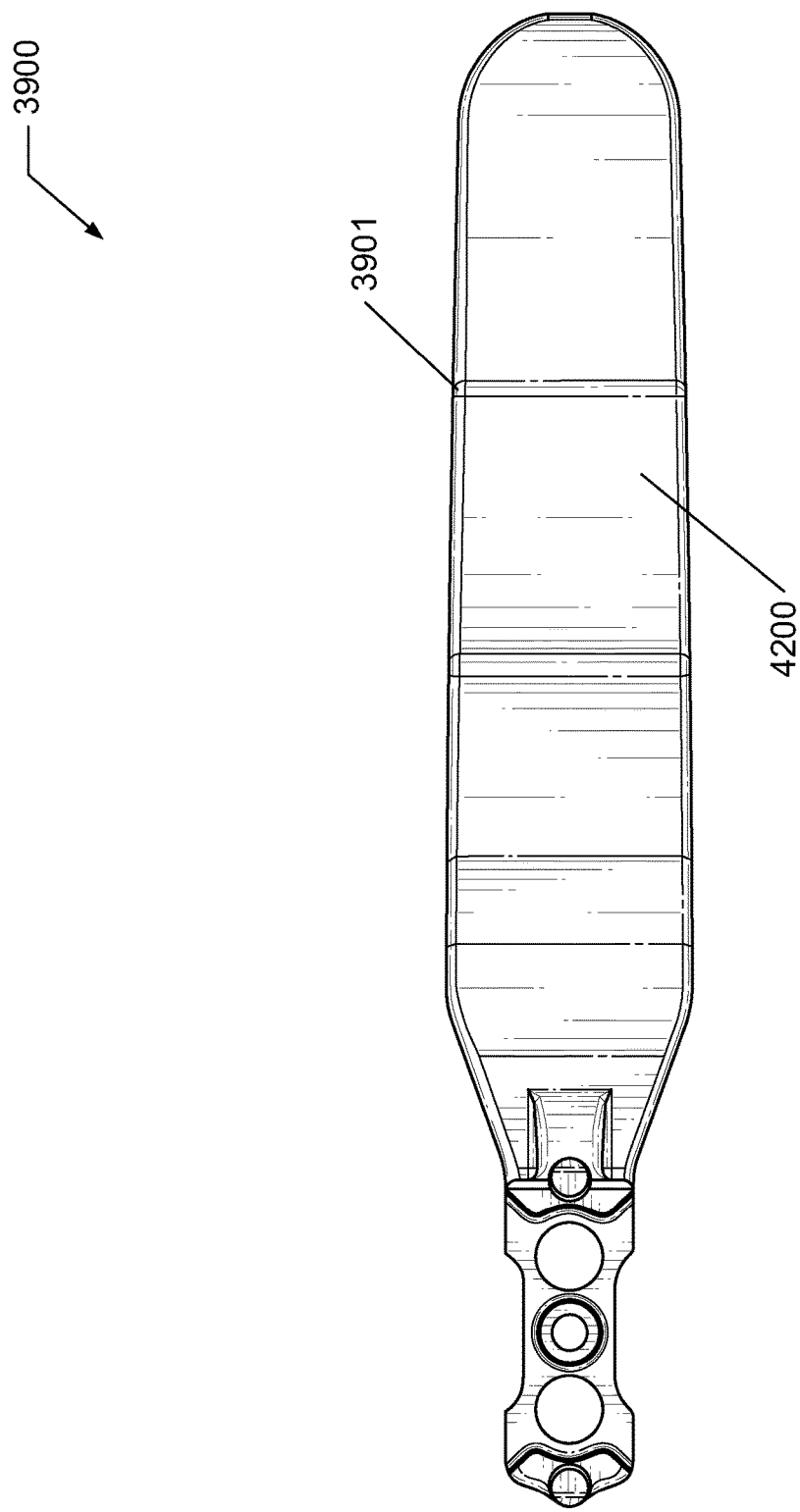
FIG. 42 shows a bottom view of an exemplary handle according to one embodiment of the present disclosure.

FIG. 42 shows a bottom view of the handle 3900 according to one embodiment of the present disclosure. In various embodiments, the first portion 3901 includes a bottom surface 4200.

FIG. 43 shows a side view of a target pin 4300, according to one embodiment of the present disclosure. In one or more embodiments, the target pin 4300 is configured to penetrate into a target site. For example, the target pin 4300 is inserted through a boring apparatus and directed into an approximate center point of a vertebra (e.g., for aligning boreholes according to a center point of the vertebra).

In various embodiments, the target pin 4300 includes a shaft 4301 connected to a top body 4302 and a bottom body 4304. In at least one embodiment, the shaft 4301 is integrally formed with the top body 4302 and/or the bottom body 4304. In some embodiments, the top body 4302 and/or the bottom body 4304 attaches to the shaft 4301 via any suitable means including but not limited to threaded connections, press fittings, luer locks, bayonet fittings, adhesives, magnetic connections, and snap fittings. In at least one embodiment, the top body 4302 receives a portion of the shaft 4301. In one or more embodiments, the top body 4302 includes a top section 4303.

In various embodiments, the shaft 4301 includes a cylindrical shape and extends from the bottom section 4304 to the top body 4302. A length 4323 may measure the length of the shaft 4301, extending from an edge 4311 to an edge 4313. In one or more embodiments, the length 4323 measures at least about 59.5 mm, 59.5-79.5 mm, 59.5-64.5 mm, 64.5-69.5 mm, 69.5 mm, 69.5-74.5 mm, 74.5-79.5 mm, or less than about 79.5 mm. In various embodiments, the cylindrical construct produces a diameter 4331, with a measured value of at least about 2.0 mm, 2.0-4.0 mm, 2.0-3.0 mm, 3.18 mm, 3.0-4.0 mm, or less than about 4.0 mm. In at least one embodiment, the edge 4313 transitions the shaft 4301 to the bottom section 4304. According to one embodiment, the edge 4313 includes a bevel, taper, rounded shape, or other modification to transition the shaft 4301 to the bottom body 4304.

In various embodiments, the edge 4311 defines an insertion depth of the target pin 4300 and the edge 4311 can be referred to as a "stop." In particular embodiments, the edge 4311 defines a transition between the shaft 4301 and the top body 4302. In at least one embodiment, the top body 4302 includes a cylindrical shape (e.g., or any other suitable shape, such as a prism or other solid of revolution). In various embodiments, the top body 4302 includes an indentation 4307 that allows a tool to attach to and rotate the target pin 4300. The top body 4302 may include a diameter 4332. In various embodiments, the diameter 4332 measures at least about 2.0 mm, or about 2.0-8.0 mm, 2.0-4.0 mm, 4.46 mm, 4.0-6.0 mm, 6.0-8.0 mm, or less than about 8.0 mm. In one or more embodiments, a recessed portion 4312 separates the top body 4302 from the top section 4303. In at least one embodiment, the recessed region 4313 is configured to receive an attachment mechanism of a tool or tool adapter. For example, the recessed region 4313 receives hooks 7114 of a tool adapter 7100 (FIG. 71).

The top section 4303 may demonstrate the diameter 4332 of the top body 4302. In some embodiments, a diameter of the top section 4303 is greater than, less than, or equal to the diameter 4332. In particular embodiments, the top section 4303 includes a surface 4306 that transitions the top section 4303 to a top surface shown 4401 (not shown, see FIG. 44). According to one embodiment, the surface 4306 defines a bevel, taper, rounded shape, or slope that transitions the top section 4303 to the top surface 4401.

In one or more embodiments, the top section 4303 includes a length 4324. The length 4324 may measure at least about 2.0 mm, or about 2.0-10.0 mm, 2.0-4.0 mm, 4.95 mm, 4.0-6.0 mm, 6.0-8.0 mm, 8.0-10.0 mm, or less than about 10.0 mm. A length 4322 may extend from the edge 4311 to an edge 4402 of the surface 4306, and may measure at least about 20.0 mm, or about 20.0-30.0 mm, 20.0-25.0 mm, 25.4 mm, 25.0-30.0 mm, or less than about 30.0 mm. In various embodiments, the indentation 4307 extends along the recessed portion 4312 and the top section 4303, and extends to the edge 4402.

In one or more embodiments, the edge 4313 defines a transition between the shaft 4301 and the bottom section 4304. In various embodiments, the bottom section 4304 is cylindrical in shape (e.g., or includes any other suitable shape, such as a prism or other solid of revolution). The bottom section 4303 may include a tip 4305 and a diameter 4333. The diameter 4333 may measure at least about 1.45 mm, or about 1.45-1.55 mm, 1.45-1.50 mm, 1.50 mm, 1.50-1.55 mm, or less than about 1.55 mm. In particular embodiments, a length 4321 extends from the tip 4305 to the beveled edge 4313. The length 4321 may measure at least about 9.0 mm, 9.0-15.0 mm, 9.0-12.0 mm, 12.0 mm, 12.0-15.0 mm, or less than about 15.0 mm.

Figure 44:
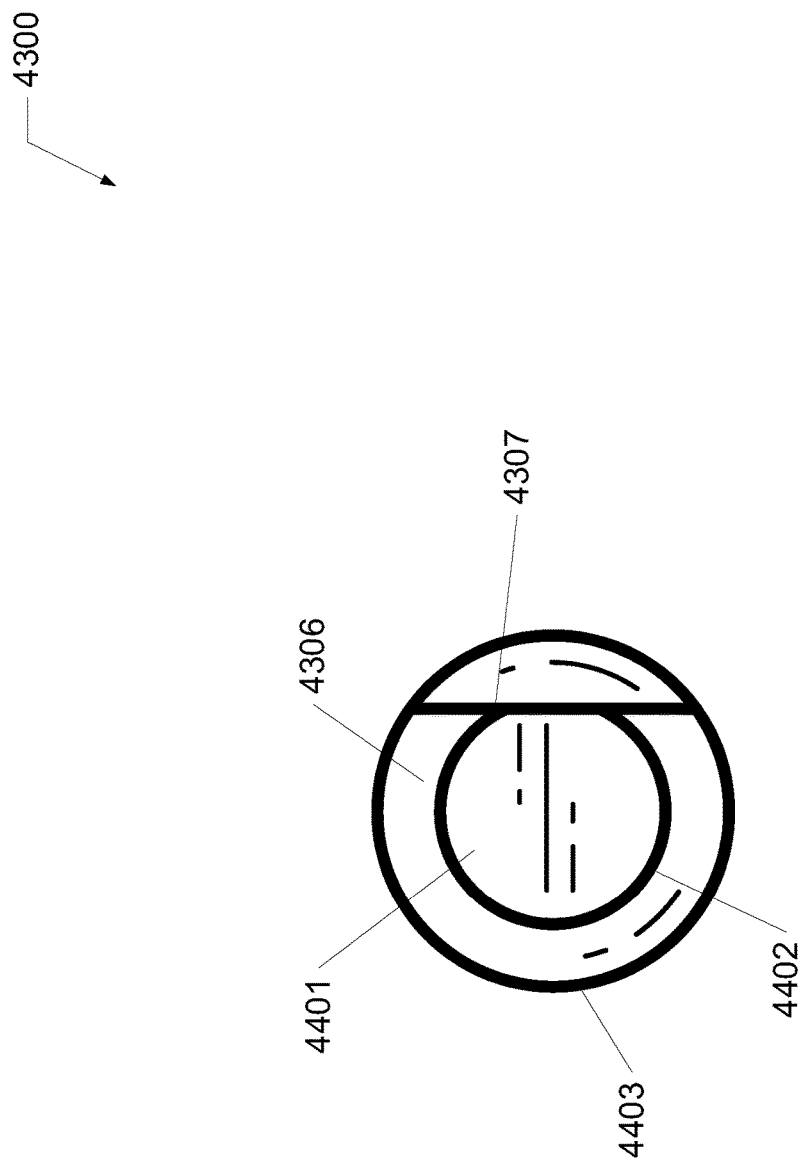
FIG. 44 shows a top view of an exemplary target pin according to one embodiment of the present disclosure.

FIG. 44 shows a top view of the target pin 4300, according to one embodiment of the present disclosure. In various embodiments, the target pin 4300 includes a top surface 4401. In one or more embodiments, the top surface 4401 is substantially smooth. In at least one embodiment, the top surface 4401 is bounded by an edge 4402 and the indentation 4307. In particular embodiments, the surface 4306 is bounded by the edge 4402, an edge 4403, and the indentation 4307. In one or more embodiments, the edges 4402, 4403 extend from the indentation 4307.

Figure 45:
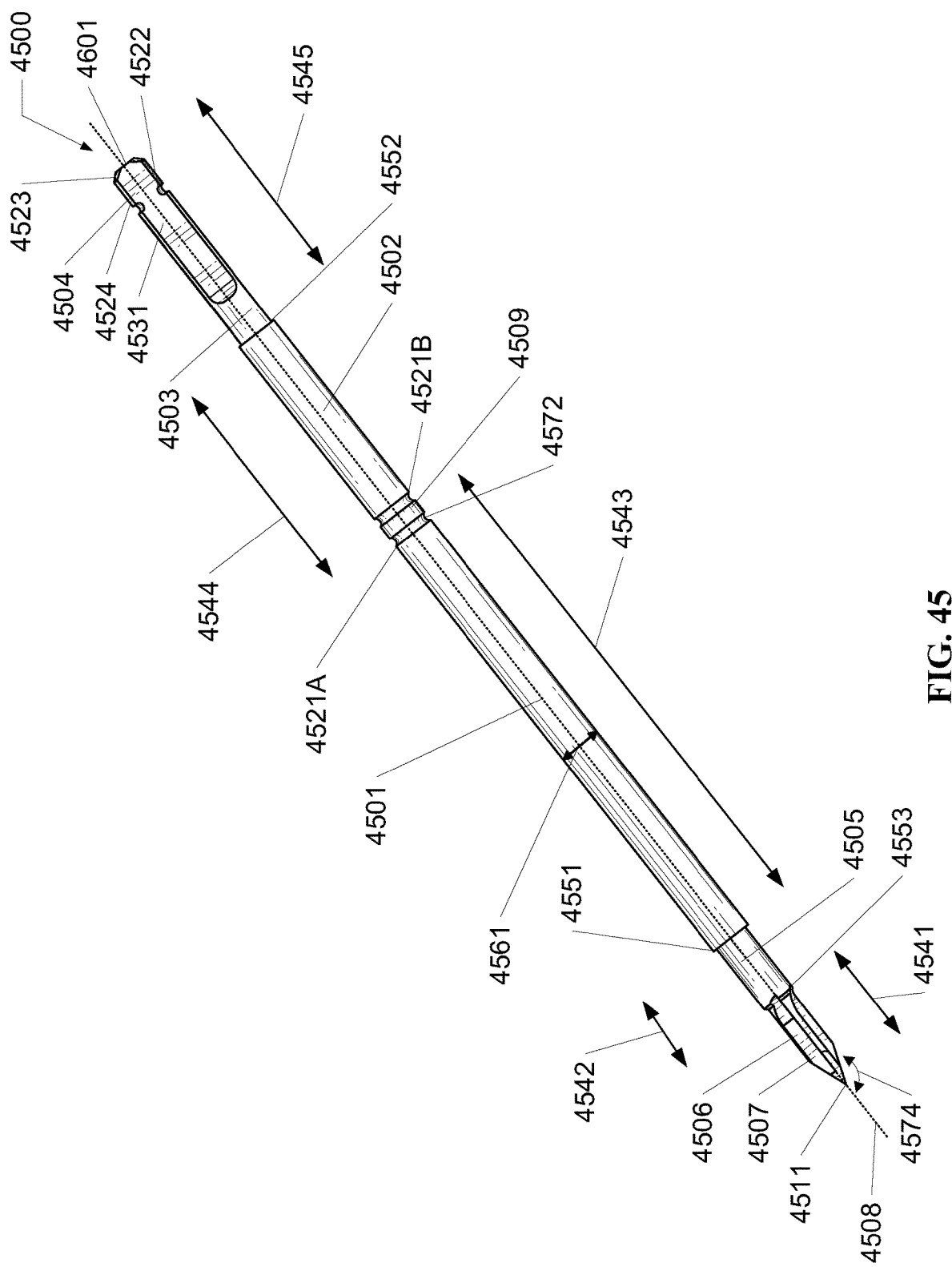
FIG. 45 shows a side view of an exemplary drill pin according to one embodiment of the present disclosure.

FIG. 45 shows a side view of a drill pin 4500, according to one embodiment of the present disclosure. In various embodiments, the drill pin 4500 includes a body 4501. In one or more embodiments, the body 4501 is bounded at both ends by an end 4551 and an end 4552. In particular embodiments, the body 4501 includes a generally cylindrical shape (e.g., or any suitable shape, such as rectangular prisms, and other prisms or solids of revolution). In one or more embodiments, the body 4501 includes a diameter 4561 and extends a length 4543. In various embodiments, the length 4543 measures the distance between the end 4551 and a stop 4521A. The length 4543 may measure at least about 57.0 mm, or about 57.0-70.0 mm, 57.0-60.0 mm, 60.0-63.0 mm, 63.5 mm, 63.0-66.0 mm, 66.0-70.0 mm, or less than about 70.0 mm. The diameter 4561 may measure at least about 3.0 mm, 3.0-7.0 mm, 3.0-5.0 mm, 5.16 mm, 5.0-7.0 mm, or less than about 7.0 mm.

According to one embodiment, the body 4501 includes stops 4521A-B that define recessed regions of the body 4501 that demonstrate a decreased diameter 4561 (e.g., as compared to other sections of the body 4501). In various embodiments, a surface 4509, isolated by stops 4521A-B, shares the same diameter 4561 as the body 4501. Each stop 4521A-B may include a radius 4572 of at least about 0.3 mm, or about 0.3-0.9 mm, 0.3-0.4 mm, 0.4-0.5 mm, 0.5-0.6 mm, 0.6 mm, 0.6-0.7 mm, 0.7-0.8 mm, 0.8-0.9 mm, or less than about 0.9 mm. In at least one embodiment, the stops 4521A-B define depths to which the drill pin 4500 may be inserted to a target site. For example, the stop 4521A defines a first insertion depth and the stop 4521B defines a second insertion depth (e.g., greater than the first insertion depth). In some embodiments, the stops 4521A-B are configured to receive an attachment mechanism of a tool or tool adapter. In various embodiments, the insertion depth of the drill pin 4500 can be a predetermined amount calculated by adding a length 4541, a length 4542, and the length 4543.

According to one embodiment, the body 4501 includes an upper portion 4502 that extends from the stop 4521B to the end 4552. In various embodiments, the upper portion 4502 includes a cylindrical shape. In at least one embodiment, the upper portion 4502 demonstrates the diameter 4561. In particular embodiments, the upper portion 4502 demonstrates a length 4544 between the stop 4521B and the end 4552. The length 4544 may measure at least 25.0 mm, or about 25.0-27.0 mm, 25.0-26.0 mm, 26.6 mm, 26.0-27.0 mm, or less than about 27.0 mm.

In particular embodiments, the drill pin 4500 includes an adapter pin 4503. For example, the drill pin 4500 receives the adapter pin 4503 at the end 4552. In various embodiments, the adapter pin 4503 includes an indentation 4531, a stop 4522, and a head 4504. In one or more embodiments, the adaptor pin 4503 includes a surface 4523 that transitions the top surface 4601 to a surface 4524 of the adapter pin 4503. In various embodiments, the surface 4523 defines a rounded, tapered, or beveled transition between the top surface 4601 and the surface 4524.

In one or more embodiments, the adapter pin 4503 is a removable component. For example, the drill pin 4500 receives the adapter pin 4503 into an aperture (not shown) at the end 4552. The attachment process of the adapter pin 4503 may include, but is not limit to, a magnetic mechanism, a screwing mechanism (e.g., via threads, a luer lock, etc.), and/or a snap fit mechanism. In some embodiments, the adapter pin 4503 and the drill pin 4500 are integrally formed or are attached via welding and/or adhesives. In one or more embodiments, the indentation 4531 extends from the top surface 4601 to at least about 10 mm down the adapter pin 4503, or about 10-30 mm, 10-20 mm, 20 mm, 20-30 mm, or less than about 30 mm down the adapter pin 4503. In various embodiments, the stop 4522 includes a radius of at least about 0.3 mm, or about 0.3-0.9 mm, 0.3-0.4 mm, 0.4-0.5 mm, 0.5-0.6 mm, 0.6 mm, 0.6-0.7 mm, 0.7-0.8 mm, 0.8-0.9 mm, or less than about 0.9 mm. In particular embodiments, the beveled edge of surface 4523 is angled relative to a center axis 4508, and measures at least about 35.0 degrees, 35.0-55.0 degrees, 35.0-40.0 degrees, 40.0-45.0 degrees, 45.0-50.0 degrees, 50.0-55.0 degrees, or less than about 55.0 degrees.

In various embodiments, the drill pin adapter 4503 includes a length 4545 that extends from the top surface 4601 to the end 4552. The length 4545 may measure at least about 20.0 mm, 20.0-30.0 mm, 20.0-25.0 mm, 25.4 mm, 25.0-30.0 mm, or less than about 30.0 mm.

In one or more embodiments, the drill pin 4500 includes a bottom section 4505 and a drilling section 4506. The bottom section 4505 may extend from the end 4551 to an end 4553, and may measure a length 4542. The length 4542 may measure at least about 7.0 mm, or about 7.0-11.0 mm, 7.0-9.0 mm, 9.0 mm, 9.0-11.0 mm, or less than about 11.0 mm. In various embodiments, the drilling section 4506 includes a drill bit 4507 and a tip 4511. In particular embodiments, the drill bit 4507 includes any suitable shape or shape combination that directs swarf (for example, bone filings or other loose drilling debris) out of a borehole. In at least one embodiment, the tip 4511 of the drilling section 4506 defines a vertex that converges all surfaces of the drilling section 4506. In at least one embodiment, the tip 4511 demonstrates an angle 4574 relative to the center axis 4508. In various embodiments, the angle 4574 measures at least about 5 degrees, or about 5-65 degrees, 5-15 degrees, 15-25 degrees, 20 degrees, 25-35 degrees, 35-45 degrees, 45-55 degrees, or 55-65 degrees, or less than about 65 degrees. In various embodiments, a length 4541 extends from the tip 4511 to the end 4553 and measures at least about 10.0 mm, or about 10.0-16.0 mm, 10.0-12.0 mm, 12.0-13.0 mm, 13.0 mm, 13.0-15.0 mm, 15.0-16.0 mm, or less than about 16.0 mm.

Figure 46:
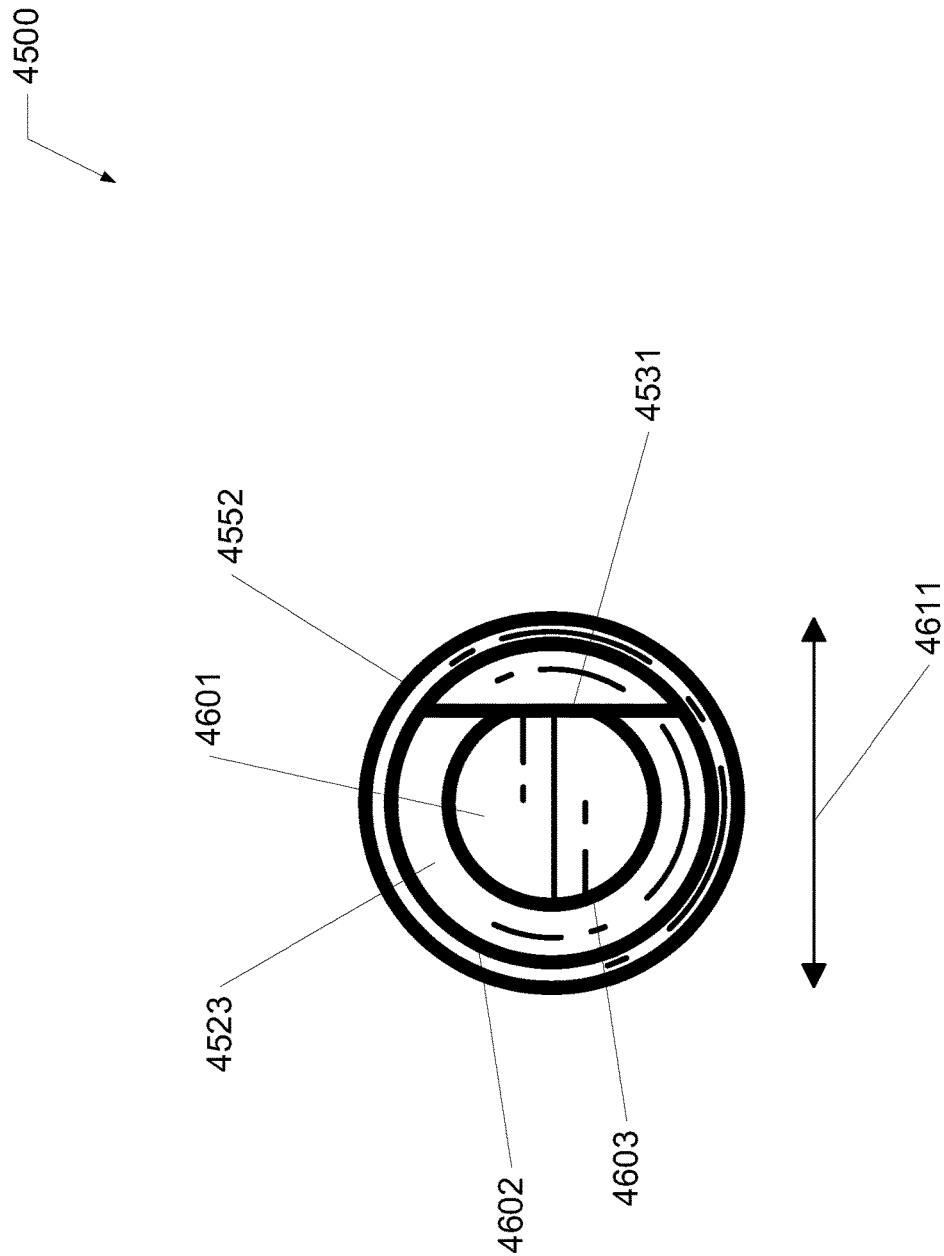
FIG. 46 show a top view of an exemplary drill pin according to one embodiment of the present disclosure.

FIG. 46 show a top view of the drill pin 4500, according to one embodiment of the present disclosure. In one or more embodiments, the drill pin 4500 includes a top surface 4601 that is bounded by an edge 4603 and the indentation 4531. In particular embodiments, the surface 4523 is bounded by the edge 2603, an edge 2602, and the indentation 4531. In various embodiments, the diameter of the edge 4602 is measured by a diameter 4611. The diameter 4611 may measure at least about 2.0 mm, 2.0-6.0 mm, 2.0-4.0 mm, 4.46 mm, 4.0-6.0 mm, or less than about 6.0 mm.

Figure 47:
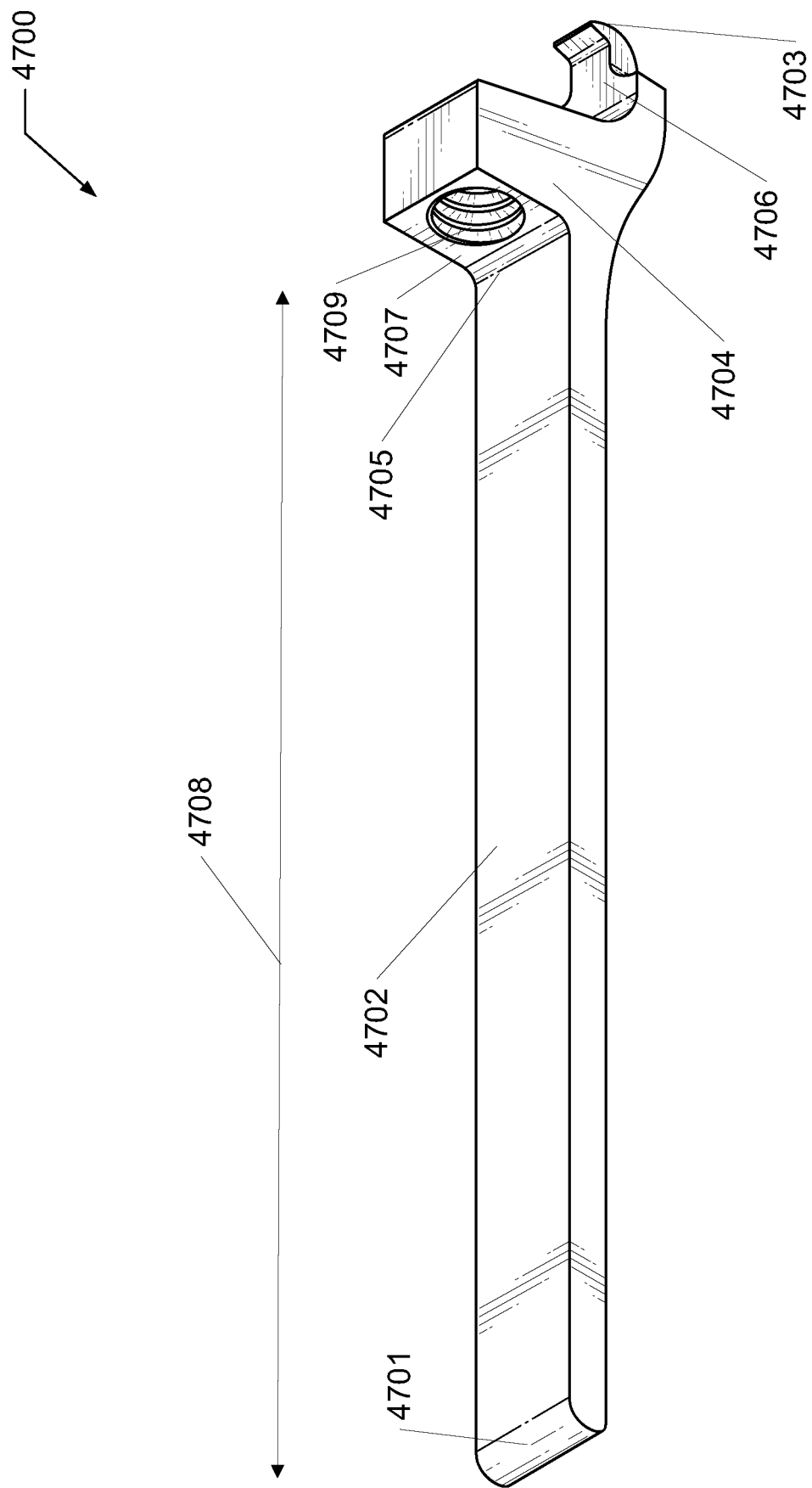
FIG. 47 shows a perspective view of an exemplary first shaft according to one embodiment of the present disclosure.

FIG. 47 shows a perspective view of a first shaft 4700, according to one embodiment of the present disclosure. In various embodiments, the first shaft 4700 is configured to attach to and deform staples described herein (e.g., in combination with a second shaft 5200 shown in FIG. 52). For example, the first shaft 4700 connects to and deforms the staple 100 (FIG. 1) during staple installation and removal procedures.

In one or more embodiments, the first shaft 4700 includes a first end 4701 and a second end 4703 opposite the first end 4701. In at least one embodiment, the first shaft 4700 includes a first portion 4702 between the first end 4701 and an end 4705. According to one embodiment, the first portion 4702 includes a generally rectangular prismatic shape (e.g., or includes any suitable shape or shape combination, such as a cylinder or other solid of revolution). In one or more embodiments, the first portion 4702 includes a length 4708 between the first end 4701 and the end 4705. In various embodiments, the length 4708 measures at least about 70.0 mm, or about 70.0-90.0 mm, 70.0-75.0 mm, 75.0-80.0 mm, 80.0-85.0 mm, 83.0 mm, 85.0-90.0 mm, or less than about 90.0 mm.

In one or more embodiments, the first shaft 4700 includes a second portion 4704 between the end 4705 and the second end 4703. In at least one embodiment, the second portion 4704 includes a generally rectangular prismatic or trapezoidal prismatic shape (e.g., or includes any suitable shape or shape combination, such as a cylinder or other solid of revolution). In various embodiments, the second portion 4704 includes a hook 4706. According to one embodiment, the hook 4706 extends from a bottom surface 5100 (see FIG. 51B) and defines the end 4703. In one or more embodiments, the hook 4706 is configured to attach to staples described herein. For example, the hook 4706 attaches to an indentation 121 of the staple 100 (FIG. 1). In various embodiments, the second portion 4704 includes an aperture 4707 that extends through the second portion 4704. In at least one embodiment, the aperture 4707 includes threads 4709 for creating a threaded connection with threads of a component inserted through the aperture 4707. In one or more embodiments, the threads 4709 are configured to mate with threads 5712 of the pin 5705 (see FIG. 57). In one or more embodiments, the threads 4709 demonstrate any suitable thread handedness and thread quantity. In various embodiments, a thread quantity of the threads 4709 is at least about 3 threads, 3-30 threads, 20 threads, or less than about 30 threads. In various embodiments, a diameter of the threads 4709 is at least about 0.1 inches, or about 0.1-0.5 inches, 0.1-0.2 inches, 0.2-0.3 inches, 0.25 inches, 0.3-0.4 inches, 0.4-0.5 inches, or less than about 0.5 inches. In some embodiments, the first portion 4702 includes an aperture that extends outward and is aligned with the aperture 4707 of the second portion 4704. For example, the first portion 4702 includes a rectangular prism-shaped portion that extends outward from the first portion 4702. In this example, the extending portion includes an aperture that is aligned with the aperture 4707 and configured to receive the rod 5700 (e.g., the rod 5700 may be passed through the aperture of the first portion 4702 and through the aperture 4707). In the same example, the extending portion can maintain a separation distance between the first shaft 4700 and the second shaft 5200 (e.g., when the shafts are brought into a parallel orientation).

In one or more embodiments, the first portion 4702 and the second portion 4704 are integrally formed. In some embodiments, the first portion 4702 and the second portion 4704 are attached via any suitable mechanism including, but not limited to, welds, adhesives, threaded connections, bayonet fittings, press fittings, magnetic connections, and snap connections.

Figure 48:
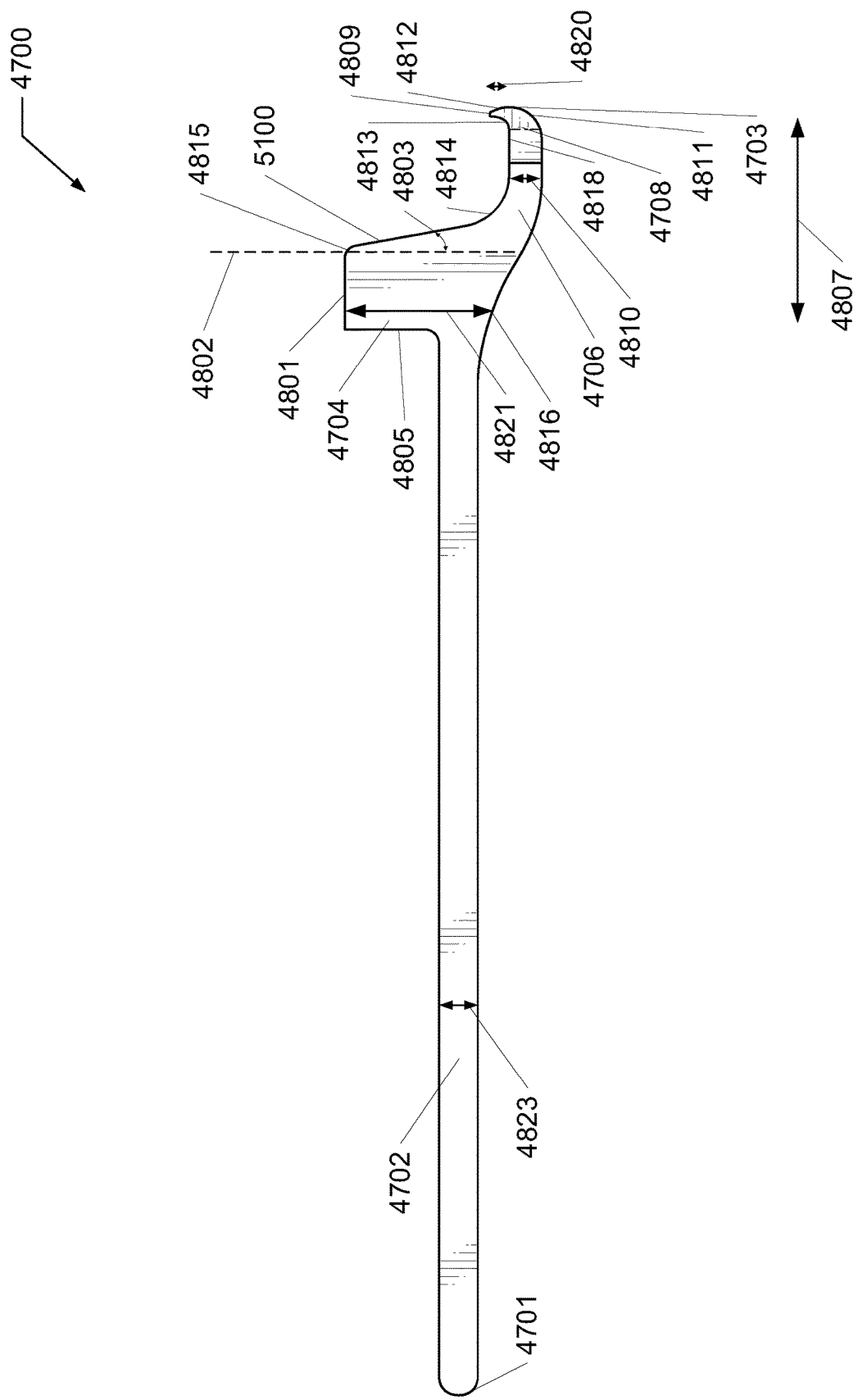
FIG. 48 shows a side view of an exemplary first shaft according to one embodiment of the present disclosure.

FIG. 48 shows a side view of the first shaft 4700, according to one embodiment of the present disclosure. In particular embodiments, the hook 4706 includes radii 4811, 4812, 4813, 4814. The radius 4811 may measure at least about 1.0 mm, or about 1.0-4.0 mm, 1.0-2.0 mm, 2.5 mm, 2.0-3.0 mm, 3.0-4.0 mm, or less than about 4.0 mm. The radius 4812 may measure at least about 0.5 mm, or about 0.5-1.5 mm, 0.5-1.0 mm, 1.0 mm, 1.0-1.5 mm, or less than about 1.5 mm. The radius 4813 may measure at least about 0.25 mm, or about 0.25-0.75 mm, 0.25-0.5 mm 0.5 mm, 0.5-0.75 mm, or less than about 0.75 mm. The radius 4814 may measure at least about 3.0 mm, 3.0-5.0 mm, 3.0-4.0 mm, 4.0 mm, 4.0-5.0 mm, or less than about 5.0 mm.

In one or more embodiments, the second portion 4704 includes radii 4815, 4816. The radius 4815 may measure at least about 0.5 mm, 0.5-1.5 mm, 0.5-1.0 mm, 1.0 mm, 1.0-1.5 mm, or less than about 1.5 mm. In various embodiments, the radius 4815 defines a transition from a front surface 4801 of the second portion 4704 to a bottom surface 5100 of the second portion 4704. In at least one embodiment, the radius 4816 measures at least about 15.0 mm, 15.0-25.0 mm, 15.0-20.0 mm, 20.0 mm, 20.0-25.0 mm, or less than about 25.0 mm. In at least one embodiment, the bottom surface 5100 is oriented at an angle 4803 relative to a vertical axis 4802. In one or more embodiments, the angle 4803 measures at least about 5 degrees, about 5-45 degrees, 5-10 degrees, 10 degrees, 10-15 degrees, 15-20 degrees, 20-25 degrees, 25-30 degrees, 30-35 degrees, 35-40 degrees, degrees, or less than about 45 degrees.

In various embodiments, the hook 4706 includes a tip 4809. According to one embodiment, a separation distance 4807 between a top surface 4805 of the second portion 4704 and the tip 4809 measures at least about 10.0 mm, or about 10.0-30.0 mm, 10.0-15.0 mm, 16.4 mm, 15.0-20.0 mm, 20.0-25.0 mm, or 25.0-30.0 mm, or less than about 30.0 mm. In one or more embodiments, the hook 4706 includes a thickness 4810 that measures at least about 0.5 mm, or about 0.5-5.0 mm, 0.5-1.0 mm, 1.0-1.5 mm, 1.5-2.0 mm, 2.0-2.5 mm, 2.5 mm, 2.5-3.0 mm, 3.0-3.5 mm, 3.5-4.0 mm, 4.0-4.5 mm, or 4.5-5.0 mm, or less than about 5.0 mm. In various embodiments, a separation distance 4820 between the tip 4809 and an inner surface 4818 of the hook 4706 measures at least about 0.5 mm, or about 0.5-5.0 mm, 0.5-1.0 mm, 1.0-1.5 mm, 1.5-2.0 mm, 2.0-2.5 mm, 2.5 mm, 2.5-3.0 mm, 3.0-3.5 mm, 3.5-4.0 mm, 4.0-4.5 mm, or 4.5-5.0 mm, or less than about mm.

In one or more embodiments, the second portion 4704 includes a thickness 4821 that measures at least about 5.0 mm, or about 5.0-15.0 mm, about 5.0-7.0 mm, 7.0-9.0 mm, 8.8 mm, 9.0-11.0 mm, 9.8 mm, 10.8 mm, 11.0-13.0 mm, 11.8 mm, 12.8 mm, 13.0-15.0 mm, or less than about 15.0 mm. In at least one embodiment, the first portion 4702 includes a thickness 4823 that measures at least about 1.0 mm, or about 1.0-10.0 mm, 1.0-2.0 mm, 2.0-3.0 mm, 3.0-4.0 mm, 3.0 mm, 5.0-6.0 mm, 6.0-7.0 mm, 7.0-8.0 mm, 8.0-9.0 mm, or 9.0-10.0 mm, or less than about 10.0 mm.

Figure 49:
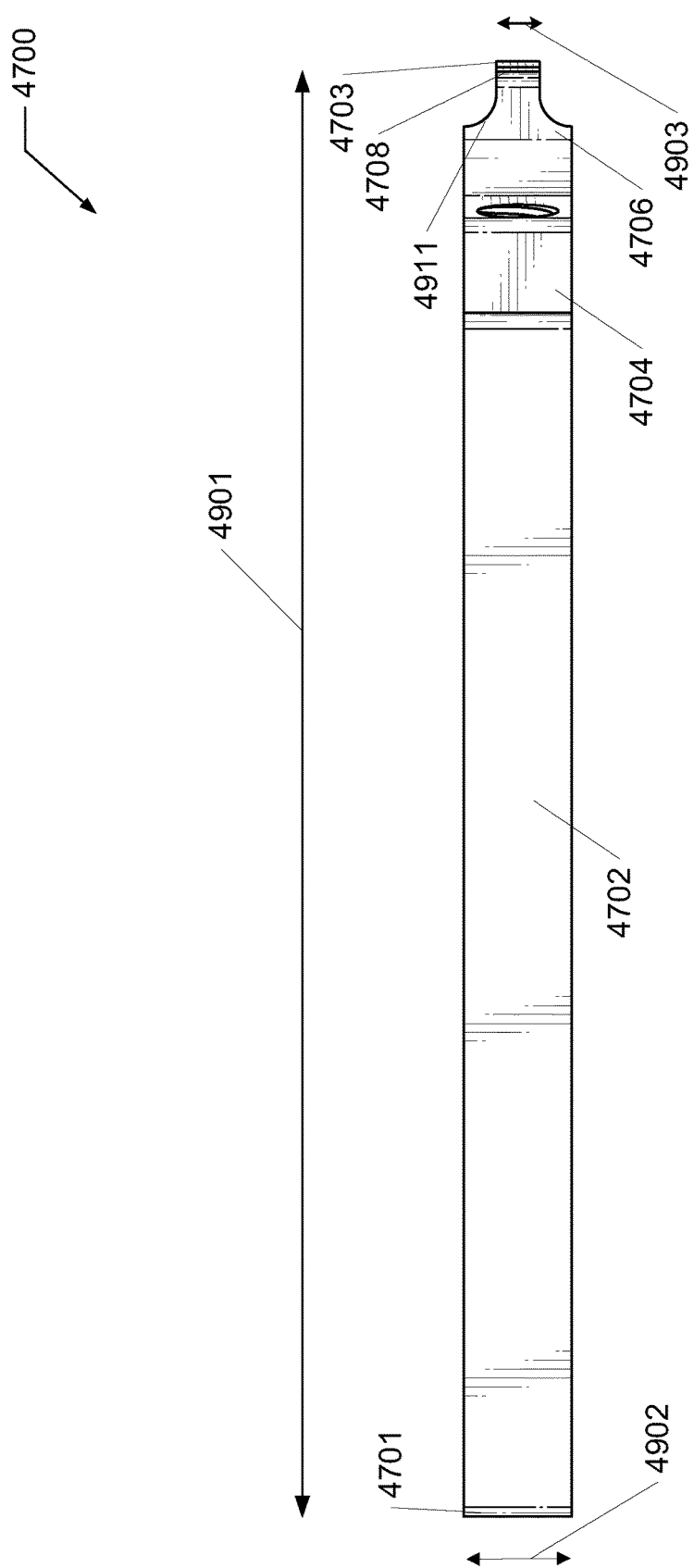
FIG. 49 shows a front view of an exemplary first shaft according to one embodiment of the present disclosure.

FIG. 49 shows a front view of the first shaft 4700, according to one embodiment of the present disclosure. In various embodiments, the first shaft 4700 includes a length 4901 between the ends 4701, 4703. The length 4901 may measure at least about 80.0 mm, or about 80.0-120.0 mm, 80.0-85.0 mm, 85.0-90.0 mm, 90.0-95.0 mm, 95.0-100.0 mm, 100.4 mm, 100.0-105.0 mm, 105.0-110.0 mm, 110.0-115.0 mm, 115.0-120.0 mm, or less than about 120.0 mm. In particular embodiments, the first portion 4702 and the second portion 4704 include a depth 4902. The depth 4902 may measure at least about 6.0 mm, or about 6.0-8.0 mm, 6.0-7.0 mm, 7.5 mm, 7.0-8.0 mm, or less than about 8.0 mm. The depth of the first portion 4702 may be greater than, less than, or equal to the depth of the second portion 4702. In at least one embodiment, the hook 4706 includes a depth 4903 that measures at least about 2.0 mm, or about 2.0-4.0 mm, 2.0-3.0 mm, 3.0 mm, 3.0-4.0 mm, or less than about 4.0 mm. In some embodiments, the depth 4903 is greater than, less than, or equal to the depth 4902.

In one or more embodiments, the hook 4706 includes a radius 4911 that transitions the second portion 4704 to the hook 4706. The radius 4911 may measure at least about 3.5 mm, 3.5-5.5 mm, 3.5-4.0 mm, 4.0-4.5 mm, 4.5 mm, 4.5-5.0 mm, 5.0-5.5 mm, or less than about 5.5 mm.

Figure 50:
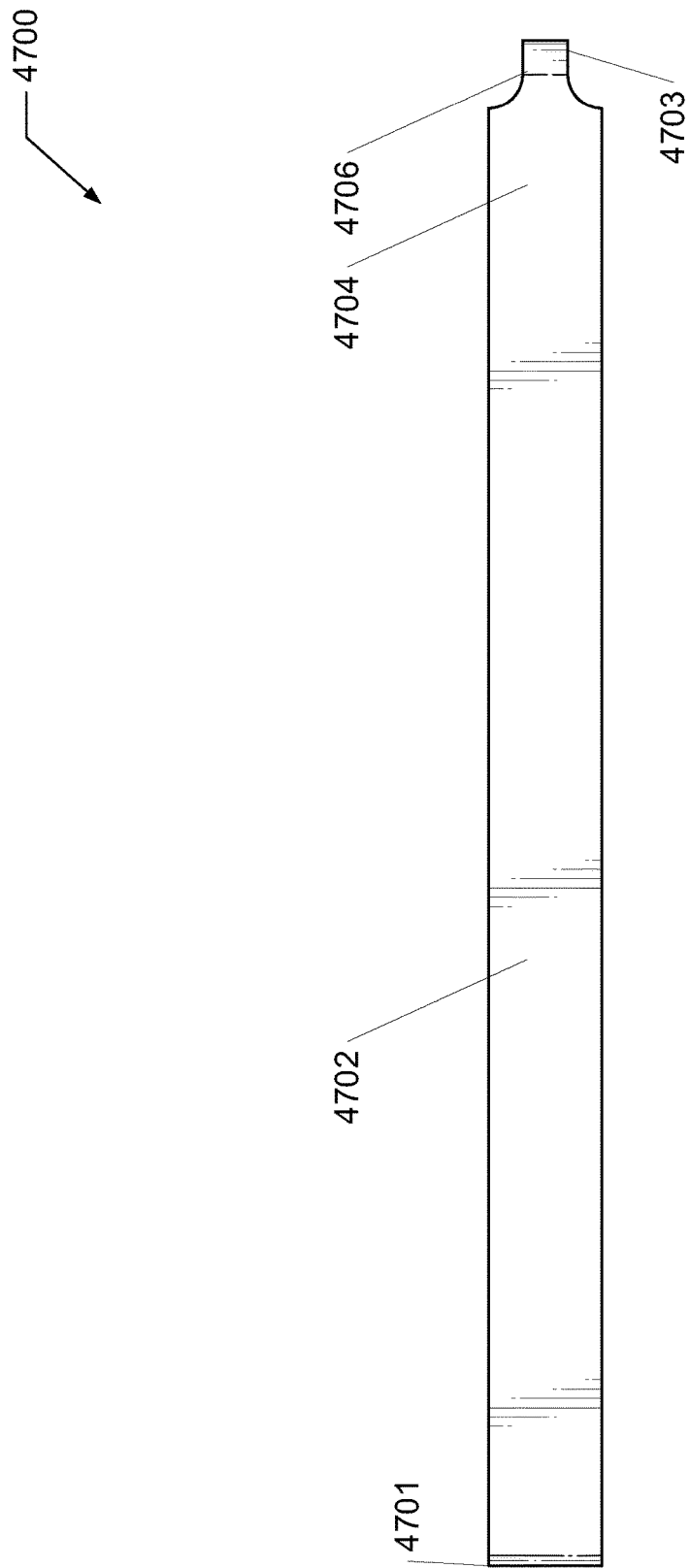
FIG. 50 shows a back view of an exemplary first shaft according to one embodiment of the present disclosure.

FIG. 50 shows a back view of the first shaft 4700, according to one embodiment of the present disclosure.

Figure 51A:
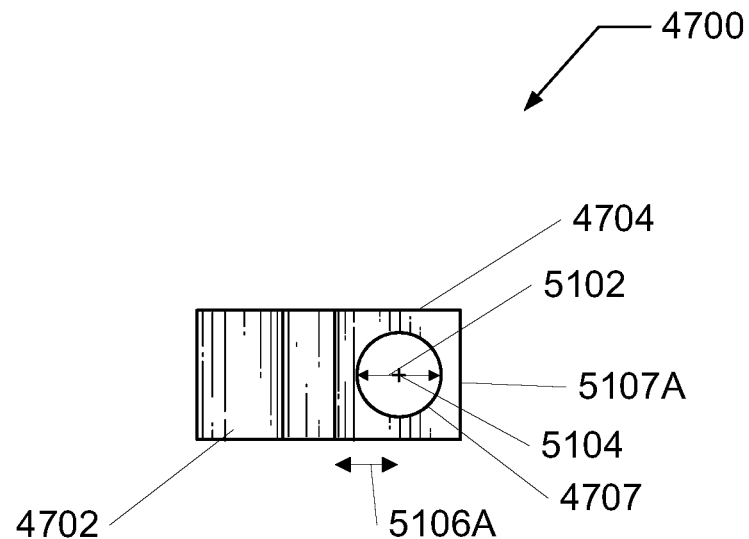
FIG. 51A shows a top view of an exemplary first shaft according to one embodiment of the present disclosure.

FIG. 51A shows a top view of the first shaft 4700, according to one embodiment of the present disclosure. In particular embodiments, the aperture 4707 includes a diameter 5102. The diameter 5102 may measure at least about 4.0 mm, or about 4.0-7.0 mm, 4.0-5.0 mm, 5.33 mm, 5.0-6.0 mm, 6.0-7.0 mm, or less than about 7.0 mm.

In at least one embodiment, a separation distance 5106A between the first portion 4702 and a center point 5104 of the aperture 4707 measures at least about 1.0 mm, or about 1.0-8.0 mm, 1.0-2.0 mm, 2.0-3.0 mm, 3.0-4.0 mm, 4.0 mm, 4.0-5.0 mm, 5.0-6.0 mm, 6.0-7.0 mm, or 7.0-8.0 mm, or less than about 8.0 mm.

Figure 51B:
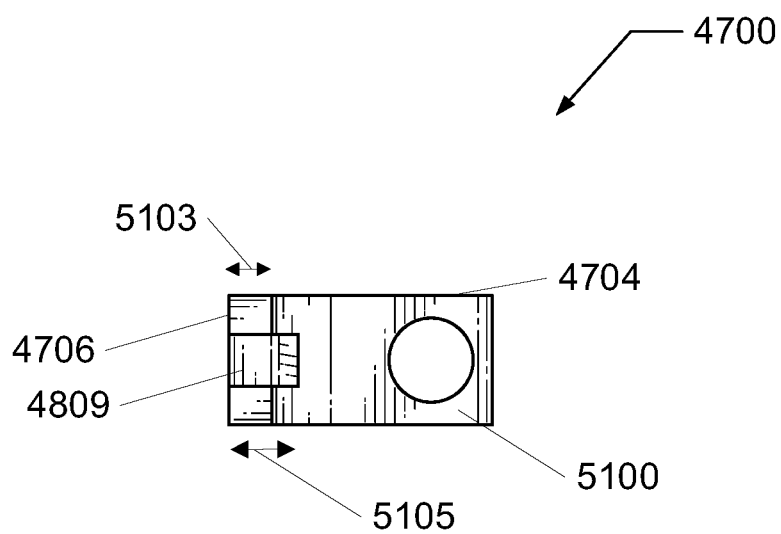
FIG. 51B shows a bottom view of an exemplary first shaft according to one embodiment of the present disclosure.

FIG. 51B shows a bottom view of the first shaft 4700, according to one embodiment of the present disclosure. In one or more embodiments, the hook 4706 includes a depth 5103 and the tip 4809 of the hook 4706 includes a depth 5105. In at least one embodiment, the depth 5103 measures at least about 3.0 mm, or about 3.0-5.0 mm, 3.0-4.0 mm, 4.0 mm, 4.0-5.0 mm, or less than about 5.0 mm. In one or more embodiments, the depth 5105 measures at least about 1.0 mm, or about 1.0-4.0 mm, 1.0-2.0 mm, 2.5 mm, 2.0-3.0 mm, 3.0-4.0 mm, or less than about 4.0 mm. The depth 5105 may be greater than, less than, or equal to the depth 5103.

FIG. 52 shows a perspective view of a second shaft 5200, according to one embodiment of the present disclosure. In various embodiments, the second shaft 5200 is configured to attach to and deform staples described herein (e.g., in combination with a first shaft 4700 shown in FIG. 47). For example, the second shaft 5200 connects to and deforms the staple 100 (FIG. 1) during staple installation and removal procedures.

In one or more embodiments, the second shaft 5200 includes a first end 5201 and a second end 5203 opposite the first end 5201. In at least one embodiment, the second shaft 5200 includes a first portion 5202 between the first end 5201 and an end 5205. According to one embodiment, the first portion 5202 includes a generally rectangular prismatic shape (e.g., or includes any suitable shape or shape combination, such as a cylinder or other solid of revolution). In one or more embodiments, the first portion 5202 includes a length 5208 between the first end 5201 and the end 5205. In various embodiments, the length 5208 measures at least about 70.0 mm, or about 70.0-90.0 mm, 70.0-75.0 mm, 75.0-80.0 mm, 80.0-85.0 mm, 83.0 mm, 85.0-90.0 mm, or less than about 90.0 mm.

In one or more embodiments, the second shaft 5200 includes a second portion 5204 between the end 5205 and the second end 5203. In at least one embodiment, the second portion 5204 includes a generally rectangular prismatic or trapezoidal prismatic shape (e.g., or includes any suitable shape or shape combination, such as a cylinder or other solid of revolution). In various embodiments, the second portion 5204 includes a hook 5206. According to one embodiment, the hook 5206 extends from a bottom surface 5600 (see FIG. 56B) and defines the end 5203. In one or more embodiments, the hook 5206 is configured to attach to staples described herein. For example, the hook 5206 attaches to an indentation 123 of the staple 100 (FIG. 1). In various embodiments, the second portion 5204 includes an aperture 5207 that extends through at least part of the second portion 5204. In one or more embodiments, the aperture 5207 is configured to receive a component for deforming a spacer and/or staple attached to the second shaft 5200. In one example, the aperture 5207 receives an end 5713 of the pin 5705 (see FIG. 57) and, when received, the end 5713 extends from the aperture 5207 (e.g., past the end 5203). In this example, the end 5713 can contact and apply a downward force to a spacer or staple attached to the second shaft 5200.

In one or more embodiments, the second portion 5204 includes one or more prongs 5211, a channel 5213A, and a channel 5213B. According to one embodiment, the prongs 5211 and channels 5213A-B are configured to receive a spacer, such as, for example, a spacer 3200 (FIG. 32). In at least one embodiment, the prongs 5211 and channels 5213A-B match a footprint of the spacer 3200.

In one or more embodiments, the first portion 5202 and the second portion 5204 are integrally formed. In some embodiments, the first portion 5202 and the second portion 5204 are attached via any suitable mechanism including, but not limited to, welds, adhesives, threaded connections, bayonet fittings, press fittings, magnetic connections, and snap connections.

Figure 53A:
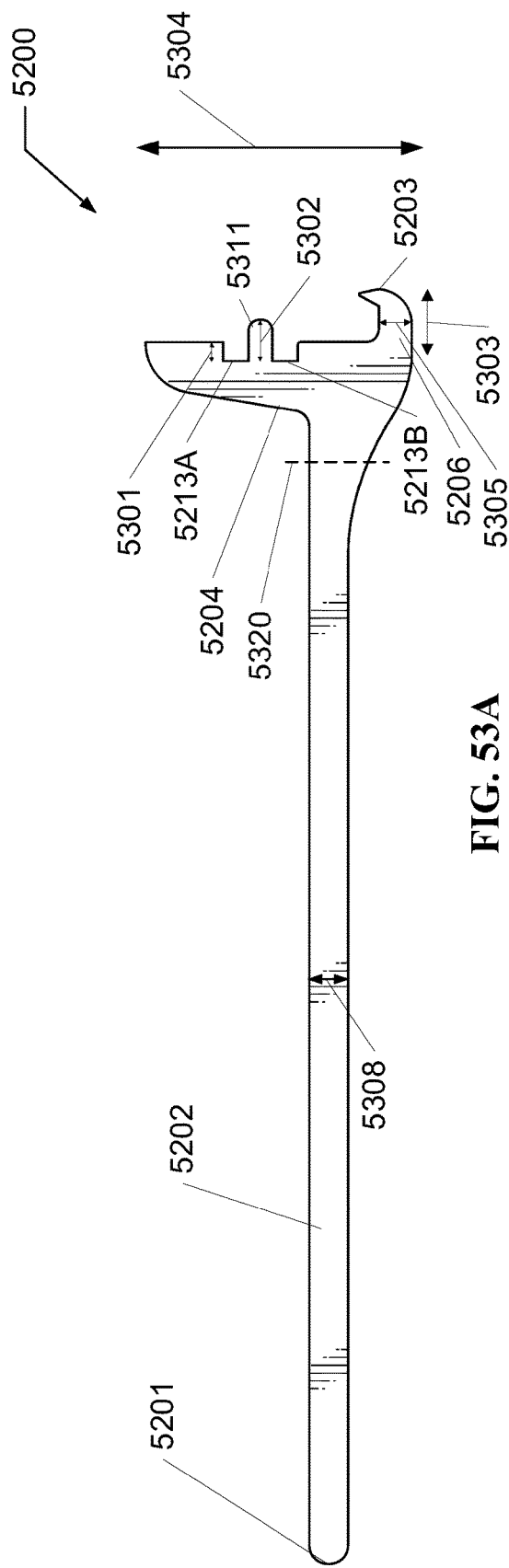
FIG. 53A shows a side view of an exemplary second shaft according to one embodiment of the present disclosure.

FIG. 53A shows a side view of the second shaft 5200, according to one embodiment of the present disclosure. In one or more embodiments, the channels 5213A-B include a depth 5301. The depth 5301 may measure at least about 1.0 mm, or about, 1.0-2.0 mm, 1.0-1.5 mm, 1.5-2.0 mm, or less than about 2.0 mm. In at least one embodiment, the prongs 5311 include a length 5302. The length 5302 may measure at least about 2.5 mm, 2.0-6.0 mm, 2.0-3.0 mm, 3.25 mm, 3.0-4.0 mm, 4.0-5.0 mm, 5.0-6.0 mm, or less than about 6.0 mm. In one or more embodiments, the hook 5206 includes a length 5303 that measures at least about 3.0 mm, or about 3.0-7.0 mm, 3.0-5.0 mm, 5.6 mm, 5.0-7.0 mm, or less than about 7.0 mm. In at least one embodiment, the hook 5206 includes a thickness 5305 that measures at least about 2.0 mm, or about 2.0-3.0 mm, 2.0-2.5 mm, 2.5 mm, 2.5-3.0 mm, or less than about 3.0 mm. In particular embodiments, the second portion includes a depth 5304. In various embodiments, the depth 5304 measures at least about 10.0 mm, or about 10.0-20.0 mm, 10.2 mm, 10.0-12.0 mm, 12.2 mm, 12.0-14.0 mm, 14.2 mm, 14.0-16.0 mm, 16.0-18.0 mm, 18.0-20.0 mm, or less than about 20.0 mm. In various embodiments, the first portion 5202 includes a depth 5308 that measures at least 2.0 mm, or 2.0-10.0 mm, 2.0-3.0 mm, 3.0 mm, 3.0-4.0 mm, 4.0-5.0 mm, 5.0-6.0 mm, 6.0-7.0 mm, 7.0-8.0 mm, 8.0-9.0 mm, or 9.0-10.0 mm, or less than about 10.0 mm.

Figure 53B:
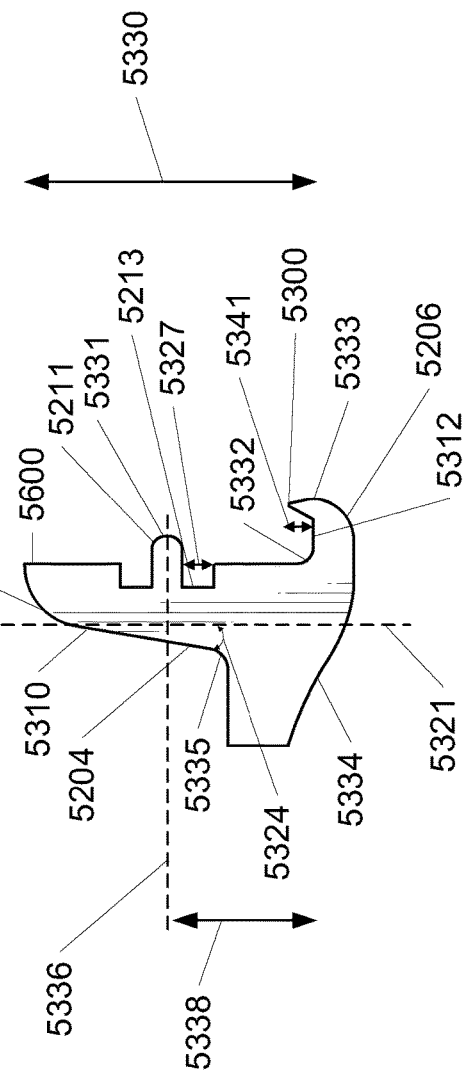
FIG. 53B shows a sectional view of an exemplary second shaft according to one embodiment of the present disclosure.

In various embodiments, a section line 5320 denotes a sectional view of the second shaft 5200 shown in FIG. 53B.

FIG. 53B shows a sectional view of the second shaft 5200. In at least one embodiment, the prongs 5211 includes a radius 5331. The radius 5331 may measure at least about 0.5 mm, or about 0.5-1.5 mm, 0.5-0.75 mm, 0.75 mm, 0.75-1.0 mm, 1.0-1.25 mm, 1.25-1.5 mm, or less than about 1.5 mm. In one or more embodiments, the hook 5206 includes a radius 5332 for transitioning the second portion 5204 to the hook 5206. The radius 5332 may measure at least about 0.5 mm, or about 0.5-1.5 mm, 0.5-1.0 mm, 1.0 mm, 1.0-1.5 mm, or less than about 1.5 mm.

In at least one embodiment, the hook 5206 includes a tip 5300. In at least one embodiment, the tip 5300 includes a radius 5333 for transitioning from the tip 5300 to the hook 5206. In particular embodiments, the radius 5333 measures at least about 0.5 mm, or about 0.5-1.5 mm, 0.5-1.0 mm, 1.0 mm, 1.0-1.5 mm, or less than about 1.5 mm. According to one embodiment, the second portion 5204 includes a radii 5334, 5335 for transitioning from the first portion 5202 (see FIG. 52) to the second portion 5204. In one or more embodiments, the radius 5334 measures at least about 10 mm, or about 10-30 mm, 10-20 mm, 20 mm, 20-30 mm or less than about 30 mm. In various embodiments, the radius 5335 measures at least about 0.5 mm, or about 0.5-1.5 mm, 0.5-1.0 mm, 1.0 mm, 1.0-1.5 mm, or less than about 1.5 mm. In particular embodiments, the second portion 5204 includes a radius 5336 that transitions a side surface 5310 of the second portion 5204 to the bottom surface 5600 (see also, FIG. 56). The radius 5336 may measure at least 3.0 mm, or about 3.0-5.0 mm, 3.0-4.0 mm, 4.0 mm, 4.0-5.0 mm, or less than about 5.0 mm.

In at least one embodiment, at least a portion of the side surface 5310 is oriented at an angle 5324 relative to a vertical axis 5321. In one or more embodiments, the angle 5324 measures at least about 5 degrees, about 5-45 degrees, 5-10 degrees, 10 degrees, 10-15 degrees, 15-20 degrees, 20-25 degrees, 25-30 degrees, 30-35 degrees, 35-40 degrees, 40-45 degrees, or less than about 45 degrees. In at least one embodiment, a separation distance 5341 between an inner surface 5312 of the hook 5206 and the tip 5300 measures at least about 1.0 mm, or about 1.0-2.0 mm, 1.0-1.5 mm, 1.5 mm, 1.5-2.0 mm, or less than about 2.0 mm. In one or more embodiments, the channel 5213 includes a width 5327 that measures at least about 0.5 mm, or about 0.5-4.0 mm, 0.5-1.0 mm, 1.0-1.5 mm, 1.5-2.0 mm, 2.0 mm, 2.0-2.5 mm, 2.5-3.0 mm, 3.0-3.5 mm, or 3.5-4.0 mm, or less than about 4.0 mm.

In various embodiments a separation distance 5330 between the side surface 5310 of the second portion 5204 and the inner surface 5312 of the hook 5206 measures at least about 5.0 mm, or about 5.0-25.0 mm, or 5.0-10.0 mm, 10.0-15.0 mm, 10.2 mm, 12.2 mm, 14.2 mm, 15.0-20.0 mm, 16.2 mm, 18.2 mm, or 20.0-25.0 mm, or less than about 25.0 mm. In one or more embodiments, a separation distance 5338 between a center axis 5336 of the prongs 5211 and the inner surface 5312 of the hook 5206 measures at least about 2.0 mm, or about 2.0-12.0 mm, 2.0-4.0 mm, 4.0-6.0 mm, 5.2 mm, 6.0-8.0 mm, 6.2 mm, 7.2 mm, 8.0-10.0 mm, 8.2 mm, 9.2 mm, or 10.0-12.0 mm, or less than about 12.0 mm.

Figure 54:
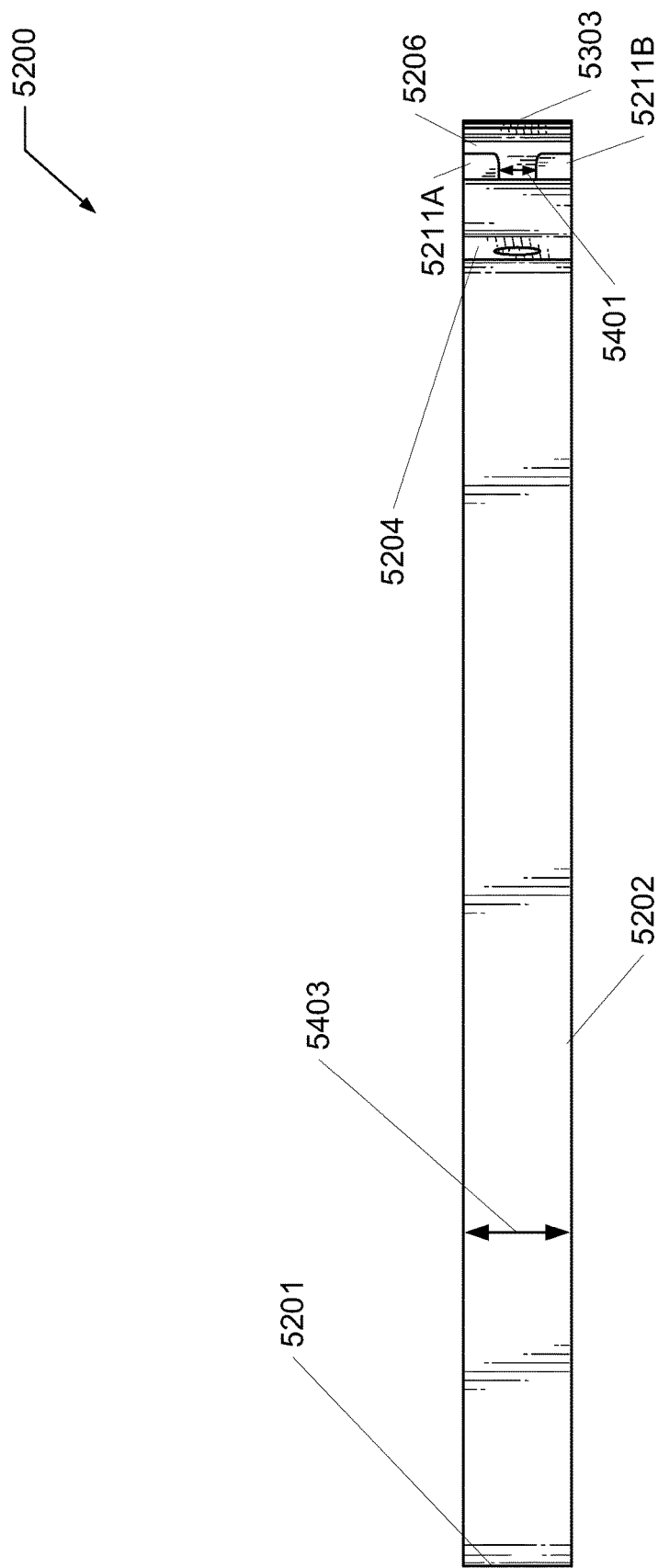
FIG. 54 shows a front view of an exemplary second shaft according to one embodiment of the present disclosure.

FIG. 54 shows a front view of the second shaft 5200, according to one embodiment of the present disclosure. In one or more embodiments, prongs 5211A, 5211B are separated by a separation distance 5401. In at least one embodiment, the separation distance 5401 measures at least about 0.5 mm, or about 0.5-6.0 mm, 0.5-1.0 mm, 1.0-1.5 mm, 1.5-2.0 mm, 2.0 mm, 2.0-2.5 mm, 2.5-3.0 mm, 3.0-3.5 mm, 3.1 mm, 3.5-4.0 mm, 4.0-4.5 mm, 4.5-5.0 mm, 5.0-5.5 mm, 5.5-6.0 mm, or less than about 6.0 mm. In various embodiments, the first portion 5202, second portion 5204, and hook 5206 include a thickness 5403 that measures at least about 2.0 mm, or about 2.0-12.0 mm, 2.0-4.0 mm, 4.0-6.0 mm, 6.0-8.0 mm, 7.5 mm, 8.0-10.0 mm, or 10.0-12.0 mm, or less than about 12.0 mm. In some embodiments, the first portion 5202, second portion 5204, and hook 5206 can vary in thickness. For example, the hook 5206 can demonstrate a decreased thickness as compared to the first portion 5202 and the second portion 5204.

Figure 55:
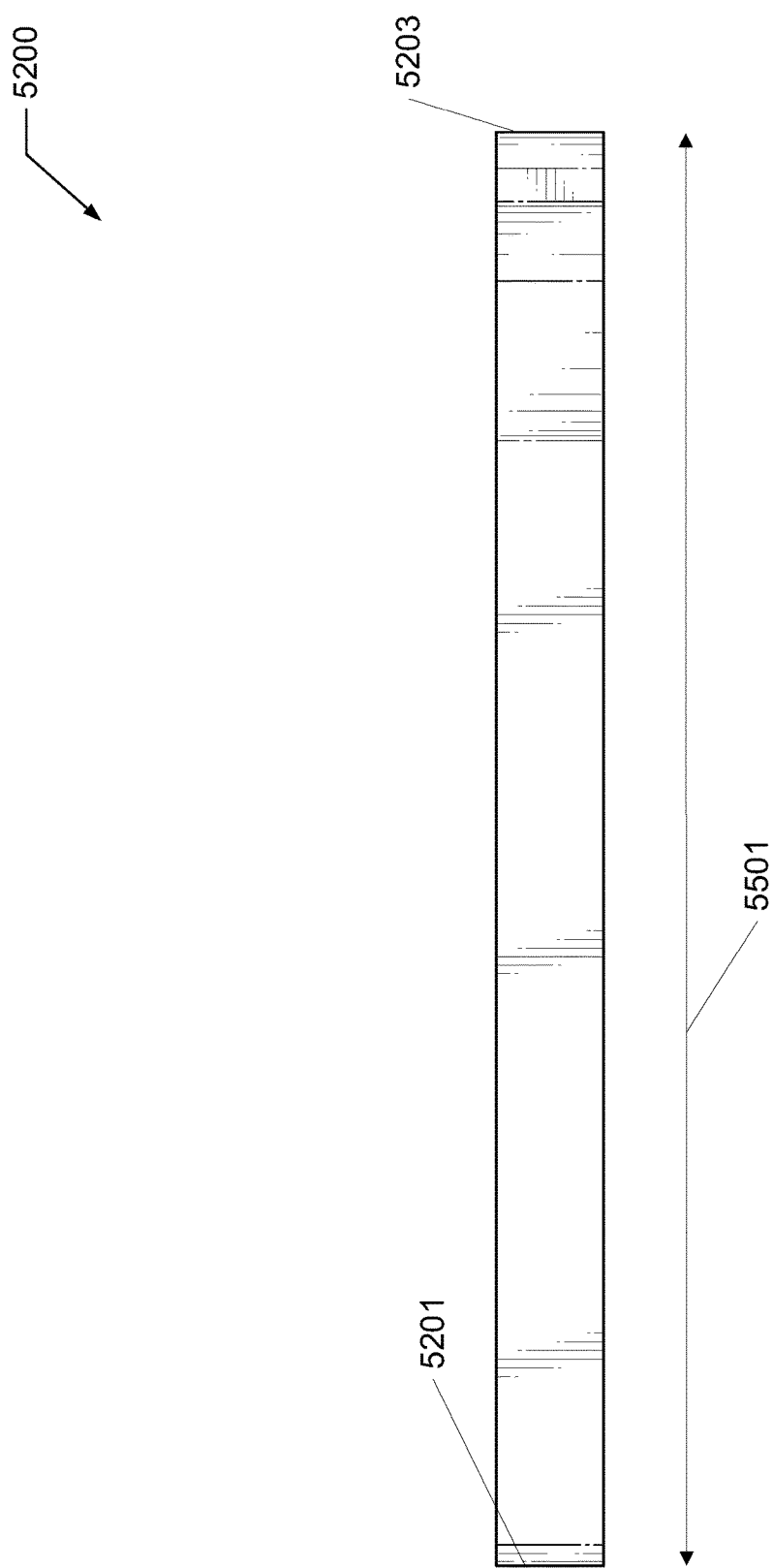
FIG. 55 shows a back view of an exemplary second shaft according to one embodiment of the present disclosure.

FIG. 55 shows a back view of the second shaft 5200, according to one embodiment of the present disclosure. In one or more embodiments, the second shaft 5200 includes a length 5501 between the ends 5201, 5203. In one or more embodiments, the length 5501 measures at least about 50.0 mm, or about 50.0-200.0 mm, or 50.0-75.0 mm, 75.0-100.0 mm, 99.1 mm, 100.0-125.0 mm, 125.0-150.0 mm, 150.0-175.0 mm, or 175.0-200.0 mm, or less than about 200.0 mm.

Figure 56A:
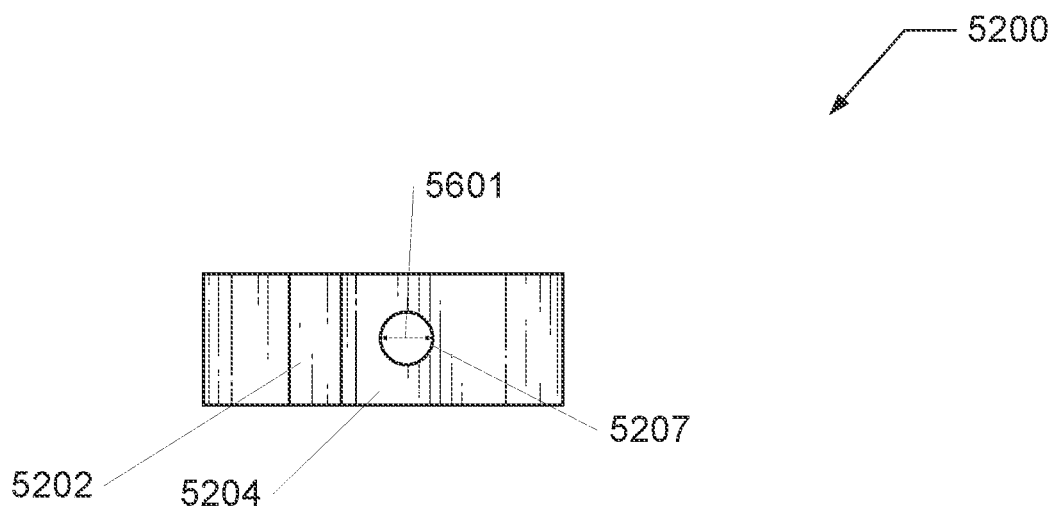
FIG. 56A shows a top view of an exemplary second shaft according to one embodiment of the present disclosure.

FIG. 56A shows a top view of the second shaft 5200, according to one embodiment of the present disclosure. In various embodiments, the aperture 5207 includes a diameter 5601 that measures about 2.5 mm, or about 2.5-3.5 mm, 2.5-3.0 mm, 3.1 mm, or about 3.0-3.5 mm, or less than about 3.5 mm.

Figure 56B:
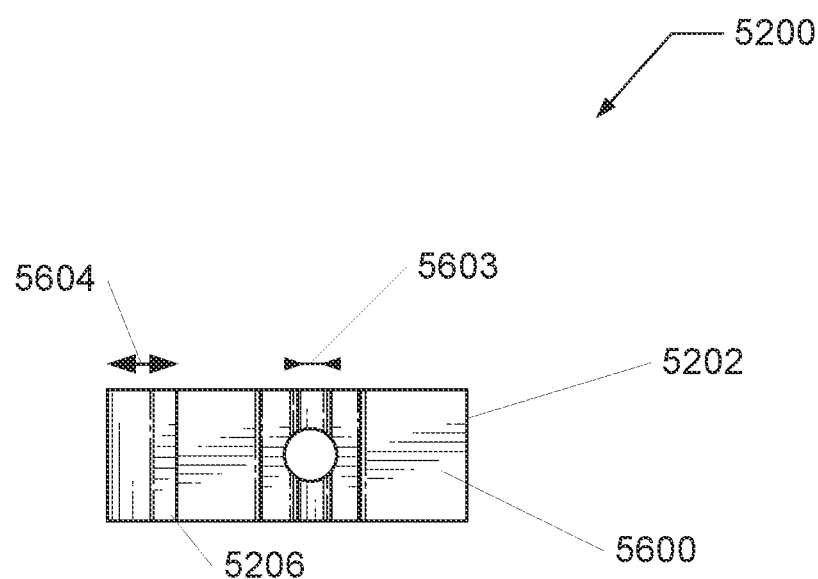
FIG. 56B shows a bottom view of an exemplary second shaft according to one embodiment of the present disclosure.

FIG. 56B shows a bottom view of the second shaft 5200, according to one embodiment of the present disclosure. In one or more embodiments, the second portion 5204 includes a bottom surface 5600.

In one or more embodiments, the prongs 5211A-B include a width 5603. In at least one embodiment, the width 5603 measures at least about 1.0 mm, or about 1.0-3.0 mm, 1.0-1.5 mm, 1.5 mm, 1.5-2.0 mm, 2.49 mm, 2.0-2.5 mm, or about 2.5-3.0 mm, or less than about 3.0 mm. In various embodiments, the hook 5206 includes a width 5604 that measures at least about 2.0 mm, or about 2.0-6.0 mm, 2.0-4.0 mm, 4.0 mm, 4.0-6.0 mm, or less than about 6.0 mm.

Figure 57:
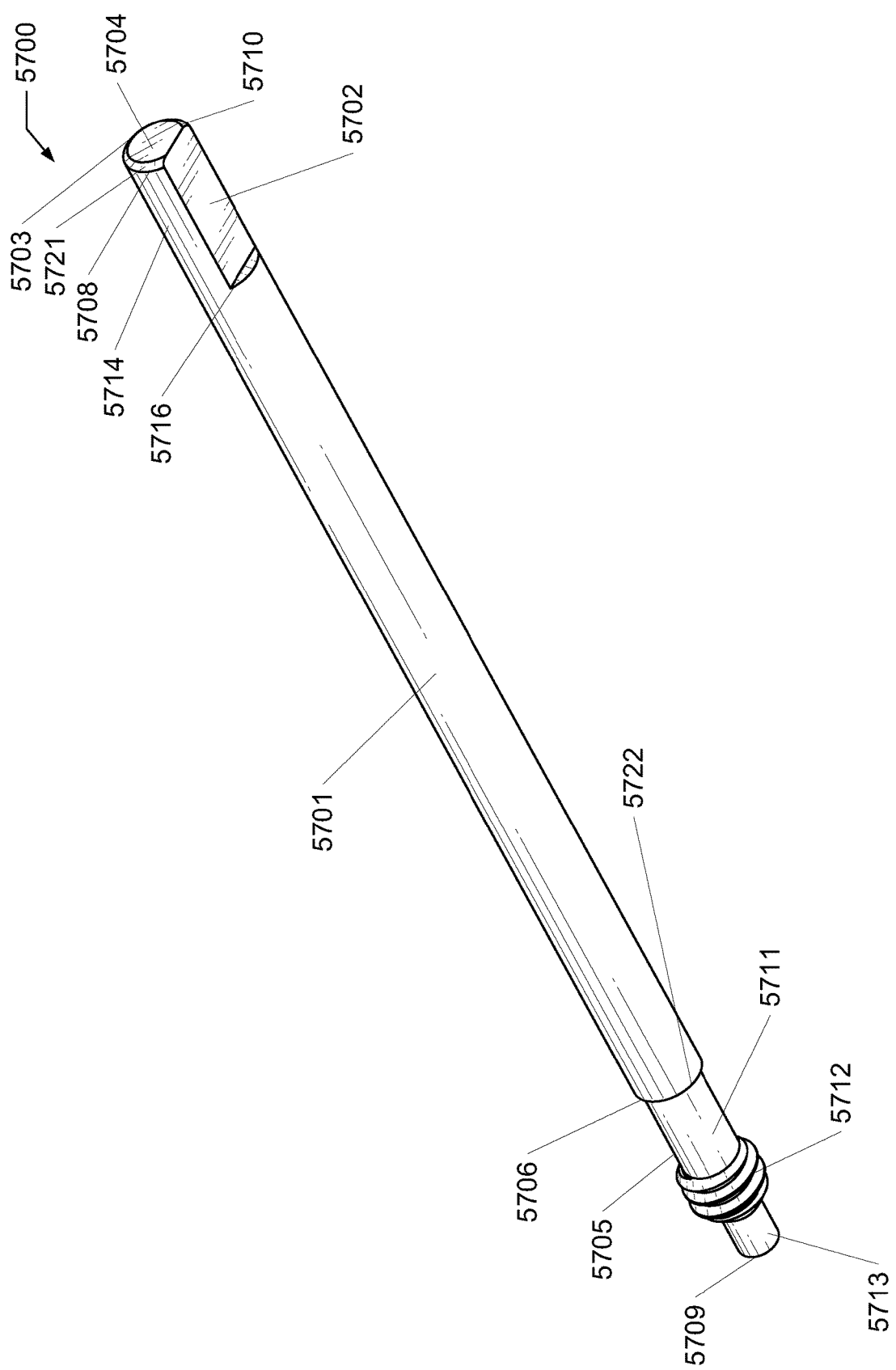
FIG. 57 shows a perspective view of an exemplary rod according to one embodiment of the present disclosure.

FIG. 57 shows a perspective view of a rod 5700, according to one embodiment of the present disclosure. According to one embodiment, the rod 5700 is configured to be inserted through the first shaft 4700 (FIG. 47) and the second shaft 5200 (FIG. 52). In some embodiments, the rod 5700 is configured to be inserted through the first shaft 4700 and a pin 5705 connected to the rod 5700 is configured to be inserted through the second shaft 5200. In at least one embodiment, the rod 5700 is configured to apply (e.g., or to cause the pin 5705 to apply) a pushing force to the spacer 3200 (FIG. 32) or a staple described herein (for example, staple 100 shown in FIG. 1).

In particular embodiments, the rod 5700 includes a body 5701. In various embodiments, the body 5701 extends between a first end 5703 and a second end 5706. In one or more embodiments, the body 5701 includes an indentation 5702 and a top surface 5704. In at least one embodiment, the rod 5700 includes a pin 5705. According to one embodiment, the pin 5705 is a separate component that is received by the rod 5700. For example, the rod 5700 receives the pin 5705 within an aperture (not shown) at the edge 5722. In this example, the pin 5705 can secure to the rod 5700 by any suitable means, including, but not limited to, press fitting, adhesives, magnetism, welding, threading, snap fitting, or bayonet fitting. In one or more embodiments, the rod 5700 receives the pin 5705 at the second end 5706, and the pin 5705 extends to an end 5709.

In at least one embodiment, the body 5701 is cylindrical in shape (e.g., or includes any other suitable shape, such as a prism or other solid of revolution). In various embodiments, toward the first end 5703 the body 5701 includes a first edge 5708 and a second edge 5710. In one or more embodiments, the body 5701 includes a sloped surface 5721 between the first edge 5708 and the second edge 5710. In various embodiments, the sloped surface 5721, the first edge 5708, and/or the second edge 5710 include a chamfer, curve, or other suitable modification for transitioning a surface 5714 of the body 5701 to the sloped surface 5721, and for transitioning the sloped surface 5721 to the top surface 5704. In at least one embodiment, toward the second end 5706 the body 5701 includes an edge 5722. According to one embodiment, the edge 5722 transitions the body 5701 to the pin 5705. The edge 5722 may include any suitable modification or structure (e.g., bevel, curve, etc.) for transitioning the body 5701 to the pin 5705.

In one or more embodiments, the indentation 5702 extends from an edge 5716 body 5701 to the top surface 5704. In at least one embodiment, the indention 5702 is configured to allow a handle to rotate the rod 5700 (for example, handle 6500 shown in FIG. 65).

In particular embodiments, the pin 5705 includes a pin body 5711, threads 5712 that extend from the pin body 5711, and a second body 5713 configured to apply a pushing force to a second shaft 5200 (FIG. 52), a spacer 3200 (FIG. 32), and/or a staple described herein (for example, staple 100 shown in FIG. 1). The second body 5713 and the body 5711 may be integrally formed or connected via any suitable mechanism (e.g., threads, adhesives, welds, press fittings, snap fittings, bayonet fittings, etc.). The second body 5713 and the body 5711 may include a generally cylindrical shape or any suitable shape or shape combination (e.g., other solids of rotation, polygon-based prisms, etc.).

Figure 58:
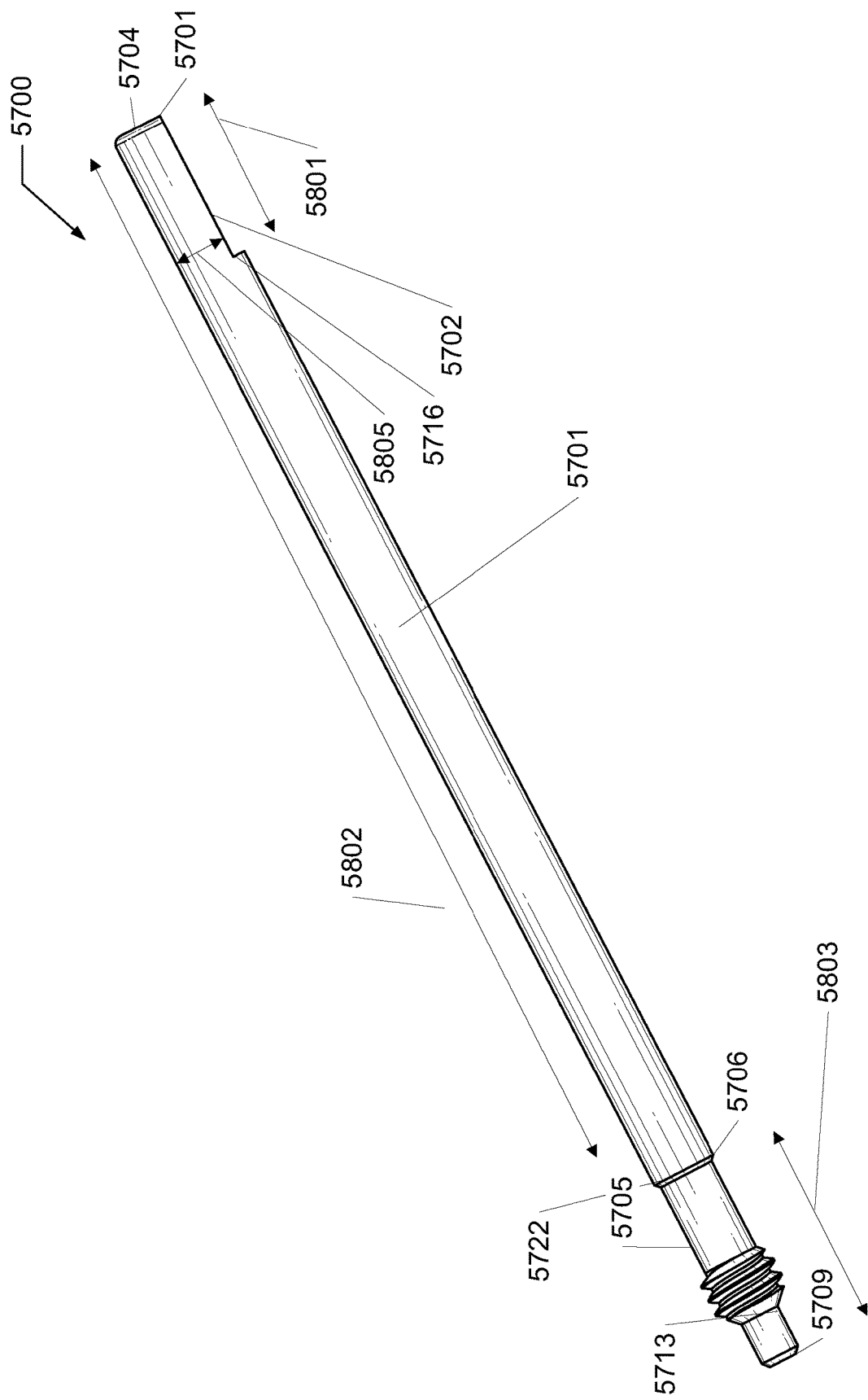
FIG. 58 shows a side view of an exemplary rod according to one embodiment of the present disclosure.

FIG. 58 shows a side view of the rod 5700, according to one embodiment of the present disclosure. In at least one embodiment, the rod 5700 includes an indentation length 5801 between the edge 5716 and the first end 5703. In particular embodiments, the indentation length 5801 measures at least about 10.0 mm, or about 10.0-14.0 mm, 10.0-12.0 mm, 12.5 mm, 12.0-14.0 mm, or less than about 14.0 mm. In various embodiments, the body 5701 includes a length 5802 between the first end 5703 and the second end 5706. In at least one embodiment, the length 5802 measures at least about mm, or about 90.0-110.0 mm, 90.0-95.0 mm, 94.4 mm, 95.0-100.0 mm, 100.0-105.0 mm, 105.0-110.0 mm, or less than about 110.0 mm. In one or more embodiments, the pin 5705 includes a length 5803 that measures a distance from which the pin 5705 extends from the end 5706 of the body 5701. The length 5803 may measure at least about 14.0 mm, or about 14.0-18.0 mm, 14.0-16.0 mm, 16.6 mm, 16.0-18.0 mm, or less than about 18.0 mm. In various embodiments, the indentation 5702 includes a depth 5805. The length 5805 may measure at least about 3.0 mm, or about 3.0-5.0 mm, 3.0-4.0 mm, 4.28 mm, 4.0-5.0 mm, or less than about 5.0 mm.

Figure 59:
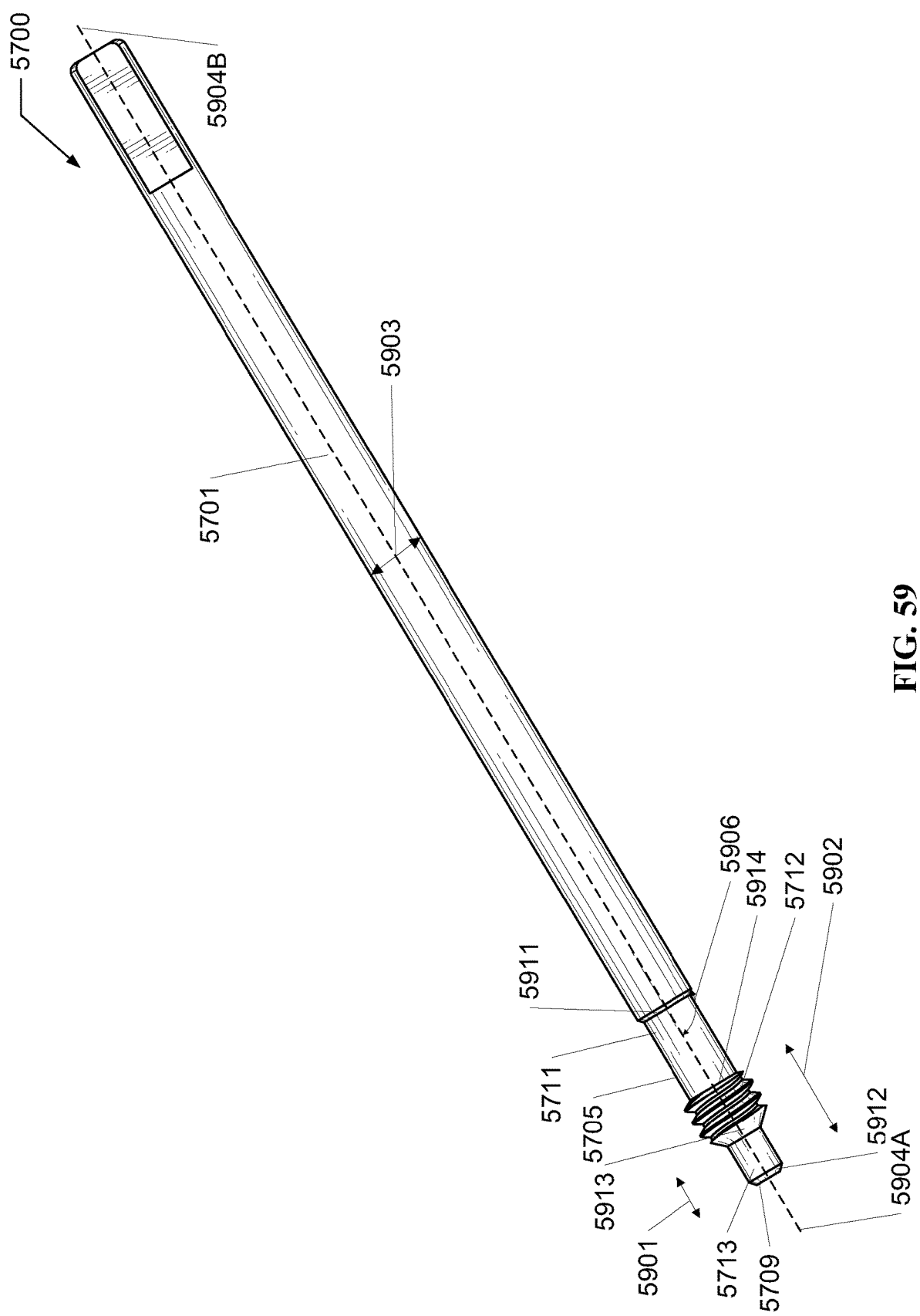
FIG. 59 shows a front view of an exemplary rod according to one embodiment of the present disclosure.

FIG. 59 shows a front view of the rod 5700, according to one embodiment of the present disclosure. In various embodiments, the pin 5705 includes chamfers 5911, 5912, and 5913. The chamfers 5911, 5912, and 5913 may each include an angle 5906 relative to a center axis 5904A-B of the rod 5700. In various embodiments, the angle 5906 measures at least about 35.0 degrees, 35.0-55.0 degrees, 35.0-40.0 degrees, 40.0-45.0 degrees, 45.0-50.0 degrees, 50.0-55.0 degrees, or less than about 55.0 degrees. The chamfers 5911, 5912, 5913 can demonstrate equal or variable angles 5906.

In at least one or more embodiments, the pin 5705 includes a length 5901 and 5902. In various embodiments, the length 5901 extends from the end 5709 to the chamfer 5913, and the length 5901 measures at least 3.0 mm, or about 3.0-5.0 mm, 3.0-4.0 mm, 4.0 mm, 4.0-5.0 mm, or less than about 5.0 mm. In particular embodiments, the length 5902 extends from the end 5709 to a first thread 5914 of the threads 5712. In at least one embodiment, the length 5902 measures at least about 8.0 mm, 8.0-10.0 mm, 8.0-9.0 mm, 9.0 mm, 9.0-10.0 mm, or less than about 10.0 mm.

In at least one embodiment, the body 5701 includes a diameter 5903. The diameter 5903 may measure at least about 4.0 mm, or about 4.0-6.0 mm, 4.0-5.0 mm, 5.35 mm, 5.0-6.0 mm, or less than about 6.0 mm.

Figure 60:
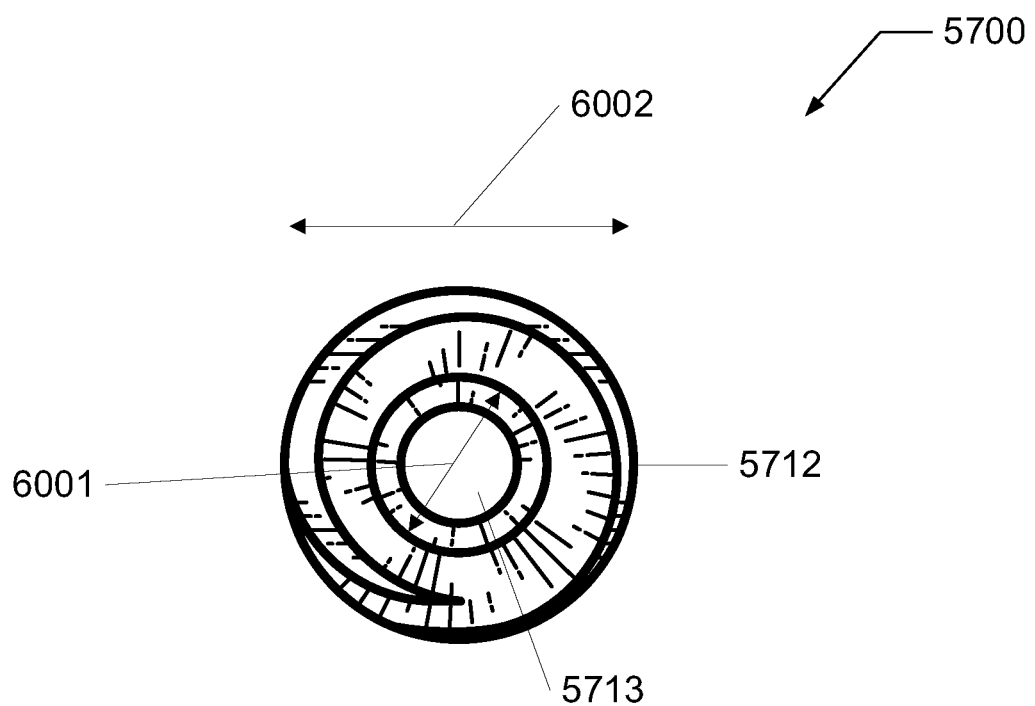
FIG. 60 shows a bottom view of an exemplary rod according to one embodiment of the present disclosure.

FIG. 60 shows a bottom view of the rod 5700, according to one embodiment of the present disclosure. In particular embodiments, the second body 5713 of the pin 5705 includes a diameter 6001 that measures at least about 2.0 mm, or about 2.0-4.0 mm, 2.0-3.0 mm, 3.10 mm, 3.0-4.0 mm, or less than about 4.0 mm. In various embodiments, the threads 5712 include a diameter 6002 that measures at least about 4.0 mm, or about 4.0-7.0 mm, 4.0-5.0 mm, 5.0-6.0 mm, 6.15 mm, 6.0-7.0 mm, or less than about 7.0 mm.

Figure 61:
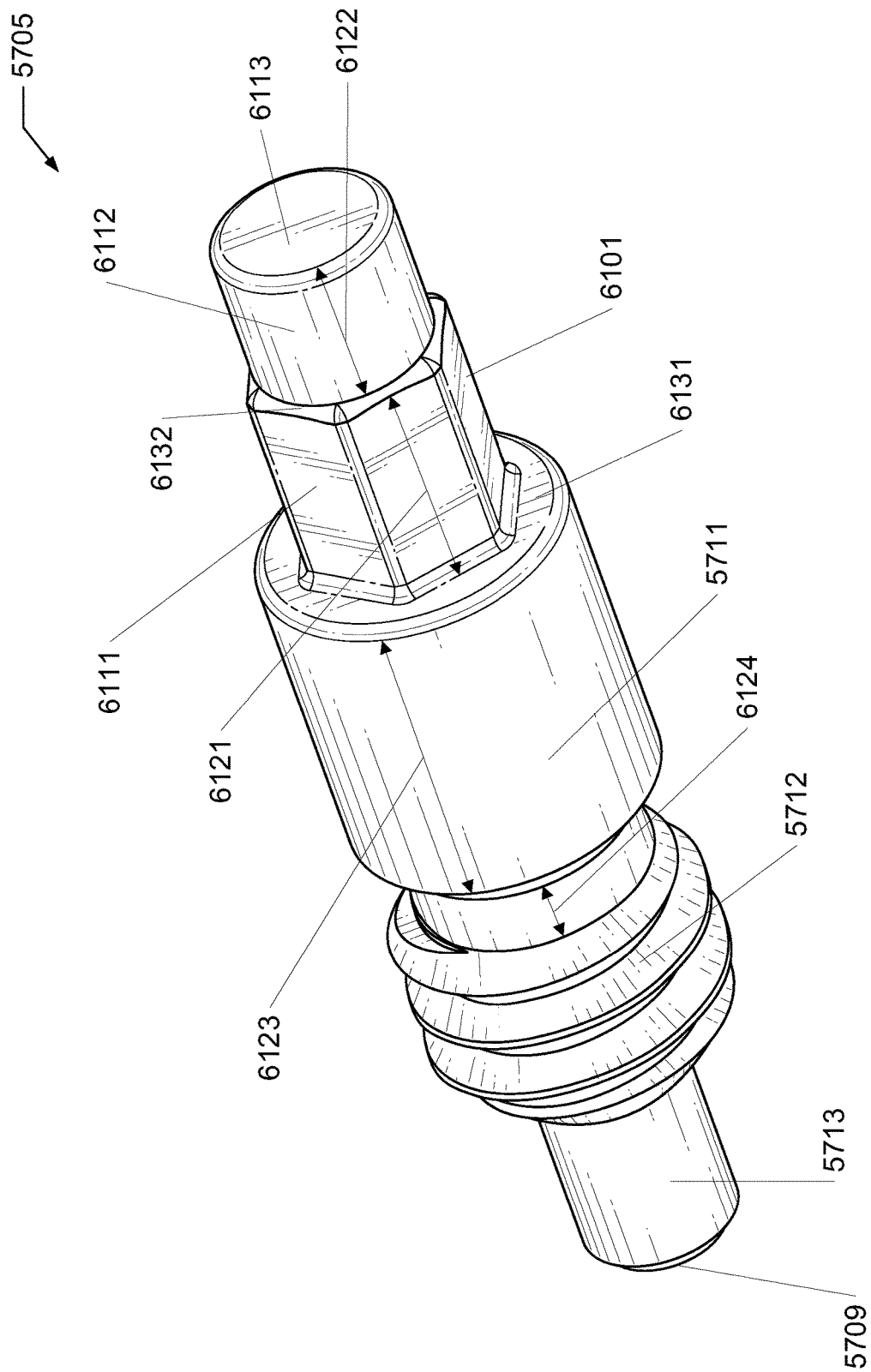
FIG. 61 shows a perspective view of an exemplary pin according to one embodiment of the present disclosure.

FIG. 61 shows a perspective view of the pin 5705, according to one embodiment of the present disclosure. In particular embodiments, the pin 5705 can be referred to as a rod screw. In at least one embodiment, a thread quantity of the threads 5712 is at least about 3 threads, 3-30 threads, 20 threads, or less than about 30 threads. In various embodiments, a diameter of the threads 5712 is at least about 0.1 inches, or about 0.1-0.5 inches, 0.1-0.2 inches, 0.2-0.3 inches, 0.25 inches, 0.3-0.4 inches, 0.4-0.5 inches, or less than about 0.5 inches.

In various embodiments, between a surface 6131 and a top surface 6113, the pin 5705 includes an attachment portion 6101 that is configured to be received by the drill pin 5700 (FIG. 57). In one or more embodiments, the attachment portion 6101 includes a top surface 6113, a head 6112, and a base 6111. In at least one embodiment, the base 6111 and the head 6112 can conform to any three-dimensional shape or shape combination (e.g., hexagonal, rectangular, cylindrical, square, octagonal, etc.). The base 6111 may include a length 6121, which may extend from a surface 6131 to an edge 6132. In various embodiments, the length 6121 may measure at least about 3.0 mm, or about 3.0-6.0 mm, 3.0-4.0 mm, 4.5 mm, 4.0-5.0 mm, 5.0-6.0 mm, or less than about 6.0 mm. In particular embodiments, the attachment portion 6101 includes a length 6122, which measures the distance between the edge 6132 and the top surface 6113. The length 6122 may measure at least about 2.0 mm, 2.0-4.0 mm, 2.0-3.0 mm, 3.0 mm, 3.0-4.0 mm, or less than about 4.0 mm. In various embodiments, the pin body 5711 extends a length 6123. The length 6123 may measure at least about 5.0 mm, 5.0-7.0 mm, 5.0-6.0 mm, 6.5 mm, 6.0-7.0 mm, or less than about 7.0 mm.

In at least one embodiment, the pin 5705 includes a separation distance 6124, between the threads 5712 and the pin body 5711. The separation distance 6124 may measure at least about 0.0 mm, 0.0-3.0 mm, 0.0-1.0 mm, 1.3 mm, 1.0-2.0 mm, 2.0-3.0 mm, or less than about 3.0 mm.

Figure 62A:
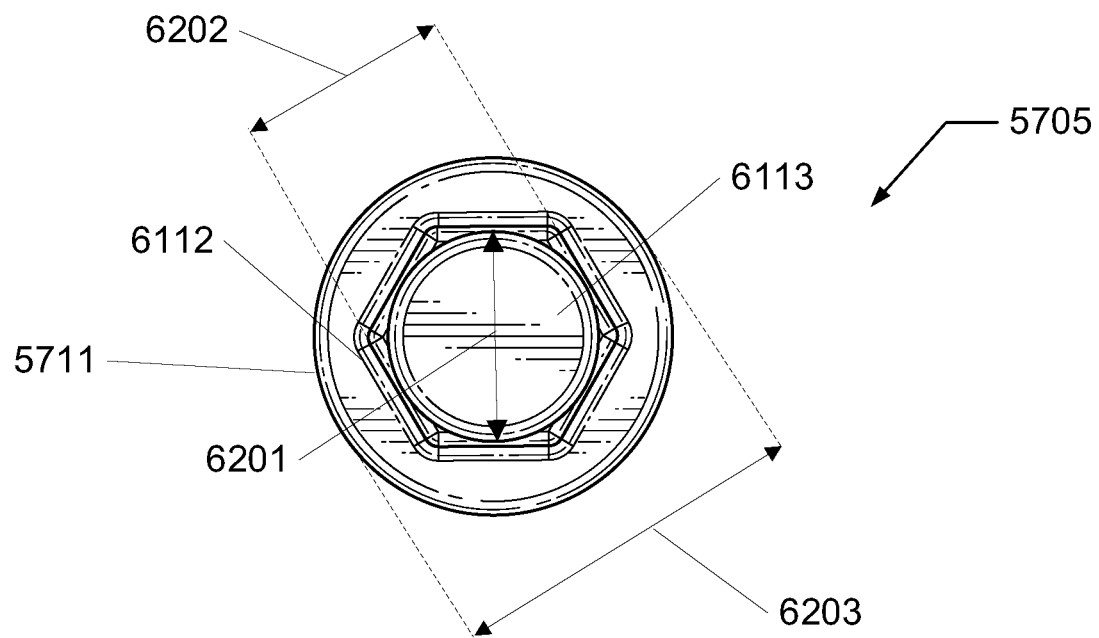
FIG. 62A shows a top view of an exemplary pin according to one embodiment of the present disclosure.

FIG. 62A shows a top view of the pin 5705, according to one embodiment of the present disclosure. In various embodiments, the top surface 6113 includes a diameter 6201 that measures at least about 2.0 mm, or about 2.0-4.0 mm, 2.0-3.0 mm, 3.63 mm, 3.0-4.0 mm, or less than about 4.0 mm. In at least one embodiment, the base 6112 includes a diameter 6202 that measures at least about 2.0 mm, or about 2.0-4.0 mm, 2.0-3.0 mm, 3.8 mm, 3.0-4.0 mm, or less than about 4.0 mm. In one or more embodiments, the pin body 5711 includes a diameter 6203 that measures at least about 5.0 mm, or about 5.0-7.0 mm, 5.0-6.0 mm, 6.2 mm, 6.0-7.0 mm, or less than about 7.0 mm.

Figure 62B:
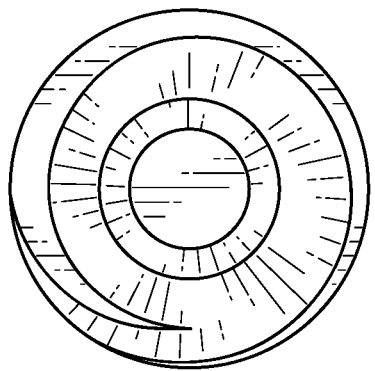
FIG. 62B shows a bottom view of an exemplary pin according to one embodiment of the present disclosure.

FIG. 62B show a bottom view of the pin 5705, according to one embodiment of the present disclosure.

Figure 63:
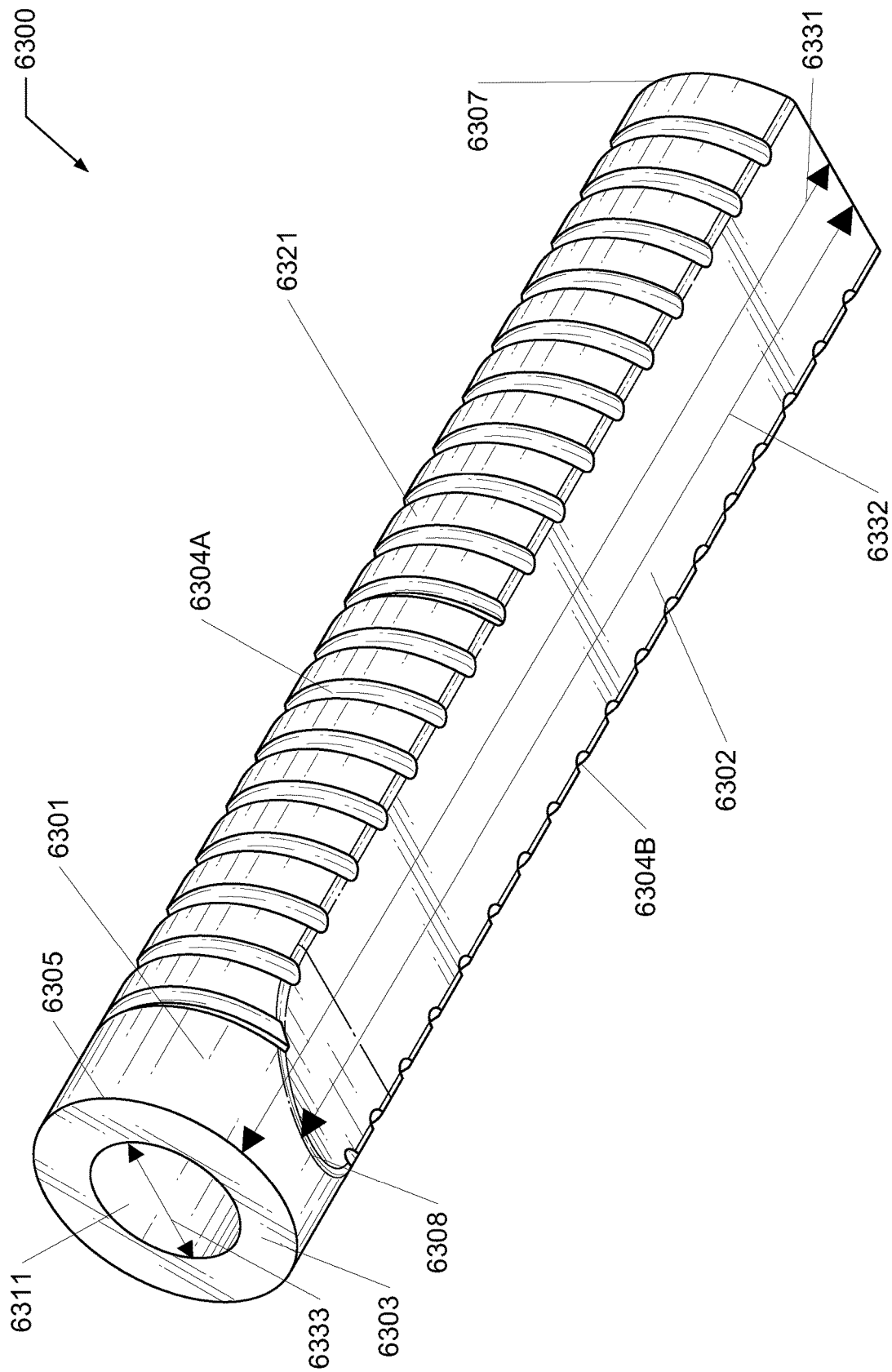
FIG. 63 shows a perspective view of an exemplary sleeve according to one embodiment of the present disclosure.

FIG. 63 shows a perspective view of a sleeve 6300, according to one embodiment of the present disclosure. In at least one embodiment, the sleeve 6300 can be referred to as a sleeve portion. In various embodiments, the sleeve 6300 is configured to slide over portions of the first shaft 4700 (FIG. 47) and the second shaft 5200 (FIG. 52) and, thereby, maintain a position of the first shaft 4700 relative to the second shaft 5200.

In particular embodiments, the sleeve 6300 includes a body 6301 between a first end 6305 and a second end 6307. In one or more embodiments, the body 6301 includes a generally cylindrical shape or includes any suitable shape or shape combination (e.g., solids of revolution, rectangular prisms, etc.). In at least one embodiment, the body includes indentations 6302, 6304A-B. In at least one embodiment, the indentations 6304A-B define ridges 6321 for improving grip of the sleeve 6300.

In one or more embodiments, the body 6301 includes a top surface 6303. In various embodiments, the top surface 6303 includes an aperture 6311 that extends from the first end 6205 to the second end 6307. In one or more embodiments, the aperture 6311 includes a generally cylindrical shape, or includes any suitable shape or shape combination (for example, solids of revolution, polygon-derived prisms, etc.).

In various embodiments, the body 6301 includes a length 6331 between the first end 6305 and the second end 6307. In at least one embodiment, the length 6331 measures at least about 90.0 mm, 90.0-110.0 mm, 90.0-100.0 mm, 100.0 mm, 100.0-110.0 mm, or less than about 110.0 mm. According to one embodiment, the indentation 6302 includes a length 6332 between the second end 6307 and an edge 6308 of the indentation 6302. In one or more embodiments, the length 6332 measures at least 93 mm, or about 93.0-95.0 mm, 93.0-94.0 mm, 94.83 mm, 94.0-95.0 mm, or less than about 95.0 mm. According to one embodiment, the aperture 6311 includes a diameter 6333 that measures at least about 9.0 mm, 9.0-13.0 mm, 9.0-10.0 mm, 10.0-11.0 mm, 11.3 mm, 11.0-12.0 mm, 12.0-13.0 mm, or less than about 13.0 mm.

Figure 64:
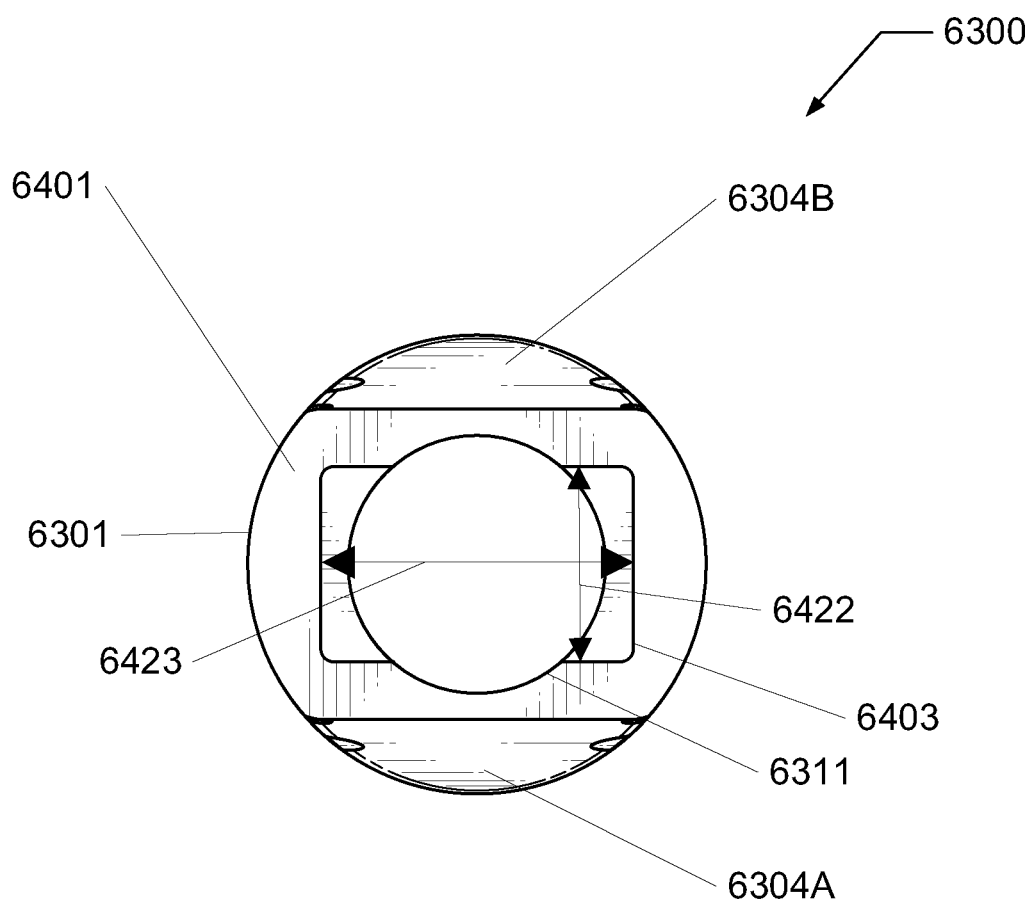
FIG. 64 shows a bottom view of an exemplary sleeve according to one embodiment of the present disclosure.

FIG. 64 shows a bottom view of the sleeve 6300, according to one embodiment of the present disclosure. In at least one embodiment, the body 6301 includes a bottom surface 6401. In one or more embodiments, the body 6301 includes a second aperture 6403 that extends from the bottom surface 6401 into the aperture 6311. In various embodiments, the second aperture 6403 includes a generally rectangular shape, or includes any suitable shape or shape combination (for example, circular, square, trapezoid, etc.). In at least one embodiment, the second aperture 6403 is configured to receive a portion of the first shaft 4700 (FIG. 47) and a portion of the second shaft 5200 (FIG. 52). In some embodiments, the second aperture 6403 allows the sleeve 6300 to be slid over the first shaft 4700 and the second shaft 5200 such that the second aperture 6403 receives a second portion 4704 of the first shaft 4700 and a second portion 5204 of the second shaft 5200. In some embodiments, the second aperture 6403 extends into the body 6301 to a depth of at least about 0.5 mm, or about 0.5-5.0 mm, 0.5-1.0 mm, 1.0-2.0 mm, 2.0-3.0 mm, 3.0 mm, 3.0-4.0 mm, or 4.0-5.0 mm, or less than about 5.0 mm.

In one or more embodiments, the second aperture 6403 includes a length 6423 that measures at least about 11.0 mm, 11.0-15.0 mm, 11.0-12.0 mm, 12.0-13.0 mm, 13.6 mm, 13.0-14.0 mm, 14.0-15.0 mm, or less than about 15.0 mm. In one or more embodiments, the second aperture 6403 includes a width 6422 that measures at least about 7.0 mm, 7.0-9.0 mm, 7.0-8.0 mm, 8.5 mm, 8.0-9.0 mm, or less than about 9.0 mm.

FIG. 65A shows a perspective view of a handle 6500, according to one embodiment of the present disclosure. In at least one embodiment, the handle 6500 is referred to as a "knob" and is configured to secure the staple installation tool 2600 to the staple 2601. According to one embodiment, the handle 6500 is configured to attach to and control rotation of the rod 5700 (FIG. 57).

In various embodiments, the handle 6500 includes a head 6501, a body 6502, and a base 6503. In various embodiments, the head 6501, body 6502, and base 6503 connect at edge locations 6521 and 6522. In at least one embodiment, the head 6501 includes one or more indentations 6512, a top surface 6511, and divots 6513. The indentations 6512 may include any suitable shape (e.g., circular, rectangular, square). In one example, the head 6501 includes two indentations 6512 on opposed sides, and each indentation 6512 includes a generally circular shape. In various embodiments, the one or more indentations 6512 and the divots 6513 are configured to improve grip of the handle 6500.

FIG. 65B shows a side view of the handle 6500, according to one embodiment of the present disclosure. In particular embodiments, the head 6501 includes absences 6532. In various embodiments, the absences 6532 occur around the head 6501. In one or more embodiments, the edge 6522 and an edge 6523 are chamfers with angles, relative to the center axis of handle 6500, measuring at least about 35.0 degrees, 35.0-55.0 degrees, 35.0-40.0 degrees, 40.0-45.0 degrees, 45.0-50.0 degrees, 50.0-55.0 degrees, or less than about 55.0 degrees.

In at least one embodiment of the present disclosure, the handle 6500 includes length 6541, 6542, and 6543. In particular embodiments, the length 6541 measures a distance between the edge 6523 and the edge 6522. The length 6541 may measure at least about 19.0 mm, or about 19.0-21.0 mm, 19.5 mm, 19.0-20.0 mm, 20.0-21.0 mm, 21.0 mm, or less than about 21.0 mm. In various embodiments, the length 6542 measures a distance between the edge 6521 and the edge 6522. The length 6542 may measure at least 49.0 mm, or about 49.0-50.0 mm, 49.0-49.5 mm, 49.5 mm, 49.5-50.0 mm, or less than about 50.0 mm. In one or more embodiments, the length 6543 measures a distance between the top surface 6511 and the edge 6521. The length 6543 may measure at least about 30 mm, or about 30-40 mm, 30-35 mm, 35 mm, 35-40 mm, or less than about 40 mm.

Figure 66:
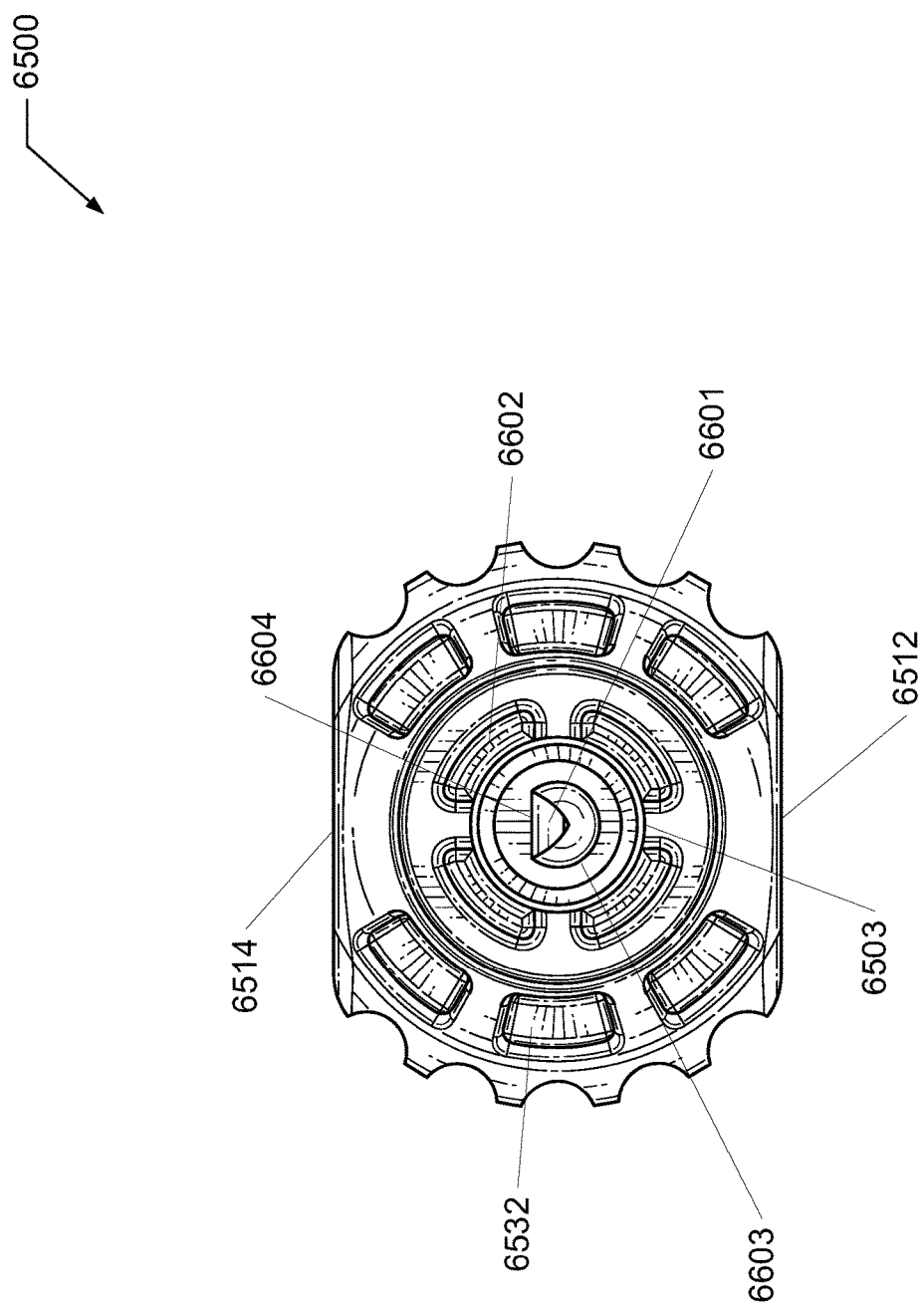
FIG. 66 shows a bottom view of an exemplary handle according to one embodiment of the present disclosure.

FIG. 66 shows a bottom view of the handle 6500, according to one embodiment of the present disclosure. In particular embodiments, the base 6503 includes an aperture 6601. In at least one embodiment of the present disclosure, the aperture 6601 is bounded by an edge 6604 and an edge 6603, where the edge 6604 is linear and the edge 6603 is circular. In particular embodiments, the connection of edges 6603 and 6604 create a circular segment for the aperture 6601. In various embodiments, the handle 6500 includes recessed portions 6602 that are distributed about the handle 6500 at 90 degree increments (e.g., or any other suitable increment. In at least one embodiment, the recessed portions 6602 reduce a mass of the handle 6500, thereby improving precision and accuracy of handle movements by a user.

Figure 74:
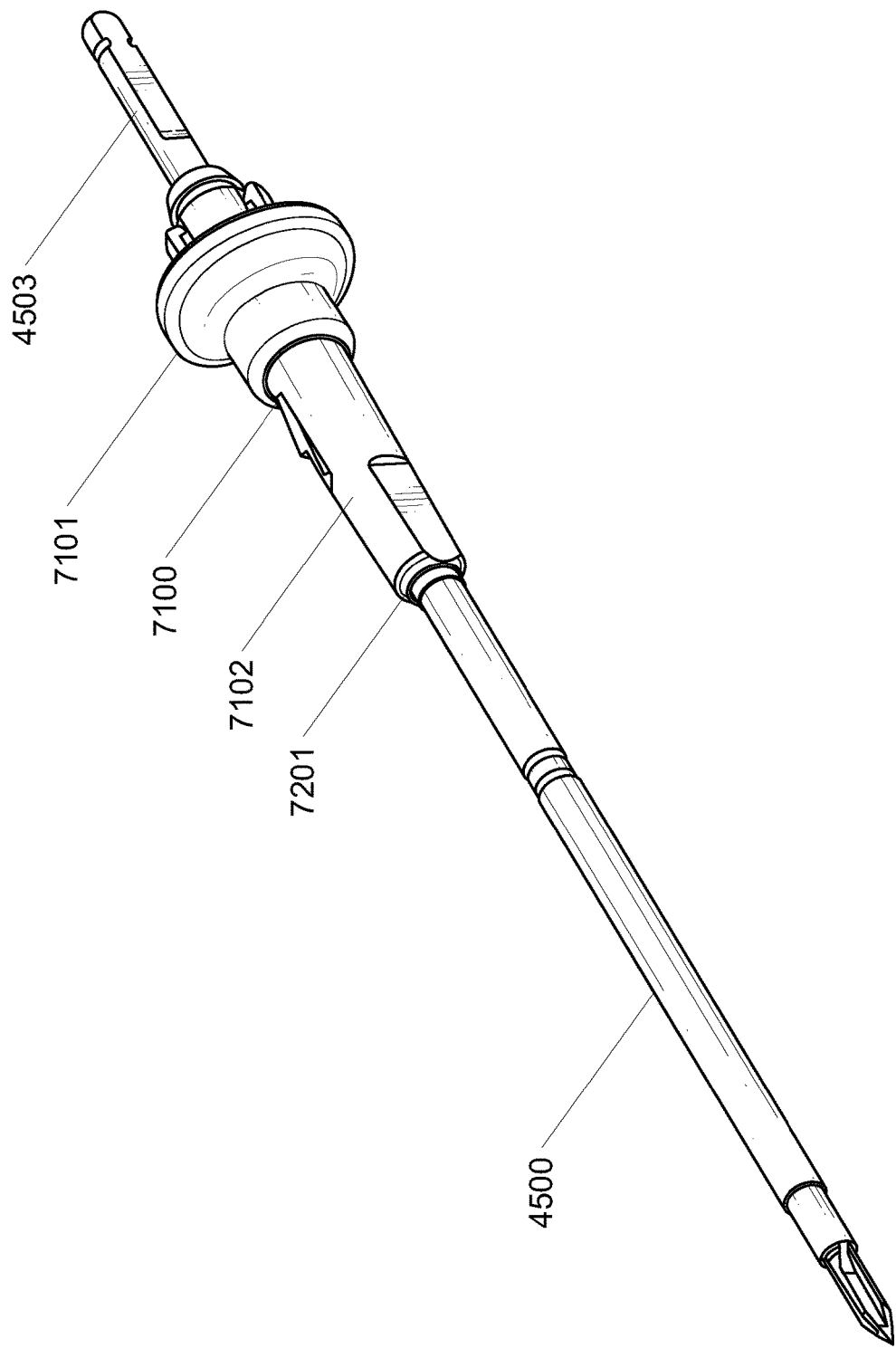
FIG. 74 shows a perspective view of an exemplary drill pin and an exemplary tool adapter configured to an unlocked state according to one embodiment of the present disclosure.

FIG. 67 shows a perspective view of an adapter pin 4503, according to one embodiment of the present disclosure. In at least one embodiment, the adapter pin 4503 is received by a drill pin 4500 (FIG. 45) and a tool adapter 7100 (FIG. 71, see also FIG. 74). According to one embodiment, the adapter pin 4503 allows for rapid, secure connection and disconnection of a tool (e.g., such as a drill or other driver) or a tool adapter 7100 to the drill pin 4500.

In various embodiments, the adapter pin 4503 includes a shaft 6702 between a first end 6701 and a second end 6703. According to one embodiment, the shaft 6702 includes a generally cylindrical shape. In one or more embodiments, the shaft 6702 includes a first side portion 6705 toward the first end 6701 and includes a second side portion 6707 toward the second end 6703. In at least one embodiment, the first end 6701 is configured to be received by the drill pin 4500 or the tool adapter 7100. In various embodiments, toward the first end 6701 the first side portion 6705 includes threads 6709 for engaging with threaded elements of the drill pin 4500, tool adapter 7100, or other tool. According to one embodiment, the threads 6709 include a radius 6711 of at least about 0.2 mm, or about 0.1-3.0 mm, 0.2-3.0 mm, 0.1-0.5 mm, 0.5-1.0 mm, 0.6 mm, 1.0-1.5 mm, 1.5-2.0 mm, 2.0-2.5 mm, or 2.5-3.0 mm, or less than about 3.0 mm. In one or more embodiments, toward the second end 6703, the second side portion 6707 includes a stop 6713. According to one embodiment, the stop 6713 is configured to receive a hook, prong, or other structure for locking the adapter pin 4503 to the tool adapter 7100 (e.g., or a tool, such as a drill).

In at least one embodiment, the shaft 6702 includes sloped portions 6715A, 6715B for transitioning the shaft 6702 to the first side portion 6705 and the second side portion 6707. In one or more embodiments, the first side portion 6705 and the second side portion 6707 demonstrate a generally cylindrical shape between a first edge 6717A, B and a second edge 6719A, B. According to one embodiment, the first side portion 6705 and the second side portion 6707 include a flat surface 6721A, B between the first edge 6717A, B and the second edge 6719A, B. In at least one embodiment, the cylindrical shape and flat surface 6721A, B allow the adapter pin 4503 to be rotated via a tool connected at the second end 6703 and to rotate a component connected at the first end 6701.

FIG. 68 shows a top view of the adapter pin 4503, according to one embodiment of the present disclosure. In at least one embodiment, the shaft 6702 includes a diameter 6801 that measures at least about 2.0 mm, or about 2.0-8.0 mm, 2.0-3.0 mm, 3.0-4.0 mm, 4.0-5.0 mm, 4.46 mm, 5.0-6.0 mm, 6.0-7.0 mm, or about 7.0-8.0 mm, or less than about 8.0 mm.

FIG. 69 shows a side view of the adapter pin 4503, according to one embodiment of the present disclosure. According to one embodiment, the adapter pin 4503 includes a length 6901 between the first end 6701 and the second end 6703. In various embodiments, the length 6901 measures at least about 30.0 mm, or about 30.0-70.0 mm, 30.0-40.0 mm, 40.0-50.0 mm, 50.8 mm, 50.0-60.0 mm, or about 60.0-70.0, or less than about 70.0 mm. In at least one embodiment, the first side portion 6705 and the second side portion 6707 include a thickness 6903. According to one embodiment, the thickness 6903 measures at least about 2.0 mm, or about 2.0-5.0 mm, 2.0-3.0 mm, 3.0-4.0 mm, 3.05 mm, 3.53 mm, or 4.0-5.0 mm, or less than about 5.0 mm. In at least one embodiment, the first end 6701 and the second end 6703 demonstrate a thickness 6903 of about 3.53 mm.

In one or more embodiments, the shaft 6702 includes an end 6902 approximate the sloped portion 6715A and an end 6904 approximate the sloped portion 6715B. In at least one embodiment, the shaft 6702 includes radii 6911A-B that transition the ends 6902, 6904 to the sloped portions 6915A-B. In various embodiments, the radii 6911A-B measure at least about 0.5 mm, or about 0.5-4.0 mm, 0.5-1.0 mm, 1.0-1.5 mm, 1.59 mm, 1.5-2.0 mm, 2.0-2.5 mm, 2.5-3.0 mm, 3.0-3.5 mm, or 3.5-4.0 mm, or less than about 4.0 mm.

In various embodiments, the first side portion 6705 includes a length 6905 between the first end 6701 and the end 6902. In at least one embodiment, the length 6905 measures at least about 5.0 mm, or about 5.0-12.0 mm, 5.0-6.0 mm, 6.0-7.0 mm, 7.0-8.0 mm, 8.4 mm, 8.0-9.0 mm, 9.0-10.0 mm, 10.0-11.0 mm, 11.0-12.0 mm, or less than about 12.0 mm. In one or more embodiments, the second side portion 6705 includes a length 6907 between the second end 6703 and the end 6904. In various embodiments, the length 6907 measures at least about 10.0 mm, or about 10.0-30.0 mm, 10.0-15.0 mm, 15.0-20.0 mm, 18.5 mm, 20.0-25.0 mm, 25.0-30.0 mm, or less than about 30.0 mm. In at least one embodiment, a distance 6909 between the stop 6713 and the second end 6703 measures at least about 2.0 mm, about 2.0-8.0 mm, 2.0-3.0 mm, 3.0-4.0 mm, 4.0-5.0 mm, 4.95 mm, 5.0-6.0 mm, 6.0-7.0 mm, or 7.0-8.0 mm, or less than about 8.0 mm.

FIG. 70 shows a side view of the adapter pin 4503. In one or more embodiments, the stops 6713A, 6713B include a radius 7001. In various embodiments, the radius 7001 measures at least about 0.2 mm, or about 0.1-3.0 mm, 0.2-3.0 mm, 0.1-0.5 mm, 0.5-1.0 mm, 0.6 mm, 1.0-1.5 mm, 1.5-2.0 mm, 2.0-2.5 mm, or 2.5-3.0 mm, or less than about 3.0 mm.

FIG. 71 shows a perspective view of a tool adapter 7100, according to one embodiment of the present disclosure. In particular embodiments, the tool adapter 7100 includes a plunger 7101, a shaft 7102, and an adapter pin 4503. In various embodiments, the plunger 7101 slides over the shaft 7102, while the pin adapter is placed into a top end 7103. In one or more embodiments, the plunger 7101 includes a compressed profile, with a disk region 7113 dividing a bottom portion 7111 and a top portion 7112. The bottom portion 7111 and the top portion 7112 may extend continuously through the surface of the circular disk region 7113. In at least one embodiment, the bottom portion 7112 includes hooks 7114 configured to enable and disable a locked state of the tool adapter 7100. In some embodiments, the hooks 7114 are spaced apart by gaps 7115. In particular embodiments, the hooks 7114 engage a stop 7121A (e.g., corresponding to an unlocked state) or a stop 7121B (e.g., corresponding to a locked state). The plunger 7101 may slide across the shaft 7102, and may become removably coupled to the shaft 7102 once the hooks 7114 connect with either of the stops 7121A-B.

In various embodiments, the shaft 7102 includes an indentation 7131 and a bottom end 7106, and the shaft 7102 is substantially cylindrical in shape (e.g., or includes any other suitable shape, such as a prism or other solid of revolution). The shaft 7102 may extend from the top end 7103 to the bottom end 7106. In one or more embodiments, the adapter pin 4503 includes an indentation 7132 and a stop 7122, and the adapter pin 4503 is substantially cylindrical in shape (e.g., or includes any other suitable shape, such as a prism or other solid of revolution). In at least one embodiment, the adapter pin 4503 is locked into place on the inside of the shaft 7102 by means of engaging a stop, magnetic attachment, threaded attachment, and/or any other forms of fastening.

FIG. 72 shows a bottom view of the tool adapter 7100, according to one embodiment of the present disclosure. In at least one embodiment of the present disclosure, the disk portion 7113 of the plunger 7101 is substantially cylinder in shape (e.g., or any other suitable shape, such as a prism or other solid of revolution). In various embodiments, the top end 7106 includes an aperture 7201.

FIG. 73A shows a side view of the tool adapter 7100 in an unlocked state, according to one embodiment of the present disclosure. In an unlocked state, the hooks 7114 of the plunger 7101 may engage the stop 7121B. In particular embodiments, the shaft 7102 includes a locking mechanism 7301. In various embodiments, the locking mechanism 7301 includes a protruding edge 7302, and a hook 7303. In at least one embodiment of the present disclosure, the protruding edge 7302 is higher relative to a surface 7304.

FIG. 73B shows a side view of the tool adapter 7100 in a locked state, according to one embodiment of the present disclosure. In one or more embodiments, the shaft 7102 includes an opening 7305. In various embodiments, the plunger 7101 is moved towards the opening 7305, and the hooks 7114 engage the stop 7121A once the locations are aligned. In particular embodiments, the plunger 7101, in a locked state, may apply pressure to the protruding edge 7302 of the locking mechanism 7301. Applying pressure to the protruding edge 7302 may lower the hook 7303. Lowering the hook 7303 may allow the shaft 7102 to engage a desired attachment.

FIG. 74 shows a perspective view of the drill pin 4500 and the tool adapter 7100 configured to an unlocked state, according to one embodiment of the present disclosure. In various embodiments, the drill pin 4500 is inserted into the aperture 7201. In particular embodiments, the tool adapter 7100 is moved from an unlocked state to a locked state by sliding the plunger 7101 towards the drill pin 4500. According to one embodiment, the drill pin 4500 includes an adapter pin (not shown) and the tool adapter 7100 securely connects to the adapter pin to attach to the drill pin 4500. As the plunger 7101 progresses over the shaft 7102, the hooks 7114 may engage with the stop 7121A (not pictured) when aligned (e.g., as shown in FIG. 73B). Once the locked position is engaged, the plunger may apply pressure to the locking mechanism 7301. In particular embodiments, engaging the locking mechanism 7301 allows the hook 7303 (not pictured) to engage a stop 4522 on an adapter pin 4503 attached to the drill pin 4500 (see FIG. 45). In particular embodiments, engaging the hook 7303 on the stop 4522 locks the drill pin 4500 inside the shaft 7102.

Figure 75:
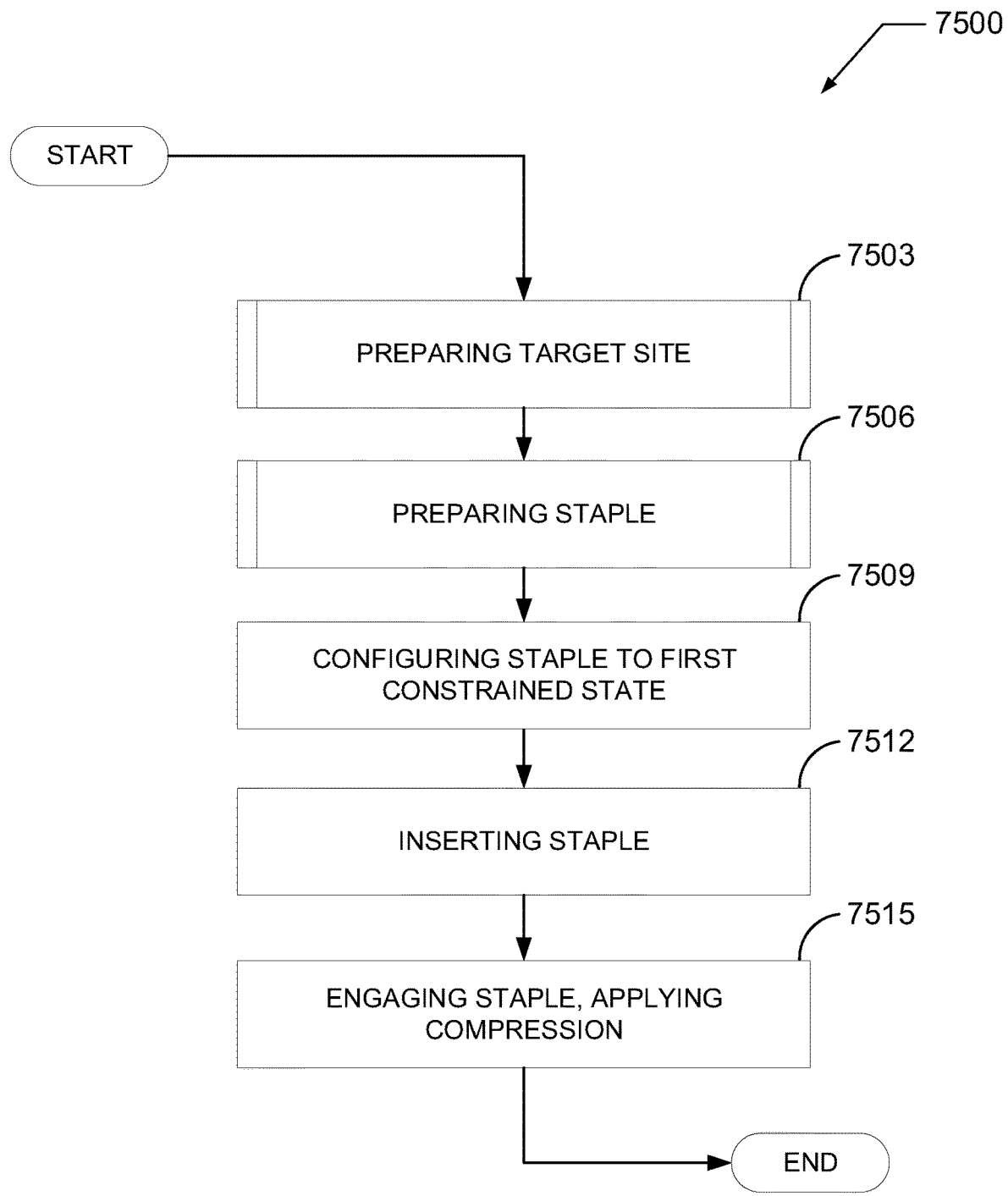
FIG. 75 shows a flowchart of an exemplary staple installation process, according to one embodiment of the present disclosure.

FIG. 75 shows an exemplary staple insertion process 7500. In at least one embodiment, a user (e.g., a surgeon or technician) performs the process 7500 to insert a staple to a target site and apply compressive forces to the target site via the staple. As will be understood by one having ordinary skill in the art, the steps and processes shown in FIG. 75 (and those of all other flowcharts and sequence diagrams shown and described herein) may operate concurrently and continuously, are generally asynchronous and independent, and are not necessarily performed in the order shown. In one or more embodiments, the process 7500 is performed following an insertion of an implant between two or more bony structures. In one example, a user inserts a spinal fusion cage into an intervertebral space between two adjacent vertebrae. In the same example, the user performs the process 7500 (e.g., or a subset of the steps thereof) to insert a staple into the adjacent vertebrae such that the staple is aligned over the inserted spinal cage and compresses the adjacent vertebrae toward the spinal cage.

Figure 76:
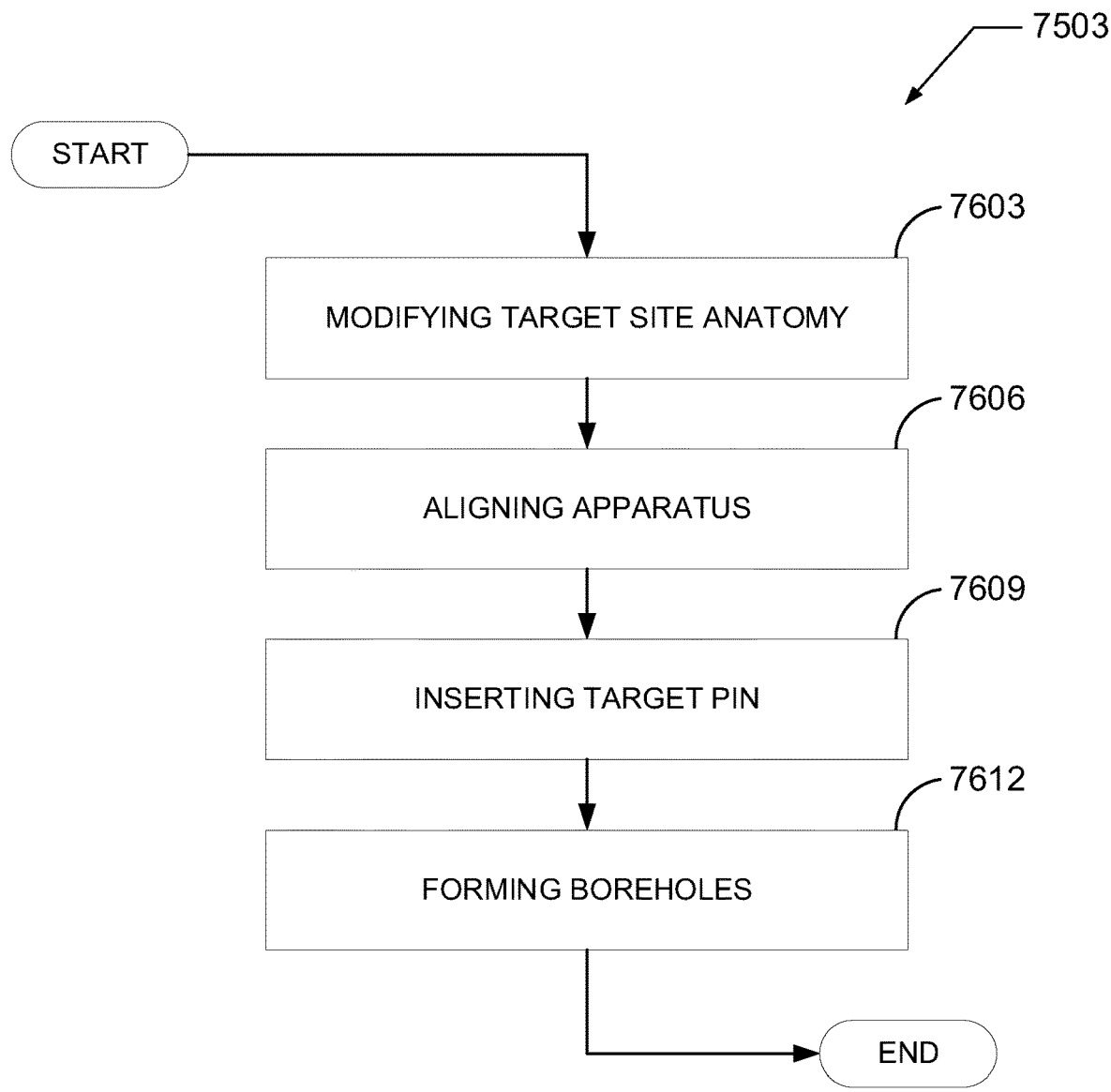
FIG. 76 shows a flowchart of an exemplary target site preparation process, according to one embodiment of the present disclosure.

At step 7503, the process 7500 includes preparing a target site for the insertion of a staple. In one example, the target site includes a pair of adjacent vertebrae. In various embodiments, preparing the target site for the insertion of a staple includes any necessary surgical techniques for preparing the location for a staple installation. In at least one embodiment, additional details of one or more techniques performed at step 7503 are shown in FIG. 76 and described in the corresponding description.

Figure 77:
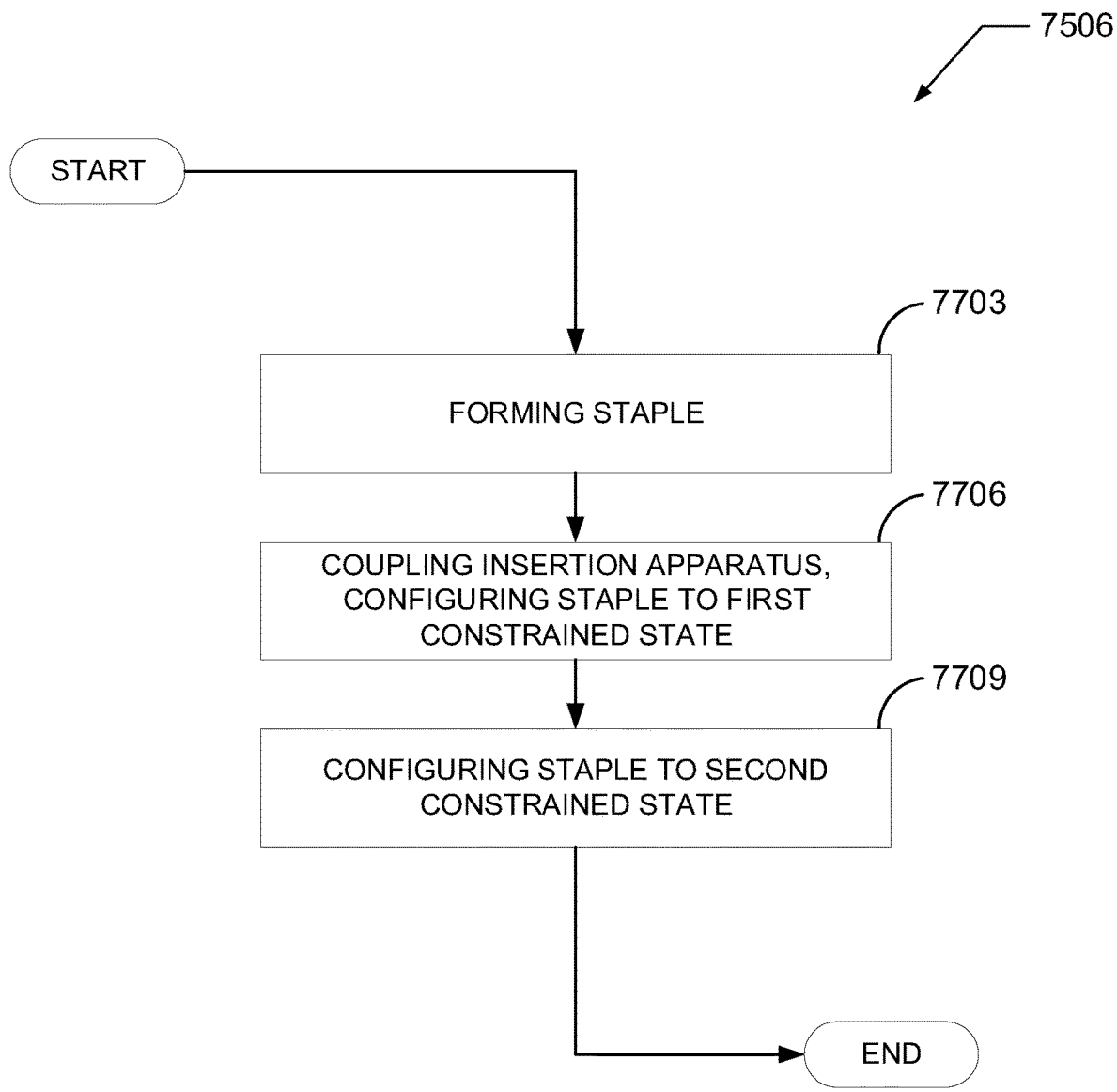
FIG. 77 shows a flowchart of an exemplary staple preparation process, according to one embodiment of the present disclosure.

At step 7506, the process 7500 includes preparing a staple for applying compression at a target site. In one example, preparing the staple includes forming the staple such that the staple demonstrates a bias toward a first state (e.g., a non-deformed state). In at least one embodiment, the bias towards the first state allows the staple to be deformed from the first state and undergo contraction toward the first state upon release from the deformation (e.g., the force of the contraction being used to apply compressive forces to the target site). In various embodiments, engaging contraction of the staple refers to releasing the staple from a deformed state (e.g., also referred to as a "constrained state"). In at least one embodiment, additional details of one or more techniques performed at step 7506 are shown in FIG. 77 and described in the corresponding description.

At step 7509, the process 7500 includes configuring the staple to a first constrained state (e.g., in which the staple may be inserted to boreholes at the target site). In various embodiments, configuring the staple to the first constrained state includes coupling a staple installation tool to the staple (for example, staple installation tool 2600 shown in FIG. 26). In particular embodiments, the staple installation tool 2600 attaches to the staple, deforms the staple to the first constrained state, and maintains the staple in the first constrained state during insertion of the staple to the target site. In various embodiments, the staple installation tool 2600 deforms the staple by applying a downward force to a base member of the staple and applying upward forces to opposite sides of the base member. In one or more embodiments, the staple installation tool applies a variable amount of force to the staple to deform the staple according to the necessities of the particular surgical application or target site. For example, a rod of the staple installation tool can be rotated (e.g., via a knob or handle) to increase or decrease the downward force on the base member and, thereby, cause further deformation or contraction of the staple. In one example, a manufacturer provides the staple to a user in the form of a kit in which the staple installation tool is attached to the staple and the staple is deformed to a second constrained state. In this example, the second constrained state includes opposed pairs of the staple legs being oriented away from each other. Continuing the example, to configure the staple from the second constrained state to the first constrained state, a user rotates a knob of the staple installation tool to rotate the rod and, thereby, reduce a downward force applied to the staple base member. In the same example, the user rotates the knob until the staple legs are oriented substantially parallel, thereby achieving the first constrained state.

At step 7512, the process 7500 includes inserting the staple into the target site. For example, a user inserts the staple into boreholes formed into adjacent vertebrae such that portions of the staple lie within each vertebra and the staple is aligned over an implant inserted into the intervertebral space between the vertebrae.

At step 7515, the process 7500 includes engaging the staple. In various embodiments, engaging the staple causes the staple to contract towards a non-deformed state and, thereby, apply compressive forces at the target site. In one or more embodiments, engaging the staple includes decoupling the staple installation tool from the staple such that the staple is allowed to recover from the constrained state (e.g., by contracting inward toward the non-deformed state).

FIG. 76 shows an exemplary target site preparation process 7503 (e.g., referred to as step 7503 when performed during the process 7500 of FIG. 75).

At step 7603, the process 7600 includes modifying target site anatomy. In one example, a user exposes and prepares a fusion site to receive one or more implants (e.g., cage implants, staples, etc.). A user can expose the fusion site (e.g., or other target site) can include making one or more incisions and using appropriate surgical instruments and techniques to remove or displace tissues and expose bony structures into which the staple will be inserted. In another example, a user removes osteophytes from anterior portions of vertebrae to prevent the osteophytes from inhibiting seating of a staple inserted to the vertebrae. In at least one embodiment, modifying target site anatomy includes inserting an implant between two or more bony structures at the target site. In one example, a user inserts a spinal fusion cage into an intervertebral space between two adjacent vertebrae. In some embodiments, inserting the implant includes aligning an anterior edge of the implant with an anterior edge of the first bony structure and an anterior edge of the second bony structure.

At step 7606, the process 7600 includes aligning a boring apparatus (e.g., boring apparatus 3600 shown in FIG. 36) against the target site. For example, a user aligns a boring apparatus against two adjacent vertebrae such that a central window of the boring apparatus is centered over the intervertebral space and, in some embodiments, centered over an implant inserted to the intervertebral space. In the same example, a first pair of corners of the boring apparatus contact a first vertebra of the adjacent vertebrae, and a second pair of corners, opposite the first pair of corners, contact a second vertebra of the adjacent vertebrae.

At step 7609, the process 7600 includes inserting a targeting pin through the aligned boring apparatus and into the target site. In at least one embodiment, the inserted targeting pin affixes the boring apparatus to the target site anatomy. In one example, following boring apparatus alignment to two adjacent vertebrae, a user inserts the targeting pin through the boring apparatus and into a first vertebra of the two adjacent vertebrae. In some embodiments, inserting the targeting pin includes verifying (e.g., via a fluoroscopy or other suitable medical image) a trajectory of the targeting pin relative to the first vertebra and the second vertebra. According to one embodiment, the trajectory includes a tip of the targeting pin being directed towards or into the first vertebrae.

At step 7612, the process 7600 includes forming boreholes in the target site via the aligned and affixed boring apparatus. According to one embodiment, each borehole is configured to receive a leg of a staple, and the boreholes are arranged to align with the staple in a first constrained state. In at least one embodiment, forming the boreholes includes inserting drilling pins through the boring apparatus and into the target site and removing material from the target site via rotation of the drilling pins. In one example, forming a borehole includes driving a first drilling pin through a first boring aperture of the boring apparatus and into a first vertebra of two adjacent vertebrae. In various embodiments, four drilling pins are inserted through the boring apparatus and rotated into the target site such that a first pair of boreholes are formed in a first bony structure and a second pair of boreholes are formed in a second bony structure. In some embodiments, the drilling pins are inserted in an alternating sequence in which a first drilling pin is inserted to a first bony structure, a second drilling pin is inserted to a second bony structure, a third drilling pin is inserted to the first bony structure, and a fourth drilling pin is inserted to a fourth bony structure.

FIG. 77 shows an exemplary staple preparation process 7506. (e.g., referred to as step 7506 when performed during the process 7500 of FIG. 75). In some embodiments, the process 7506 is performed by a manufacturer (e.g., or other suitable entity) prior to delivery of the staple (e.g., and related elements, such as alignment and insertion tools) to a user.

At step 7703, the process 7506 includes forming the staple, according to one embodiment of the present disclosure. In particular embodiments, the staple is manufactured in a non-constrained state from a single block of material. The staple may be formed into a non-constrained state during manufacturing by maintaining the staple within a martensite temperature range. In various embodiments, the staple can be deformed to a constrained state while the staple is maintained within the austenite temperature range. In one example, the staple can be maintained within the martensite temperature range during manufacturing to produce an acute leg angle (e.g., such that the staple legs are directed inwards to provide a bias towards a contracted staple state). Continuing with the same example, the staple can be deformed into a constrained state (e.g., the legs are substantially parallel) during manufacturing by maintaining the staple in the austenite temperature range. In at least one embodiment, the austenite temperature range includes ambient temperature and human body temperatures such that the staple maintains a bias towards a contracted state during preparation, insertion, and operation.

At step 7706, the process 7506 includes coupling the staple installation tool to the staple and, thereby, configuring the staple to the first constrained state. In particular embodiments, the installation tool 2600 is coupled to the staple for configuration and installment purposes. In one or more embodiments, the insertion apparatus is synonymous with the installation tool 2600. In at least one embodiment, the staple is configured to the first constrained state by applying a downward force to the staple base member and applying upward forces to opposite sides of the base member.

At step 7709, the process 7506 includes configuring the staple to a second constrained state via the attached staple installation tool. In various embodiments, configuring the staple to the second constrained state includes increasing the downward force applied to the staple base member. In at least one embodiment, increasing the downward force (e.g., which may also cause an increase the upward forces) causes the staple to further deform such that the opposed pairs of staple legs are oriented away from each other. In particular embodiments, the staple is configured to the second constrained state during shipment to a user in order to resist or tolerate external events (e.g., shocks, vibrations, etc.) and internal events (e.g., material creep, fitting creep, etc.) that may cause the staple to partially recover toward the non-deformed state.

Figure 78:
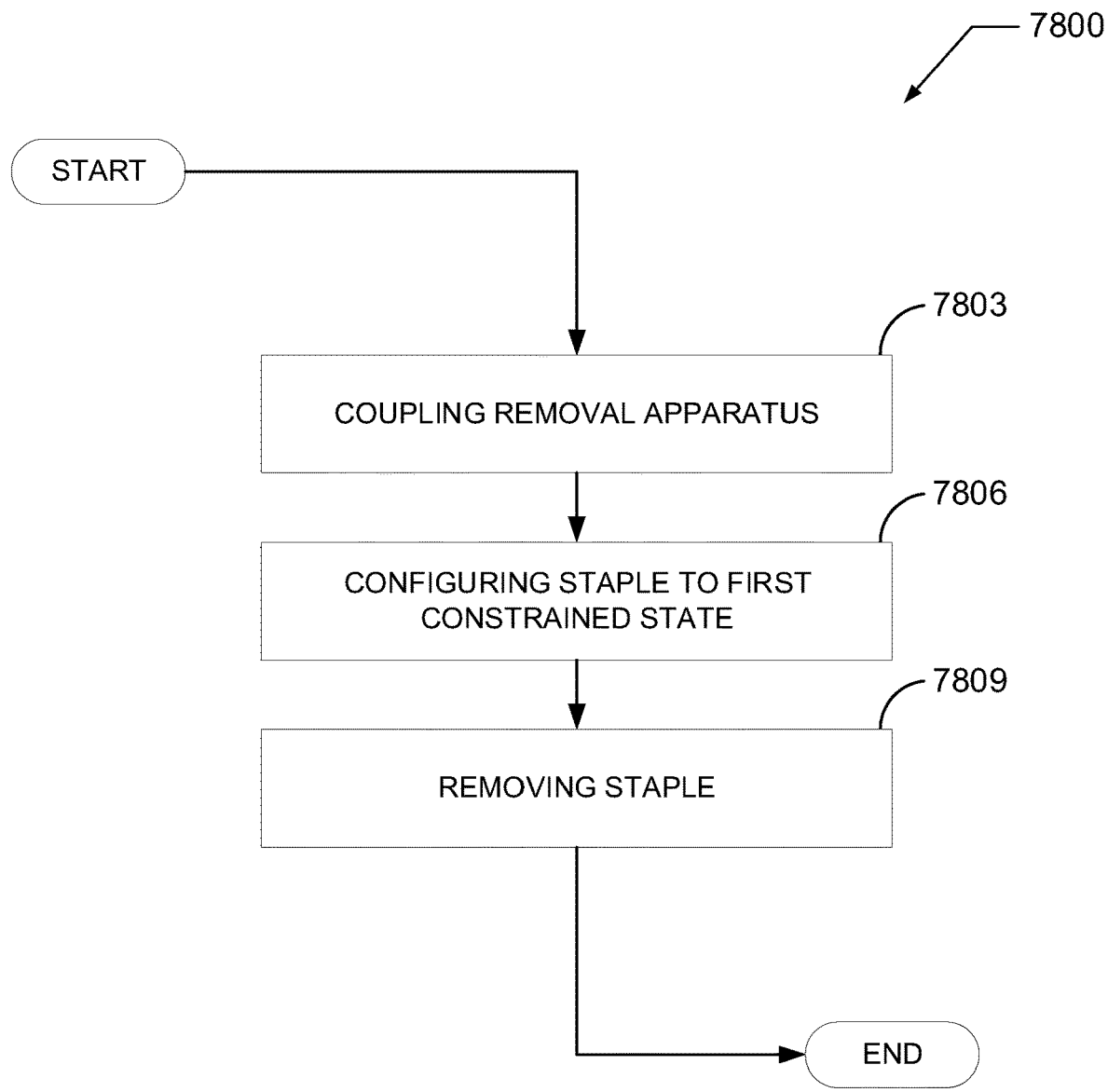
FIG. 78 shows a flowchart of an exemplary staple removal process, according to one embodiment of the present disclosure.

FIG. 78 shows an exemplary staple removal process 7800.

At step 7803, the process 7800 includes coupling a staple removal apparatus to the staple. In various embodiments, the staple removal apparatus includes the staple installation tool 2600 (FIG. 26) excluding a spacer (e.g., spacer 3200 shown in FIGS. 26-29). In one or more embodiments, coupling the staple removal apparatus to the staple includes attaching a first hooked portion of the staple removal apparatus to a first indentation of the staple and attaching a second hooked portion of the staple removal apparatus to a second indentation of the staple (e.g., opposite the first indentation). In at least one embodiment, coupling the staple removal apparatus includes orienting the first and second hooked portions (while attached to the staple) to a substantially parallel position, sliding a sleeve over the first and second hooked portions, and inserting a rod through the sleeve and the first and second hooked portions to maintain the substantially parallel position.

At step 7806, the process 7800 includes configuring the staple to the first constrained state via the staple removal apparatus. According to one embodiment, in the first constrained state the legs of the staple are substantially parallel, thereby allowing the staple to be removed more easily dislodged and removed from the target site via the boreholes. In at least one embodiment, step 7806 occurs during step 7803. For example, the act of orienting the first and second hooked portions to a parallel position while attached to the staple causes the staple removal apparatus to apply upward forces to the staple. Continuing the example, the upwards forces cause the staple to deform such that legs of the staple are drawn to substantially parallel positions. In at least one embodiment, configuring the staple to the first constrained state includes rotating the rod of the staple removal apparatus such that the staple removal apparatus applies a downward force to the staple (e.g., in opposition to the upward forces of the first and second hooked portions). In some embodiments, the rod is rotated further into or out of the staple removal apparatus to precisely and accurately control the deformation of the staple to the first constrained state.

At step 7809, the process 7800 includes removing the staple from the target site. In various embodiments, removing the staple includes pulling the staple removal apparatus away from the target site (e.g., while the staple removal apparatus is coupled to the staple). In some embodiments, removing the staple from the target site includes verifying an orientation of the staple legs under fluoroscopy (e.g., or another suitable imaging technique). In one example, a user performs fluoroscopy to confirm that the legs of the staple are substantially parallel and/or aligned with corresponding boreholes.

While various aspects have been described in the context of a preferred embodiment, additional aspects, features, and methodologies of the claimed systems will be readily discernible from the description herein, by those of ordinary skill in the art. Many embodiments and adaptations of the disclosure and claimed systems other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

Aspects, features, and benefits of the claimed devices and methods for using the same will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the devices and methods for using the same to the precise forms disclosed. Many modifications and variations are possible in light of the above teaching.

The embodiments were chosen and described in order to explain the principles of the devices and methods for using the same and their practical application so as to enable others skilled in the art to utilize the devices and methods for using the same and various embodiments and with various modifications as are suited to the particular use contemplated. Alternative embodiments will become apparent to those skilled in the art to which the present devices and methods for using the same pertain without departing from their spirit and scope. Accordingly, the scope of the present devices and methods for using the same is defined by the appended claims rather than the foregoing description and the exemplary embodiments described therein.

What is claimed is:

1. A method comprising:
   aligning a boring apparatus against a first vertebra and a second vertebra;
   inserting a targeting pin into the first vertebra via an affixing aperture extending through the boring apparatus;
   driving, through a plurality of boring apertures extending through the boring apparatus, at least one drill pin into the first vertebra and at least one drill pin into the second vertebra, thereby creating a plurality of boring apertures;
   inserting, via a staple installation tool, a nitinol staple into the plurality of boring apertures in a constrained state; and
   transitioning, via the staple installation tool, the nitinol staple from the constrained state to an unconstrained state and thereby compressing the first vertebra and the second vertebra.

2. The method of claim 1, wherein transitioning the nitinol staple from the constrained state to the unconstrained state comprises detaching the staple installation tool from the nitinol staple.

3. The method of claim 1, further comprising expanding, via the staple installation tool, the nitinol staple to the constrained state prior to inserting the nitinol staple into the plurality of boring apertures.

4. The method of claim 1, further comprising inserting an implant into an intervertebral space between the first vertebra and the second vertebra.

5. The method of claim 4, further comprising aligning an aperture of the boring apparatus with the implant.

6. The method of claim 1, further comprising exposing and preparing a fusion site.

7. The method of claim 1, further comprising verifying, via a fluoroscopy image, a trajectory of the targeting pin relative to the first vertebra and the second vertebra.

8. The method of claim 1, further comprising determining that a tip of the targeting pin is directed towards the first vertebra.

9. The method of claim 1, wherein driving, through the plurality of boring apertures extending through the boring apparatus, at least one drill pin into the first vertebra and at least one drill pin into the second vertebra comprises:
   driving, through a first boring aperture extending through the boring apparatus, a first drill pin into the second vertebra;
   driving, through a second boring aperture extending through the boring apparatus, a second drill pin into the first vertebra;
   driving, through a third boring aperture extending through the boring apparatus, a third drill pin into the second vertebra; and
   driving, through a fourth boring aperture extending through the boring apparatus, a fourth drill pin into the first vertebra.

10. The method of claim 9, wherein:
   the first drill pin and the third drill pin comprise a first length;
   the second drill pin and the fourth drill pin comprise a second length; and
   the first length is greater than the second length.

11. The method of claim 1, wherein the nitinol staple comprises at least two legs.

12. The method of claim 11, wherein the nitinol staple comprises at least four legs.

13. A method, comprising:
   positioning a first side of a body of a boring apparatus against a first vertebra of a pair of vertebrae, the pair of vertebrae comprising the first vertebra and a second vertebra adjacent to the first vertebra;
   inserting, through an affixing aperture extending from a second side of the body of the boring apparatus to the first side, a targeting pin into the first vertebra;
   driving, through a plurality of boring apertures extending from the second side to the first side of the body, a plurality of drill pins into a respective one of the first vertebra and the second vertebra;
   inserting, via a staple installation tool:
      a first pair of legs of a staple into a first set of a plurality of apertures corresponding to the first vertebra; and
      a second pair of legs of the staple into a second set of the plurality of apertures corresponding to the second vertebra; and
   engaging, via the staple installation tool, contraction of the staple with the first pair of legs and the second pair of legs positioned in the plurality of apertures in the pair of vertebrae.

14. The method of claim 13, wherein inserting the first pair of legs of the staple into the first set of the plurality of apertures and the second pair of legs of the staple into the second set of the plurality of apertures is performed while the staple is in a constrained state.

15. The method of claim 14, wherein engaging contraction of the staple comprises allowing the staple to transition from the constrained state to an unconstrained state.

16. The method of claim 15, wherein allowing the staple to transition from the constrained state to the unconstrained state comprises detaching the staple installation tool from the staple.

17. The method of claim 13, further comprising expanding, via the staple installation tool, the staple to a constrained state prior to inserting the staple into the first pair of legs of the staple into the first set of the plurality of apertures and the second pair of legs of the staple into the second set of the plurality of apertures.

18. The method of claim 13, wherein the staple comprises a trapezoidal-shaped nitinol bridge.

19. The method of claim 13, further comprising inserting an implant into an intervertebral space between the first vertebra and the second vertebra.

20. The method of claim 19, wherein contraction of the staple with the first pair of legs and the second pair of legs positioned in the plurality of apertures in the pair of vertebrae causes compression of the implant between the first vertebra and the second vertebra.

* * * * *